United States Patent
Fenical et al.

(10) Patent No.: US 9,481,662 B2
(45) Date of Patent: Nov. 1, 2016

(54) SERINIQUINONES, MELANOMA-SPECIFIC ANTICANCER AGENTS

(71) Applicant: The Regents of the University of California, Oakland, CA (US)

(72) Inventors: William Fenical, Del Mar, CA (US); Paul R. Jensen, San Diego, CA (US); James J. La Clair, San Diego, CA (US); Lynnie Trzoss, San Diego, CA (US); Takashi Fukuda, Ibaraki (JP)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/606,938

(22) Filed: Jan. 27, 2015

(65) Prior Publication Data
US 2015/0148314 A1 May 28, 2015

Related U.S. Application Data

(63) Continuation of application No. PCT/US2013/052382, filed on Jul. 26, 2013.

(60) Provisional application No. 61/676,427, filed on Jul. 27, 2012.

(51) Int. Cl.
*C07D 333/74* (2006.01)
*C07D 333/50* (2006.01)
*C07D 209/80* (2006.01)
*C07D 307/77* (2006.01)
*G01N 33/50* (2006.01)
*C07D 209/56* (2006.01)
*C07D 307/92* (2006.01)
*C07D 339/08* (2006.01)
*C07D 409/06* (2006.01)
*C07D 409/12* (2006.01)
*C07D 495/04* (2006.01)
*C07F 9/6574* (2006.01)
*A61K 31/381* (2006.01)

(52) U.S. Cl.
CPC ........... *C07D 333/74* (2013.01); *C07D 209/56* (2013.01); *C07D 209/80* (2013.01); *C07D 307/77* (2013.01); *C07D 307/92* (2013.01); *C07D 333/50* (2013.01); *C07D 339/08* (2013.01); *C07D 409/06* (2013.01); *C07D 409/12* (2013.01); *C07D 495/04* (2013.01); *C07F 9/65742* (2013.01); *G01N 33/5011* (2013.01); *A61K 31/381* (2013.01)

(58) Field of Classification Search
CPC ...................................... C07D 333/74
USPC ................... 514/410, 96; 548/418
See application file for complete search history.

(56) References Cited

FOREIGN PATENT DOCUMENTS

WO    WO-9731936 A2    9/1997
WO    WO-2008066301 A1    6/2008

OTHER PUBLICATIONS

King, Med. Chem. Principle and Practice (1994), pp. 206-208.*
Laatsch, H., "Synthesis of Hydroxylated Binaphthoquinones via Amine/Hydroxyl Exchange—The Reaction of 2,2'-Binapthyl-I,4;I',4'-diquinones with Piperidine," Zeitschrift fur Naturforschung B: A Journal of Chemical Sciences, 44(10):1271-1278 (1989).
Martins et al., "Photolysis of 2-amino- and 2-methylamino-1,4-naphthoquinone," Tetrahedron, 44(2):591-598 (1988).
Kayser et al., "In vitro leishmanicidal activity of monomeric and dimeric naphthoquinones," Acta Tropica 77(3):307-314 (2000).
International Search Report for PCT/US2013/052382 issued Nov. 20, 2013, 6 pages.

* cited by examiner

*Primary Examiner* — Taofiq A Solola
(74) *Attorney, Agent, or Firm* — Mintz Levin Cohn Ferris Glovsky and Popeo, P.C.

(57) ABSTRACT

There are provided, inter alia, derivatives of seriniquinone and methods useful for the treatment of cancer, and in particular treatment of melanoma and prostate cancer.

19 Claims, 26 Drawing Sheets seriniquinone (1)

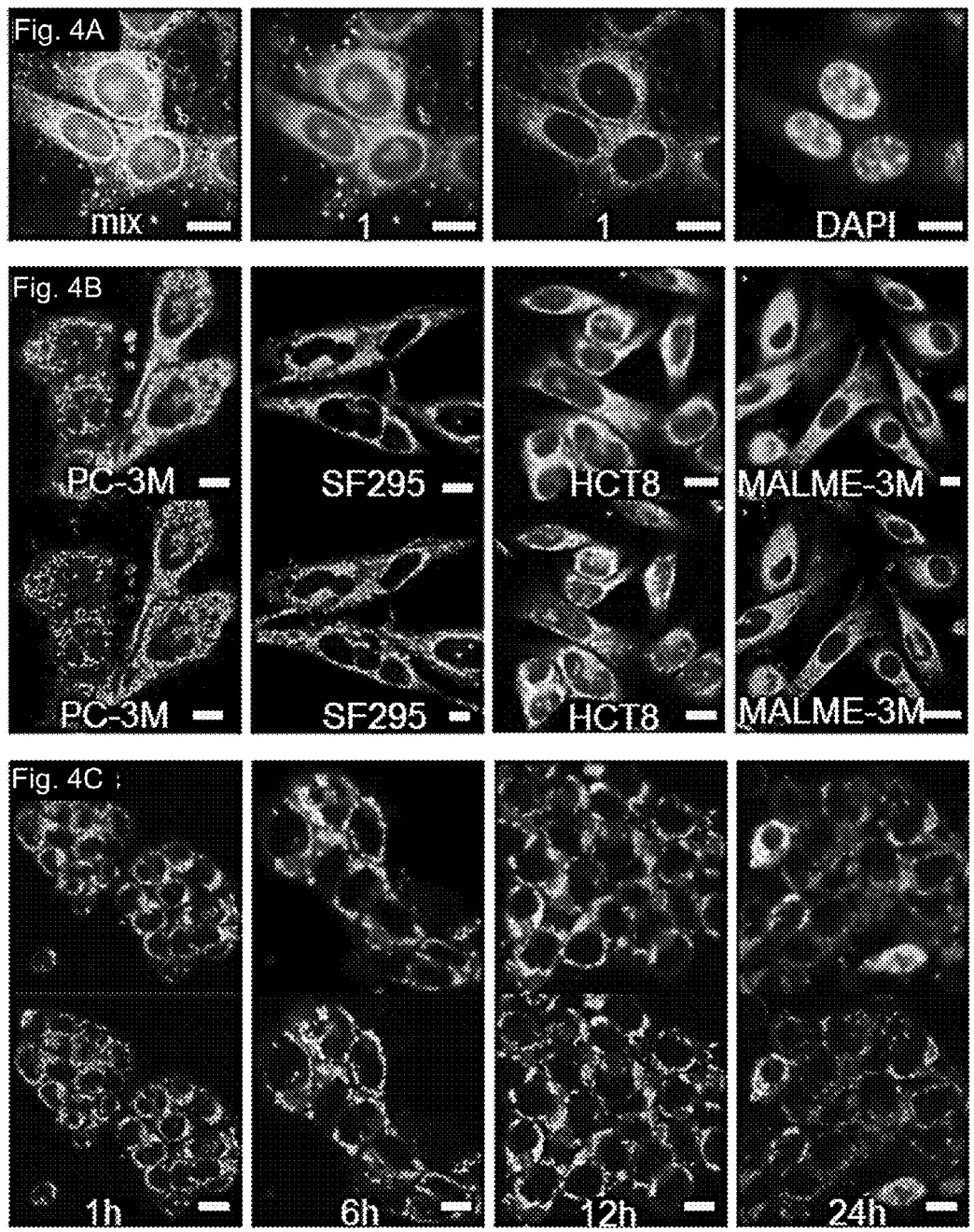

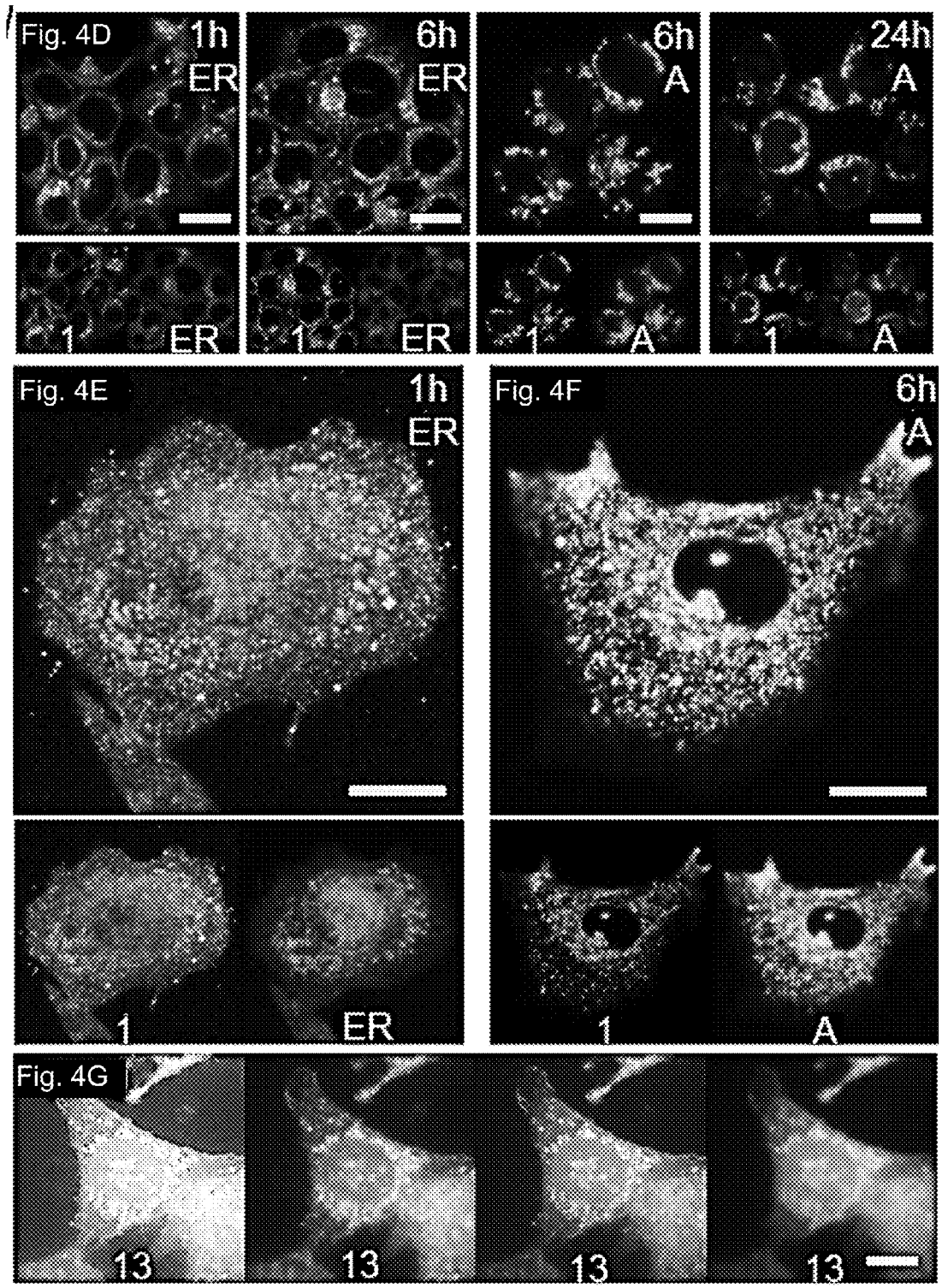

Fig. 5A

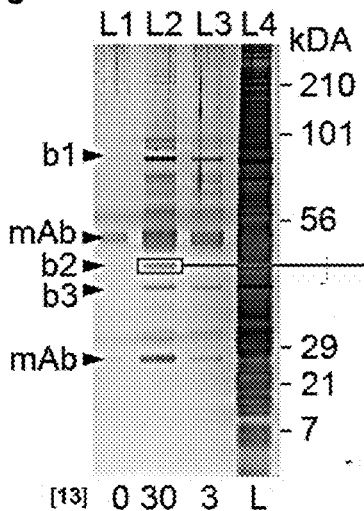

Fig. 5B

▨ 19 aa signal peptide  ▨ 13 aa propeptide
▨ 30 aa PIF-core/Y-P30 peptide  ▨ 47 aa DCD-1 peptide MRFMTLLFLTALAGALVCAYDPEAASAPGSGNPCHEA
SAAQKENAGEDPGLARQAPKPRKQRSSLLEKGLDGA
KKAVGGLGKLGKDAVEDLESVGKGAVDVKDVLDSVL MGKVKVGVNGFGRIGRLVTRAAFNSGKVDIVAINDPFI
DLNYMVYMFQYDSTHGKFHGTVKAENGKLVINGNPIT
IFQERDPSKIKWGDAGAEYVVESTGVFTTMEKAGAHL
QGGAKRVIISAPSADAPMFVMGVNHEKYDNSLKIISNA
SCTTNCLAPLAKVIHDNFGIVEGLMTTVHAITATQKTV
DGPSGKLWRDGRGALQNIIPASTGAAKAVGKVIPELN
GKLTGMAFRVPTANVSVVDLTCRLEKPAKYDDIKKVV
KQASEGPLKGILGYTEHQVVSSDFNSDTHSSTFDAGA
GIALNDHFVKLISWYDNEFGYSNRVVDLMAHMASKE

Fig. 5C

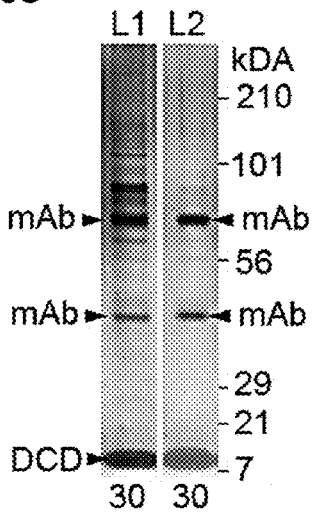

Fig. 5D

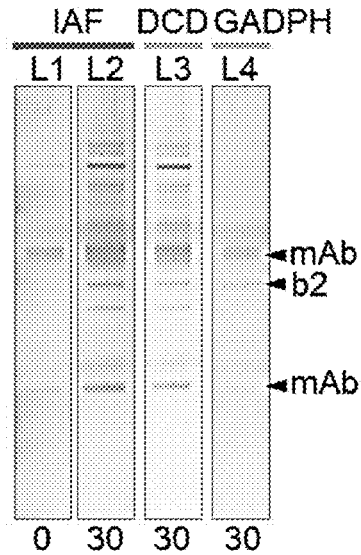

Fig. 5E

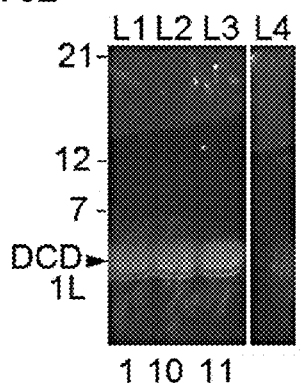

Fig. 12:

| Panel/ Cell Line | Log10 GI50 | GI50 | Log10 TGI | TGI | Log10 LC50 | LC50 |
|---|---|---|---|---|---|---|
| Leukemia | | | | | | |
| CCRF-CEM | -5.72 | | -5.31 | | -4.37 | |
| HL-60(tb) | -5.82 | | -5.44 | | -5.07 | |
| K-562 | -5.99 | | -5.39 | | -4.00 | |
| MOLT-4 | -5.79 | | -5.39 | | -4.86 | |
| RPMI-8226 | -5.89 | | -5.29 | | -4.14 | |
| SR | -6.18 | | -5.29 | | -4.00 | |
| Non-small cell lung cancer | | | | | | |
| A549/ATCC | -5.90 | | -5.41 | | -4.61 | |
| EKVX | -5.45 | | -4.54 | | -4.00 | |
| HOP-62 | -5.82 | | -5.48 | | -5.13 | |
| HOP-92 | -6.56 | | -4.75 | | -4.00 | |
| NCI-H226 | -5.80 | | -5.39 | | -4.14 | |
| NCI-H23 | -6.68 | | -6.23 | | -4.30 | |
| NCI-H322M | -6.59 | | -5.91 | | -5.39 | |
| NCI-H460 | -6.07 | | -5.60 | | -5.18 | |
| NCI-H522 | -6.20 | | -5.61 | | -5.13 | |
| Colon cancer | | | | | | |
| COLO 205 | -5.84 | | -5.52 | | -5.20 | |
| HCC-2998 | -6.39 | | -5.81 | | -5.35 | |
| HCT-116 | -5.80 | | -5.22 | | -4.00 | |
| HCT-15 | -6.36 | | -5.61 | | -4.50 | |
| HT29 | -5.55 | | -5.16 | | -4.09 | |
| KM12 | -5.68 | | -5.23 | | -4.56 | |
| SW-620 | -6.05 | | -5.59 | | -5.15 | |
| CNS cancer | | | | | | |
| SF-268 | -5.73 | | -5.08 | | -4.20 | |
| SF-295 | -5.75 | | -5.40 | | -5.05 | |
| SF-539 | -5.84 | | -5.53 | | -5.22 | |
| SNB-19 | -6.13 | | -5.14 | | -4.40 | |
| SNB-75 | -6.77 | | -6.26 | | -5.64 | |
| U251 | -5.90 | | -4.94 | | -4.16 | |
| Melanoma | | | | | | |
| LOX IMVI | -6.66 | | -5.77 | | -4.21 | |
| MALME-3M | -7.24 | | -6.61 | | -6.09 | |
| M14 | -6.83 | | -6.45 | | -6.06 | |
| MDA-MB-43 | -6.83 | | -6.42 | | -6.01 | |
| SK-MEL-2 | -6.19 | | -5.57 | | -5.04 | |
| SK-MEL-28 | -6.55 | | -6.10 | | -5.39 | |
| SK-MEL-5 | -6.88 | | -6.58 | | -6.27 | |
| UACC-257 | -5.75 | | -5.48 | | -5.21 | |
| UACC-62 | -5.79 | | -5.43 | | -5.07 | |
| Ovarian Cancer | | | | | | |
| IGROV1 | -6.00 | | -5.30 | | -4.42 | |
| OVCAR-3 | -6.53 | | -5.93 | | -5.01 | |
| OVCAR-4 | -5.64 | | -5.12 | | -4.50 | |
| OVCAR-5 | -5.73 | | -5.46 | | -5.19 | |
| OVCAR-8 | -5.70 | | -4.96 | | -4.00 | |
| NCI/ADR-RI | -5.78 | | -5.16 | | -4.00 | |
| SK-OV-3 | -5.53 | | -4.77 | | -4.29 | |
| Renal Cancer | | | | | | |
| 786-0 | -5.51 | | -4.96 | | -4.37 | |
| A498 | -5.62 | | 5.25 | | -4.75 | |
| ACHN | -5.83 | | -4.91 | | -4.31 | |
| CAKI-1 | -5.69 | | -5.21 | | -4.40 | |
| RXF 393 | -5.92 | | -4.92 | | -4.39 | |
| SN12C | -5.96 | | -5.57 | | -5.18 | |
| TK-0 | -5.19 | | -4.71 | | -4.29 | |
| UO-31 | -6.58 | | -5.25 | | -4.54 | |
| Prostate Cancer | | | | | | |
| PC-3 | -5.76 | | -4.99 | | -4.00 | |
| DU-145 | -6.77 | | -6.51 | | -6.24 | |
| Breast Cacner | | | | | | |
| MCF7 | -5.98 | | -5.55 | | -5.11 | |
| MDA-MB-23 | -6.14 | | -4.00 | | -4.00 | |
| HS 578T | -5.91 | | -5.20 | | -4.00 | |
| BT-549 | -6.22 | | -5.68 | | -5.30 | |
| T-47D | -5.50 | | -4.46 | | -4.00 | |
| MDA-MB-46 | -5.85 | | -5.20 | | -4.35 | |
| MID | -6.04 | | -5.42 | | -4.73 | |
| Delta | 1.2 | | 1.19 | | 1.54 | |
| Range | 2.05 | | 2.61 | | 2.27 | |

Fig. 13A

| | Time | | Mean Optical Densities | | | | | Log10 Concentration | | | | | Percent Growth | | | | | |
|---|---|---|---|---|---|---|---|---|---|---|---|---|---|---|---|---|---|---|
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 | | | |
| Leukemia | | | | | | | | | | | | | | | | | | |
| CCRF-CEM | 0.526 | 1.245 | 1.723 | 1.199 | 1.122 | 0.333 | 0.222 | 104 | 94 | 83 | -37 | -58 | 1.88E-06 | 4.93E-06 | 4.23E-05 | | | |
| HL-60(tb) | 0.435 | 0.829 | 0.796 | 0.839 | 0.724 | 0.180 | 0.191 | 92 | 103 | 73 | -59 | -56 | 1.50E-06 | 3.59E-06 | 8.50E-06 | | | |
| K-562 | 0.104 | 0.574 | 0.544 | 0.502 | 0.343 | 0.070 | 0.053 | 93 | 85 | 51 | -33 | -49 | 1.02E-06 | 4.03E-06 | 1.00E-04 | | | |
| MOLT-4 | 0.299 | 0.874 | 0.864 | 0.849 | 0.738 | 0.155 | 0.116 | 98 | 96 | 76 | -46 | -61 | 1.63E-06 | 4.10E-06 | 1.38E-05 | | | |
| RPMI-8226 | 0.611 | 1.483 | 1.451 | 1.305 | 1.143 | 0.507 | 0.302 | 96 | 78 | 59 | -23 | -54 | 1.27E-06 | 5.19E-06 | 7.22E-05 | | | |
| SR | 0.420 | 1.215 | 1.065 | 0.994 | 0.779 | 0.343 | 0.314 | 81 | 72 | 45 | -18 | -25 | 6.61E+07 | 5.13E-06 | 1.00E-04 | | | |
| Non-small cell lung cancer | | | | | | | | | | | | | | | | | | |
| 549/ATCC | 0.232 | 1.204 | 1.244 | 1.251 | 0.818 | 0.134 | 0.088 | 104 | 105 | 80 | -42 | -62 | 1.26E-06 | 3.87E-06 | 2.46E-05 | | | |
| EKVX | 0.962 | 2.092 | 1.917 | 1.743 | 1.714 | 1.372 | 0.550 | 84 | 69 | 67 | 36 | -43 | 3.52E-06 | 2.87E-05 | 1.00E-04 | | | |
| HOP-62 | 0.611 | 1.307 | 1.201 | 1.230 | 1.148 | 0.209 | 0.297 | 84 | 88 | 75 | -68 | -55 | 1.50E-06 | 3.34E-06 | 7.44E-06 | | | |
| HOP-92 | 0.392 | 0.949 | 0.865 | 0.762 | 0.546 | 0.451 | 0.269 | 85 | 68 | 28 | 11 | -31 | 2.65E-07 | 1.78E-05 | 1.00E-04 | | | |
| NCI-H226 | 0.814 | 1.415 | 1.364 | 1.286 | 1.263 | 0.423 | 0.405 | 91 | 78 | 75 | -48 | -50 | 1.59E-06 | 4.08E-06 | 7.26E-05 | | | |
| NCI-H23 | 0.509 | 1.355 | 1.262 | 1.237 | 0.379 | 0.320 | 0.227 | 89 | 86 | -26 | -37 | -55 | 2.10E-07 | 5.90E-07 | 5.04E-05 | | | |
| NCI-H322M | 0.975 | 2.111 | 1.920 | 1.880 | 1.067 | 0.130 | 0.068 | 83 | 80 | 8 | -87 | -93 | 2.60E-07 | 1.22E-06 | 4.10E-06 | | | |
| NCI-H460 | 0.266 | 1.874 | 2.001 | 1.837 | 1.014 | 0.078 | 0.056 | 108 | 96 | 47 | -71 | -79 | 8.54E-07 | 2.49E-06 | 5.64E-06 | | | |
| NCI-H522 | 0.334 | 0.816 | 0.802 | 0.761 | 0.529 | 0.123 | 0.056 | 97 | 89 | 40 | -71 | -83 | 6.31E-07 | 2.45E-06 | 7.45E-06 | | | |
| Colon cancer | | | | | | | | | | | | | | | | | | |
| COLO 205 | 0.353 | 1.217 | 1.221 | 1.126 | 1.003 | 0.067 | 0.062 | 100 | 89 | 75 | -81 | -82 | 1.45E-06 | 3.03E-06 | 6.33E-06 | | | |
| HCC-2998 | 0.732 | 0.925 | 0.904 | 0.914 | 0.774 | 0.079 | 0.067 | 89 | 94 | 22 | -89 | -91 | 4.06E-07 | 1.57E-06 | 4.43E-06 | | | |
| HCT-116 | 0.174 | 1.306 | 1.235 | 1.208 | 0.936 | 0.142 | 0.121 | 94 | 91 | 67 | -19 | -30 | 1.59E-06 | 6.06E-06 | 1.00E-04 | | | |
| HCT-15 | 0.226 | 1.446 | 1.404 | 1.286 | 0.582 | 0.121 | 0.105 | 96 | 87 | 29 | -46 | -54 | 4.36E-07 | 2.43E-06 | 3.16E-06 | | | |
| HT29 | 0.314 | 1.551 | 1.568 | 1.891 | 1.647 | 0.251 | 0.148 | 101 | 111 | 108 | -20 | -53 | 2.83E-06 | 6.97E-06 | 8.09E-05 | | | |
| KM12 | 0.226 | 1.021 | 1.044 | 1.039 | 0.910 | 0.169 | 0.041 | 103 | 102 | 86 | -25 | -62 | 2.11E-06 | 5.93E-06 | 2.73E-05 | | | |
| SW-620 | 0.156 | 0.811 | 0.829 | 0.836 | 0.463 | 0.052 | 0.022 | 103 | 104 | 47 | -67 | -86 | 8.82E-07 | 2.59E-06 | 7.13E-06 | | | |
| CNS cancer | | | | | | | | | | | | | | | | | | |
| SF-268 | 0.371 | 1.063 | 1.071 | 1.047 | 0.853 | 0.349 | 0.144 | 101 | 98 | 71 | -6 | -61 | 1.88E-06 | 6.34E-06 | 6.24E-05 | | | |
| SF-295 | 0.799 | 2.326 | 2.250 | 2.245 | 2.100 | 0.343 | 0.263 | 95 | 95 | 85 | -57 | -67 | 1.76E-06 | 3.97E-06 | 8.92E-06 | | | |
| SF-539 | 0.65 | 1.869 | 1.743 | 1.718 | 1.577 | 0.100 | 0.015 | 90 | 88 | 76 | -65 | -98 | 1.45E-06 | 2.97E-06 | 6.09E-06 | | | |
| SNB-19 | 0.421 | 1.389 | 1.371 | 1.272 | 0.652 | 0.390 | 0.092 | 98 | 88 | 44 | -7 | -78 | 7.74E-07 | 7.21E-06 | 3.99E-05 | | | |
| SNB-75 | 0.705 | 1.095 | 0.966 | 0.989 | 0.528 | 0.034 | 0.045 | 67 | 73 | -25 | -95 | -93 | 1.70E-07 | 5.54E-07 | 2.27E-05 | | | |
| U251 | 0.201 | 1.216 | 1.189 | 1.135 | 0.761 | 0.240 | 0.080 | 97 | 92 | 55 | 4 | -60 | 1.26E-06 | 1.15E-05 | 6.93E-05 | | | |

Fig. 13B

| Panel/Cell Line | Time Zero | Ctrl | Mean Optical Densities -8.0 | -7.0 | -6.0 | -5.0 | -4.0 | Log10 Concentration Percent Growth -8.0 | -7.0 | -6.0 | -5.0 | -4.0 | GI50 | TGI | LC50 |
|---|---|---|---|---|---|---|---|---|---|---|---|---|---|---|---|
| Melanoma | | | | | | | | | | | | | | | |
| LOX IMVI | 0.23 | 1.621 | 1.495 | 1.193 | 0.413 | 0.128 | 0.112 | 91 | 69 | 13 | -44 | -52 | 2.20E-07 | 1.69E-06 | 6.14E-05 |
| MALME-3M | 0.714 | 1.280 | 1.225 | 0.924 | 0.293 | 0.048 | 0.049 | 90 | 37 | -59 | -93 | -93 | 5.70E-08 | 2.43E-07 | 8.05E-07 |
| M14 | 0.378 | 1.411 | 1.407 | 1.121 | 0.159 | 0.086 | 0.047 | 100 | 72 | -58 | -83 | -88 | 1.48E-07 | 3.58E-07 | 8.69E-07 |
| MDA-MB-435 | 0.434 | 1.861 | 1.863 | 1.412 | 0.210 | 0.131 | 0.087 | 103 | 71 | -52 | -70 | -80 | 1.48E-07 | 3.79E-07 | 9.70E-07 |
| SK-MEL-2 | 0.391 | 0.891 | 0.921 | 0.871 | 0.589 | 0.186 | 0.107 | 106 | 96 | 39 | -53 | -73 | 6.51E-07 | 2.66E-06 | 9.21E-06 |
| SK-MEL-28 | 0.247 | 0.635 | 0.673 | 0.636 | 0.219 | 0.064 | 0.012 | 110 | 101 | -12 | -74 | -95 | 2.83E-07 | 7.89E-07 | 4.12E-06 |
| SK-MEL-5 | 0.278 | 1.488 | 1.139 | 1.212 | 0.015 | 0.017 | 0.008 | 86 | 70 | -85 | -94 | -97 | 1.32E-07 | 2.65E-07 | 5.34E-07 |
| UACC-257 | 0.447 | 1.190 | 1.182 | 1.204 | 1.152 | 0.054 | 0.039 | 99 | 102 | -95 | -94 | -97 | 1.76E-06 | 3.31E-06 | 6.20E-06 |
| UACC-62 | 0.521 | 1.975 | 1.783 | 1.734 | 1.681 | 0.210 | 0.160 | 87 | 83 | 801 | -60 | -69 | 1.64E-06 | 3.73E-06 | 8.52E-06 |
| Ovarian Cancer | | | | | | | | | | | | | | | |
| IGROV1 | 0.136 | 0.576 | 0.443 | 0.382 | 0.357 | 0.107 | 0.040 | 70 | 56 | 50 | -22 | -71 | 1.01E-06 | 4.99E-06 | 3.79E-05 |
| OVCAR-3 | 0.208 | 0.616 | 0.610 | 0.578 | 0.223 | 0.103 | 0.071 | 98 | 91 | 4 | -51 | -66 | 2.93E-07 | 1.17E-06 | 9.70E-06 |
| OVCAR-4 | 0.407 | 1.046 | 1.032 | 1.038 | 0.953 | 0.360 | 0.046 | 98 | 99 | 85 | -12 | -89 | 2.31E-06 | 7.58E-06 | 3.14E-05 |
| OVCAR-5 | 0.525 | 1.006 | 0.990 | 1.023 | 1.008 | 0.079 | 0.098 | 97 | 104 | 100 | -85 | -81 | 1.87E-06 | 3.48E-06 | 5.48E-05 |
| OVCAR-8 | 0.225 | 0.994 | 0.992 | 0.935 | 0.774 | 0.234 | 0.167 | 100 | 92 | 71 | 1 | -26 | 2.01E-06 | 1.10E-06 | 1.00E-04 |
| NCI/ADR-RES | 0.497 | 1.376 | 1.349 | 1.380 | 1.112 | 0.432 | 0.417 | 97 | 100 | 70 | -13 | -16 | 1.74E-06 | 6.96E-06 | 1.00E-04 |
| SK-OV-3 | 0.533 | 1.455 | 1.328 | 1.297 | 1.234 | 0.829 | 0.125 | 84 | 81 | 73 | 24 | -80 | 2.94E-06 | 1.69E-05 | 5.12E-05 |
| Renal Cancer | | | | | | | | | | | | | | | |
| 786-0 | 0.698 | 1.961 | 2.039 | 1.972 | 1.908 | 0.737 | 0.138 | 106 | 101 | 96 | 3 | -81 | 3.12E-06 | 1.09E-05 | 4.31E-05 |
| A498 | 0.614 | 1.353 | 1.454 | 1.432 | 1.363 | 0.402 | 0.023 | 114 | 111 | 101 | -35 | -96 | 2.39E-06 | 5.57E-06 | 1.78E-05 |
| ACHN | 0.339 | 1.387 | 1.229 | 1.104 | 0.898 | 0.423 | 0.081 | 65 | 73 | 53 | 8 | -76 | 1.18E-06 | 1.24E-05 | 4.89E-05 |
| CAKI-1 | 0.927 | 2.381 | 2.237 | 2.297 | 2.124 | 0.728 | 0.291 | 90 | 94 | 82 | -21 | -69 | 2.05E-06 | 6.21E-06 | 4.02E-05 |
| RXF 393 | 0.585 | 1.198 | 1.206 | 1.158 | 0.915 | 0.635 | 0.073 | 101 | 93 | 54 | 8 | -88 | 1.21E-06 | 1.12E-05 | 4.05E-05 |
| SN12C | 0.523 | 1.793 | 1.684 | 1.554 | 1.217 | 0.138 | 0.186 | 91 | 81 | 55 | -74 | -64 | 1.09E-06 | 2.57E-06 | 8.54E-06 |
| TK-10 | 0.612 | 1.307 | 1.372 | 1.359 | 1.380 | 0.859 | 0.086 | 109 | 107 | 111 | 35 | -86 | 6.40E-06 | 1.96E-05 | 5.08E-05 |
| UO-31 | 0.513 | 1.267 | 1.057 | 0.951 | 0.805 | 0.446 | 0.037 | 72 | 58 | 39 | -13 | -93 | 2.61E-07 | 5.57E-06 | 2.90E-05 |
| Prostate Cancer | | | | | | | | | | | | | | | |
| PC-3 | 0.168 | 0.570 | 0.525 | 0.478 | 0.433 | 0.169 | 0.109 | 89 | 77 | 86 | | -35 | 1.75E-06 | 1.02E-05 | 1.00E-04 |
| DU-145 | 0.275 | 0.906 | 0.956 | 0.875 | 0.008 | 0.003 | 0.005 | 108 | 95 | -97 | -99 | -98 | 1.72E-07 | 3.31E-07 | 5.69E-07 |
| Breast Cancer | | | | | | | | | | | | | | | |
| MCF7 | 0.238 | 1.135 | 1.027 | 0.966 | 0.706 | 0.089 | 0.073 | 88 | 81 | 52 | -63 | -69 | 1.04E-06 | 2.85E-08 | 7.76E-06 |
| MDA-MB-231/ | 0.456 | 1.266 | 1.157 | 1.000 | 0.838 | 0.547 | 0.465 | 86 | 67 | 47 | 11 | 1 | 7.71E-07 | 1.00E-04 | 1.00E-04 |
| HS 578T | 0.395 | 0.893 | 0.917 | 0.905 | 0.676 | 0.339 | 0.242 | 105 | 102 | 56 | -14 | -39 | 1.23E-06 | 6.27E-06 | 1.00E-04 |
| BT-549 | 1.085 | 2.198 | 2.153 | 1.997 | 1.543 | 0.122 | 0.227 | 96 | 82 | 41 | -89 | -79 | 6.06E-07 | 2.07E-06 | 5.03E-06 |
| T-47D | 0.657 | 1.429 | 1.394 | 1.287 | 0.127 | 0.810 | 0.546 | 95 | 82 | 80 | 20 | -17 | 3.13E-06 | 3.46E-05 | 1.00E-04 |
| MDA-MB-468 | 0.245 | 0.529 | 0.521 | 0.544 | 0.500 | 0.191 | 0.086 | 91 | 105 | 90 | -22 | -65 | 2.28E-06 | 6.33E-06 | 4.47E-05 |

| Panel/Cell Line | Time Zero | Ctrl | Mean Optical Densities |  |  |  |  | Log10 Concentration Percent Growth |  |  |  |  | GI50 | TGI | LC50 |
|---|---|---|---|---|---|---|---|---|---|---|---|---|---|---|---|
| | | | -8.0 | -7.0 | -6.0 | -5.0 | -4.0 | -8.0 | -7.0 | -6.0 | -5.0 | -4.0 | | | |
| Melanoma | | | | | | | | | | | | | | | |
| LOX IMVI | 0.256 | 1.831 | 1.630 | 1.330 | 0.509 | 0.074 | 0.042 | 87 | 67 | 16 | -75 | -86 | 2.11E-07 | 1.43E-06 | 5.22E-06 |
| M14 | 0.331 | 1.074 | 1.041 | 0.733 | 0.028 | 0.025 | 0.012 | 95 | 54 | -89 | -92 | -96 | 1.07E-07 | 2.39E-07 | 5.33E-06 |
| MDA-MB-435 | 0.523 | 2.014 | 2.103 | 1.844 | 0.227 | 0.183 | 0.139 | 106 | 89 | -57 | -65 | -74 | 1.88E-07 | 4.07E-07 | 8.99E-07 |
| SK-MEL-2 | 1.221 | 2.307 | 2.270 | 2.224 | 2.126 | 1.413 | 0.198 | 97 | 92 | 83 | 18 | -84 | 3.22E-06 | 1.49E-05 | 4.64E-05 |
| SK-MEL-28 | 0.345 | 0.857 | 0.922 | 0.899 | 0.240 | 0.060 | 0.017 | 113 | 108 | -31 | -83 | -95 | 2.63E-07 | 6.02E-07 | 2.36E-06 |
| SK-MEL-5 | 0.622 | 2.309 | 2.275 | 2.035 | 0.017 | 0.018 | 0.011 | 98 | 84 | -97 | -97 | -98 | 1.54E-07 | 2.90E-07 | 5.48E-07 |
| UACC-257 | 0.958 | 1.614 | 1.581 | 1.632 | 1.395 | 0.076 | 0.028 | 95 | 103 | 66 | -92 | -97 | 1.75E-06 | 3.23E-06 | 5.97E-06 |
| UACC-62 | 0.418 | 1.446 | 1.320 | 1.275 | 1.052 | 0.059 | 0.017 | 88 | 83 | 62 | -86 | -96 | 1.20E-06 | 2.62E-06 | 5.71E-06 |
| Ovarian Cancer | | | | | | | | | | | | | | | |
| IGROV1 | 0.326 | 0.912 | 0.742 | 0.598 | 0.454 | 0.099 | 0.016 | 71 | 46 | 22 | -70 | -95 | 7.11E-08 | 1.73E-06 | 6.08E-06 |
| OVCAR-3 | 0.359 | 0.878 | 0.850 | 0.777 | 0.303 | 0.169 | 0.131 | 102 | 80 | -16 | -58 | -64 | 2.07E-07 | 8.88E-07 | 6.34E-06 |
| OVCAR-4 | 0.491 | 1.373 | 1.321 | 1.252 | 1.151 | 0.466 | 0.018 | 94 | 86 | 75 | -4 | -98 | 2.12E-06 | 9.67E-06 | 3.26E-06 |
| OVCAR-5 | 0.492 | 1.145 | 1.160 | 1.162 | 1.175 | 0.059 | 0.047 | 102 | 103 | 105 | -88 | -90 | 1.92E-06 | 3.49E-06 | 6.34E-06 |
| OVCAR-8 | 0.309 | 1.808 | 1.799 | 1.702 | 1.431 | 0.417 | 0.357 | 99 | 92 | 71 | -18 | -30 | 1.72E-06 | 6.27E-06 | 1.00E-04 |
| NCI/ADR-RES | 0.588 | 1.645 | 1.663 | 1.643 | 1.418 | 0.504 | 0.441 | 102 | 100 | 78 | -14 | -25 | 2.03E-06 | 7.01E-06 | 1.00E-04 |
| SK-OV-3 | 0.383 | 1.064 | 1.007 | 0.969 | 0.892 | 0.441 | 0.064 | 89 | 83 | 66 | -22 | -89 | 1.51E-06 | 5.65E-06 | 2.65E-05 |
| Renal Cancer | | | | | | | | | | | | | | | |
| 786-0 | 0.908 | 2.207 | 2.289 | 2.346 | 2.235 | 0.772 | 0.082 | 106 | 111 | 102 | -15 | -91 | 2.79E-06 | 7.44E-06 | 2.89E-05 |
| A498 | 0.348 | 1.471 | 1.506 | 1.519 | 1.540 | 0.425 | 0.017 | 107 | 109 | 113 | -55 | -98 | 2.97E-06 | 4.70E-06 | 9.31E-06 |
| ACHN | 0.377 | 1.688 | 1.512 | 1.370 | 1.102 | 0.851 | 0.058 | 87 | 76 | 55 | 6 | -85 | 1.28E-06 | 1.15E-05 | 4.09E-05 |
| CAKI-1 | 0.991 | 2.535 | 2.449 | 2.313 | 2.347 | 1.507 | 0.983 | 94 | 86 | 88 | 33 | -1 | 4.96E-06 | 9.44E-05 | 1.00E-04 |
| RXF 393 | 0.488 | 0.580 | 0.746 | 0.698 | 0.647 | 0.464 | 0.051 | 134 | 109 | 83 | -30 | -90 | 2.46E-06 | 9.78E-06 | 3.58E-05 |
| SN12C | 0.397 | 1.358 | 1.257 | 1.180 | 0.711 | 0.037 | 0.026 | 89 | 81 | 33 | -91 | -93 | 4.41E-07 | 1.84E-06 | 4.67E-06 |
| UO-31 | 0.411 | 1.053 | 0.879 | 0.821 | 0.641 | 0.258 | 0.016 | 73 | 64 | 36 | -57 | -96 | 3.13E-07 | 3.09E-06 | 1.64E-05 |
| Prostate Cancer | | | | | | | | | | | | | | | |
| DU-145 | 0.243 | 0.799 | 0.843 | 0.676 | 0.503 | 0.005 | 0.003 | 108 | 78 | -99 | -99 | -99 | 1.44E-07 | 2.76E-07 | 5.29E-07 |
| Breast Cancer | | | | | | | | | | | | | | | |
| MCF7 | 0.216 | 1.001 | 0.988 | 0.857 | 0.576 | 0.060 | 0.056 | 98 | 82 | 46 | -72 | -74 | 7.63E-07 | 2.44E-06 | 6.48E-06 |
| MDA-MB-231/ATCC | 0.493 | 1.124 | 1.025 | 0.821 | 0.695 | 0.533 | 0.330 | 84 | 52 | 32 | 6 | -33 | 1.26E-07 | 1.44E-05 | 1.00E-04 |
| HS 578T | 0.571 | 0.344 | 0.929 | 0.838 | 0.503 | 0.351 | 0.277 | 96 | 87 | -12 | -39 | -51 | 2.37E-07 | 7.58E-07 | 7.68E-05 |
| T-47D | 0.512 | 1.039 | 1.007 | 0.959 | 0.927 | 0.533 | 0.316 | 94 | 85 | 79 | 4 | -28 | 2.42E-06 | 1.24E-05 | 1.00E-04 |
| MDA-MB-468 | 0.446 | 0.922 | 0.949 | 0.910 | 0.916 | 0.379 | 0.167 | 106 | 97 | 99 | -15 | -63 | 2.66E-06 | 7.38E-06 | 5.44E-05 |

SERINIQUINONES, MELANOMA-SPECIFIC ANTICANCER AGENTS

CROSS-REFERENCES TO RELATED APPLICATIONS

This application is a continuation of International Appl. No. PCT/US2013/052382, filed Jul. 26, 2013, which claims priority to U.S. Provisional Application No. 61/676,427, filed Jul. 27, 2012, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant number CA044848 awarded by the National Institutes of Health. The Government may have certain rights in this invention.

REFERENCE TO A "SEQUENCE LISTING," A TABLE, OR A COMPUTER PROGRAM LISTING APPENDIX SUBMITTED ON A COMPACT DISK

Sequence Listing written in file 88654-929759_ST25.TXT, created on Jan. 21, 2015, 5,831 bytes, machine format IBM-PC, MS Windows operating system, is hereby incorporated by reference.

BACKGROUND OF THE INVENTION

Melanoma refers to malignant neoplasms of melanocytes and its incidence has significantly increased over the last five decades. (Wingo, P. A. et al., *Cancer* 82:1197-207 (1998); Rigel, D. S. et al., *J Am Acad Dermatol* 34:839-47 (1996)). It may develop from unrepaired DNA damage to skin cells. The damage leads to genetic mutation and formation of malignant tumors. The tumors develop in melanocytes and often resemble moles. In some instances the transformed melanocytes produce increased amounts of pigment such that the tumor can be readily seen. The proper diagnosis and early treatment of melanoma is of great importance because advanced melanoma has a poor prognosis. Treatment options for melanoma should include prevention of further growth of the tumor. One such way is to induce autophagy of melanomatic cells. Autophagy is characterized by an increase in the number of autophagosomes, vesicles surrounding cellular organelles such as Golgi complexes, polyribosomes, and the endoplasmic reticulum [Finn R S. Ann Oncol 2008: 19:1379-86]. Autophagosomes merge with lysosomes and digest these organelles, leading to cell death. There is a need for new treatment options of melanoma that may induce autophagy. Provided herein are solutions to these and other problems in the art.

BRIEF SUMMARY OF THE INVENTION

Accordingly, herein are provided, inter alia, derivatives of seriniquinone useful for the treatment of cancer, and in particular treatment of melanoma, and prostate cancer.

In a first aspect is a compound having the formula:

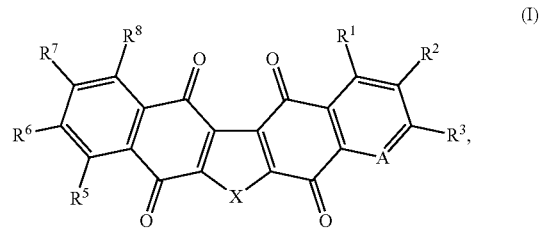

or pharmaceutically acceptable salt thereof.

A is N or —$CR^4$. X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, CN, —$CF_3$, —$CCl_3$, —$CBr_3$, —$CI_3$, —$NR^9R^{10}$, —C(O)$R^{11}$, —C(O)$NR^9R^{10}$, —$NR^{12}$C(O)$R^{11}$, —S(O)$_nR^{13}$, —S(O)$_nNR^9R^{10}$, —$NR^{12}$S(O)$_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$, $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4. If X is S and A is $CR^4$, at least one of $R^1$, $R^2$, $R^3$, $R^4$, $R^5$, $R^6$, $R^7$, and $R^8$ is not hydrogen.

In another aspect is having the formula:

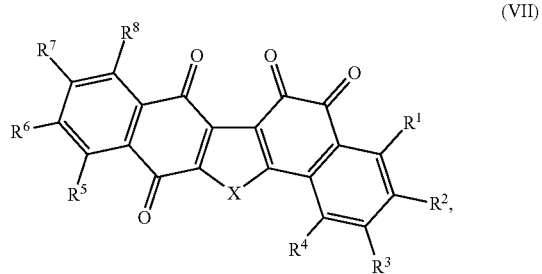

or pharmaceutically acceptable salt thereof.

X is —S—, —$NR^{21}$—, or —O—. $R^1$, $R^2$, $R^3$, $R^4$, $R^5$, $R^6$, $R^7$, and $R^8$ are each independently hydrogen, halogen, —$N_3$, —NHC=(O)$NHNH_2$, —CN, —$CF_3$, —$CCl_3$, —$CBr_3$, —$CI_3$, —$NR^9R^{10}$, —C(O)$R^{11}$, —C(O)$NR^9R^{10}$, —$NR^{12}$C(O)$R^{11}$, —S(O)$_nR^{13}$, —S(O)$_nNR^9R^{10}$, —$NR^{12}$S(O)$_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted C$_1$—C$_5$ alkyl. The symbol n is 1 to 4.

In another aspect is a compound having the formula:

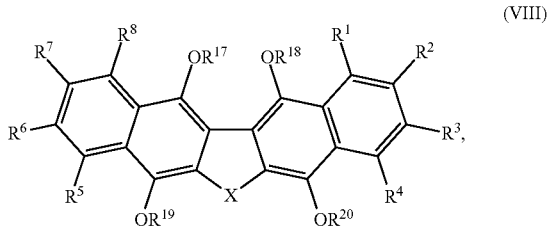

(VIII)

or pharmaceutically acceptable salt thereof.

X is —S—, —NR$^{21}$—, or —O—. $R^1$, $R^2$, $R^3$, $R^4$, $R^5$, $R^6$, $R^7$, and $R^8$ are each independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SH, NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$ are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted C$_1$-C$_5$ alkyl. The symbol n is 1 to 4. $R^{17}$, $R^{18}$, $R^{19}$, and $R^{20}$ are independently hydrogen or substituted or unsubstituted alkyl.

In another aspect is a pharmaceutical composition comprising a pharmaceutically acceptable excipient and a compound of formula (VII), (VIII), or a compound having the formula:

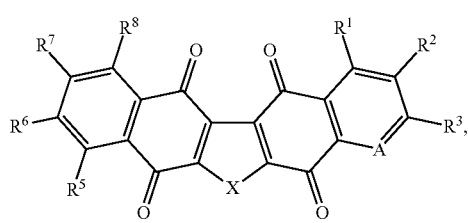

(I)

or pharmaceutically acceptable salt thereof.

A is N or —CR$^4$. X is —S—, —NR$^{21}$—, or —O—. $R^1$, $R^2$, $R^3$, $R^4$, $R^5$, $R^6$, $R^7$, and $R^8$ are independently hydrogen, halogen, —N$_3$, —NHC=(O)NHNH$_2$, CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted C$_1$-C$_5$ alkyl. The symbol n is 1 to 4.

In another aspect is a method of treating cancer in a subject in need thereof. The method includes administering to a subject a therapeutically effective amount of a compound of formula (VII), (VIII), or a compound having the formula:

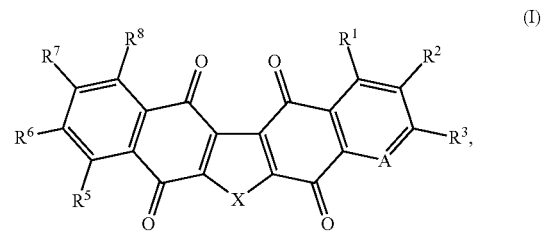

(I)

or pharmaceutically acceptable salt thereof.

A is N or —CR$^4$. X is —S—, —NR$^{21}$—, or —O—. $R^1$, $R^2$, $R^3$, $R^4$, $R^5$, $R^6$, $R^7$, and $R^8$ are independently hydrogen, halogen, —N$_3$, —NHC=(O)NHNH$_2$, CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted C$_1$-C$_5$ alkyl. The symbol n is 1 to 4.

In another aspect is a method of inhibiting a dermcidin protein. The method includes contacting a dermcidin protein with a compound of formula (VII), (VIII), or a compound having the formula:

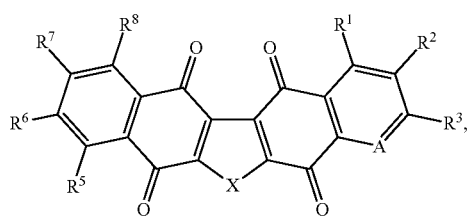

(I)

or pharmaceutically acceptable salt thereof, thereby inhibiting the dermcidin protein.

A is N or —$CR^4$—. X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, CN, —$CF_3$, —$CCl_3$, —$CBr_3$, —$Cl_3$, —$NR^9R^{10}$, —C(O)$R^{11}$, —C(O)$NR^9R^{10}$, —$NR^{12}$C(O)$R^{11}$, —S(O)$_nR^{13}$, —S(O)$_nNR^9R^{10}$, —$NR^{12}$S(O)$_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$Cl_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4.

In another aspect is a dermcidin protein covalently or non-covalently bonded to a dermcidin inhibitor.

In another aspect is a method of identifying a test compound that inhibits dermcidin. The method includes contacting a dermcidin with a test compound and detecting a decrease in activity of the dermcidin, thereby identifying a test compound that inhibits dermcidin.

BRIEF DESCRIPTION OF THE DRAWINGS

FIG. 1A depicts the marine-derived *Serinicoccus* sp. and crystals of 1 (inset), FIG. 1B shows the structure of 1, and FIG. 1C shows the summary of salient NMR data including $^1$H-$^1$H COSY (bold lines) and HMBC interactions (arrows) observed in solutions of 1 in $CDCl_3$.

FIG. 2A shows the synthesis of seriniquinone (1), FIG. 2B, shows the synthesis of IAF probe 13 arises through coupling of acid 11, a functionalized analog derived from alkene 10, to an amine terminal IAF tag 12, wherein alkene 10 was prepared at gram scales in 5 steps from α-myrcene (4) and 2,5-dichlorobenzoquinone (5) (Reagents and conditions: (a) dithiooxamide, $Et_3N$, DMF, 10 h, 50° C., 85%; (b) 30% aq. $H_2O_2$, AcOH, reflux, 3 h, 86%; (c) $MnO_2$, benzene, reflux, 48 h, 82%; (d) NaOH, MeOH, 96%; (e) $CsCO_3$, $CH_3CN$, rt, 72 h; (f) $(ClCO)_2$, DMF, $CH_2Cl_2$, 12 h, 77% (over two steps); (g) $Na_2S$, THF rt, 12 h, 63%; (h) $OsO_4$, NMO, THF, $H_2O$, 88%; (i) $NaIO_4$ on $SiO_2$, $CH_2Cl_2$, 99%; (j) Oxone, THF, $H_2O$, 72 h, 98%; (k) HATU, $EtNiPr_2$, DMF, rt, 18 h, 57%).

FIG. 3A shows seriniquinone (1) induces cell death in HCT-116 cells in a concentration and time dependent manner; FIG. 3B shows time course studies showing the optimal activity from 1 in HCT-116 cells is obtained after constant treatment with 1 over a 24 h.; FIG. 3C shows induction of autophagy by a dose dependant increase in the levels of LC3A-II and LC3B-II after treatment of HCT-116 cells with 1 for 24 h as noted by western blot analysis and that this response was significantly greater than both negative control (−, DMSO) and a positive control (+, 17 µM etoposide); FIG. 3D shows Seriniquinone (1) also induces a dose dependent arrest during DNA replication as noted by the increase in S staged cells during treatments for 18 h and 24 h.; FIG. 3E shows cell death is accompanied by DNA fragmentation suggesting that apoptotic processes are elicited. FIG. 3F shows Western blot analyses for selected cyclins, and FIG. 3G shows caspases in lysates prepared from HCT-116 cells that were treated with 1 for 24 h. (negative control (−) denotes use of DMSO and positive control (+) 17 µM etoposide—Unless noted otherwise, concentrations are provided in µM).

FIGS. 4A-4G: Subcellular localization studies. FIG. 4A shows treatment of HCT-116 cells with 5 µM 1 for 1 h results in the appearance of red and green fluorescence from 1, as given by comparative staining of the nuclei using DAPI; FIG. 4B shows similar subcellular localization was observed across a panel of cell lines that demonstrated sensitivity to 1 (cells from each line were grown to $10^6$ cells/cm then treated with 30 µM 1 for 1 h, and then imaged live); FIG. 4C shows time course analysis over 24 h. wherein within 1 h, 1 localizes within the endoplasmic reticulum (ER) then induces autophagocytosis as noted by time course imaging of PC-3 cells in media containing 30 µM 1; FIG. 4D shows counterstaining to validate the subcellular localization events wherein the initial localization in the ER and autophagocytes (ER) was confirmed counterstaining with dyes as given by ER Tracker for the ER and dansylcadavarine (HCT-116 cells were treated in media containing µM 1 and then counterstained at the given time interval); FIG. 4E shows comparable staining in MALME-3M provides clear validation of the localization; FIG. 4F shows locationzation to the ER within 1 h.; FIG. 4G shows the transition to autophagocytes at 6 h. (the IAF probe 13 undergoes comparable subcellular localization and vesicularization, such that the presence of fluorescence in images of 13 is indicative of the fluorescent IAF tag and wherein unless otherwise noted, cells were grown to $10^6$ cells/$cm^2$ then treated with solutions of compound and at the designated time, cells were washed with media, fixed and imaged on a Zeiss LSM-710 confocal microscope).

FIGS. 5A-5E: Seriniquinone (1) targets dermcidin (DCD). FIG. 5A shows silver-stained SDS PAGE gel depicting proteins immunoprecipitated from HCT-116 cell lysates treated with 3 or 30 µM 13 over 8 h wherein this response was dose dependent with an increasing level of immunoprecipitated protein when higher concentrations of 13 were applied (only the anti-IAF antibody (mAb) was observed in experiments conducted without 13). FIG. 5B shows trypsin digest LC-MS/MS of the protein band b2 at 50 kDa returned peptides corresponding to GADPH and DCD wherein the latter, DCD-derived, peptides were observed in the 30 aa PIF core, 13 aa propeptide and 49 DCD-1 peptide region and comparable analyses for bands b1 and b3 indicated that contained HSP-70 and actin, respectively, along with DCD-derived peptides. Sequence listing (FIG. 5B): MRFMTLL-FLTALAGALVCAYDPEAASAPGSGNPCHEASAAQKE-NAGEDPGLARQAPKPRK QRSSLLEKGLDGAK- KAVGGLGKLGKDAVEDLESVGKGAVDVKDVLDSVL (SEQ ID NO:3); MGKVKVGVNGFGRIGRLVTRAAFNS-GKVDIVAINDPFIDLNYMVYMFQYDSTHGKFHGTV KAENGKLVINGNPITIFQERDPSKIKWGDAGAEYV-VESTGVFTTMEKAGAHLQGGAKRVIIS APSADAPM-FVMGVNHEKYDNSLKIISNASCTTNCLAPLAKVIH-DNFGIVEGLMTTVHAITA TQKTVDGPSGKLWRDGRGALQNIIPASTGAAKAVG-KVIPELNGKLTGMAFRVPTANVSVV DLTCRLEKPA-KYDDIKKVVKQASEGPLKGILGYTEHQWSSDFNS-DTHSSTFDAGAGIALND HFVKLISWYDNEFGYSNRWDLMAHMASKE (SEQ ID NO:4). FIG. 5C shows treatment with iodoacetamide cleaves DCD peptide disulfide linkages wherein Lane L1 is a SDS page gel depicting proteins immunoprecipitated from HCT-116 cell lysates with 30 μM 13 over 8 h, then treated with 5 mM iodoacetamide at rt for 1 h prior to SDS-PAGE analysis and the arrow denotes DCD, Lane L2 is SDS PAGE gel depicting proteins from HCT-116 cell lysates that were treated for 1 h with 5 mM iodoacetamide, spin dialyzed, and then immunoprecipitated with 30 μM 13 over 8 h. and the arrow denotes DCD; FIG. 5D shows Western blot interrogation of the immunopreciptiated fractions wherein proteins in the immunopreciptiated fractions from cells treated 30 μM 13 were positive when developed with antibodies against the IAF tag and DCD, suggesting that the proteins were covalently modified by probe 13 as indicated by positive activity against the anti-IAF tag antibody but also were ligated with peptides from DCD, and the ~50 kDa band was also positive when stained with an antibody against GADPH suggesting that the ~50 kDa band contained a fusion between GADPH, 13 and DCD; FIG. 5E shows incubating the 47 amino acid DCD-1L fragment (50 μg) in 200 μL of PBS pH 7.2 containing 5% DMSO and 50 μM 1 (lane L1), 50 μM alkene 10 (lane L2) or 50 μM 13 (lane L3) at 23° C. for 24 h resulted in fluorescent bands corresponding to DCD-1L, as compared to control (no probe, lane L4).

FIG. 12: NCI 60 data for compounds herein.
FIGS. 13A-13B: NCI 60 data for compounds herein.
FIG. 15A: leukemia;
FIG. 15B: CNS cancer;
FIG. 15C: renal cancer;
FIG. 15D: non-small cell lung cancer;
FIG. 15E: melanoma;
FIG. 15F: orostate cancer;
FIG. 15G: colon cancer;
FIG. 15H: ovarian cancer;
FIG. 15I: breast cancer.
FIGS. 17A-17B: NCI 60 data for compounds herein.
FIG. 18A: leukemia;
FIG. 18B: CNS cancer;
FIG. 18C: renal cancer;
FIG. 18D: non-small cell lung cancer;
FIG. 18E: melanoma;
FIG. 18F: orostate cancer;
FIG. 18G: colon cancer;
FIG. 18H: ovarian cancer;
FIG. 199: breast cancer.

DETAILED DESCRIPTION OF THE INVENTION

I. Definitions

Figure 1A:
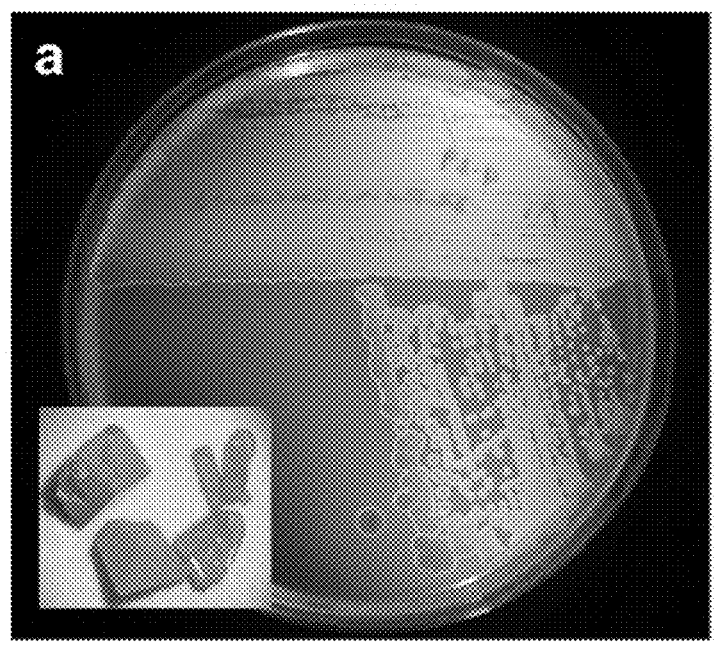
FIGS. 1A-1C: Isolation of seriniquinone (1)

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'-C(O) NR"R'", —NR"C(O)$_2$R', —NR—C(NR'R"R'")=NR"", —NR—C(NR'R")=NR''', —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'-C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, Oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:
(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_3$-C$_8$ aryl, and each substituted or unsubstituted heteroaryl is a substituted or unsubstituted C$_3$-C$_8$ heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_3$-C$_7$ aryl, and each substituted or unsubstituted heteroaryl is a substituted or unsubstituted C$_3$-C$_7$ heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_3$-C$_8$ arylene, and/or each substituted or unsubstituted heteroaryl is a substituted or unsubstituted C$_3$-C$_8$ heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_3$-C$_7$ aryl, and/or each substituted or unsubstituted heteroaryl is a substituted or unsubstituted C$_3$-C$_7$ heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_3$-C$_7$ arylene, and/or each substituted or unsubstituted heteroarylene is a substituted or unsubstituted C$_3$-C$_7$ heteroarylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "⌇⌇⌇" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound. In embodiments, a reference compound is metformin.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13}A$, $R^{13B}$, $R^{13C}$, $R^{13D}$, etc. is defined within the scope of the definition of $R^{13}$ and optionally differently.

A "nitrile" refers to an organic compound having a —CN group.

A "hydrophilic moiety" refers to a monovalent compound that increases the hydrophilicity of a compound herein, thereby increasing solubilization in a hydrophilic solution. A hydrophilic moiety may increase solubility of a compound in polar organic solvents. A hydrophilic moiety may alter the partitioning coefficient of a compound or molecule to which it is bound thereby making the molecule more or less hydrophilic. Exemplary hydrophilic moieties include moieties such as poly(oxyethylated polyols) such as poly(oxyethylated glycerol), poly(oxyethylated sorbitol), and poly (oxyethylated glucose); poly(vinyl alcohol) ("PVA"); dextran; carbohydrate-based polymers and the like (including linear chains or branched chains); polyethylene glycol moieties of formula

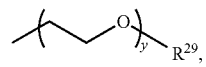

wherein y is an integer from 1 to 50 and $R^{29}$ is —OH or —OMe; polyvinylpyroolidone moieties; or poly 2-ethyl oxazoline moieties.

The hydrophilic moiety may include a moiety containing a heteroatom (e.g., oxygen or nitrogen). To improve the hydrophilicity of compounds herein a hydrophilic moiety is covalently attached at one or more positions. Such moieties may include, for example, hydrogen, halogen, substituted or unsubstituted alkyl moiety, substituted or unsubstituted heteroalkyl moiety, substituted cycloalkyl moiety, substituted or unsubstituted heteroalkyl moiety, or substituted or unsubstituted aryl moiety. In embodiments, the moiety contains an alcohol moiety (e.g. an organic moiety having an —OH bound to a carbon atom), ester linker moiety (e.g. the linker moiety —C(O)O— between two carbon atoms), ether linker moiety (e.g. the linker moiety —O— between two carbon atoms), amine (—NH$_2$) moiety, nitrile (—CN) moiety, ketone moiety (e.g. the linker moiety —C(O)— between two carbon atoms), or aldehyde (—C(O)H) moiety.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The terms "DNA" and "RNA" refer to deoxyribonucleic acid and ribonucleic acid, respectively.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Dermcidin," "Dermcidin protein," or "Dermcidin peptide" is used according to its common, ordinary meaning and refers to proteins of the same or similar names and functional fragments and homologs thereof, fragments of which known to have anti-microbial properties, and secreted by human dermal glands (e.g. SEQ ID NO. 1). The term includes any recombinant or naturally-occurring form of dermcidin, or a dermcidin preprotein, or variants thereof that maintain dermcidin activity (e.g. within at least 30%, 40%, 50%, 60%, 70%, 80%, 90%, 95%, or 100% activity compared to dermcidin). In embodiments, dermcidin (GI: 148271059), 110 amino acids) may undergo autoproteolysis yielding at least 3 peptides of at least 30 to at least 50 amino acids in length. In embodiments, at least one of the peptides in dermcidin 1.

SEQ ID NO 1: mrfmtllflt alagalvcay dpeaasapgs gnpcheasaa qkenagedpg larqapkprk qrssllekgl dgakkavggl gklgkdaved lesvgkgavh dvkdvldsvl "Dermcidin 1" (GI:409106969) (SEQ ID NO. 2) as referred to herein, includes any recombinant or naturally-occurring form of dermcidin 1, or variants thereof that maintain dermcidin activity (e.g. within at least 30%, 40%, 50%, 60%, 70%, 80%, 90%, 95%, or 100% activity compared to dermcidin).

SEQ ID NO. 2: ssllekgldg akkavgglgk lgkdavedle svgkgavhdv kdvldsvl

An "apoptosis-inducing-protein" as used herein refers to a protein that initiates an apoptotic pathway in a cell. Dermcidin may bind to an apoptosis-inducing protein. The binding is either covalent or non-covalent. When the bond is covalent, the binding is, for example, a disulfide (e.g. S—S).

A "dermcidin-seriniquinone complex" as used herein refers to dermcidin bound to a compound as disclosed herein, including embodiments thereof. The dermcidin may be bound to the compound covalently or non-covalently.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization. In some embodiments the cell is a cancer cell line such as MALME-3M or HCT-116.

The term "autophagy" or "autophagocytosis" refers to cellular self-degradative processes mediated by the lysosomal degradation pathway. Autophagocytosis is used to degrade cellular organelles. In embodiments, decreased autophagocytosis may lead to tumor progression by promoting survival of starved tumor cells.

The terms "apoptosis" and "apoptotic" generally refer to pathways associated with programmed cell death within a cell. Apoptosis may lead to fragmentation of DNA, and/or other physiological changes to a cell, causing cell death, without lysis or damage to a neighboring cell.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts",

*Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "marker" refers to any biochemical marker, serological marker, genetic marker, or other clinical or echographic characteristic that can be used to diagnose or provide a prognosis for a cancer.

The term "sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In embodiments, the sample is obtained from a human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast, lung, pancreas, skin, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

A "therapeutically effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

A "test compound" as used herein refers to an experimental compound used in a screening process to identify activity, non-activity, or other modulation of a particularized biological target or pathway.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

The term "associated" or "associated with" in the context of a substance or substance activity or function associated with a disease means that the disease is caused by (in whole or in part), or a symptom of the disease is caused by (in whole or in part) the substance or substance activity or function.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, metastatic bone cancer, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

II. Compositions

In a first aspect, a compound having formula (I), or a pharmaceutically acceptable salt thereof is provided.

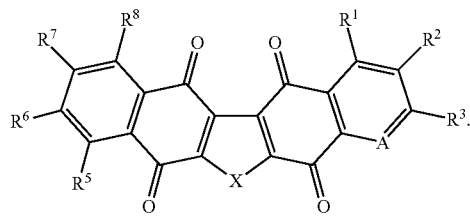

(I)

A is N or —$CR^4$—. X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, —CN, —$CF_3$, —$CCl_3$, —$CBr_3$, —$CI_3$, —$NR^9R^{10}$, —C(O)$R^{11}$, —C(O)$NR^9R^{10}$, —$NR^{12}$C(O)$R^{11}$, —S(O)$_nR^{13}$, —S(O)$NR^9R^{10}$, —$NR^{12}$S(O)$_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$, $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4. If X is S and A is $CR^4$, at least one of $R^1$, $R^2$, $R^3$, $R^4$, $R^5$, $R^6$, $R^7$, and $R^8$ is not hydrogen.

In one embodiment, when X is S and A is $CR^4$, at least one of $R^1$, $R^2$, $R^3$, $R^4$, $R^5$, $R^6$, $R^7$, and $R^8$ is not substituted or unsubstituted $C_1$-$C_{10}$ alkyl. In one embodiment, when X is S and A is $CR^4$, at least one of $R^1$, $R^2$, $R^3$, $R^4$, $R^5$, $R^6$, $R^7$, and $R^8$ is not substituted or unsubstituted $C_1$-$C_5$ alkyl. In one embodiment, when X is S and A is $CR^4$, at least one of $R^1$, $R^2$, $R^3$, $R^4$, $R^5$, $R^6$, $R^7$, and $R^8$ is not substituted or unsubstituted $C_1$-$C_3$ alkyl. In one embodiment, when X is S and A is $CR^4$, at least one of $R^1$, $R^2$, $R^3$, $R^4$, $R^5$, $R^6$, $R^7$, and $R^8$ is not unsubstituted $C_1$-$C_3$ alkyl. In one embodiment, when X is S and A is $CR^4$, at least one of $R^1$, $R^2$, $R^3$, $R^4$, $R^5$, $R^6$, $R^7$, and $R^8$ is not methyl. In one embodiment, when X is S and A is $CR^4$, at least one of $R^1$, $R^2$, $R^3$, $R^4$, $R^5$, $R^6$, $R^7$, and $R^8$ is not hydrogen.

A may be N. A may be —$CR^4$—. X may be —S—. X may be —$NR^{21}$—. X may be —O—. $R^1$, $R^2$, $R^3$, $R^4$, $R^5$, $R^6$, $R^7$, and $R^8$ may be a hydrophilic moiety. $R^1$, $R^3$, $R^4$, $R^5$, $R^6$, $R^7$, and $R^8$ may be hydrogen.

$R^1$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, $R^{1a}$-substituted or unsubstituted alkyl (e.g. $C_1$ to $C_8$ alkyl), $R^{1a}$-substituted or unsubstituted heteroalkyl (e.g. 2 to 8 membered heteroalkyl), $R^{1a}$-substituted or unsubstituted cycloalkyl (e.g. $C_3$-$C_8$ cycloalkyl), $R^{1a}$-substituted or unsubstituted heterocycloalkyl (e.g. 3 to 6 membered heterocycloalkyl), $R^{1a}$-substituted or unsubstituted aryl (e.g. phenyl), or $R^{1a}$-substituted or unsubstituted heteroaryl (e.g. 5 or 6 membered heteroaryl).

$R^{1a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, $R^{1b}$-substituted or unsubstituted alkyl (e.g. $C_1$ to $C_8$ alkyl), $R^{1b}$-substituted or unsubstituted heteroalkyl (e.g. 2 to 8 membered heteroalkyl), $R^{1b}$-substituted or unsubstituted cycloalkyl (e.g. $C_3$-$C_8$ cycloalkyl), $R^{1b}$-substituted or unsubstituted heterocycloalkyl (e.g. 3 to 6 membered heterocycloalkyl), $R^{1b}$-substituted or unsubstituted aryl (e.g. phenyl), or $R^{1b}$-substituted or unsubstituted heteroaryl (e.g. 5 or 6 membered heteroaryl).

$R^{1b}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^1$ may be substituted or unsubstituted $C_1$-$C_{20}$ alkyl. $R^1$ may be unsubstituted $C_1$-$C_{20}$ alkyl. $R^1$ may be substituted $C_1$-$C_{20}$ alkyl. $R^1$ may be substituted or unsubstituted 2 to 20 membered heteroalkyl. $R^1$ may be unsubstituted 2 to 20 membered heteroalkyl. $R^1$ may be substituted 2 to 20 membered heteroalkyl. $R^1$ may be substituted or unsubstituted $C_1$-$C_8$ alkyl. $R^1$ may be unsubstituted $C_1$-$C_8$ alkyl. $R^1$ may be substituted $C_1$-$C_8$ alkyl. $R^1$ may be substituted or unsubstituted 2 to 8 membered heteroalkyl. $R^1$ may be unsubstituted 2 to 8 membered heteroalkyl. $R^1$ may be substituted 2 to 8 membered heteroalkyl. $R^1$ may be substituted or unsubstituted $C_1$-$C_4$ alkyl. $R^1$ may be unsubstituted $C_1$-$C_4$ alkyl. $R^1$ may be substituted $C_1$-$C_4$ alkyl. $R^1$ may be substituted or unsubstituted 2 to 4 membered heteroalkyl. $R^1$ may be unsubstituted 2 to 4 membered heteroalkyl. $R^1$ may be substituted 2 to 4 membered heteroalkyl.

$R^1$ may be substituted or unsubstituted 2 to 20 membered cycloalkyl. $R^1$ may be unsubstituted 2 to 20 membered cycloalkyl. $R^1$ may be substituted 2 to 20 membered cycloalkyl. $R^1$ may be substituted or unsubstituted 2 to 20 membered heterocycloalkyl. $R^1$ may be unsubstituted 2 to 20 membered heterocycloalkyl. $R^1$ may be substituted 2 to 20 membered heterocycloalkyl. $R^1$ may be substituted or unsubstituted 2 to 8 membered cycloalkyl. $R^1$ may be unsubstituted 2 to 8 membered cycloalkyl. $R^1$ may be substituted 2 to 8 membered cycloalkyl. $R^1$ may be substituted or unsubstituted 2 to 8 membered heterocycloalkyl. $R^1$ may be unsubstituted 2 to 8 membered heterocycloalkyl. $R^1$ may be substituted 2 to 8 membered heterocycloalkyl.

$R^1$ may be substituted or unsubstituted 5 to 20 membered aryl. $R^1$ may be unsubstituted 5 to 20 membered aryl. $R^1$ may be substituted 5 to 20 membered aryl. $R^1$ may be substituted or unsubstituted 5 to 20 membered heteroaryl. $R^1$ may be unsubstituted 5 to 20 membered heteroaryl. $R^1$ may be substituted 5 to 20 membered heteroaryl. $R^1$ may be substituted or unsubstituted 5 to 8 membered aryl. $R^1$ may be unsubstituted 5 to 8 membered aryl. $R^1$ may be substituted 5 to 8 membered aryl. $R^1$ may be substituted or unsubstituted 5 to 8 membered heteroaryl. $R^1$ may be unsubstituted 5 to 8 membered heteroaryl. $R^1$ may be substituted 5 to 8 membered heteroaryl.

$R^1$ may be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$. $R^1$ may be hydrogen.

$R^2$ may independently be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, $R^{2a}$-substituted or unsubstituted alkyl (e.g. $C_1$ to $C_8$ alkyl), $R^{2a}$-substituted or unsubstituted heteroalkyl (e.g. 2 to 8 membered heteroalkyl), $R^{2a}$-substituted or unsubstituted cycloalkyl (e.g. $C_3$-$C_8$ cycloalkyl), $R^{2a}$-substituted or unsubstituted heterocycloalkyl (e.g. 3 to 6 membered heterocycloalkyl), $R^{2a}$-substituted or unsubstituted aryl (e.g. phenyl), or $R^{2a}$-substituted or unsubstituted heteroaryl (e.g. 5 or 6 membered heteroaryl).

$R^{2a}$ is independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, $R^{2b}$-substituted or unsubstituted alkyl (e.g. $C_1$ to $C_8$ alkyl), $R^{2b}$-substituted or unsubstituted heteroalkyl (e.g. 2 to 8 membered heteroalkyl), $R^{2b}$-substituted or unsubstituted cycloalkyl (e.g. $C_3$-$C_8$ cycloalkyl), $R^{2b}$-substituted or unsubstituted heterocycloalkyl (e.g. 3 to 6 membered heterocycloalkyl), $R^{2b}$-substituted or unsubstituted aryl (e.g. phenyl), or $R^{2b}$-substituted or unsubstituted heteroaryl (e.g. 5 or 6 membered heteroaryl).

$R^{2b}$ is independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^2$ may be substituted or unsubstituted $C_1$-$C_{20}$ alkyl. $R^2$ may be unsubstituted $C_1$-$C_{20}$ alkyl. $R^2$ may be substituted $C_1$-$C_{20}$ alkyl. $R^2$ may be substituted 2 to 20 membered heteroalkyl. $R^2$ may be unsubstituted 2 to 20 membered heteroalkyl. $R^2$ may be substituted 2 to 20 membered heteroalkyl. $R^2$ may be substituted or unsubstituted $C_1$-$C_8$ alkyl. $R^2$ may be unsubstituted $C_1$-$C_8$ alkyl. $R^2$ may be substituted $C_1$-$C_8$ alkyl. $R^2$ may be substituted or unsubstituted 2 to 8 membered heteroalkyl. $R^2$ may be unsubstituted 2 to 8 membered heteroalkyl. $R^2$ may be substituted 2 to 8 membered heteroalkyl. $R^2$ may be substituted or unsubstituted $C_1$-$C_4$ alkyl. $R^2$ may be unsubstituted $C_1$-$C_4$ alkyl. $R^2$ may be substituted $C_1$-$C_4$ alkyl. $R^2$ may be substituted or unsubstituted 2 to 4 membered heteroalkyl. $R^2$ may be unsubstituted 2 to 4 membered heteroalkyl. $R^2$ may be substituted 2 to 4 membered heteroalkyl.

$R^2$ may be substituted or unsubstituted 2 to 20 membered cycloalkyl. $R^2$ may be unsubstituted 2 to 20 membered cycloalkyl. $R^2$ may be substituted 2 to 20 membered cycloalkyl. $R^2$ may be substituted or unsubstituted 2 to 20 membered heterocycloalkyl. $R^2$ may be unsubstituted 2 to 20 membered heterocycloalkyl. $R^2$ may be substituted 2 to 20 membered heterocycloalkyl. $R^2$ may be substituted or unsubstituted 2 to 8 membered cycloalkyl. $R^2$ may be unsubstituted 2 to 8 membered cycloalkyl. $R^2$ may be substituted 2 to 8 membered cycloalkyl. $R^2$ may be substituted or unsubstituted 2 to 8 membered heterocycloalkyl. $R^2$ may be unsubstituted 2 to 8 membered heterocycloalkyl. $R^2$ may be substituted 2 to 8 membered heterocycloalkyl.

$R^2$ may be substituted or unsubstituted 5 to 20 membered aryl. $R^2$ may be unsubstituted 5 to 20 membered aryl. $R^2$ may be substituted 5 to 20 membered aryl. $R^2$ may be substituted or unsubstituted 5 to 20 membered heteroaryl. $R^2$ may be unsubstituted 5 to 20 membered heteroaryl. $R^2$ may be substituted 5 to 20 membered heteroaryl. $R^2$ may be substituted or unsubstituted 5 to 8 membered aryl. $R^2$ may be unsubstituted 5 to 8 membered aryl. $R^2$ may be substituted 5 to 8 membered aryl. $R^2$ may be substituted or unsubstituted 5 to 8 membered heteroaryl. $R^2$ may be unsubstituted 5 to 8 membered heteroaryl. $R^2$ may be substituted 5 to 8 membered heteroaryl.

$R^2$ may be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$. $R^2$ may be hydrogen.

$R^2$ may be substituted or unsubstituted heteroalkyl, substituted or unsubstituted heterocycloalkyl, substituted or unsubstituted aryl, or substituted or unsubstituted heteroaryl. $R^2$ may be substituted or unsubstituted heteroalkyl. $R^2$ may be $R^{2a}$-substituted heteroalkyl, wherein $R^{2a}$ is as described herein, including embodiments thereof. The $R^{2a}$-substituted heteroalkyl may be $-(CH_2)_2C(O)-R^{2a}$, wherein $R^{2a}$ is as described herein, including embodiments thereof. The $R^{2a}$-substituted heteroalkyl may be $-O-(CH_2)_2-R^{2a}$.

$R^3$ may independently be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, $R^{3a}$-substituted or unsubstituted alkyl (e.g. $C_1$ to $C_8$ alkyl), $R^{3a}$-substituted or unsubstituted heteroalkyl (e.g. 2 to 8 membered heteroalkyl), $R^{3a}$-substituted or unsubstituted cycloalkyl (e.g. $C_3$-$C_8$ cycloalkyl), $R^{3a}$-substituted or unsubstituted heterocycloalkyl (e.g. 3 to 6 membered heterocycloalkyl), $R^{3a}$-substituted or unsubstituted aryl (e.g. phenyl), or $R^{3a}$-substituted or unsubstituted heteroaryl (e.g. 5 or 6 membered heteroaryl).

$R^{3a}$ is independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, $R^{3b}$-substituted or unsubstituted alkyl (e.g. $C_1$ to $C_8$ alkyl), $R^{3b}$-substituted or unsubstituted heteroalkyl (e.g. 2 to 8 membered heteroalkyl), $R^{3b}$-substituted or unsubstituted cycloalkyl (e.g. $C_3$-$C_8$ cycloalkyl), $R^{3b}$-substituted or unsubstituted heterocycloalkyl (e.g. 3 to 6 membered heterocycloalkyl), $R^{3b}$-substituted or unsubstituted aryl (e.g. phenyl), or $R^{3b}$-substituted or unsubstituted heteroaryl (e.g. 5 or 6 membered heteroaryl).

$R^{3b}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^3$ may be substituted or unsubstituted $C_1$-$C_{20}$ alkyl. $R^3$ may be unsubstituted $C_1$-$C_{20}$ alkyl. $R^3$ may be substituted $C_1$-$C_{20}$ alkyl. $R^3$ may be substituted or unsubstituted 2 to 20 membered heteroalkyl. $R^3$ may be unsubstituted 2 to 20 membered heteroalkyl. $R^3$ may be substituted 2 to 20 membered heteroalkyl. $R^3$ may be substituted or unsubstituted $C_1$-$C_8$ alkyl. $R^3$ may be unsubstituted $C_1$-$C_8$ alkyl. $R^3$ may be substituted $C_1$-$C_8$ alkyl. $R^3$ may be substituted or unsubstituted 2 to 8 membered heteroalkyl. $R^3$ may be unsubstituted 2 to 8 membered heteroalkyl. $R^3$ may be substituted 2 to 8 membered heteroalkyl. $R^3$ may be substituted or unsubstituted $C_1$-$C_4$ alkyl. $R^3$ may be unsubstituted $C_1$-$C_4$ alkyl. $R^3$ may be substituted $C_1$-$C_4$ alkyl. $R^3$ may be substituted or unsubstituted 2 to 4 membered heteroalkyl. $R^3$ may be unsubstituted 2 to 4 membered heteroalkyl. $R^3$ may be substituted 2 to 4 membered heteroalkyl.

$R^3$ may be substituted or unsubstituted 2 to 20 membered cycloalkyl. $R^3$ may be unsubstituted 2 to 20 membered cycloalkyl. $R^3$ may be substituted 2 to 20 membered cycloalkyl. $R^3$ may be substituted or unsubstituted 2 to 20 membered heterocycloalkyl. $R^3$ may be unsubstituted 2 to 20 membered heterocycloalkyl. $R^3$ may be substituted 2 to 20 membered heterocycloalkyl. $R^3$ may be substituted or unsubstituted 2 to 8 membered cycloalkyl. $R^3$ may be unsubstituted 2 to 8 membered cycloalkyl. $R^3$ may be substituted 2 to 8 membered cycloalkyl. $R^3$ may be substituted or unsubstituted 2 to 8 membered heterocycloalkyl. $R^3$ may be unsubstituted 2 to 8 membered heterocycloalkyl. $R^3$ may be substituted 2 to 8 membered heterocycloalkyl.

$R^3$ may be substituted or unsubstituted 5 to 20 membered aryl. $R^3$ may be unsubstituted 5 to 20 membered aryl. $R^3$ may be substituted 5 to 20 membered aryl. $R^3$ may be substituted or unsubstituted 5 to 20 membered heteroaryl. $R^3$ may be unsubstituted 5 to 20 membered heteroaryl. $R^3$ may be substituted 5 to 20 membered heteroaryl. $R^3$ may be substituted or unsubstituted 5 to 8 membered aryl. $R^3$ may be unsubstituted 5 to 8 membered aryl. $R^3$ may be substituted 5 to 8 membered aryl. $R^3$ may be substituted or unsubstituted 5 to 8 membered heteroaryl. $R^3$ may be unsubstituted 5 to 8 membered heteroaryl. $R^3$ may be substituted 5 to 8 membered heteroaryl.

$R^3$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$. $R^3$ may be hydrogen.

$R^4$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{4a}$-substituted or unsubstituted alkyl (e.g. $C_1$ to $C_8$ alkyl), $R^{4a}$-substituted or unsubstituted heteroalkyl (e.g. 2 to 8 membered heteroalkyl), $R^{4a}$-substituted or unsubstituted cycloalkyl (e.g. $C_3$-$C_8$ cycloalkyl), $R^{4a}$-substituted or unsubstituted heterocycloalkyl (e.g. 3 to 6 membered heterocycloalkyl), $R^{4a}$-substituted or unsubstituted aryl (e.g. phenyl), or $R^{4a}$-substituted or unsubstituted heteroaryl (e.g. 5 or 6 membered heteroaryl).

$R^{4a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{4b}$-substituted or unsubstituted alkyl (e.g. $C_1$ to $C_8$ alkyl), $R^{4b}$-substituted or unsubstituted heteroalkyl (e.g. 2 to 8 membered heteroalkyl), $R^{4b}$-substituted or unsubstituted cycloalkyl (e.g. $C_3$-$C_8$ cycloalkyl), $R^{4b}$-substituted or unsubstituted heterocycloalkyl (e.g. 3 to 6 membered heterocycloalkyl), $R^{4b}$-substituted or unsubstituted aryl (e.g. phenyl), or $R^{4b}$-substituted or unsubstituted heteroaryl (e.g. 5 or 6 membered heteroaryl).

$R^{4b}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^4$ may be substituted or unsubstituted $C_1$-$C_{20}$ alkyl. $R^4$ may be unsubstituted $C_1$-$C_{20}$ alkyl. $R^4$ may be substituted $C_1$-$C_{20}$ alkyl. $R^4$ may be substituted or unsubstituted 2 to 20 membered heteroalkyl. $R^4$ may be unsubstituted 2 to 20 membered heteroalkyl. $R^4$ may be substituted 2 to 20 membered heteroalkyl. $R^4$ may be substituted or unsubstituted $C_1$-$C_8$ alkyl. $R^4$ may be unsubstituted $C_1$-$C_8$ alkyl. $R^4$ may be substituted $C_1$-$C_8$ alkyl. $R^4$ may be substituted or unsubstituted 2 to 8 membered heteroalkyl. $R^4$ may be unsubstituted 2 to 8 membered heteroalkyl. $R^4$ may be substituted 2 to 8 membered heteroalkyl. $R^4$ may be substituted or unsubstituted $C_1$-$C_4$ alkyl. $R^4$ may be unsubstituted $C_1$-$C_4$ alkyl. $R^4$ may be substituted $C_1$-$C_4$ alkyl. $R^4$ may be substituted or unsubstituted 2 to 4 membered heteroalkyl. $R^4$ may be unsubstituted 2 to 4 membered heteroalkyl. $R^4$ may be substituted 2 to 4 membered heteroalkyl.

$R^4$ may be substituted or unsubstituted 2 to 20 membered cycloalkyl. $R^4$ may be unsubstituted 2 to 20 membered cycloalkyl. $R^4$ may be substituted 2 to 20 membered cycloalkyl. $R^4$ may be substituted or unsubstituted 2 to 20 membered heterocycloalkyl. $R^4$ may be unsubstituted 2 to 20 membered heterocycloalkyl. $R^4$ may be substituted 2 to 20 membered heterocycloalkyl. $R^4$ may be substituted or unsubstituted 2 to 8 membered cycloalkyl. $R^4$ may be unsubstituted 2 to 8 membered cycloalkyl. $R^4$ may be substituted 2 to 8 membered cycloalkyl. $R^4$ may be substituted or unsubstituted 2 to 8 membered heterocycloalkyl. $R^4$ may be unsubstituted 2 to 8 membered heterocycloalkyl. $R^4$ may be substituted 2 to 8 membered heterocycloalkyl.

$R^4$ may be substituted or unsubstituted 5 to 20 membered aryl. $R^4$ may be unsubstituted 5 to 20 membered aryl. $R^4$ may be substituted 5 to 20 membered aryl. $R^4$ may be substituted or unsubstituted 5 to 20 membered heteroaryl. $R^4$ may be unsubstituted 5 to 20 membered heteroaryl. $R^4$ may be substituted 5 to 20 membered heteroaryl. $R^4$ may be substituted or unsubstituted 5 to 8 membered aryl. $R^4$ may be unsubstituted 5 to 8 membered aryl. $R^4$ may be substituted 5 to 8 membered aryl. $R^4$ may be substituted or unsubstituted 5 to 8 membered heteroaryl. $R^4$ may be unsubstituted 5 to 8 membered heteroaryl. $R^4$ may be substituted 5 to 8 membered heteroaryl.

$R^4$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$. $R^4$ may be hydrogen.

$R^5$ may independently be hydrogen, halogen, —$N_3$, —$CF_3$, —$CCl_3$, —$CBr_3$, —$CI_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{5a}$-substituted or unsubstituted alkyl (e.g. C$_1$ to C$_8$ alkyl), R$^{5a}$-substituted or unsubstituted heteroalkyl (e.g. 2 to 8 membered heteroalkyl), R$^{5a}$-substituted or unsubstituted cycloalkyl (e.g. C$_3$-C$_8$ cycloalkyl), R$^{5a}$-substituted or unsubstituted heterocycloalkyl (e.g. 3 to 6 membered heterocycloalkyl), R$^{5a}$-substituted or unsubstituted aryl (e.g. phenyl), or R$^5$-substituted or unsubstituted heteroaryl (e.g. 5 or 6 membered heteroaryl).

R$^{5a}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{5b}$-substituted or unsubstituted alkyl (e.g. C$_1$ to C$_8$ alkyl), R$^{5b}$-substituted or unsubstituted heteroalkyl (e.g. 2 to 8 membered heteroalkyl), R$^{5b}$-substituted or unsubstituted cycloalkyl (e.g. C$_3$-C$_8$ cycloalkyl), R$^{5b}$-substituted or unsubstituted heterocycloalkyl (e.g. 3 to 6 membered heterocycloalkyl), R$^{5b}$-substituted or unsubstituted aryl (e.g. phenyl), or R$^{5b}$-substituted or unsubstituted heteroaryl (e.g. 5 or 6 membered heteroaryl).

R$^{5b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

R$^5$ may be substituted or unsubstituted C$_1$-C$_{20}$ alkyl. R$^5$ may be unsubstituted C$_1$-C$_{20}$ alkyl. R$^5$ may be substituted C$_1$-C$_{20}$ alkyl. R$^5$ may be substituted or unsubstituted 2 to 20 membered heteroalkyl. R$^5$ may be unsubstituted 2 to 20 membered heteroalkyl. R$^5$ may be substituted 2 to 20 membered heteroalkyl. R$^5$ may be substituted or unsubstituted C$_1$-C$_8$ alkyl. R$^5$ may be unsubstituted C$_1$-C$_8$ alkyl. R$^5$ may be substituted C$_1$-C$_8$ alkyl. R$^5$ may be substituted or unsubstituted 2 to 8 membered heteroalkyl. R$^5$ may be unsubstituted 2 to 8 membered heteroalkyl. R$^5$ may be substituted 2 to 8 membered heteroalkyl. R$^5$ may be substituted or unsubstituted C$_1$-C$_4$ alkyl. R$^5$ may be unsubstituted C$_1$-C$_4$ alkyl. R$^5$ may be substituted C$_1$-C$_4$ alkyl. R$^5$ may be substituted or unsubstituted 2 to 4 membered heteroalkyl. R$^5$ may be unsubstituted 2 to 4 membered heteroalkyl. R$^5$ may be substituted 2 to 4 membered heteroalkyl.

R$^5$ may be substituted or unsubstituted 2 to 20 membered cycloalkyl. R$^5$ may be unsubstituted 2 to 20 membered cycloalkyl. R$^5$ may be substituted 2 to 20 membered cycloalkyl. R$^5$ may be substituted or unsubstituted 2 to 20 membered heterocycloalkyl. R$^5$ may be unsubstituted 2 to 20 membered heterocycloalkyl. R$^5$ may be substituted 2 to 20 membered heterocycloalkyl. R$^5$ may be substituted or unsubstituted 2 to 8 membered cycloalkyl. R$^5$ may be unsubstituted 2 to 8 membered cycloalkyl. R$^5$ may be substituted 2 to 8 membered cycloalkyl. R$^5$ may be substituted or unsubstituted 2 to 8 membered heterocycloalkyl. R$^5$ may be unsubstituted 2 to 8 membered heterocycloalkyl. R$^5$ may be substituted 2 to 8 membered heterocycloalkyl.

R$^5$ may be substituted or unsubstituted 5 to 20 membered aryl. R$^5$ may be unsubstituted 5 to 20 membered aryl. R$^5$ may be substituted 5 to 20 membered aryl. R$^5$ may be substituted or unsubstituted 5 to 20 membered heteroaryl. R$^5$ may be unsubstituted 5 to 20 membered heteroaryl. R$^5$ may be substituted 5 to 20 membered heteroaryl. R$^5$ may be substituted or unsubstituted 5 to 8 membered aryl. R$^5$ may be unsubstituted 5 to 8 membered aryl. R$^5$ may be substituted 5 to 8 membered aryl. R$^5$ may be substituted or unsubstituted 5 to 8 membered heteroaryl. R$^5$ may be unsubstituted 5 to 8 membered heteroaryl. R$^5$ may be substituted 5 to 8 membered heteroaryl.

R$^5$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$. R$^5$ may be hydrogen.

R$^6$ may independently be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{6a}$-substituted or unsubstituted alkyl (e.g. C$_1$ to C$_8$ alkyl), R$^{6a}$-substituted or unsubstituted heteroalkyl (e.g. 2 to 8 membered heteroalkyl), R$^{6a}$-substituted or unsubstituted cycloalkyl (e.g. C$_3$-C$_8$ cycloalkyl), R$^{6a}$-substituted or unsubstituted heterocycloalkyl (e.g. 3 to 6 membered heterocycloalkyl), R$^{6a}$-substituted or unsubstituted aryl (e.g. phenyl), or R$^{6a}$-substituted or unsubstituted heteroaryl (e.g. 5 or 6 membered heteroaryl).

R$^{6a}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{6b}$-substituted or unsubstituted alkyl (e.g. C$_1$ to C$_8$ alkyl), R$^{6b}$-substituted or unsubstituted heteroalkyl (e.g. 2 to 8 membered heteroalkyl), R$^{6b}$-substituted or unsubstituted cycloalkyl (e.g. C$_3$-C$_8$ cycloalkyl), R$^{6b}$-substituted or unsubstituted heterocycloalkyl (e.g. 3 to 6 membered heterocycloalkyl), R$^{6b}$-substituted or unsubstituted aryl (e.g. phenyl), or R$^{6b}$-substituted or unsubstituted heteroaryl (e.g. 5 or 6 membered heteroaryl).

R$^{6b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

R$^6$ may be substituted or unsubstituted C$_1$-C$_{20}$ alkyl. R$^6$ may be unsubstituted C$_1$-C$_{20}$ alkyl. R$^6$ may be substituted C$_1$-C$_{20}$ alkyl. R$^6$ may be substituted or unsubstituted 2 to 20 membered heteroalkyl. R$^6$ may be unsubstituted 2 to 20 membered heteroalkyl. R$^6$ may be substituted or unsubstituted C$_1$-C$_8$ alkyl. R$^6$ may be unsubstituted C$_1$-C$_8$ alkyl. R$^6$ may be substituted C$_1$-C$_8$ alkyl. R$^6$ may be substituted or unsubstituted 2 to 8 membered heteroalkyl. R$^6$ may be unsubstituted 2 to 8 membered heteroalkyl. R$^6$ may be substituted 2 to 8 membered heteroalkyl. R$^6$ may be substituted or unsubstituted C$_1$-C$_4$ alkyl. R$^6$ may be unsubstituted C$_1$-C$_4$ alkyl. R$^6$ may be substituted C$_1$-C$_4$ alkyl. R$^6$ may be substituted or unsubstituted 2 to 4 membered heteroalkyl. R$^6$ may be unsubstituted 2 to 4 membered heteroalkyl. R$^6$ may be substituted 2 to 4 membered heteroalkyl.

R$^6$ may be substituted or unsubstituted 2 to 20 membered cycloalkyl. R$^6$ may be unsubstituted 2 to 20 membered cycloalkyl. R$^6$ may be substituted 2 to 20 membered cycloalkyl. R$^6$ may be substituted or unsubstituted 2 to 20 membered heterocycloalkyl. R$^6$ may be unsubstituted 2 to 20 membered heterocycloalkyl. R$^6$ may be substituted 2 to 20 membered heterocycloalkyl. R$^6$ may be substituted or unsubstituted 2 to 8 membered cycloalkyl. R$^6$ may be unsubstituted 2 to 8 membered cycloalkyl. R$^6$ may be substituted 2 to 8 membered cycloalkyl. R$^6$ may be substituted or unsubstituted 2 to 8 membered heterocycloalkyl. $R^6$ may be unsubstituted 2 to 8 membered heterocycloalkyl. $R^6$ may be substituted 2 to 8 membered heterocycloalkyl.

$R^6$ may be substituted or unsubstituted 5 to 20 membered aryl. $R^6$ may be unsubstituted 5 to 20 membered aryl. $R^6$ may be substituted 5 to 20 membered aryl. $R^6$ may be substituted or unsubstituted 5 to 20 membered heteroaryl. $R^6$ may be unsubstituted 5 to 20 membered heteroaryl. $R^6$ may be substituted 5 to 20 membered heteroaryl. $R^6$ may be substituted or unsubstituted 5 to 8 membered aryl. $R^6$ may be unsubstituted 5 to 8 membered aryl. $R^6$ may be substituted 5 to 8 membered aryl. $R^6$ may be substituted or unsubstituted 5 to 8 membered heteroaryl. $R^6$ may be unsubstituted 5 to 8 membered heteroaryl. $R^6$ may be substituted 5 to 8 membered heteroaryl.

$R^6$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$. $R^6$ may be hydrogen.

$R^7$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, $R^{7a}$-substituted or unsubstituted alkyl (e.g. $C_1$ to $C_8$ alkyl), $R^{7a}$-substituted or unsubstituted heteroalkyl (e.g. 2 to 8 membered heteroalkyl), $R^{7a}$-substituted or unsubstituted cycloalkyl (e.g. $C_3$-$C_8$ cycloalkyl), $R^{7a}$-substituted or unsubstituted heterocycloalkyl (e.g. 3 to 6 membered heterocycloalkyl), $R^{7a}$-substituted or unsubstituted aryl (e.g. phenyl), or $R^{7a}$-substituted or unsubstituted heteroaryl (e.g. 5 or 6 membered heteroaryl).

$R^{7a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, $R^{7b}$-substituted or unsubstituted alkyl (e.g. $C_1$ to $C_8$ alkyl), $R^{7b}$-substituted or unsubstituted heteroalkyl (e.g. 2 to 8 membered heteroalkyl), $R^{7b}$-substituted or unsubstituted cycloalkyl (e.g. $C_3$-$C_8$ cycloalkyl), $R^{7b}$-substituted or unsubstituted heterocycloalkyl (e.g. 3 to 6 membered heterocycloalkyl), $R^{7b}$-substituted or unsubstituted aryl (e.g. phenyl), or $R^{7b}$-substituted or unsubstituted heteroaryl (e.g. 5 or 6 membered heteroaryl).

$R^{7b}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

$R^7$ may be substituted or unsubstituted $C_1$-$C_{20}$ alkyl. $R^7$ may be unsubstituted $C_1$-$C_{20}$ alkyl. $R^7$ may be substituted $C_1$-$C_{20}$ alkyl. $R^7$ may be substituted or unsubstituted 2 to 20 membered heteroalkyl. $R^7$ may be unsubstituted 2 to 20 membered heteroalkyl. $R^7$ may be substituted 2 to 20 membered heteroalkyl. $R^7$ may be substituted or unsubstituted $C_1$-$C_8$ alkyl. $R^7$ may be unsubstituted $C_1$-$C_8$ alkyl. $R^7$ may be substituted $C_1$-$C_8$ alkyl. $R^7$ may be substituted or unsubstituted 2 to 8 membered heteroalkyl. $R^7$ may be unsubstituted 2 to 8 membered heteroalkyl. $R^7$ may be substituted 2 to 8 membered heteroalkyl. $R^7$ may be substituted or unsubstituted $C_1$-$C_4$ alkyl. $R^7$ may be unsubstituted $C_1$-$C_4$ alkyl. $R^7$ may be substituted $C_1$-$C_4$ alkyl. $R^7$ may be substituted or unsubstituted 2 to 4 membered heteroalkyl. $R^7$ may be unsubstituted 2 to 4 membered heteroalkyl. $R^7$ may be substituted 2 to 4 membered heteroalkyl.

$R^7$ may be substituted or unsubstituted 2 to 20 membered cycloalkyl. $R^7$ may be unsubstituted 2 to 20 membered cycloalkyl. $R^7$ may be substituted 2 to 20 membered cycloalkyl. $R^7$ may be substituted or unsubstituted 2 to 20 membered heterocycloalkyl. $R^7$ may be unsubstituted 2 to 20 membered heterocycloalkyl. $R^7$ may be substituted 2 to 20 membered heterocycloalkyl. $R^7$ may be substituted or unsubstituted 2 to 8 membered cycloalkyl. $R^7$ may be unsubstituted 2 to 8 membered cycloalkyl. $R^7$ may be substituted 2 to 8 membered cycloalkyl. $R^7$ may be substituted or unsubstituted 2 to 8 membered heterocycloalkyl. $R^7$ may be unsubstituted 2 to 8 membered heterocycloalkyl. $R^7$ may be substituted 2 to 8 membered heterocycloalkyl.

$R^7$ may be substituted or unsubstituted 5 to 20 membered aryl. $R^7$ may be unsubstituted 5 to 20 membered aryl. $R^7$ may be substituted 5 to 20 membered aryl. $R^7$ may be substituted or unsubstituted 5 to 20 membered heteroaryl. $R^7$ may be unsubstituted 5 to 20 membered heteroaryl. $R^7$ may be substituted 5 to 20 membered heteroaryl. $R^7$ may be substituted or unsubstituted 5 to 8 membered aryl. $R^7$ may be unsubstituted 5 to 8 membered aryl. $R^7$ may be substituted 5 to 8 membered aryl. $R^7$ may be substituted or unsubstituted 5 to 8 membered heteroaryl. $R^7$ may be unsubstituted 5 to 8 membered heteroaryl. $R^7$ may be substituted 5 to 8 membered heteroaryl.

$R^7$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$. $R^7$ may be hydrogen.

$R^8$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, $R^{8a}$-substituted or unsubstituted alkyl (e.g. $C_1$ to $C_8$ alkyl), $R^{8a}$-substituted or unsubstituted heteroalkyl (e.g. 2 to 8 membered heteroalkyl), $R^{8a}$-substituted or unsubstituted cycloalkyl (e.g. $C_3$-$C_8$ cycloalkyl), $R^{8a}$-substituted or unsubstituted heterocycloalkyl (e.g. 3 to 6 membered heterocycloalkyl), $R^{8a}$-substituted or unsubstituted aryl (e.g. phenyl), or $R^{8a}$-substituted or unsubstituted heteroaryl (e.g. 5 or 6 membered heteroaryl).

$R^{8a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, $R^{8b}$-substituted or unsubstituted alkyl (e.g. $C_1$ to $C_8$ alkyl), $R^{8b}$-substituted or unsubstituted heteroalkyl (e.g. 2 to 8 membered heteroalkyl), $R^{8b}$-substituted or unsubstituted cycloalkyl (e.g. $C_3$-$C_8$ cycloalkyl), $R^{8b}$-substituted or unsubstituted heterocycloalkyl (e.g. 3 to 6 membered heterocycloalkyl), $R^{8b}$-substituted or unsubstituted aryl (e.g. phenyl), or $R^{8b}$-substituted or unsubstituted heteroaryl (e.g. 5 or 6 membered heteroaryl).

$R^{8b}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

$R^8$ may be substituted or unsubstituted $C_1$-$C_{20}$ alkyl. $R^8$ may be unsubstituted $C_1$-$C_{20}$ alkyl. $R^8$ may be substituted $C_1$-$C_{20}$ alkyl. $R^8$ may be substituted or unsubstituted 2 to 20 membered heteroalkyl. R⁸ may be unsubstituted 2 to 20 membered heteroalkyl. R⁸ may be substituted 2 to 20 membered heteroalkyl. R⁸ may be substituted or unsubstituted $C_1$-$C_8$ alkyl. R⁸ may be unsubstituted $C_1$-$C_8$ alkyl. R⁸ may be substituted $C_1$-$C_8$ alkyl. R⁸ may be substituted or unsubstituted 2 to 8 membered heteroalkyl. R⁸ may be unsubstituted 2 to 8 membered heteroalkyl. R⁸ may be substituted 2 to 8 membered heteroalkyl. R⁸ may be substituted or unsubstituted $C_1$-$C_4$ alkyl. R⁸ may be unsubstituted $C_1$-$C_4$ alkyl. R⁸ may be substituted $C_1$-$C_4$ alkyl. R⁸ may be substituted or unsubstituted 2 to 4 membered heteroalkyl. R⁸ may be unsubstituted 2 to 4 membered heteroalkyl. R⁸ may be substituted 2 to 4 membered heteroalkyl.

R⁸ may be substituted or unsubstituted 2 to 20 membered cycloalkyl. R⁸ may be unsubstituted 2 to 20 membered cycloalkyl. R⁸ may be substituted 2 to 20 membered cycloalkyl. R⁸ may be substituted or unsubstituted 2 to 20 membered heterocycloalkyl. R⁸ may be unsubstituted 2 to 20 membered heterocycloalkyl. R⁸ may be substituted 2 to 20 membered heterocycloalkyl. R⁸ may be substituted or unsubstituted 2 to 8 membered cycloalkyl. R⁸ may be unsubstituted 2 to 8 membered cycloalkyl. R⁸ may be substituted 2 to 8 membered cycloalkyl. R⁸ may be substituted or unsubstituted 2 to 8 membered heterocycloalkyl. R⁸ may be unsubstituted 2 to 8 membered heterocycloalkyl. R⁸ may be substituted 2 to 8 membered heterocycloalkyl.

R⁸ may be substituted or unsubstituted 5 to 20 membered aryl. R⁸ may be unsubstituted 5 to 20 membered aryl. R⁸ may be substituted 5 to 20 membered aryl. R⁸ may be substituted or unsubstituted 5 to 20 membered heteroaryl. R⁸ may be unsubstituted 5 to 20 membered heteroaryl. R⁸ may be substituted 5 to 20 membered heteroaryl. R⁸ may be substituted or unsubstituted 5 to 8 membered aryl. R⁸ may be unsubstituted 5 to 8 membered aryl. R⁸ may be substituted 5 to 8 membered aryl. R⁸ may be substituted or unsubstituted 5 to 8 membered heteroaryl. R⁸ may be unsubstituted 5 to 8 membered heteroaryl. R⁸ may be substituted 5 to 8 membered heteroaryl.

R⁸ may be hydrogen, halogen, —N₃, —CF₃, —CCl₃, —CBr₃, —CI₃, —CN, —CHO, —OH, —NH₂, —COOH, —CONH₂, —NO₂, —SH, —SO₂, —SO₂Cl, —SO₃H, —SO₄H, —SO₂NH₂, —NHNH₂, —ONH₂, —NHC(O)NHNH₂. R⁸ may be hydrogen.

The compound of formula (I) may have formula:

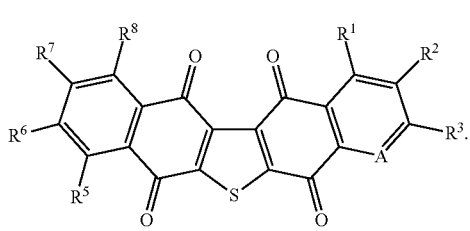

(II)

A, R¹, R², R³, R⁴, R⁵, R⁶, R⁷, R⁸, R⁹, R¹⁰ R¹¹, R¹², R¹³, R¹⁴, R¹⁵, and R¹⁶ are as described herein, including embodiments thereof.

The compound of formula II may have formula:

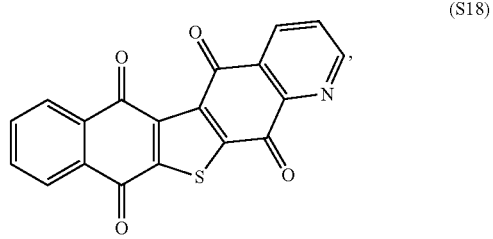 [SMILES: O=c1c2ccccc2c(=O)c2c1sc1c(=O)c3ncccc3c(=O)c12]

(S18)

or a pharmaceutically acceptable salt thereof.

The compound of formula (I) may have formula:

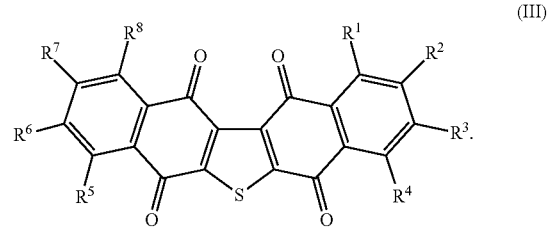

(III)

R¹, R², R³, R⁴, R⁵, R⁶, R⁷, R⁸, R⁹, R¹⁰ R¹¹, R¹², R¹³, R¹⁴, R¹⁵, and R¹⁶ are as described herein, including embodiments thereof.

The compound of formula (III) may have formula:

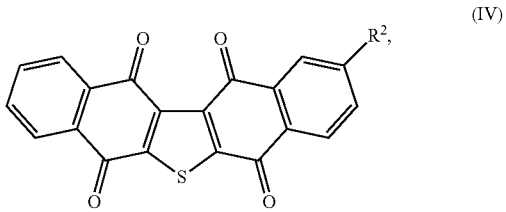

(IV)

or a pharmaceutically acceptable salt thereof.

R² is as described herein, including embodiments thereof. R² may be substituted or unsubstituted heteroalkyl, substituted or unsubstituted heterocycloalkyl, substituted or unsubstituted aryl, or substituted or unsubstituted heteroaryl. R² may be substituted or unsubstituted heteroalkyl. R² may be $R^{2a}$-substituted heteroalkyl, wherein $R^{2a}$ is hydrogen, halogen, —N₃, —CF₃, —CCl₃, —CBr₃, —CI₃, —CN, —CHO, —OH, —NH₂, —COOH, —CONH₂, —NO₂, —SH, —SO₂, —SO₂Cl, —SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The $R^{2a}$-substituted heteroalkyl may be —(CH₂)₂C(O)—$R^{2a}$. $R^{2a}$ is as described herein, including embodiments thereof.

The compounds of formula (III) may have formula:
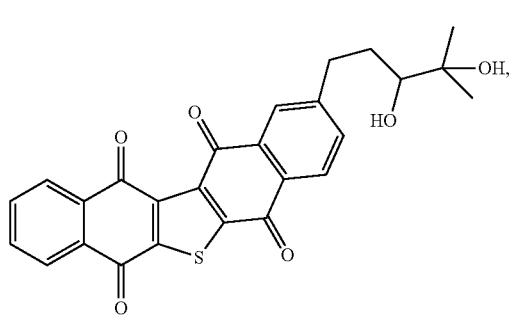
(S1)
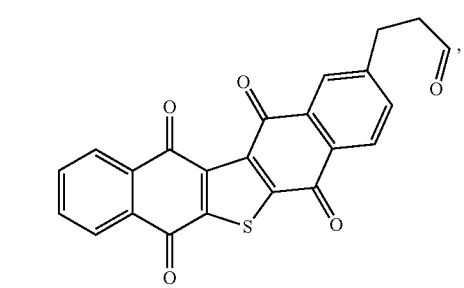
(S2)
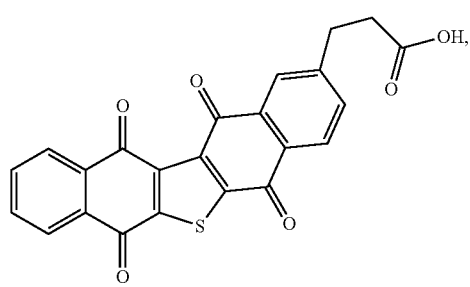
(S3)
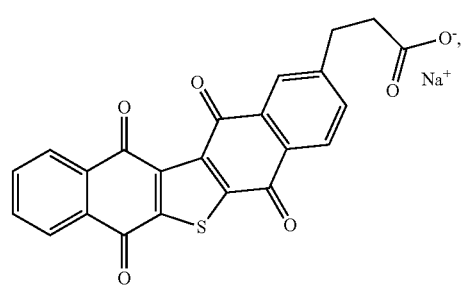
(S4)
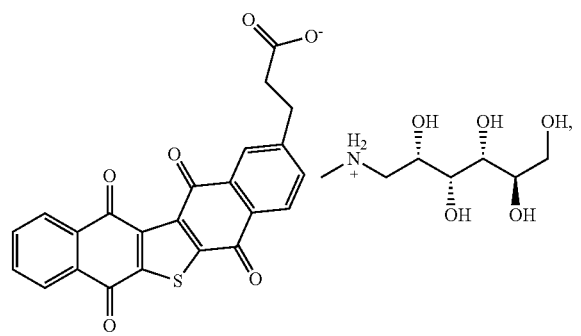
(S5)
or a pharmaceutically acceptable salt thereof.
The compound of formula (III) may have formula:
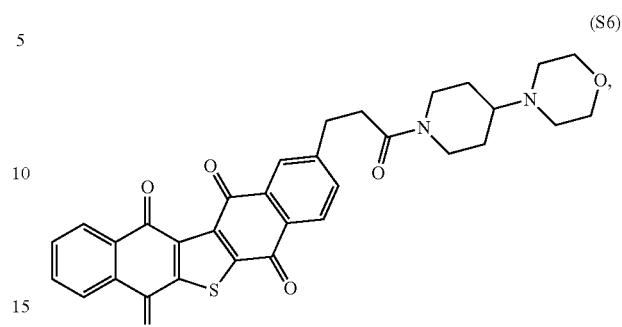
(S6)
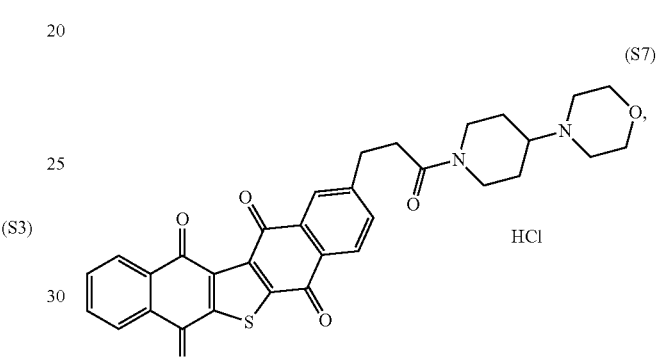
(S7)
or a pharmaceutically acceptable salt thereof.
The compound of formula (III) may have formula:
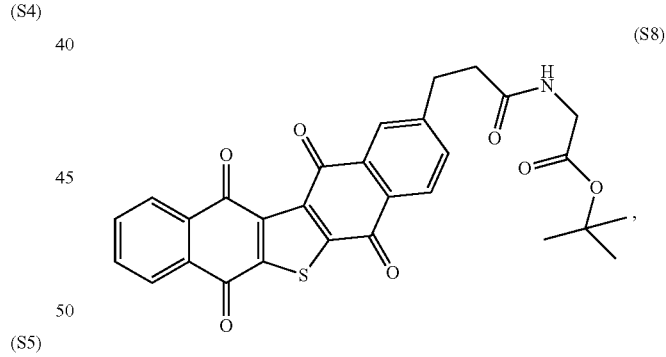
(S8)
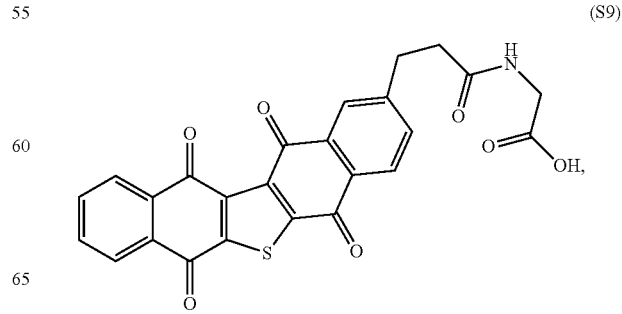
(S9)

(S12)

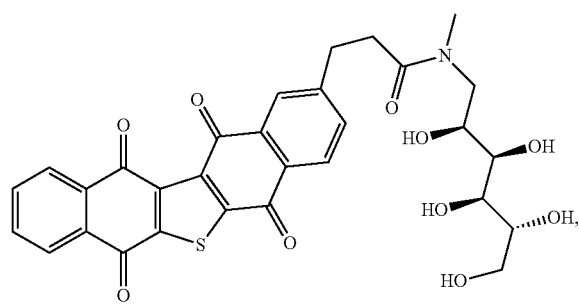

or a pharmaceutically acceptable salt thereof.

The compound of formula (III) may have formula:

(S10)

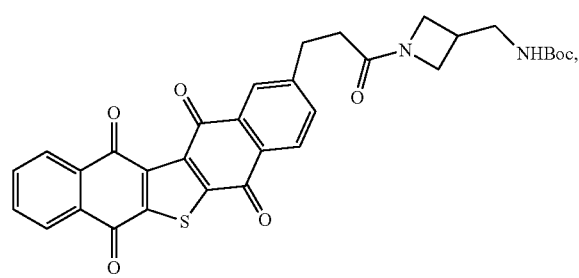

(S11)

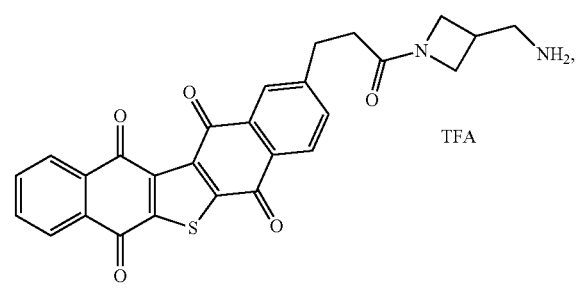

or a pharmaceutically acceptable salt thereof.

The compound of formula (III) may have formula:

(S13)

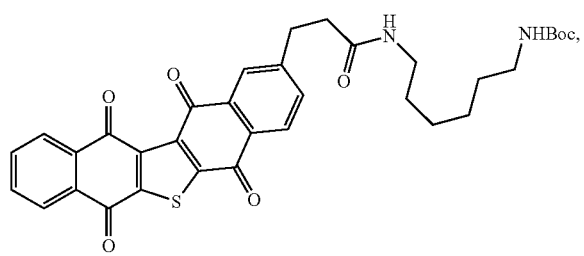

(S14)

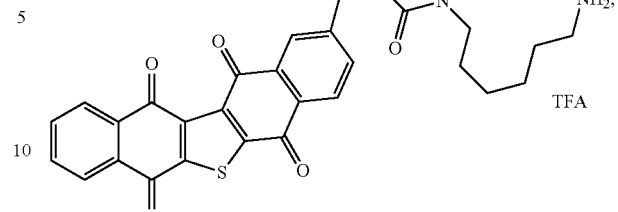

or a pharmaceutically acceptable salt thereof.

The compound of formula (III) may have formula:

(S15)

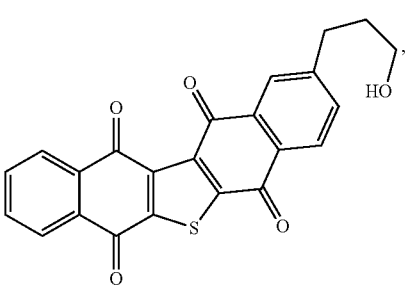

or a pharmaceutically acceptable salt thereof.

The compound of formula (III) may have formula:

(S16)

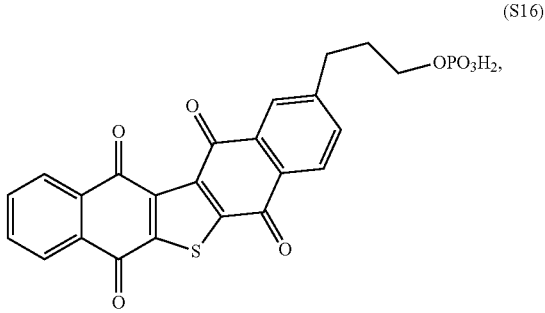

(S17)

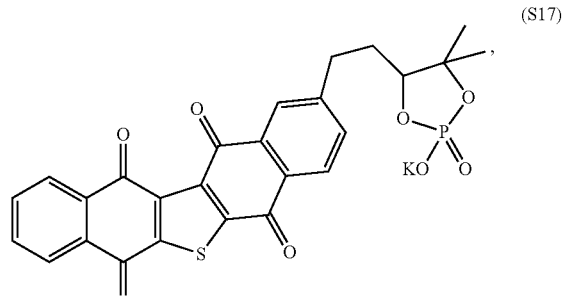

or a pharmaceutically acceptable salt thereof.

The compound of formula (III) may have formula:

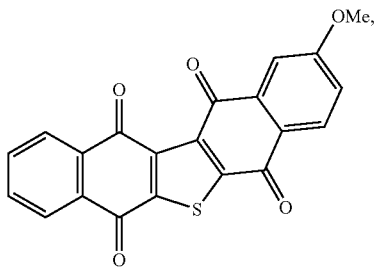
(S27)

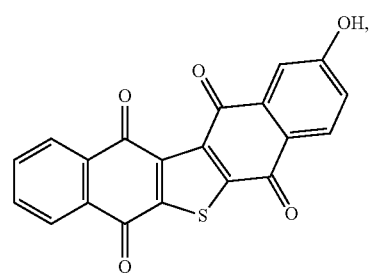
(S28)

or a pharmaceutically acceptable salt thereof.

The compound of formula (III) may have formula:

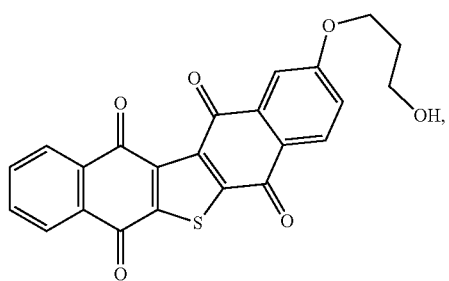
(S29)

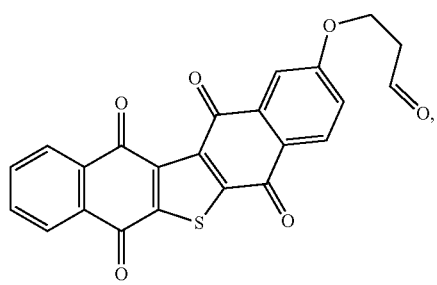
(S30)

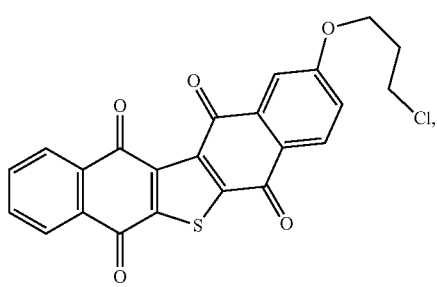
(S31)

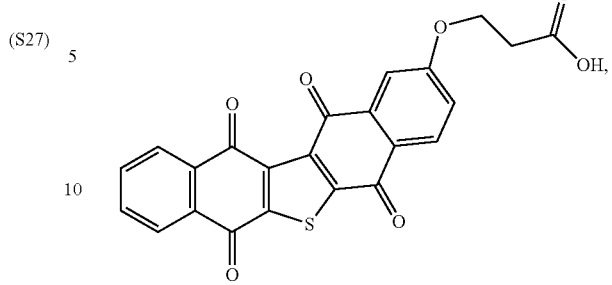
(S32)

or a pharmaceutically acceptable salt thereof.

The compound of formula (III) may have formula:

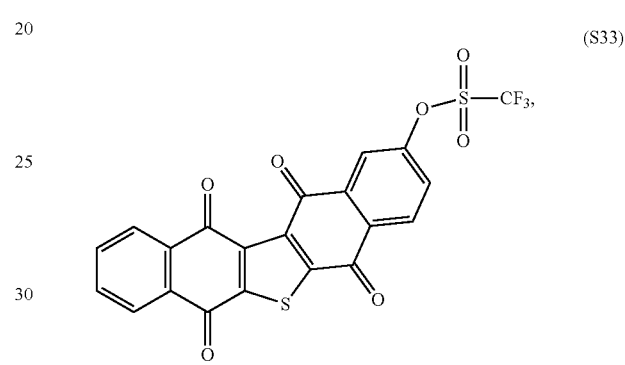
(S33)

or a pharmaceutically acceptable salt thereof.

The compound of formula (III) may have formula:

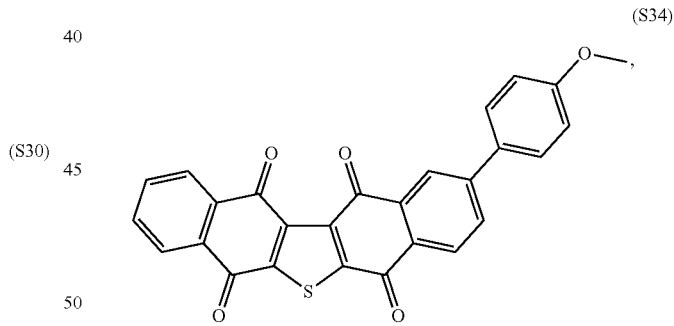
(S34)

or a pharmaceutically acceptable salt thereof.

The compound of formula (I) may have formula:

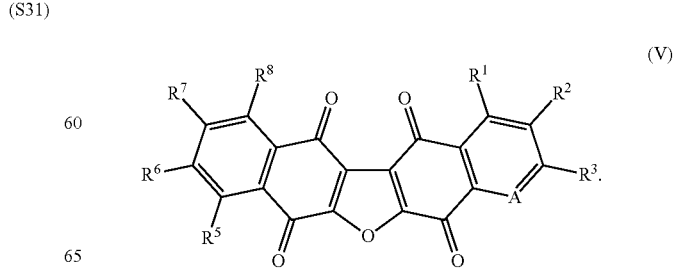
(V)

A, $R^1$, $R^2$, $R^3$, $R^4$, $R^5$, $R^6$, $R^7$, $R^8$, $R^9$, $R^{10}$ $R^{11}$, $R^{12}$, $R^{13}$, $R^{14}$, $R^{15}$, and $R^{16}$ are as described herein, including embodiments thereof.

$R^2$ may be substituted or unsubstituted heteroalkyl, substituted or unsubstituted heterocycloalkyl, substituted or unsubstituted aryl, or substituted or unsubstituted heteroaryl. $R^2$ may be substituted or unsubstituted heteroalkyl. $R^2$ may be $R^{2a}$-substituted heteroalkyl, wherein $R^{2a}$ is hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The $R^{2a}$-substituted heteroalkyl may be —$(CH_2)_2C(O)$—$R^{2a}$. $R^{2a}$ is as described herein, including embodiments thereof.

The compound of formula (V) may have formula:

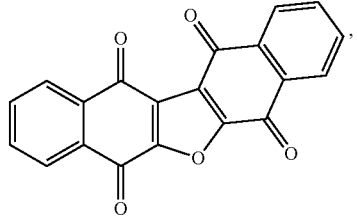

(S19)

or a pharmaceutically acceptable salt thereof.

The compound of formula (I) may have formula:

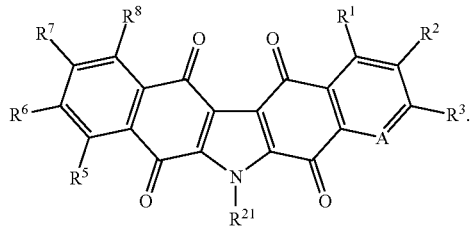

(VI)

A, $R^1$, $R^2$, $R^3$, $R^4$, $R^5$, $R^6$, $R^7$, $R^8$, $R^9$, $R^{10}$ $R^{11}$, $R^{12}$, $R^{13}$, $R^{14}$, $R^{15}$, $R^{16}$ and $R^{21}$ are as described herein, including embodiments thereof.

$R^2$ may be substituted or unsubstituted heteroalkyl, substituted or unsubstituted heterocycloalkyl, substituted or unsubstituted aryl, or substituted or unsubstituted heteroaryl. $R^2$ may be substituted or unsubstituted heteroalkyl. $R^2$ may be $R^{2a}$-substituted heteroalkyl, wherein $R^{2a}$ is hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The $R^{2a}$-substituted heteroalkyl may be —$(CH_2)_2C(O)$—$R^{2a}$. $R^{2a}$ is as described herein, including embodiments thereof.

$R^{21}$ may be hydrogen, substituted or unsubstituted methyl, substituted or unsubstituted ethyl, substituted or unsubstituted propyl. $R^{21}$ may be unsubstituted methyl. $R^{21}$ may be hydrogen.

The compound of formula (VI) may have formula:

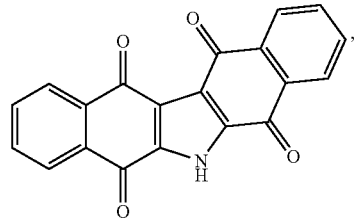

(S21)

or a pharmaceutically acceptable salt thereof.

In another aspect, a compound having formula (VII) or a pharmaceutically acceptable salt thereof is provided.

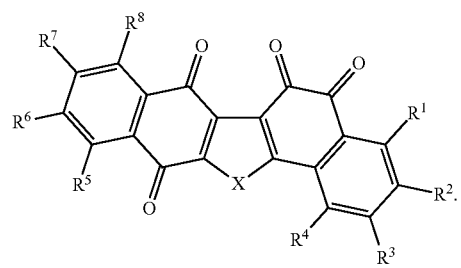

(VII)

X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, —CN, —$CF_3$, —$CCl_3$, —$CBr_3$, —$CI_3$, —$NR^9R^{10}$, —$C(O)R^{11}$, —$C(O)NR^9R^{10}$, —$NR^{12}C(O)R^{11}$, —$S(O)_nR^{13}$, —$S(O)_nNR^9R^{10}$, —$NR^{12}S(O)_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4.

X, $R^1$, $R^2$, $R^3$, $R^4$, $R^5$, $R^6$, $R^7$, $R^8$, $R^9$, $R^{10}$ $R^{11}$, $R^{12}$, $R^{13}$, $R^{14}$, $R^{15}$, $R^{16}$ and $R^{21}$ are as described herein, including embodiments thereof.

X may be —O—. $R^2$ may be substituted or unsubstituted heteroalkyl, substituted or unsubstituted heterocycloalkyl, substituted or unsubstituted aryl, or substituted or unsubstituted heteroaryl. $R^2$ may be substituted or unsubstituted heteroalkyl. $R^2$ may be $R^{2a}$-substituted heteroalkyl, wherein $R^{2a}$ is hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The $R^{2a}$-substituted heteroalkyl may be —$(CH_2)_2C(O)$—$R^{2a}$. $R^{2a}$ is as described herein including embodiments thereof.

$R^1$, $R^2$, $R^3$, $R^4$, $R^5$, $R^6$, $R^7$, and $R^8$ may be hydrogen or a hydrophilic moiety. $R^1$, $R^2$, $R^3$, $R^4$, $R^5$, $R^6$, $R^7$, and $R^8$ may be hydrogen. $R^1$, $R^2$, $R^3$, $R^4$, $R^5$, $R^6$, $R^7$, and $R^8$ may be a hydrophilic moiety.

The compound of formula (VII) may have formula:

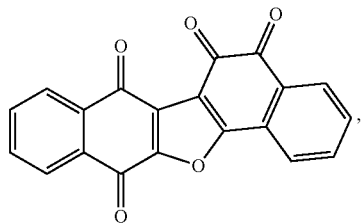

(S20)

or a pharmaceutically acceptable salt thereof.

In another aspect a compound having formula (VIII) or a pharmaceutically acceptable salt thereof is provided.

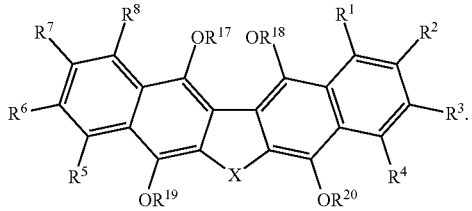

(VIII)

X is —S—, —$NR^{21}$—, or —O—. $R^1$, $R^2$, $R^3$, $R^4$, $R^5$, $R^6$, $R^7$, and $R^8$ are each independently hydrogen, halogen, —$N_3$, —NHC=(O)$NHNH_2$, —CN, —$CF_3$, —$CCl_3$, —$CBr_3$, —$CI_3$, —$NR^9R^{10}$, —$C(O)R^{11}$, —$C(O)NR^9R^{10}$, —$NR^{12}C(O)R^{11}$, —$S(O)_nR^{13}$, —$S(O)_nNR^9R^{10}$, —$NR^{12}S(O)_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$, $R^{11}$, $R^{12}$, $R^{13}$, $R^{14}$, $R^{15}$, and $R^{16}$ are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{17}$, $R^{18}$, $R^{19}$, and $R^{20}$ are independently hydrogen or substituted or unsubstituted alkyl. $R^{21}$ is hydrogen or unsubstituted $C_1$-$C_5$ alkyl. The symbol n is 1 to 4.

X, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{21}$ are as described herein, including embodiments thereof.

$R^1$, $R^2$, $R^3$, $R^4$, $R^5$, $R^6$, $R^7$, and $R^8$ may be a hydrophilic moiety. $R^1$, $R^2$, $R^3$, $R^4$, $R^5$, $R^6$, $R^7$, and $R^8$ may be hydrogen, substituted or unsubstituted alkyl, substituted or unsubstituted heteroalkyl, substituted or unsubstituted heterocycloalkyl, or substituted or unsubstituted aryl. $R^2$ may be substituted or unsubstituted heteroalkyl, substituted or unsubstituted heterocycloalkyl, substituted or unsubstituted aryl, or substituted or unsubstituted heteroaryl. $R^2$ may be substituted or unsubstituted heteroalkyl. $R^2$ may be $R^{2a}$-substituted heteroalkyl, wherein $R^{2a}$ is hydrogen, halogen, —$N_3$, —$CF_3$, —$CCl_3$, —$CBr_3$, —$CI_3$, —CN, —CHO, —OH, —$NH_2$, —COOH, $CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The $R^{2a}$-substituted heteroalkyl may be —$(CH_2)_2C(O)$—$R^{2a}$. $R^{2a}$ is as described herein, including embodiments thereof.

$R^{17}$, $R^{18}$, $R^{19}$, and $R^{20}$ may be identical. $R^{17}$, $R^{18}$, $R^{19}$, and $R^{20}$ may be different. $R^{17}$, $R^{18}$, $R^{19}$, and $R^{20}$ may independently be hydrogen or substituted or unsubstituted alkyl. $R^{17}$, $R^{18}$, $R^{19}$, and $R^{20}$ may independently be hydrogen or unsubstituted alkyl. $R^{17}$, $R^{18}$, $R^{19}$, and $R^{20}$ may independently be hydrogen, methyl, or acetyl. $R^{17}$, $R^{18}$, $R^{19}$, and $R^{20}$ may be hydrogen. $R^{17}$, $R^{18}$, $R^{19}$, and $R^{20}$ may be methyl. $R^{17}$, $R^{18}$, $R^{19}$, and $R^{20}$ may be acetyl.

The compound of formula (VIII) may have formula:

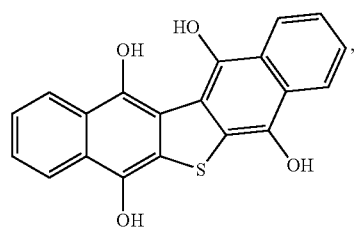

(S23)

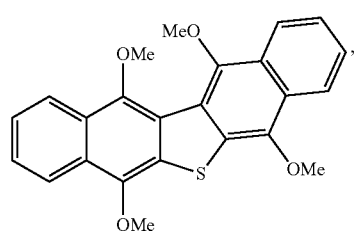

(S24)

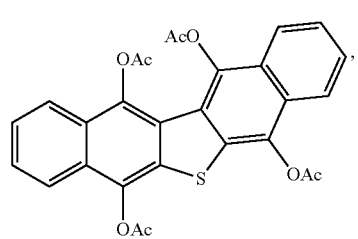

(S22)

or a pharmaceutically acceptable salt thereof.

The compound of formula (VIII) may have formula:

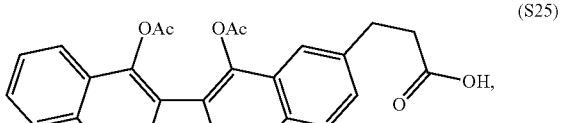
(S25)

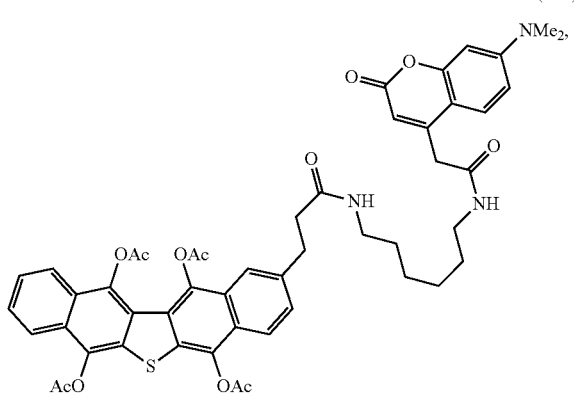
(S26)

or a pharmaceutically acceptable salt thereof.

III. Pharmaceutical Compositions

In another aspect, a pharmaceutical composition is provided. The pharmaceutical composition includes a pharmaceutically acceptable excipient and a compound of formula (VII), (VIII), or a compound having the formula:

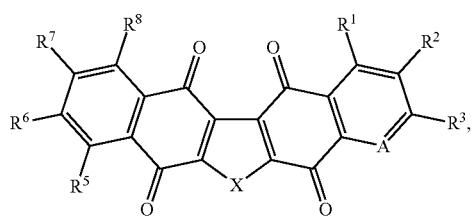
(I)

or a pharmaceutically acceptable salt thereof.

A is N or —$CR^4$—. X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, CN, —$CF_3$, —$CCl_3$, —$CBr_3$, —$CI_3$, —$NR^9R^{10}$, —C(O)$R^{11}$, —C(O)$NR^9R^{10}$, —$NR^{12}$C(O)$R^{11}$, —S(O)$_nR^{13}$, —S(O)$_nNR^9R^{10}$, —$NR^{12}$S(O)$_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$, $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4.

$R^1$, $R^2$, $R^3$, $R^4$, $R^5$, $R^6$, $R^7$, $R^8$ $R^9$, $R^{10}$ $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are as described herein, including embodiments thereof. The pharmaceutical composition may include a compound as set forth in Table 1 and/or Table 2, including embodiments thereof.

The pharmaceutical compositions include optical isomers, diastereomers, or pharmaceutically acceptable salts of the inhibitors disclosed herein (including embodiments) (e.g. agents, modulators, inhibitors, antagonists). The compound included in the pharmaceutical composition may be covalently attached to a carrier moiety, as described above. Alternatively, the compound included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

1. Formulations

The compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from compounds having formula (I), (II), (III), (IV), (V), (VI), (VII), (VIII), or pharmaceutically acceptable salts thereof, pharmaceutical carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum *acacia* and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include:

Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity-building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The compositions described herein (including embodiments) can be delivered transdermally, by a topical route, formulated as applicator sticks, solutions, suspensions, emulsions, gels, creams, ointments, pastes, jellies, paints, powders, and aerosols.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The compounds described herein can be used in combination with one another, with other active agents known to be useful in treating cancer (e.g. breast cancer, lung cancer, non-small cell lung cancer, melanoma, metastatic cancer, colon cancer, prostate cancer, or ovarian cancer).

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

In embodiments, a pharmaceutical composition as described herein includes a compound selected from the compounds set forth in Table 1 and/or Table 2.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat leukemia (e.g., chronic lyphocytic leukemia), such compositions will contain amounts of active ingredients effective to achieve the desired result (e.g. increasing the extent of cancer cell death in the patient).

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

IV. Methods of Treating

In another embodiment, a method of treating cancer in a subject in need thereof is provided. The method includes administering to a subject a therapeutically effective amount of a compound of formula (VII), (VIII), or a compound having the formula:

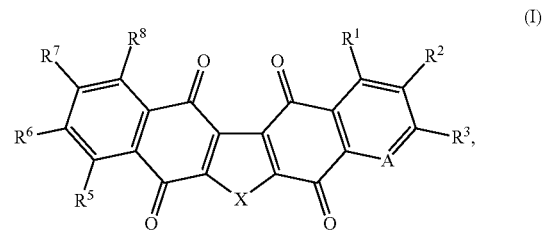

(I)

or a pharmaceutically acceptable salt thereof.

A is N or —$CR^4$. X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, CN, —$CF_3$, —$CCl_3$, —$CBr_3$, —$CI_3$, —$NR^9R^{10}$, —$C(O)R^{11}$, —$C(O)NR^9R^{10}$, —$NR^{12}C(O)R^{11}$, —$S(O)_nR^{13}$, —$S(O)_nNR^9R^{10}$, —$NR^{12}S(O)_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4.

$R^1$, $R^2$, $R^3$, $R^4$, $R^5$, $R^6$, $R^7$, $R^8$, $R^9$, $R^{10}$ $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are as described herein, including embodiments thereof. The method may include a compound as set forth in Table 1 and/or Table 2, including embodiments thereof.

The cancer may be non-small cell lung cancer, colon cancer, CNS cancer, ovarian cancer, renal cancer, breast cancer, melanoma, or prostate cancer. In embodiments, the cancer is non-small cell lung cancer. In embodiments, the cancer is colon cancer. In embodiments, the cancer is CNS cancer. In embodiments, the cancer is ovarian cancer. In embodiments, the cancer is renal cancer. In embodiments, the cancer is breast cancer. In embodiments, the cancer is melanoma or prostate cancer. In embodiments, the cancer is melanoma. In embodiments, the cancer is prostate cancer.

V. Methods of Inhibiting

In another aspect a method of inhibiting a dermcidin protein is provided. The method includes contacting a dermcidin protein with a compound having formula (VII), (VIII), or a compound having formula:

(I)

or a pharmaceutically acceptable salt thereof, thereby inhibiting the dermcidin protein.

A is N or —$CR^4$. X is —S—, —$NR^{21}$—, or —O—. $R^1$, $R^2$, $R^3$, $R^4$, $R^5$, $R^6$, $R^7$, and $R^8$ are independently hydrogen, halogen, —$N_3$, —NHC=(O)$NHNH_2$, CN, —$CF_3$, —$CCl_3$, —$CBr_3$, —$CI_3$, —$NR^9R^{10}$, —C(O)$R^{11}$, —C(O)$NR^9R^{10}$, —$NR^{12}$C(O)$R^{11}$, —S(O)$_nR^{13}$, —S(O)$NR^9R^{10}$, —$NR^{12}$S(O)$_nR^{13}$, —$NO_2$, —$OR^{14}$, —$SR^{14}$, —$NR^{15}$, —$OCOR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl. $R^9$, $R^{10}$ $R^{11}$, $R^{12}$, $R^{13}$, $R^{14}$, $R^{15}$, and $R^{16}$, are independently hydrogen, halogen, —CN, —$CF_3$, —$CCl_3$, —$CBr_3$, —$CI_3$, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is hydrogen or unsubstituted $C_1$-$C_5$ alkyl. The symbol n is 1 to 4.

$R^1$, $R^2$, $R^3$, $R^4$, $R^5$, $R^6$, $R^7$, $R^8$ $R^9$, $R^{10}$ $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are as described herein, including embodiments thereof. The method may include a compound as set forth in Table 1 and/or Table 2, including embodiments thereof.

Dermcidin may be inhibited in vivo or in vitro. In embodiments, the inhibition of dermcidin occurs in vivo. In embodiments, the inhibition of dermcidin occurs in vitro. The inhibition of dermcidin may occur at a concentration of dermcidin inhibitor of about 0.1 nM to about 10 nM. The inhibition of dermcidin may occur at a concentration of dermcidin inhibitor of about 0.1 nM to about 5 nM. The inhibition of dermcidin may occur at a concentration of dermcidin inhibitor of about 3 nM.

The method may further include allowing the dermcidin to react with a compound as described herein, including embodiments thereof, thereby forming a dermcidin-seriniquinone complex. The dermcidin-seriniquinone complex may disrupt the binding of dermcidin to an apoptosis-initiating-protein ("AIP"). The disruption of binding may occur before dermcidin binds to an AIP or may occur after dermcidin has already binded to an AIP. The AIP is as described herein and may be HSP70. The inhibition of dermcidin may occur in a cell. When the dermcidin inhibition occurs in a cell, the inhibition may result in cellular autophagy (e.g. cell death through autophagocytosis). The dermcidin inhibition may result in inducing an apoptotic pathway (e.g. a pathway that leads to apoptosis and cell death). When the dermcidin inhibition results in inducing an apoptotic pathway, the inhibition may yield cell death as a result of cellular apoptosis.

The dermcidin inhibitor may covalently or non-covalently interact with the dermcidin. The dermcidin inhibitor may be non-covalently bonded to dermcidin. When the dermcidin inhibitor is non-covalently bonded to dermcidin, it may reversibly bind to dermcidin. The dermcidin inhibitor may be covalently bonded to dermcidin. In embodiments, when the dermcidin inhibitor is covalently bonded to dermcidin, the covalent bond is a disulfide (e.g. S—S) bond. In embodiments, when the dermcidin inhibitor is covalently bonded to dermcidin, the covalent bond with a residue that interacts with an AIP, such as, for example, a lysine or cysteine residue.

VI. Methods of Screening

In another aspect is a method of identifying a test compound that inhibits dermcidin. The method comprises contacting a dermcidin with a test compound and detecting a decrease in activity of said dermcidin thereby identifying a test compound that inhibits dermcidin.

The method may be performed in a cell. When performed in a cell, the cell may be a cancer cell, such as, for example, a melanoma cell. The cancer cell may be a cancer cell line such as, for example, a cell line for non-small cell lung cancer, colon cancer, CNS cancer, melanoma, renal cancer, prostate cancer, or breast cancer. In embodiments, the cell is a HCT-116, SF-295, SF-539, MALME-3M, M13, MDA-MB-435, SK-MEL-28, SK-MEL-5, UACC-257, UACC-62, 786-0, DU-145, or BT-549 cell. The detection may be accomplished through detection of a dermcidin-test compound complex (e.g. dermcidin bound to a test-compound). The test compound may be a compound having formula (I), (II), (III), (IV), (V), (VI), (VII), or pharmaceutically acceptable salts thereof. In embodiments, the detection may be accomplished using fluorescence detection at 250 nm, 289 nm, or 342 nm (e.g. the maxima of detectable fluorescence associated with compounds disclosed herein). The detection may be performed using a competition binding assay, a decrease in function assay, or other assay for activity known in the art. The method may be performed ex-vivo. When performed outside of a cell, the detection may be accomplished as described herein, including embodiments thereof.

VII. Protein Compositions

In another aspect, a dermcidin protein covalently or non-covalently bound to a dermcidin inhibitor is provided. The dermcidin inhibitor may be a compound of formula (VII), (VIII), or a compound having formula:

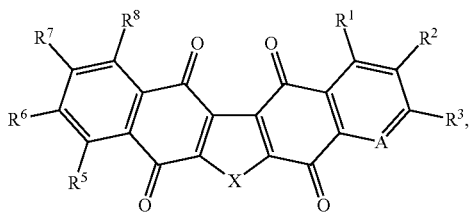

or a pharmaceutically acceptable salt thereof.

A is N or —CR$^4$. X is —S—, —NR$^{21}$—, or —O—. R$^1$, R$^2$, R$^3$, R$^4$, R$^5$, R$^6$, R$^7$, and R$^8$ are independently hydrogen, halogen, —N$_3$, —NHC═(O)NHNH$_2$, CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of R$^1$, R$^2$, R$^3$, R$^4$, R$^5$, R$^6$, R$^7$, and R$^8$ are optionally joined to form a substituted or unsubstituted aryl, substituted or unsubstituted heteroaryl, substituted or unsubstituted cycloalkyl, or substituted or unsubstituted heterocycloalkyl. R$^9$, R$^{10}$ R$^{11}$, R$^{12}$, R$^3$, R$^{14}$, R$^5$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{21}$ is hydrogen or unsubstituted C$_1$-C$_5$ alkyl. The symbol n is 1 to 4.

R$^1$, R$^2$, R$^3$, R$^4$, R$^5$, R$^6$, R$^7$, R$^8$, R$^9$, R$^{10}$ R$^{11}$, R$^{12}$, R$^{13}$, R$^{14}$, R$^{15}$, R$^{16}$, R$^{17}$, R$^{18}$, R$^{19}$, R$^{20}$, and R$^{21}$ are as described herein, including embodiments thereof. The method may include a compound as set forth in Table 1 and/or Table 2, including embodiments thereof.

The dermcidin inhibitor may covalently or non-covalently interact with dermcidin. The dermcidin inhibitor may be non-covalently bonded to dermcidin. The dermcidin inhibitor may be covalently bonded to dermcidin. In embodiments, when the dermcidin inhibitor is covalently bonded to dermcidin, the covalent bond is a disulfide (e.g. S—S) bond. In embodiments, when the dermcidin inhibitor is covalently bonded to dermcidin, the covalent bond with a residue that interacts with an AIP, such as, for example, a lysine or cysteine residue.

VIII. Embodiments:

Embodiment 1: A compound having the formula:

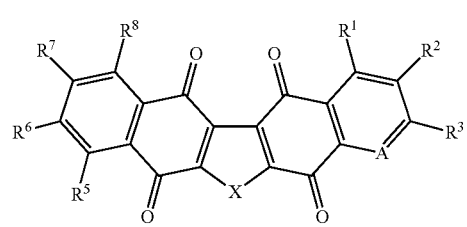

(I)

or pharmaceutically acceptable salt thereof, wherein,

A is N or —CR$^4$;

X is —S—, —NR$^{21}$—, or —O—;

R$^1$, R$^2$, R$^3$, R$^4$, R$^5$, R$^6$, R$^7$, and R$^8$ are independently hydrogen, halogen, —N$_3$, —NHC═(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of R$^1$, R$^2$, R$^3$, R$^4$, R$^5$, R$^6$, R$^7$, and R$^8$ are optionally joined to form a substituted or unsubstituted aryl, substituted or unsubstituted heteroaryl, substituted or unsubstituted cycloalkyl, or substituted or unsubstituted heterocycloalkyl;

R$^9$, R$^{10}$ R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21}$ is hydrogen or unsubstituted C$_1$-C$_5$ alkyl;

n is 1 to 4; and wherein if X is S and A is CR$^4$, at least one of R$^1$, R$^2$, R$^3$, R$^4$, R$^5$, R$^6$, R$^7$, and R$^8$ is not hydrogen.

Embodiment 2: The compound of embodiment 1, wherein R$^1$, R$^2$, R$^3$, R$^4$, R$^5$, R$^6$, R$^7$, and R$^8$ are a hydrophilic moiety.

Embodiment 3: The compound of embodiment 1, said compound having the formula:

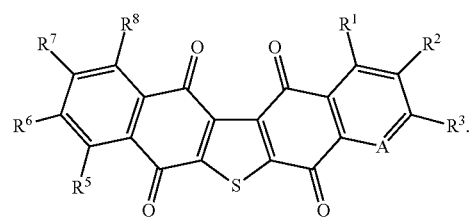

(II)

Embodiment 4: The compound of embodiment 3, said compound having the formula:

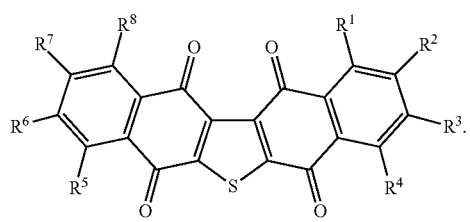

(III)

Embodiment 5: The compound of embodiments 1 or 2, said compound having the formula:

(IV)

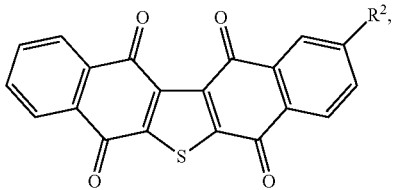

wherein R² is substituted or unsubstituted heteroalkyl, substituted or unsubstituted heterocycloalkyl, substituted or unsubstituted aryl, or substituted or unsubstituted heteroaryl.

Embodiment 6: The compound of embodiment 5, wherein said heteroalkyl is $R^{2a}$-substituted heteroalkyl, wherein $R^{2a}$ is hydrogen, halogen, —N₃, —CF₃, —CCl₃, —CBr₃, —CI₃, —CN, —CHO, —OH, —NH₂, —COOH, —CONH₂, —NO₂, —SH, —SO₂, —SO₂Cl, —SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 7: The compound of embodiment 6, wherein said $R^{2a}$-substituted heteroalkyl is —(CH₂)₂C(O)—$R^{2a}$.

Embodiment 8: The compound of embodiment 1, said compound having the formula:

(V)

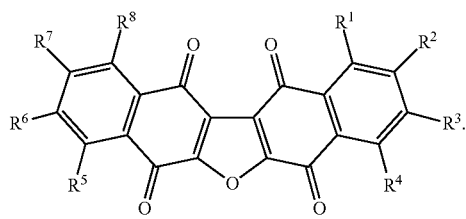

Embodiment 9: The compound of embodiment 1, said compound having the formula:

(VI)

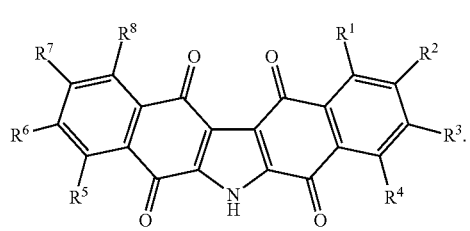

Embodiment 10: A compound having the formula:

(VII)

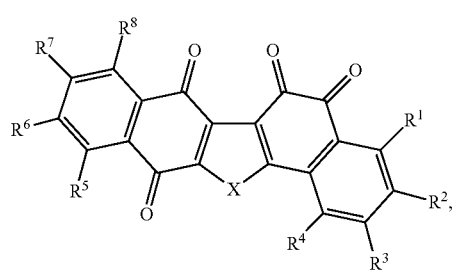

or pharmaceutically acceptable salt thereof,
wherein
X is —S—, —NR²¹—, or —O—;
R¹, R², R³, R⁴, R⁵, R⁶, R⁷, and R⁸ are independently hydrogen, halogen, —N₃, —NHC=(O)NHNH₂, —CN, —CF₃, —CCl₃, —CBr₃, —CI₃, —NR⁹R¹⁰, —C(O)R¹¹, —C(O)NR⁹R¹⁰, —NR¹²C(O)R¹¹, —S(O)ₙR¹³, —S(O)ₙNR⁹R¹⁰, —NR¹²S(O)ₙR¹³, —NO₂, —OR¹⁴, —SR¹⁴, —NR¹⁵, —OCOR¹⁶, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of R¹, R², R³, R⁴, R⁵, R⁶, R⁷, and R⁸ are optionally joined to form a substituted or unsubstituted aryl, substituted or unsubstituted heteroaryl, substituted or unsubstituted cycloalkyl, or substituted or unsubstituted heterocycloalkyl;
R⁹, R¹⁰ R¹¹, R¹², R¹³, R¹⁴, R¹⁵, and R¹⁶, are independently hydrogen, halogen, —CN, —CF₃, —CCl₃, —CBr₃, —CI₃, —OH, —NH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R²¹ is hydrogen or unsubstituted C₁-C₅ alkyl; and
n is 1 to 4.

Embodiment 11: The compound of embodiment 10, wherein X is —O—.

Embodiment 12: The compound of embodiment 11, wherein R¹, R², R³, R⁴, R⁵, R⁶, R⁷, and R⁸ are hydrogen.

Embodiment 13: The compound of embodiment 11, wherein R¹, R², R³, R⁴, R⁵, R⁶, R⁷, and R⁸ are a hydrophilic moiety.

Embodiment 14: A compound having the formula:

(VIII)

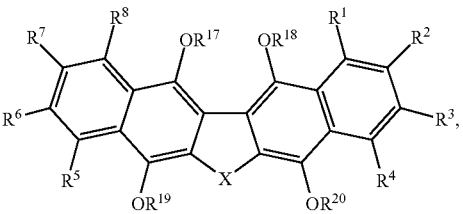

or pharmaceutically acceptable salt thereof,
wherein
X is —S—, —NR²¹—, or —O—;
R¹, R², R³, R⁴, R⁵, R⁶, R⁷, and R⁸ are independently hydrogen, halogen, —N₃, —NHC=(O)NHNH₂, —CN, —CF₃, —CCl₃, —CBr₃, —CI₃, —NR⁹R¹⁰, —C(O)R¹¹, —C(O)NR⁹R¹⁰, —NR¹²C(O)R¹¹, —S(O)ₙR¹³, —S(O)ₙNR⁹R¹⁰, —NR¹²S(O)ₙR¹³, —NO₂, —OR¹⁴, —SR¹⁴, —NR¹⁵, —OCOR¹⁶, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of R¹, R², R³, R⁴, R⁵, R⁶, R⁷, and R⁸ are optionally joined to form a substituted or unsubstituted aryl, substituted or unsubstituted heteroaryl, substituted or unsubstituted cycloalkyl, or substituted or unsubstituted heterocycloalkyl;

$R^9$, $R^{10}$, $R^{11}$, $R^{12}$, $R^{13}$, $R^{14}$, $R^{15}$, and $R^{16}$ are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is hydrogen or unsubstituted $C_1$-$C_5$ alkyl;

n is 1 to 4; and $R^{17}$, $R^{18}$, $R^{19}$, and $R^{20}$ are independently hydrogen or substituted or unsubstituted alkyl.

Embodiment 15: The compound of embodiment 14, wherein $R^1$, $R^2$, $R^3$, $R^4$, $R^5$, $R^6$, $R^7$, and $R^8$ are a hydrophilic moiety.

Embodiment 16: The compound of embodiment 14, wherein $R^{17}$, $R^{18}$, $R^{19}$, and $R^{20}$ are identical.

Embodiment 17: The compound of embodiment 16, wherein $R^{17}$, $R^{18}$, $R^{19}$, and $R^{20}$ are hydrogen, methyl, or acetyl.

Embodiment 18: The compound of embodiment 17, wherein $R^{17}$, $R^{18}$, $R^{19}$, and $R^{20}$ are acetyl.

Embodiment 19: A pharmaceutical composition comprising a pharmaceutically acceptable excipient and a compound of one of embodiments 10 to 18 or a compound having the formula:

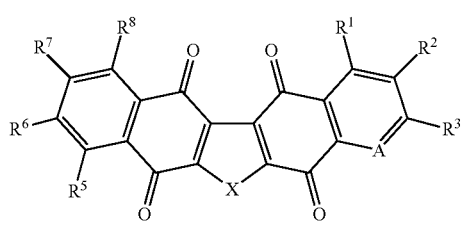

(I)

or pharmaceutically acceptable salt thereof,
wherein

A is N or —CR$^4$;

X is —S—, —NR$^{21}$—, or —O—;

$R^1$, $R^2$, $R^3$, $R^4$, $R^5$, $R^6$, $R^7$, and $R^8$ are independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl;

$R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is hydrogen or unsubstituted $C_1$-$C_5$ alkyl; and n is 1 to 4.

Embodiment 20: A method of treating cancer in a subject in need thereof, said method comprising administering to a subject a therapeutically effective amount of a compound of one of embodiments 10 to 18 or a compound having the formula:

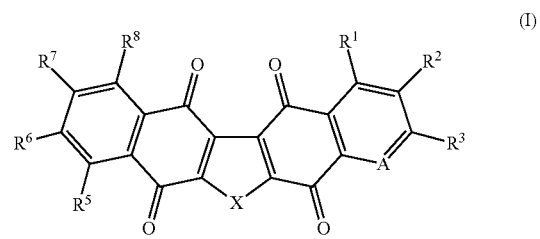

(I)

or pharmaceutically acceptable salt thereof,
wherein

A is N or —CR$^4$;

X is —S—, —NR$^{21}$—, or —O—;

$R^1$, $R^2$, $R^3$, $R^4$, $R^5$, $R^6$, $R^7$, and $R^8$ are independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of $R^1$, $R^2$, $R^3$, $R^4$, $R^5$, $R^6$, $R^7$, and $R^8$ are optionally joined to form a substituted or unsubstituted aryl, substituted or unsubstituted heteroaryl, substituted or unsubstituted cycloalkyl, or substituted or unsubstituted heterocycloalkyl;

$R^9$, $R^{10}$ $R^{11}$, $R^{12}$, $R^{13}$, $R^{14}$, $R^{15}$, and $R^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is hydrogen or unsubstituted $C_1$-$C_5$ alkyl; and n is 1 to 4.

Embodiment 21: The method of embodiment 20, wherein said cancer is melanoma or prostate cancer.

Embodiment 22: A method of inhibiting a dermcidin protein, said method comprising: contacting a dermcidin protein with a compound of one of embodiments 10 to 18 or a compound having the formula:

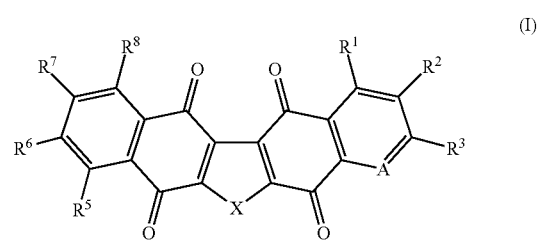

(I)

or pharmaceutically acceptable salt thereof, wherein
A is N or —CR$^4$;
X is —S—, —NR$^{21}$—, or —O—;
R$^1$, R$^2$, R$^3$, R$^4$, R$^5$, R$^6$, R$^7$, and R$^8$ are independently hydrogen, halogen, —N$_3$, —NHC=(O)NHNH$_2$, —CN, —CF$_3$, —CCl$_3$, —CBr$_3$, —CI$_3$, —NR$^9$R$^{10}$, —C(O)R$^{11}$, —C(O)NR$^9$R$^{10}$, —NR$^{12}$C(O)R$^{11}$, —S(O)$_n$R$^{13}$, —S(O)$_n$NR$^9$R$^{10}$, —NR$^{12}$S(O)$_n$R$^{13}$, —NO$_2$, —OR$^{14}$, —SR$^{14}$, —NR$^{15}$, —OCOR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two of R$^1$, R$^2$, R$^3$, R$^4$, R$^5$, R$^6$, R$^7$, and R$^8$ are optionally joined to form a substituted or unsubstituted aryl, substituted or unsubstituted heteroaryl, substituted or unsubstituted cycloalkyl, or substituted or unsubstituted heterocycloalkyl;
R$^9$, R$^{10}$, R$^{11}$, R$^{12}$, R$^{13}$, R$^{14}$, R$^{15}$, and R$^{16}$, are independently hydrogen, halogen, —CN, —CF$_3$, —CCl$_3$, —CBr$_3$, —CI$_3$, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{21}$ is hydrogen or unsubstituted C$_1$-C$_5$ alkyl; and
n is 1 to 4,
thereby inhibiting said dermcidin protein.

Embodiment 23: The method of embodiment 22, further comprising allowing said dermcidin to react with said compound, thereby forming a dermcidin-seriniquinone complex.

Embodiment 24: The method of embodiment 22, wherein said inhibition occurs within a cell and results in cellular autophagy.

Embodiment 25: A dermcidin protein covalently or non-covalently bonded to a dermcidin inhibitor.

Embodiment 26: The dermcidin protein of embodiment 25, wherein said dermcidin inhibitor is non-covalently bonded to dermcidin.

Embodiment 27: A method of identifying a test compound that inhibits dermcidin comprising:
(i) contacting a dermcidin with a test compound;
(ii) detecting a decrease in activity of said dermcidin thereby identifying a test compound that inhibits dermcidin.

Embodiment 28: The method of embodiment 27, wherein said contacting is performed in a cell.

Embodiment 29: The method of embodiment 28 wherein said cell is a cancer cell.

Embodiment 30: The method of embodiment 29 wherein said cancer cell is a melanoma cell.

Embodiment 31: The method of embodiment 27, wherein said detecting comprises detecting a dermcidin-test compound complex.

Embodiment 32: A compound with structure of Formula:

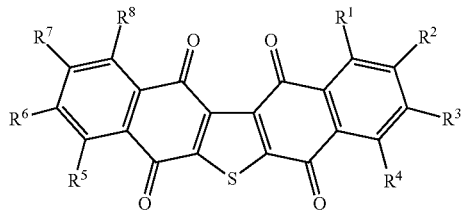

or pharmaceutically acceptable salt thereof, wherein,
R$_1$, R$_2$, R$_3$, R$_4$, R$_5$, R$_6$, R$_7$ and R$_8$ are each independently hydrogen, halogen, —CN, —CF$_3$, —NR$_9$R$_{10}$, —C(O)R$_{11}$, —C(O)NR$_9$R$_{10}$, —NR$_{12}$C(O)R$_{11}$, —S(O)$_n$R$_{13}$, —S(O)$_n$NR$_9$R$_{10}$, —NR$_{12}$S(O)$_n$R$_{13}$, —NO$_2$, —OR$_{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein two R$_1$, R$_2$, R$_3$, R$_4$, R$_5$, R$_6$, R$_7$ and R$_8$ substituents are optionally joined to form a substituted or unsubstituted aryl, substituted or unsubstituted heteroaryl, substituted or unsubstituted cycloalkyl, or substituted or unsubstituted heterocycloalkyl;
R$_9$, R$_{10}$ and R$_{12}$ are independently hydrogen, —CN, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{11}$, R$^{13}$ and R$^{14}$ are independently hydrogen, —CN, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
n is 1 or 2;
provided, however, that at least one of R$_1$, R$_2$, R$_3$, R$_4$, R$_5$, R$_6$, R$_7$ and R$_8$ is not hydrogen.

Embodiment 33: A pharmaceutical composition comprising a compound according to embodiment 32 in combination with a pharmaceutically acceptable excipient.

Embodiment 34: A method of treating cancer in a subject in need thereof, said method comprising administering to a subject an effective amount of a compound according to embodiment 32.

IX. Examples

The examples below are meant to illustrate certain embodiments of the invention, and not to limit the scope of the invention. Abbreviations, used herein as known in the chemical arts, include the following: TFA: Trifluoroacetic acid; OsO$_4$: Osmium tetraoxide; Boc: tert-Butyloxycarbonyl; NMO: N-methylmorpholine-N-oxide; NaIO$_4$: Sodium periodate; HATU: 2-(7-Aza-1H-Benzotriazole-1-yl)-1,1,3,3-tetramethyluronium hexafluorophosphate; DIPEA: di-Isopropyl ethyl amine; DMF: Dimethylformamide; DCM: Dichloromethane; MeOH: Methanol; MeCN: Acetonitrile; THF: Tetrahydrofuran; TESH: Triethylsilane; HCl: Hydrochloric acid (aqueous solution); EtOAc: Ethyl acetate; NMR: Nuclear magnetic resonance; CDCl$_3$: Deuterated chloroform; h: hour; Na$_2$SO$_4$: Anhydrous sodium sulfate; DMSO-d$_6$: Deuterated dimethyl sulfoxide; RP-HPLC: Reverse-phase high-performance liquid chromatography; CD$_3$OD: Deuterated methanol; Ether: diethyl ether; Calcd.: Calculated; LCMS: Liquid chromatography mass spectroscopy; NaHCO$_3$: Sodium bicarbonate (saturated aqueous solution).

General Methods. Unless otherwise noted, all reagents and chemical compounds were purchased from Alfa Aesar, GFS Chemicals, Strem Chemicals, Sigma-Aldrich or TCI and used without further purification. NMR spectra were recorded on a Varian Mercury Plus 400 MHz, Jeol ECA 500 MHz, Bruker DMX 500 MHz or Varian VX 500 MHz (equipped with XSens cold probe) spectrometer. FID files were processed using MestRenova version 6.0.2 (MestreLab Research) and were referenced residual solvent peaks according to S. Budavari, M. J. O'Neil, A. Smith, P. E.

Heckelman, The Merck Index, an Encyclopedia of Chemicals, Drugs, and Biologicals, Eleventh Edition, Merck Co., Inc. Rahway, N.J., 1989. HR-EIS-TOFMS data were obtained at The Scripps Research Institute, La Jolla, Calif. or at UC San Diego. Electrospray (ESI) and atmospheric pressure chemical ionization (APCI) analysis was performed using a Finnigan LCQ Deca mass spectrometer, and fast atom bombardment (FAB) analysis was carried out using a Thermo Finnigan MAT 900 XL mass spectrometer. The optical rotations were measured on a Jasco P-2000 polarimeter. UV spectra were measured on a Beckman DU800 spectrophotometer with a 1 cm cell. IR spectra were obtained with a Themo Nicolet IR100 FT-IR. Reversed-phase HPLC separation was performed using a semi-preparative C18 Luna column (250×10 mm) at a flow rate of 2.5 mL/min using Waters 600E pump and Waters Lambda-Max model 480 UV detector.

Chemical Synthesis. High purity anhydrous solvents were used at all steps. Dichloromethane, tetrahydrofuran (THF) and N,N-dimethylformamide (DMF) were obtained by passing through a solvent column composed of dry activated Al alumina. DMF was stored on oven dried 4 Å molecular sieves for 24 h prior to use. N,N-diisopropylethylamine was distilled from ninhydrin, dried ($Na_2SO_4$), and then redistilled from sodium. Water was obtained after purification via a Milli-Q water purifer (Millipore). All reactions were performed under a positive pressure of dry Ar in oven-dried thick walled round bottom flasks (ChemGlass) stirred with a Teflon coated stirbar. Flash chromatography was performed on Silica Gel 60, 230-400 mesh (EMD Chemicals). TLC analyses were conducted on 250 μm Silica Gel 60 F254 glass plates (EMD Chemicals). Visualization was achieved with UV light and stained with ceric ammonium molybdate. Melting points were corrected for cholesterol at 148-150° C. Yields and characterization data correspond to isolated, homogeneous materials. Unless otherwise noted all solvent mixtures are given in v:v ratios.

The recent synergy between natural products chemistry and chemical biology has resulted in the expanse of small molecule therapeutics and probes.[1-3] These efforts can rapidly be streamlined by integrating a program that combining the auspices of microbiology, natural product discovery, synthetic organic chemistry, and biological science under "one roof".[4] Here, is described the discovery of seriniquinone (compound 1) from culture broths of a marine actinobacterium of the genus *Serinicoccus*. The structure of 1 was elucidated by spectroscopic methods and validated the assignment by chemical synthesis. Seriniquinone (1) was found to be a potent regulator of tumor cell progression displaying enhanced efficacy in melanoma cell lines, marked by arrest at S to G2 phase and rapid induction into autophagocytotic process resulting in caspase-9 associated apoptosis. Further analyses, indicated that 1 rapidly entered tumor cells, localizing in the endoplasmic reticulum (ER). Over the next 6-8 h, the cells exposed to 1 underwent autophagy marked by the shuttling of 1 into the forming autophagocytes. Using affinity methods, we determined that seriniquinone targeted the protein dermcidin that was conjugated via disulfide linkages to an array of proteins within the tumor cell lysates. The resulting ternary, covalent adducts between 1, dermcidin, and associated cellular proteins revealed an intriguing function for dermcidin. The potent melanoma selectivity, novel mode of action, and rapid synthetic access, suggests that derivatives of seriniquinone represent a viable clinical lead.

Figure 1B:
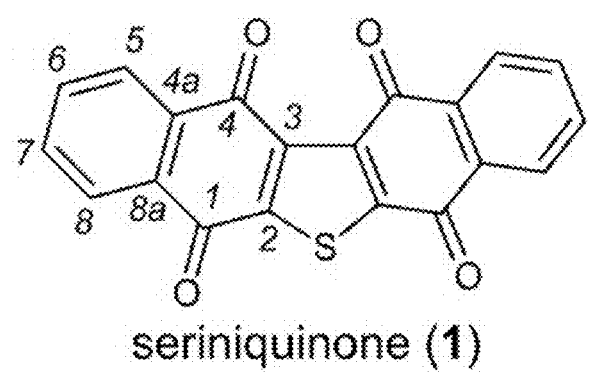

The microbial content of ocean sediments offers a rich hot bed for therapeutic discovery.[5] As part of a program to identify chemotherapeutic leads from marine bacteria,[6] yellow needles (1.2 mg/g) were identified from culture broths of a marine actinobacterium of the genus *Serinicoccus* (FIG. 1A). The structure of 1 was deduced using spectroscopic methods. HR-ESOTOF MS analysis provided an m/z of $[M+H]^+$ of 345.0210, corresponding to a formula of $C_{20}H_8O_4S$ (calcd. m/z of 345.0222), indicating 17 degrees of unsaturation. After evaluating an NMR dataset, dinaphtho[2,3-b:2',3'-d]thiophene-5,7,12,13-tetraone was proposed (1, FIG. 1B), a symmetrical compound, based on the fact that the number of the $^1H$ and $^{13}C$ signals were exactly half of that apparent from its formula. This along with correlations observed in the $^1H$-$^1H$ COSY and HMBC spectra (FIG. 1B) provided strong support for the assignment of 1. The assignment was further confirmed through a two-step synthesis (FIG. 2A).[7]

1 displayed significant activity in the NCI-60 cell line screen[8] with mean $GI_{50}$ values of 910 nM and mean $LC_{50}$ values of 18.6 μM (Supplementary Methods). This was further supported by the fact that 1 enhanced activity in melanoma cell lines with maximum activity against MALME-3M cells ($GI_{50}$ value of 60 nM). With this in hand, chemical biological methods were applied to further probe this biological response.

Figure 3A:
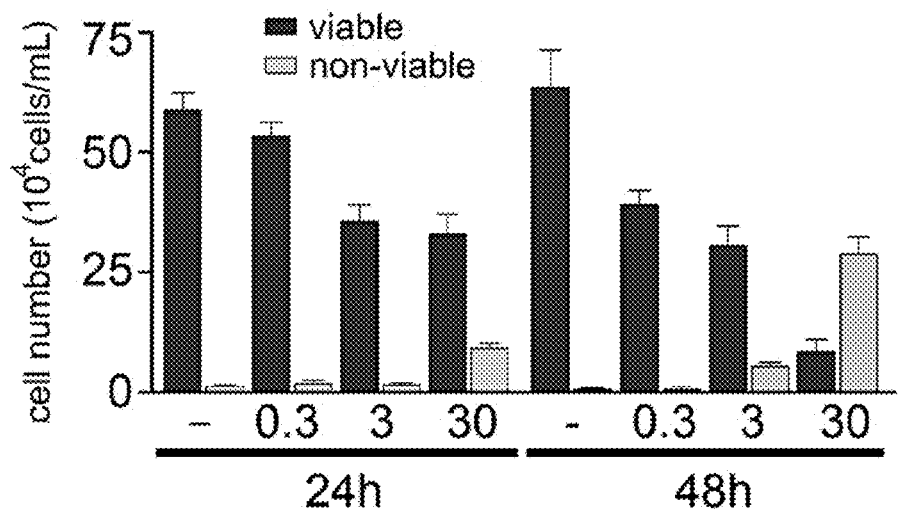
FIGS. 3A-3G: Activity data and cell cycle studies.
Figure 3B:
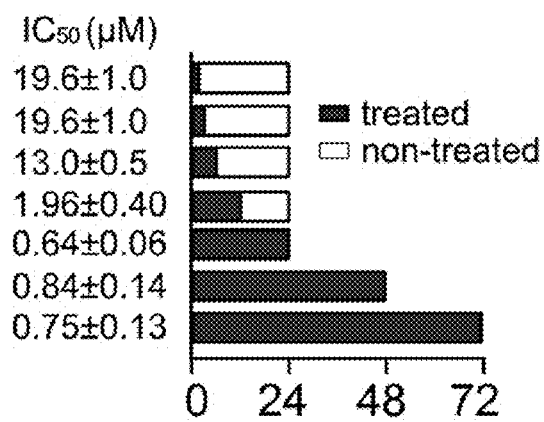
Figure 3C:
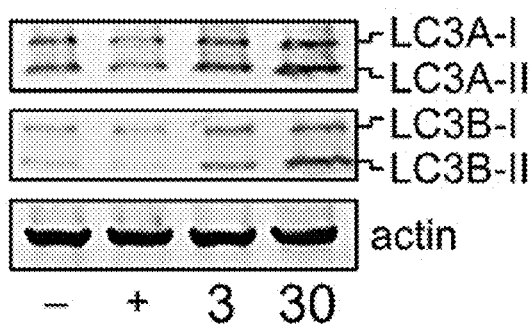

Fortunately, 1 was fluorescent with excitation maxima at 250 nm ($\epsilon$=20,800 $cm^{-1}M^{-1}$), 289 nm ($\epsilon$=24,000 $cm^{-1}M^{-1}$) and 342 nm ($\epsilon$=6900 $cm^{-1}M^{-1}$) and a broad emission from 490-680 nm. Using confocal microscopy, red and green fluorescence from 1 appeared in HCT-116 cells within minutes of addition (FIG. 3A). Comparable localization was also observed in other cell lines (FIG. 3B) including the more responsive MALME-3M cell line. Time course confocal imaging studies were then combined with conventional activity MTT assays[6] to provide a detailed correlation between cellular localization and cytostatic activity. Activity analyses delivered both a concentration and time dependence with optimal activity ($IC_{50}$ values of 640±60 nM) arising in cells that were treated with 1 over 24 h period (FIG. 4A-4B).

Figure 3D:
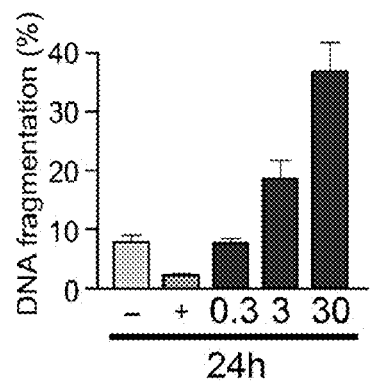
Figure 3E:
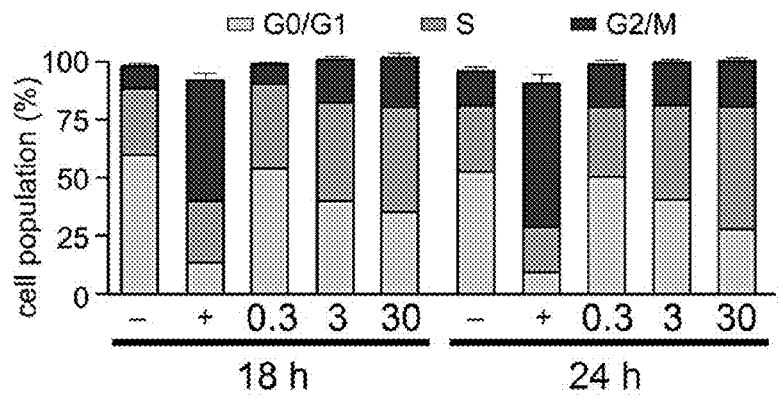
Figure 3F:
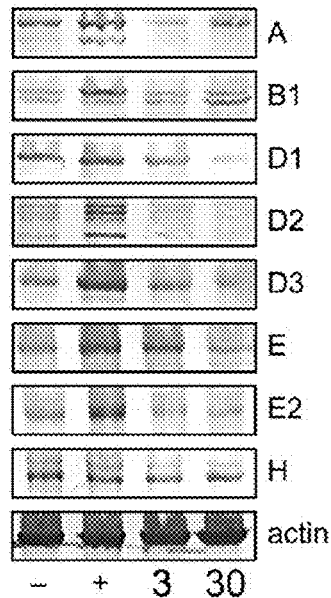

A series of blue counterstains were used to mark the subcellular distribution of 1 over a 24 h period (FIG. 3E). Counterstaining with ER tracker blue[9] indicated that 1 appeared soon after treatment in the ER.[9] After 2-3 h, vesicles formed bearing red and green fluorescence from 1. This transition was complete at 6-9 h, where red-green fluorescence from 1 correlated with the blue fluorescence from monodansylcadaverine, a stain for autophagocytes (FIG. 3D).[10] This observation was also observed in the more responsive melanoma cell lines such as MALME-3M (FIG. 3E). The fact that 1 induced autophagy was further confirmed by conversion of LC3A-I and LC3A-II to LC3B-I and LC3B-II, respectively, as indicated by Western Blot analysis (FIG. 4C).[11]

The effects of 1 were then screened for on the cell cycle. FACS analyses indicated an increasing number of cells with a subdiploid DNA suggesting a concentration dependent DNA fragmentation (FIG. 4D). The remaining cells were at the S to G2 phase, suggesting that cells treated with 1 were dying and not reentering in the cell cycle (FIG. 4E). The analysis of cyclin expression in HCT-116 treated cells reinforced this hypothesis, as it showed a strong reduction in the expression of the cyclins D1, D2 and D3 (FIG. 4F). Cyclin D-CDK complexes are essential to entry in G1.[12] As 1 failed to induce DNA fragmentation using in vitro assays (Supporting Methods), conventional apoptotic markers were turned to for further exploration. Treatment of HCT-116 cells with 1 induced cleavage of caspases 3, 7 and 9 PARP suggested that compound 1 triggers cell death through a caspase-9 dependent event, leading to DNA fragmentation (FIG. 4G).[12]

With a phenotypic model in hand, proteins targeted by 1 were screened for using an immunoaffinity fluorescent (IAF) technique developed in our laboratories.[13-14] This required synthetic preparation of an analog of 1 with a functional handle. After evaluating several different approaches, a route (FIG. 2B) was identified to alkene 10 that began with a Diels-Alder cycloaddition between α-myrcene (4) and 2,5-dichlorobenzoquinone (5).[15] The selective coupling of hydroxynapthylquinone 7 to dichloronapthylquinone 2 affording adduct 8, which after conversion to dichloride 9, provided rapid access to alkene 10. IAF probe 13 was then prepared by a 3-step oxidation of 10 to acid 11 followed by a HATU coupling to the amine terminal tag 12. Probe 13 maintained its activity with an $IC_{50}$ value of 250±80 nM in HCT-116 cells, while IAF control 14 (FIG. 2B) was inactive ($IC_{50}$ value of >50 μM). Further evidence that 13 maintained the activity of 1 was obtained from confocal imaging, were probe 13 mirrored 1 with rapid uptake in the ER followed by transport into autophagosomes, as confirmed by the co-localization of blue, from the IAF tag, and red-green fluorescence from the seriniquinone core (FIG. 3G).

Figures 2A, 2B:
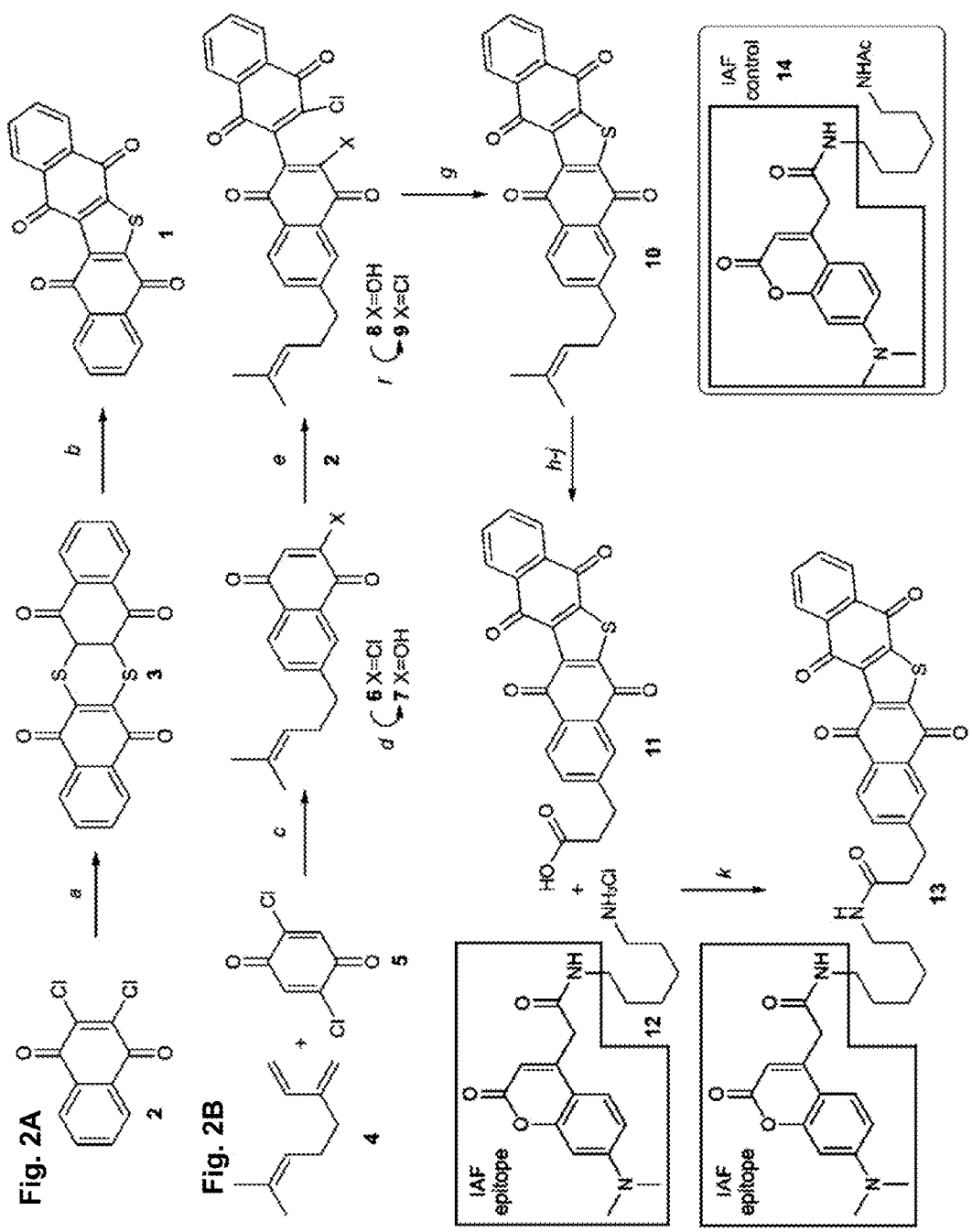
FIGS. 2A-2B: Chemical Synthesis.
Figure 3G:
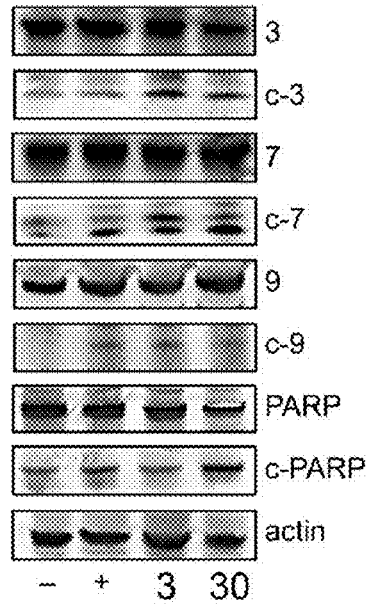
Figure 6:
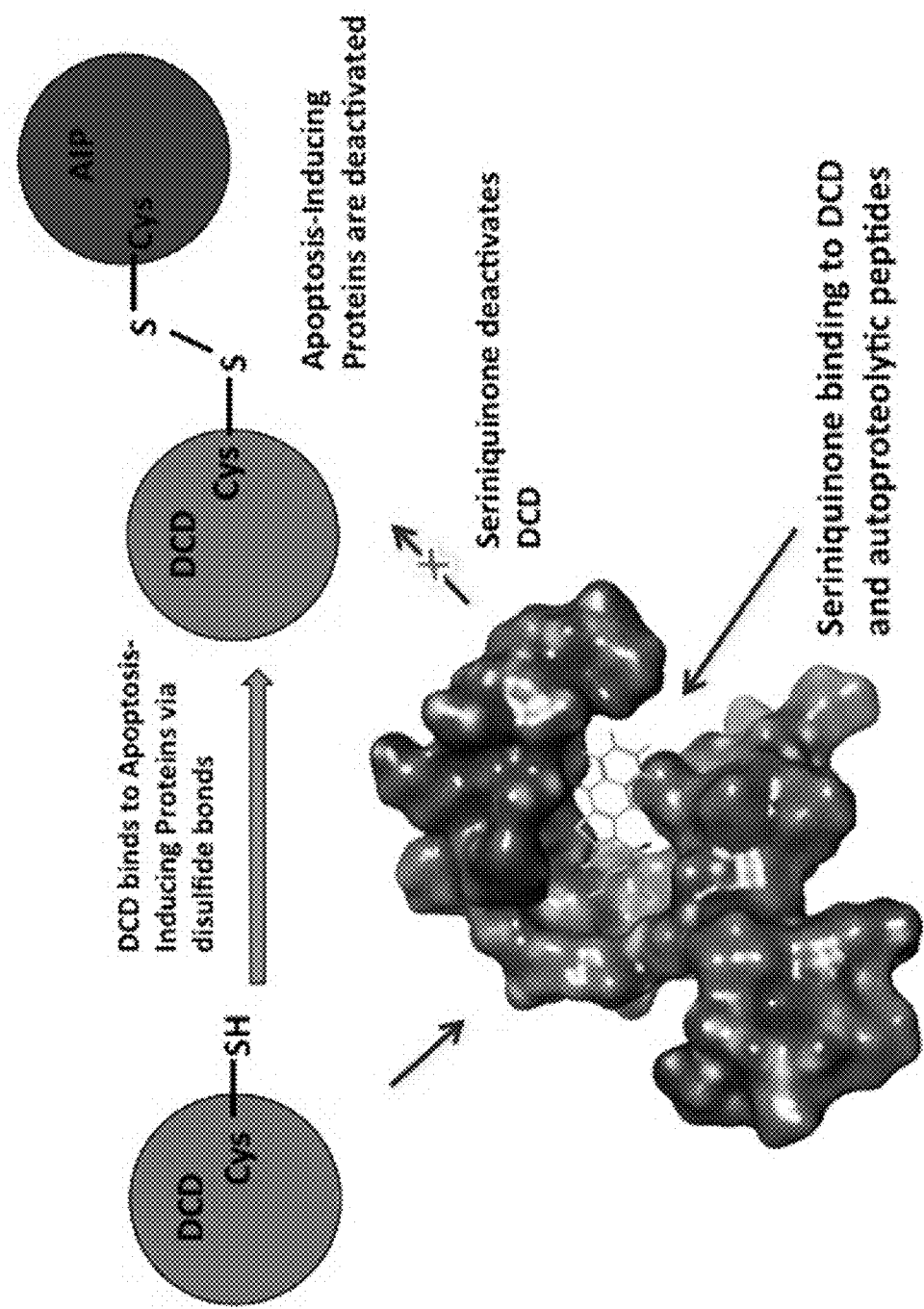
FIG. 6: Seriniquinones bind to deactivate dermcidin thereby activating apoptosis-inducing proteins.
Figure 7:
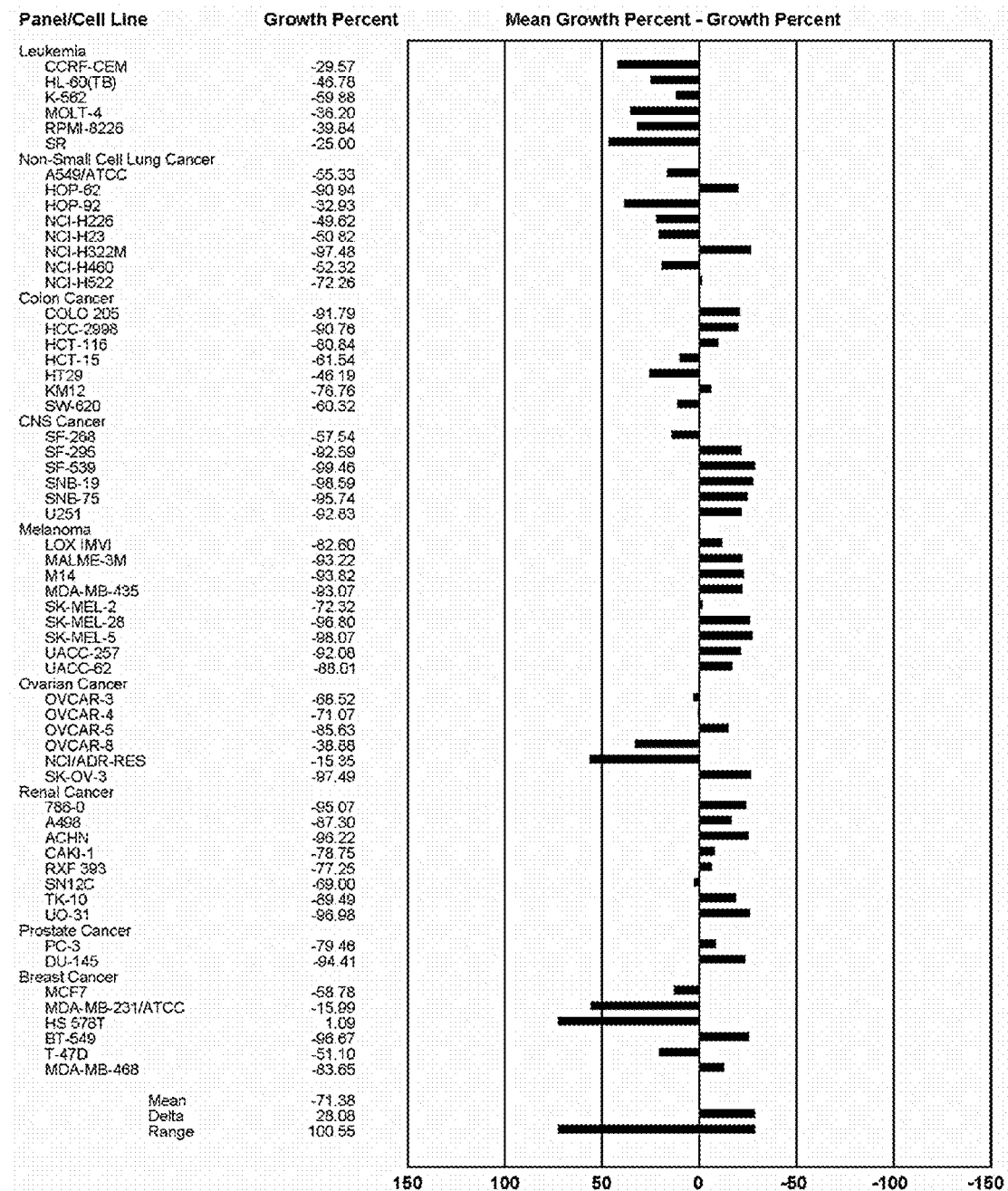
FIG. 7: NCI 60 panel for Compound S1.
Figure 8:
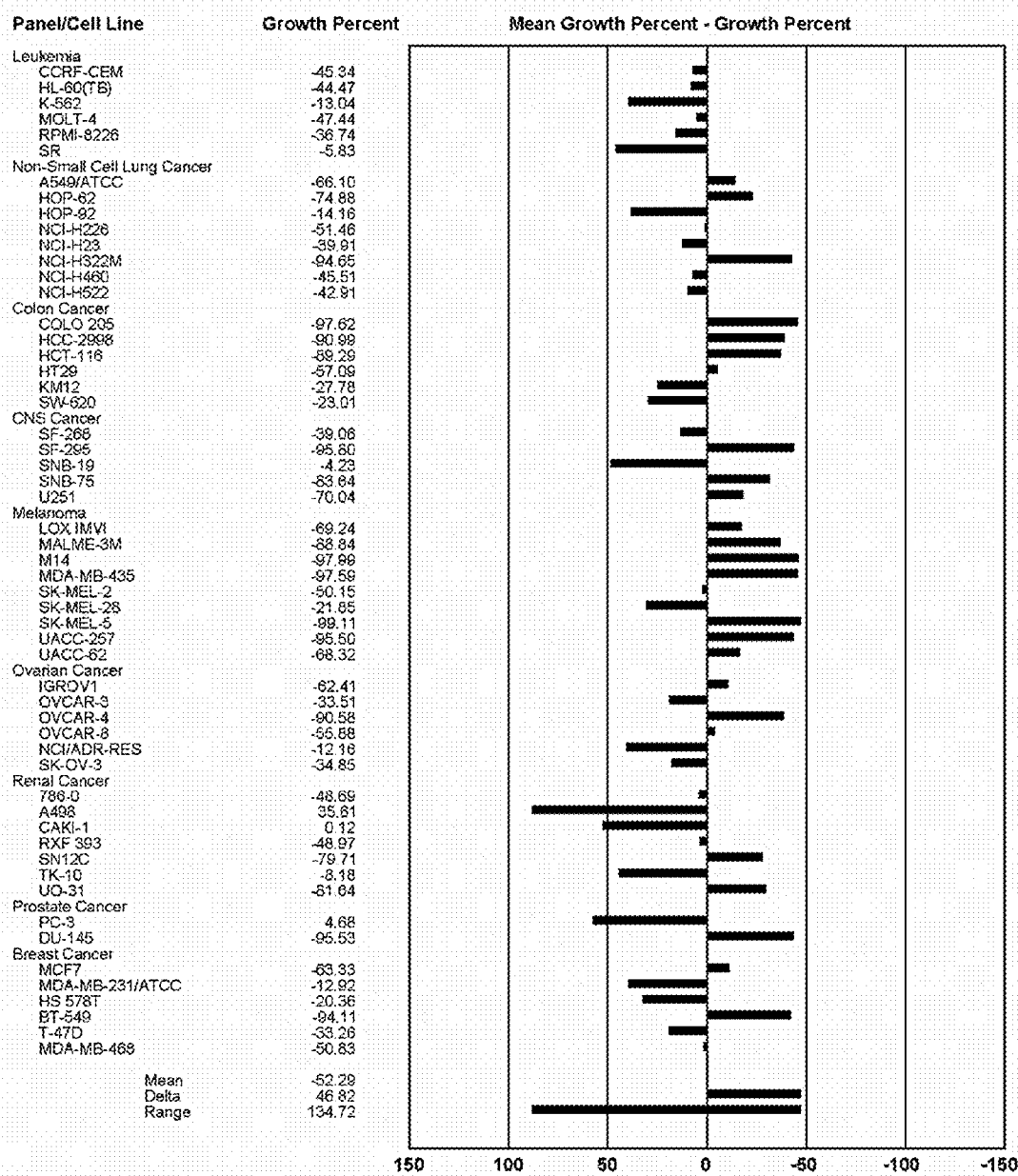
FIG. 8: NCI 60 panel for Compound S10.
Figure 9:
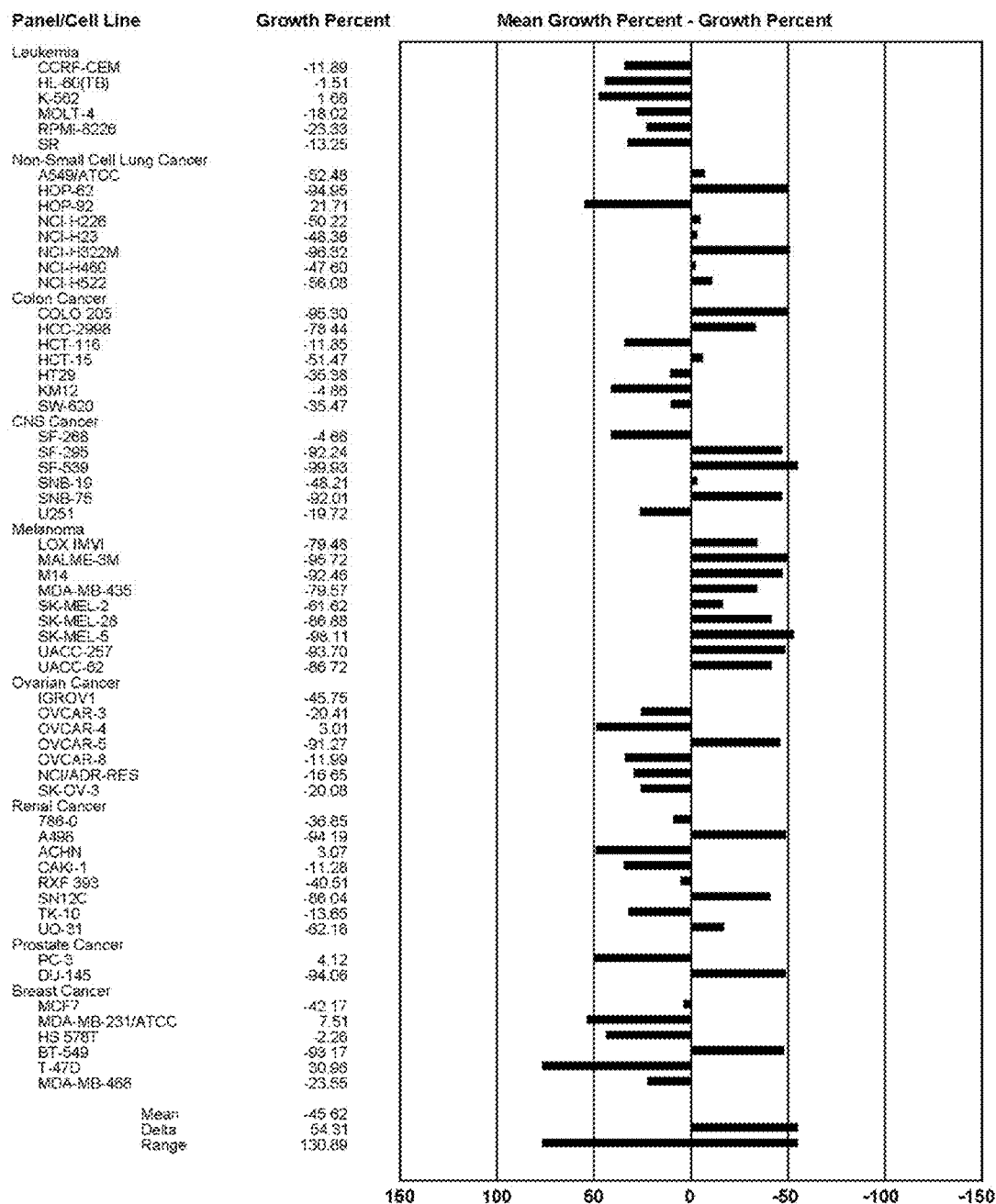
FIG. 9: NCI 60 panel for Compound S4.
Figure 10:
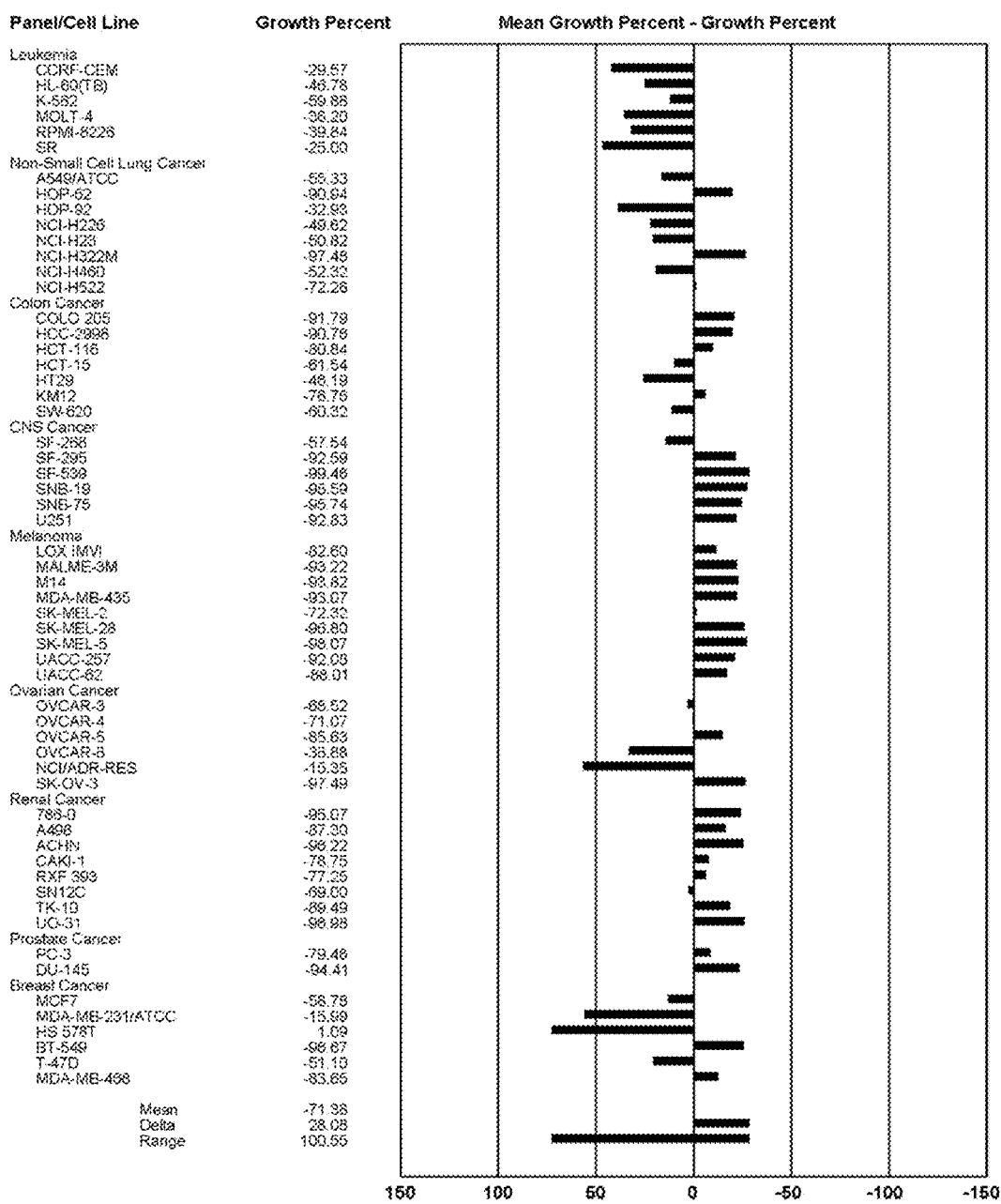
FIG. 10: NCI 60 panel for Compound S11.
Figure 11:
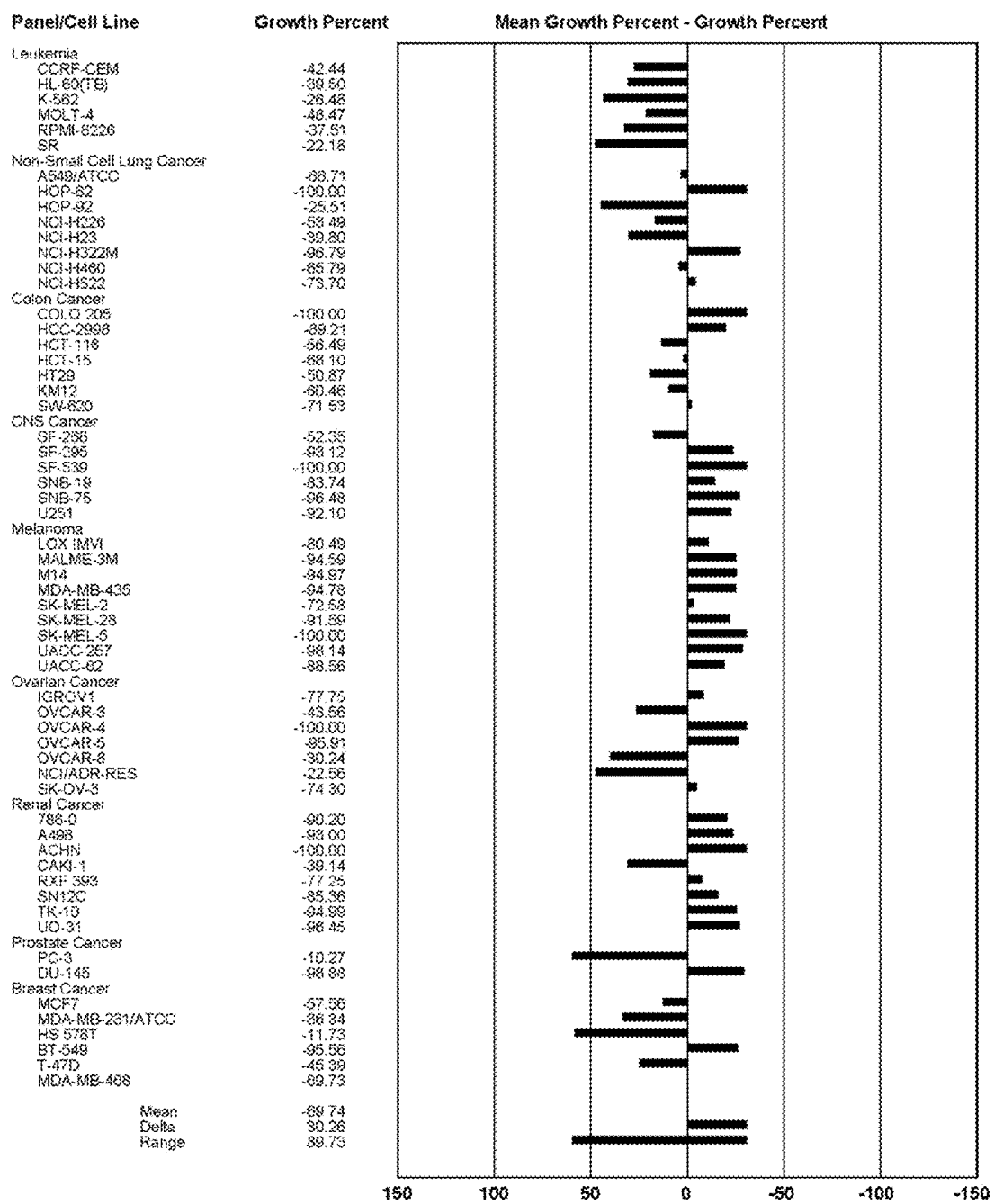
FIG. 11: NCI 60 panel for Compound S15.
Figure 14:
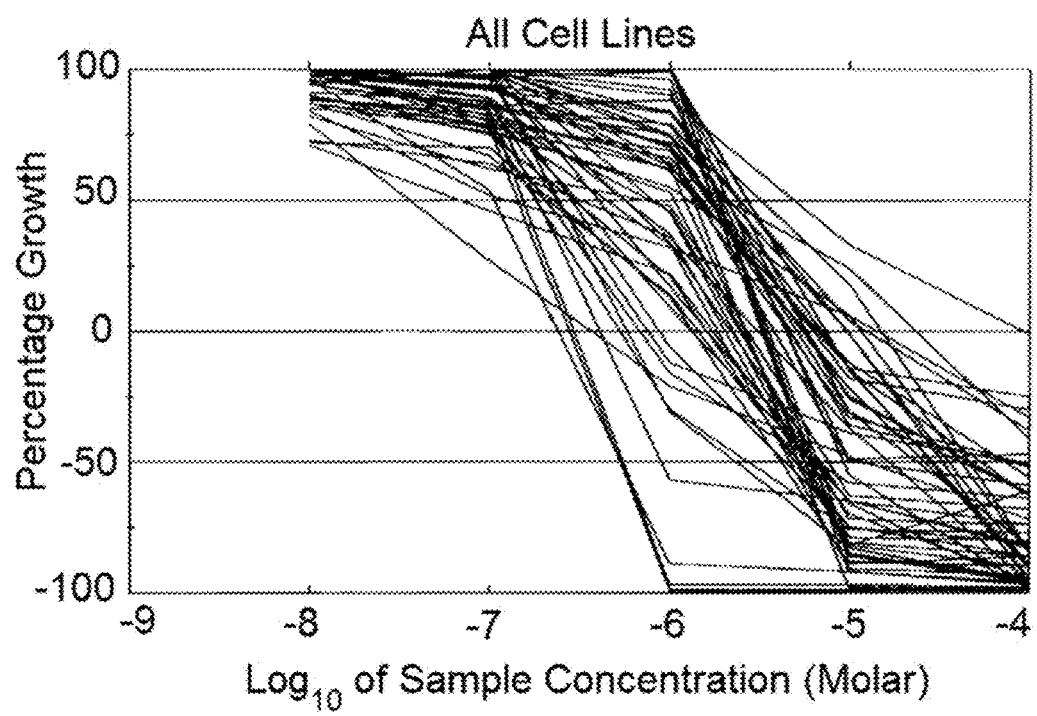
FIG. 14: NCI 60 data for compounds herein.
Figure 15A:
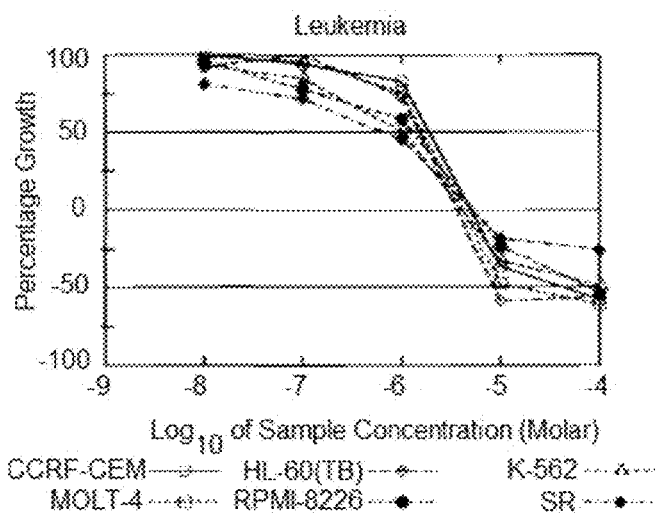
FIGS. 15A-15I: NCI 60 data for compounds herein.
Figure 15B:
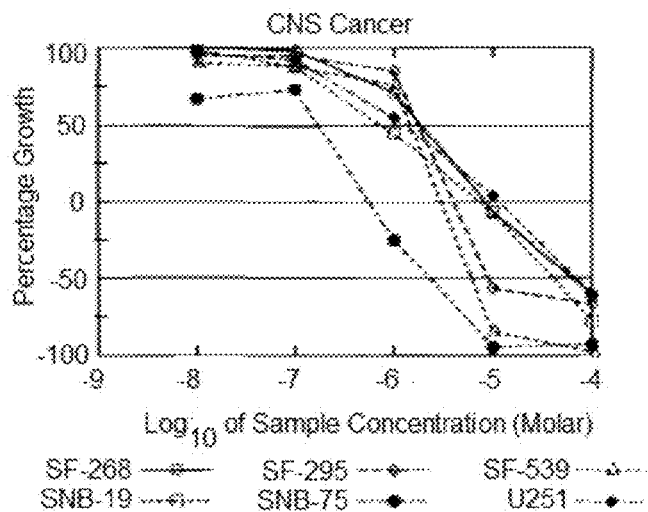
Figure 15C:
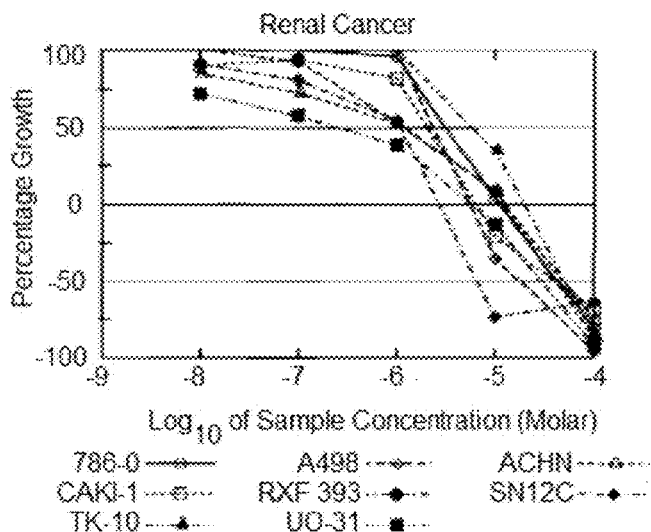
Figure 15D:
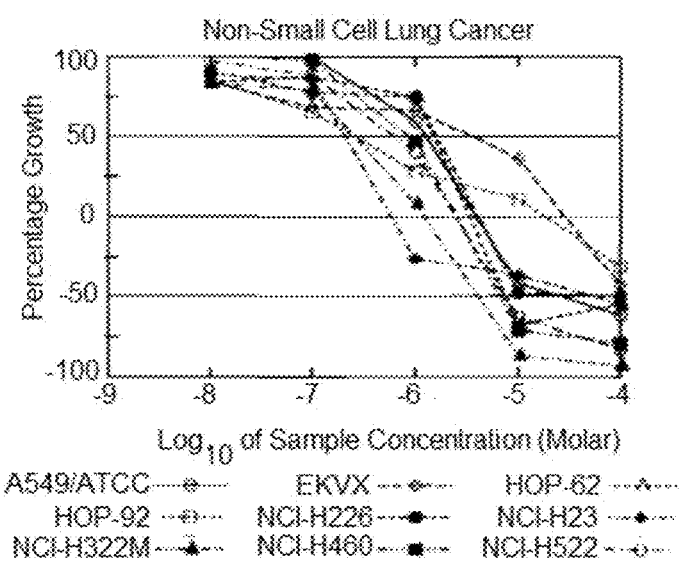
Figure 15E:
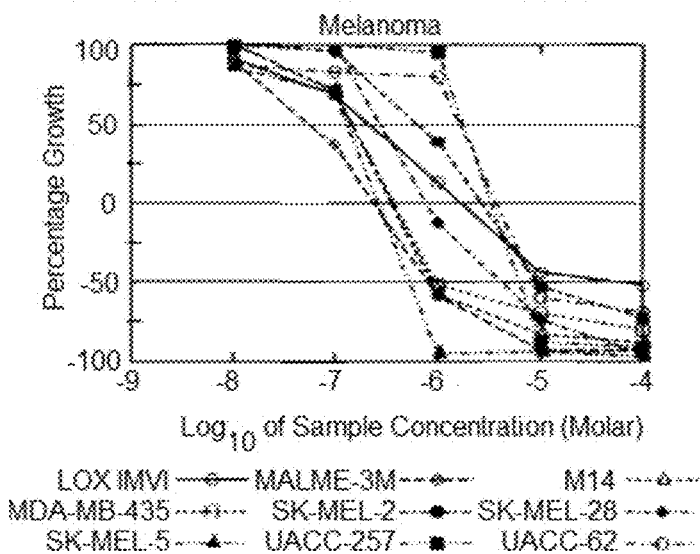
Figure 15F:
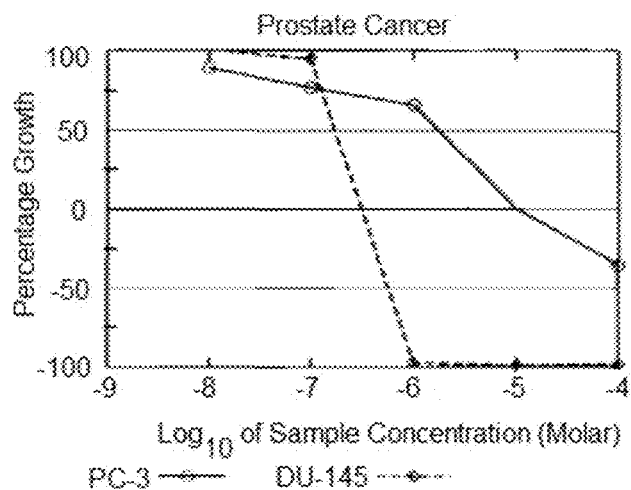
Figure 15G:
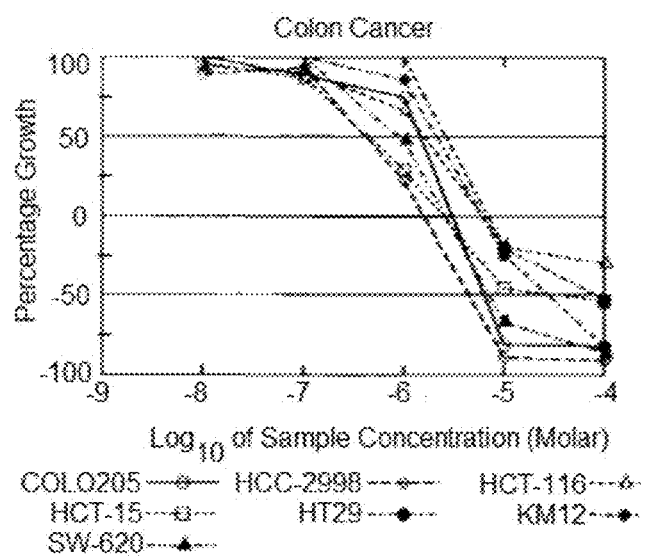
Figure 15H:
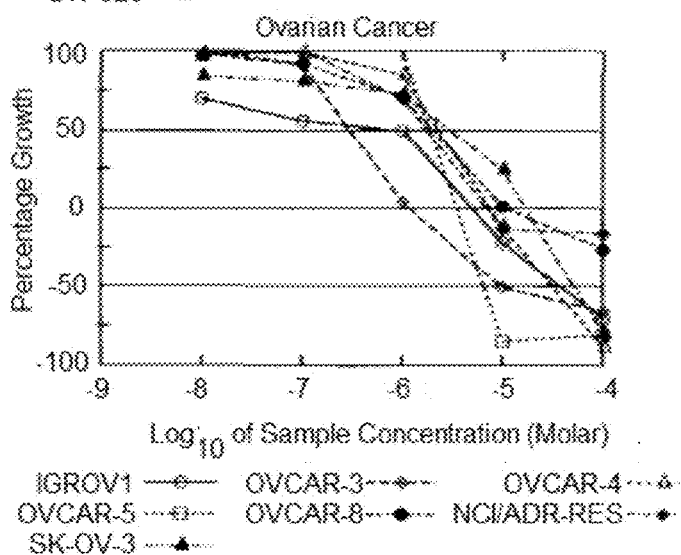
Figure 15I:
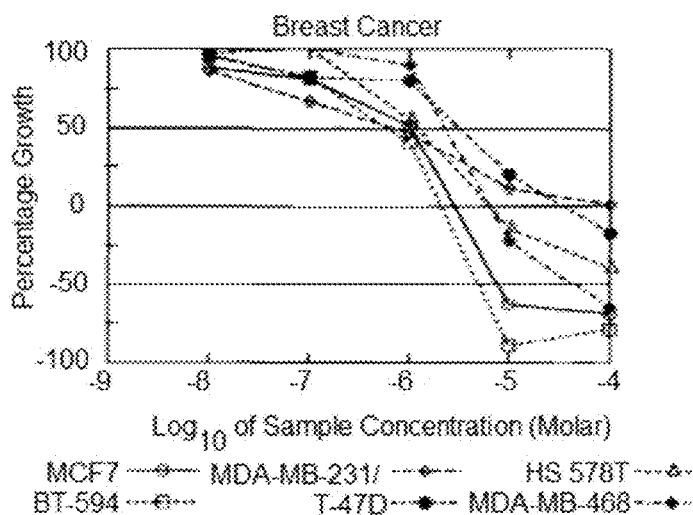
Figure 16:
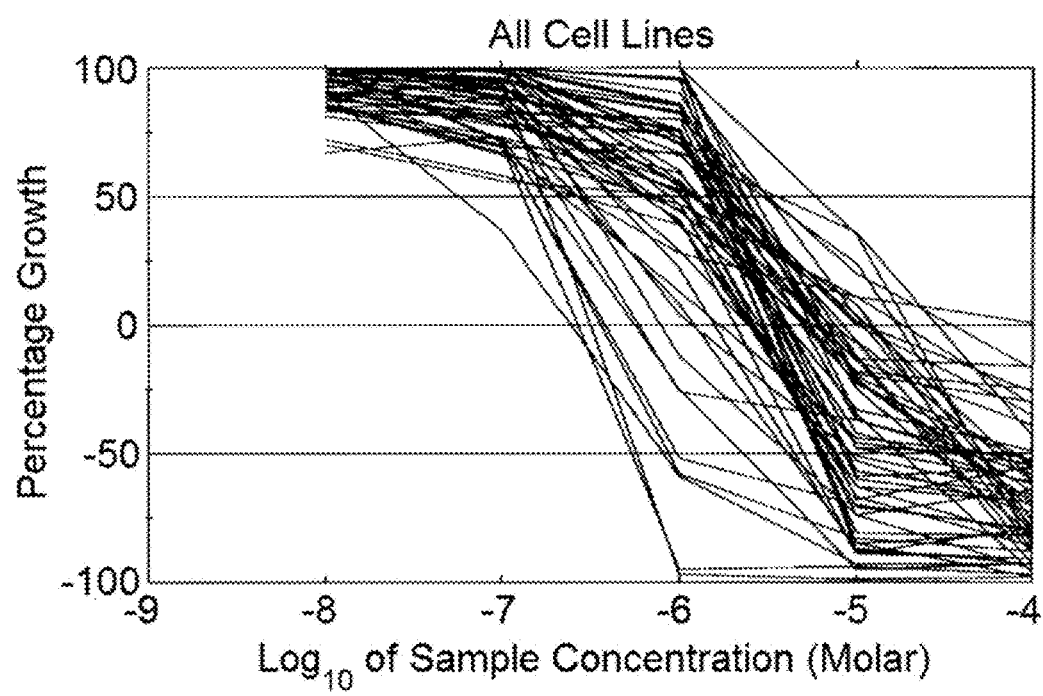
FIG. 16: NCI 60 data for compounds herein.
Figure 18A:
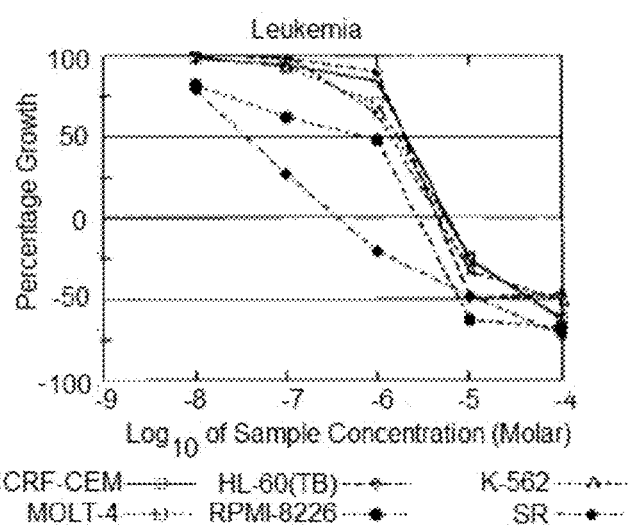
FIGS. 18A-18I: NCI 60 data for compounds herein.
Figure 18B:
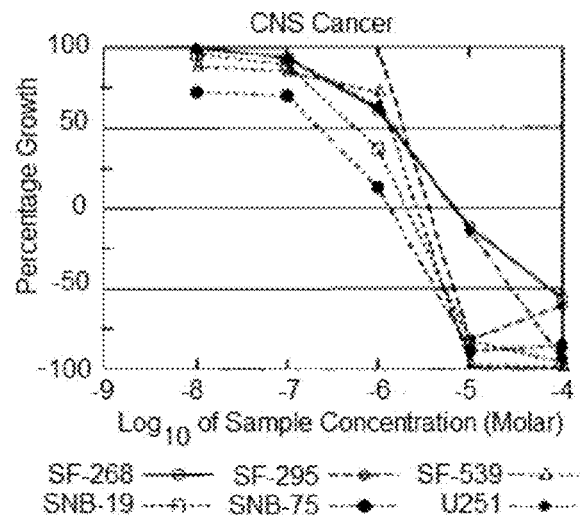
Figure 18C:
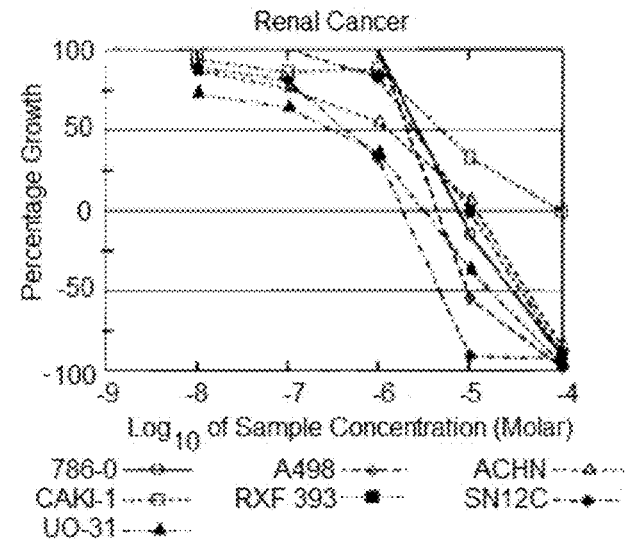
Figure 18D:
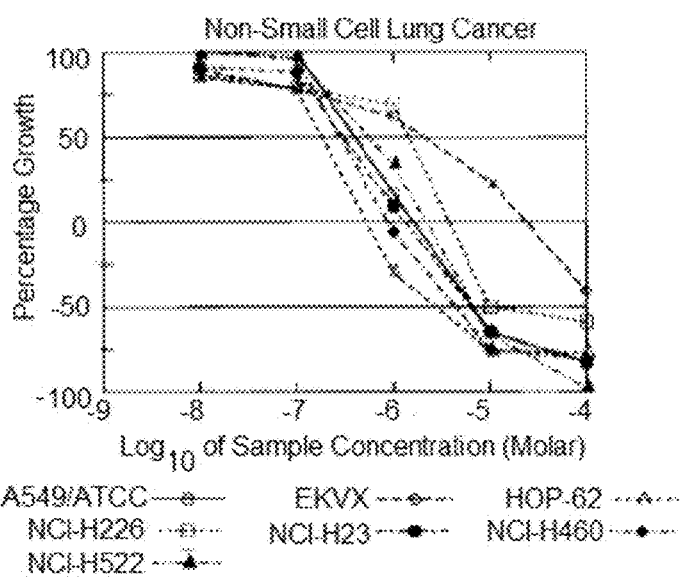
Figure 18E:
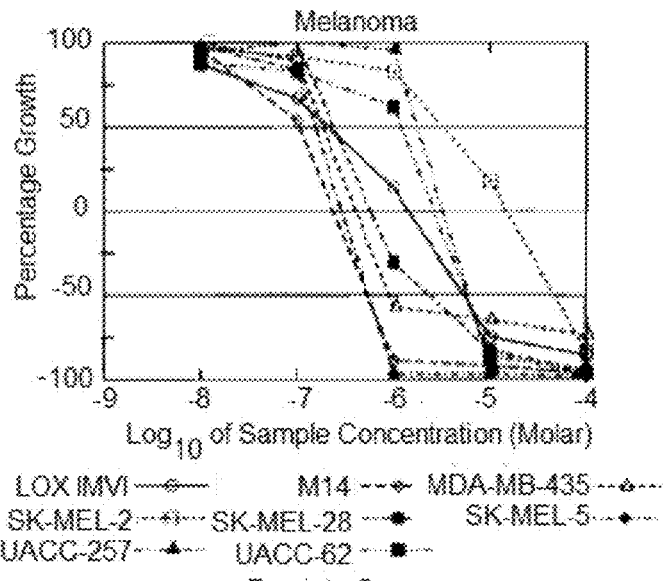
Figure 18F:
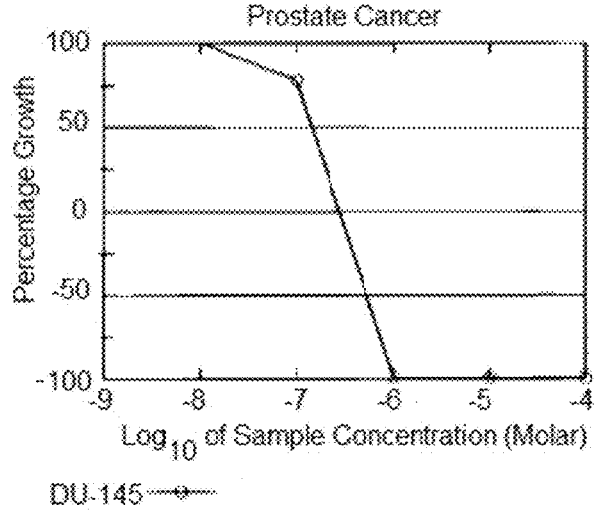
Figure 18G:
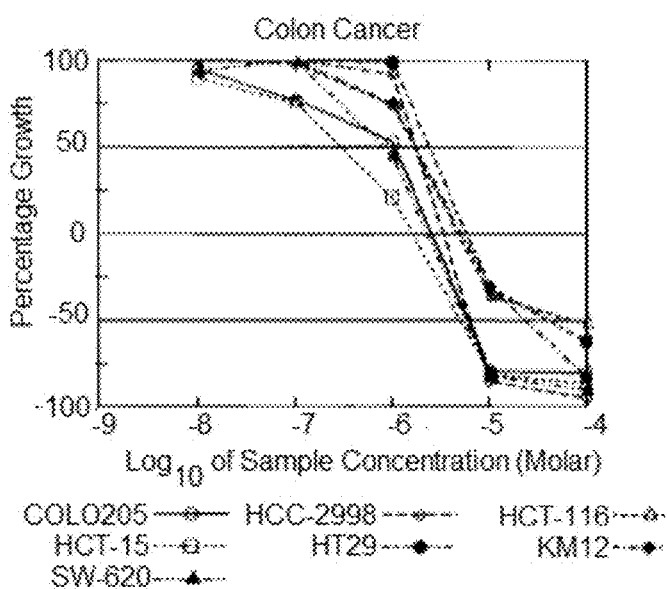
Figure 18H:
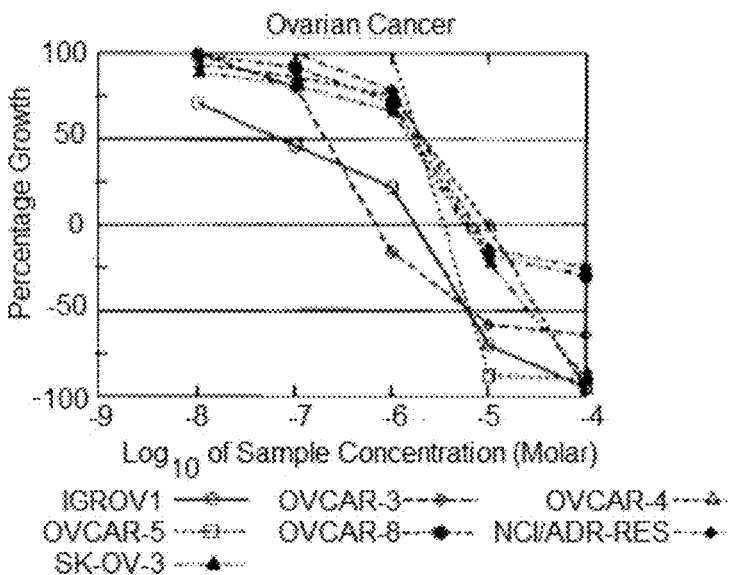
Figure 18I:
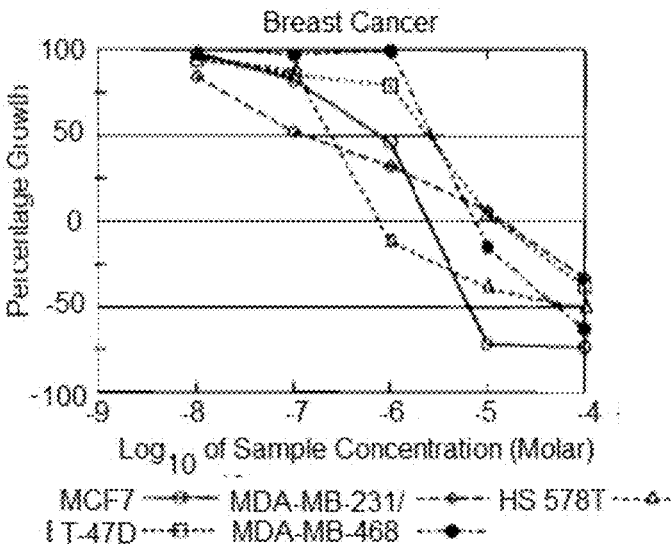

The affinity properties of 13 were then applied using a mAb elicited against the IAF epitope (FIG. 2B). Using established protocols,[13] HCT-116 cell lysates were treated for 8 h with probe 13 and immunoprecipitated with resins bearing a covalently-attached anti-IAF mAb.[14] Over multiple repetitions, a series of proteins ranging from 30-250 kDa were obtained in a manner dependent on the concentration probe 13 (FIG. 5A). Comparable results were also obtained when live cells were treated with 50 μM 13, lysed, and then immunoprecipitated (not shown). Trypsin digestion coupled with LC-MS/MS analyses was then applied to identify the proteins in the more abundant bands. LC-MS/MS data indicated that the band at 50 kDa (band b2, FIG. 5A) corresponded to glyceraldehyde 3-phosphate dehydrogenase (GADPH) with significant sequence coverage over multiple analyses (FIG. 5B). In addition to peptides from GADPH, peptides were also found in the 50 kDa band (b1, FIG. 5A) that corresponded to the 30 aa PIF core, 13 aa propeptide, and 47 aa DCD-1 peptide region of dermcidin (DCD) (FIG. 5B). Mass spectral analyses of two other bands at ~46 kDa (b2, FIG. 5A) and ~85 Kda (b3, FIG. 5A), returned actin and HSP70, respectively, along with comparable fragments of DCD.

The fact that peptides from the DCD were observed in each of the bands but not in gel controls or IP experiments without 13 (lane L1, FIG. 5A) was recently supported by a study that identified DCD peptides during the analysis of Hsp70.[16] In these studies, DCD was observed linked to Hsp70 by means of a disulfide bond, which was released upon treatment with iodoacetamide. Interested if this was the case in this experimentation, the immunoprecipitated fractions were treated with 5 mM iodoacetamide prior to gel analysis. As indicated (Lane L1, FIG. 5C), a low molecular weight band corresponding to DCD appeared. This observation indicated that the immunoprecipitated bands (b1-b3, FIG. 5A) contained a disulfide-linked DCD protein. This observation was further evaluated by repeating the immunoprecipitation experiment after treating the cell lysates with iodoacetamide (lane L2, FIG. 5C) and observed the liberation of DCD, thereby suggesting that DCD was indeed a primary target of probe 13.

Using GADPH (band b2, FIG. 5A) as a model, this observation was further confirmed by western blot analysis. As shown in FIG. 5D, the immunoprecipitated band b2 was found to contain not only the IAF tag from probe 13, as shown by a positive blot using an anti-IAF antibody (lane L2, FIG. 5D), but also DCD (lane L3, FIG. 5D) and GADPH (lane L4, FIG. 5D) when compared to control (lane L1, FIG. 5D). Combined, this evidence suggested that peptides from DCD were not only covalently modified by 13 but were also ligated via a disulfide bond to GADPH.

The reactivity between 1 and DCD was then examined. Using the 47 amino acid DCD-1 as a model, incubation at 37° C. for 24 h was found sufficient to allow 50 μM solutions of 1, alkene 10 or acid 11 to covalently label DCD-1L, as indicated by the presence of a fluorescent labeled band at ~5 kDa in a denatured SDS-PAGE gel. These studies now provided initial support for the formation of a unique trimeric covalent adduct, compound 15, between 1, DCD and targeted proteins such as GADPH. While the structure of adduct 15 is the subject of further study, the formation of 15, as indicated by chemical methods and western blot analyses (FIG. 5D) may suggest a new mechanistic intermediate in the triggering of autophagy. The targeting of 1 to DCD suggests a new role for DCD in autophagy, and provides further recent evidence[16] that DCD forms disulfide conjugates with diverse proteins.

In whole, this study defines the isolation, structure elucidation, chemical synthesis and chemical biological evaluation of a novel natural product, seriniquinone (1). The fact that analogs can be rapidly assembled with improved biological activity and pharmacological properties suggests further preclinical development for melanoma is warranted.

Example 1

Synthesis of seriniquinone. A schematic depiction of one synthetic route of seriniquinone from the substituted naphthoquinone is provided in Scheme 1 that follows.[7]

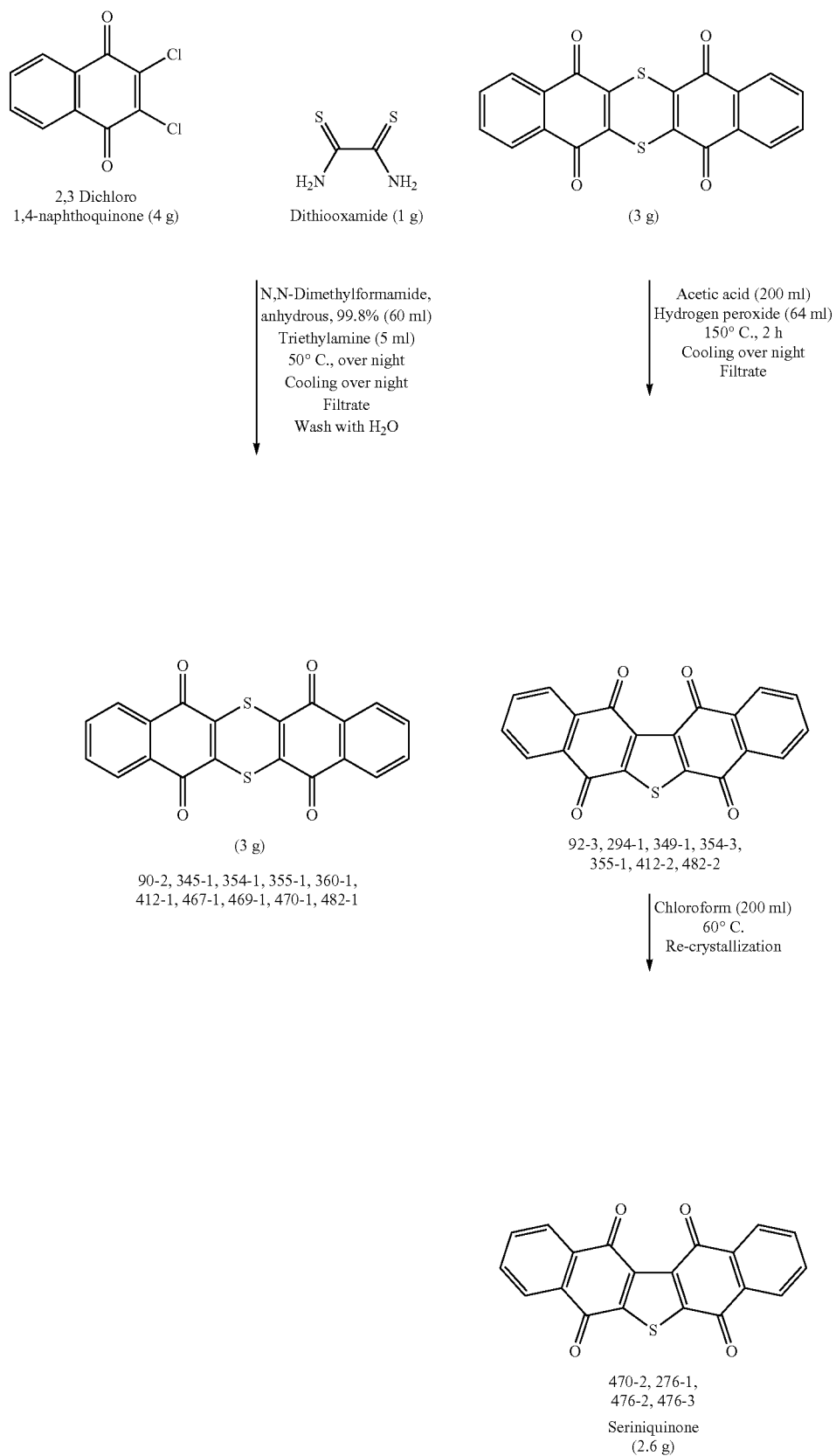

Example 2
Synthesis of substituted seriniquinone. A schematic depiction of the synthesis of a substituted seriniquinone from the substituted naphthoquinone is provided in Scheme 2 that follows.
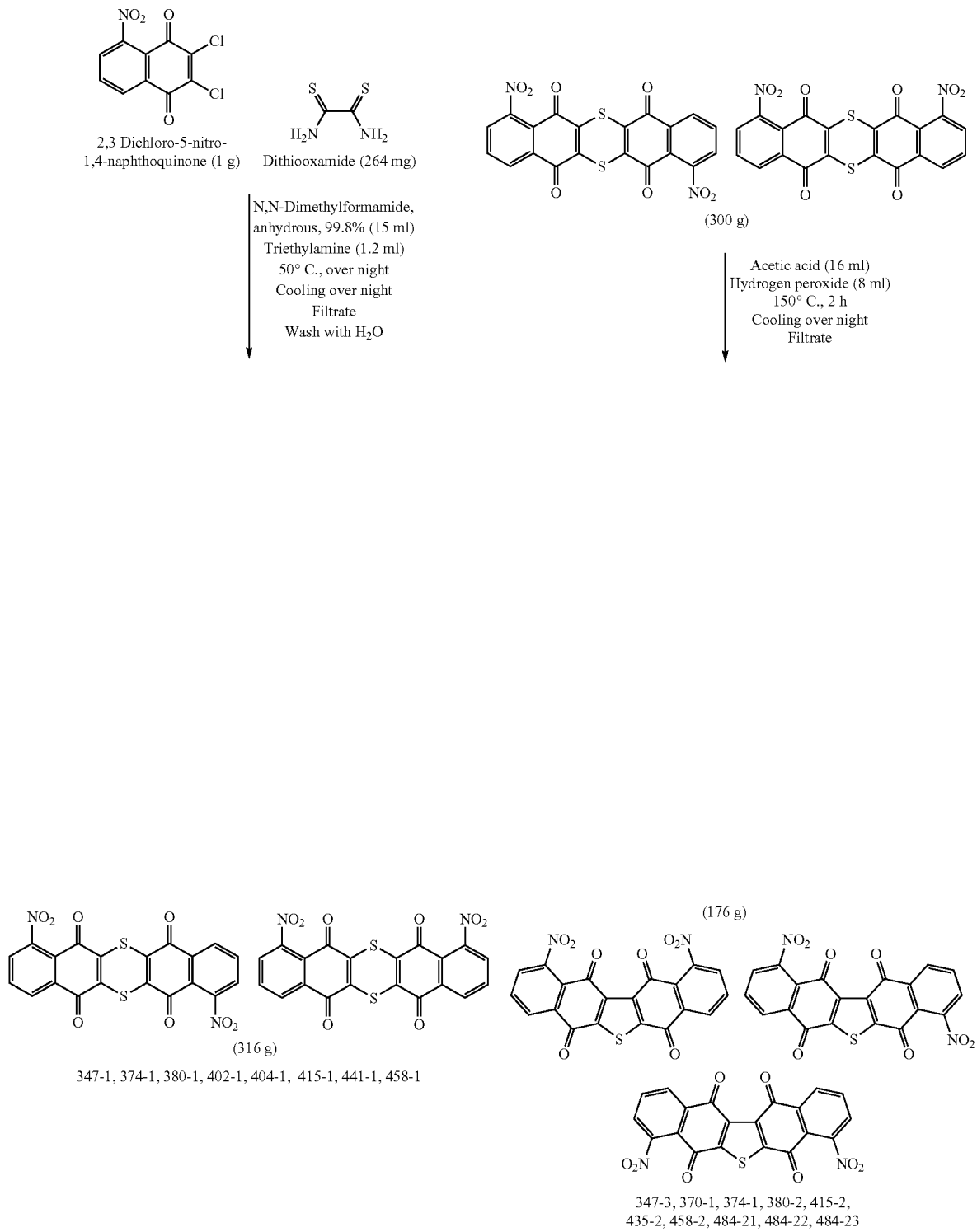

Example 3
Synthesis of substituted seriniquinone. A further schematic depiction of the synthesis of an unsubstituted or substituted seriniquinone from the substituted naphthoquinone is provided in Scheme 3 following.
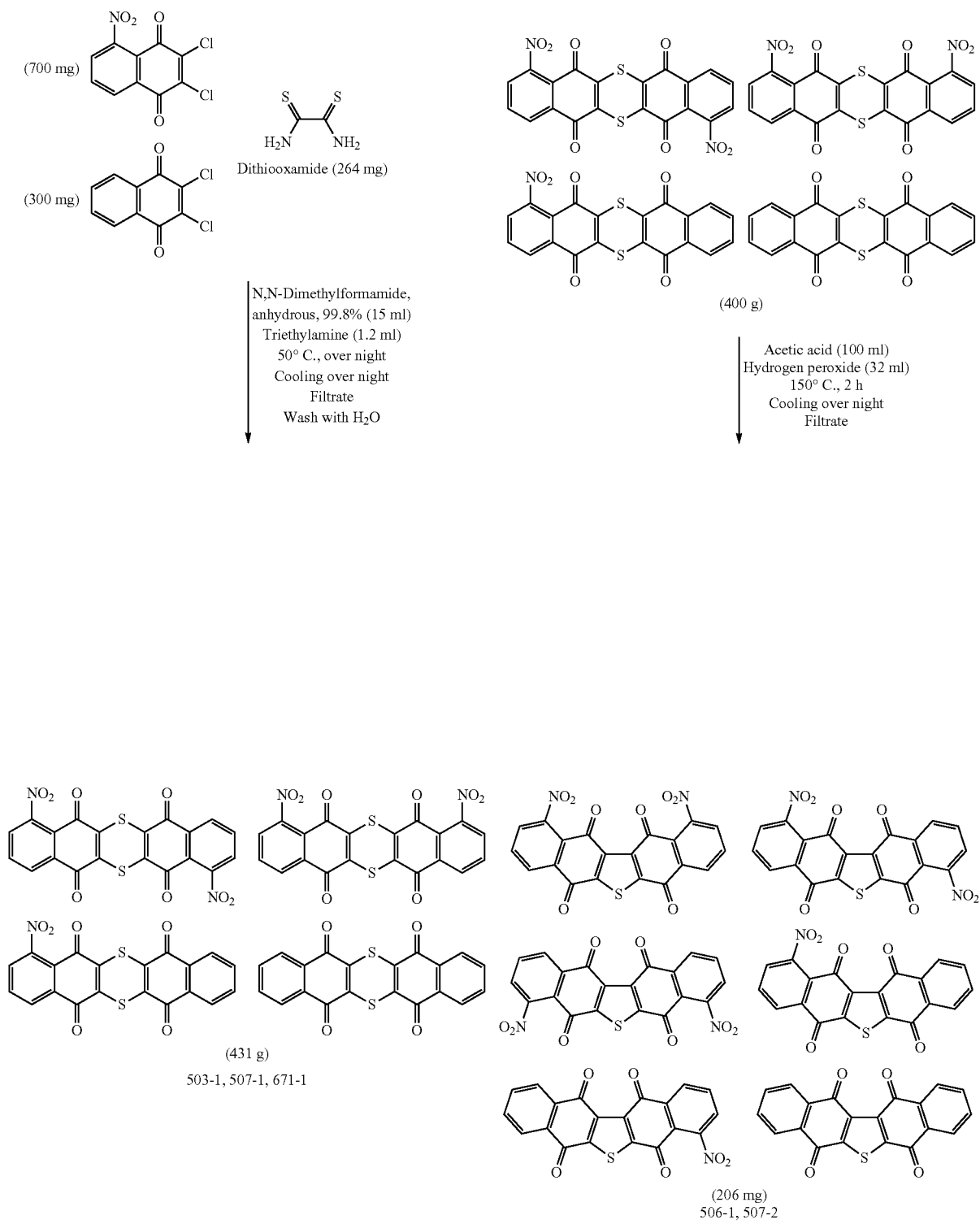
Scheme 3.

Example 4
Synthesis and purification of substituted seriniquinones. A schematic depiction of the synthesis and purification of an amine-substituted seriniquinone from the nitro-substituted compound is provided in Scheme 4 following.
Scheme 4.
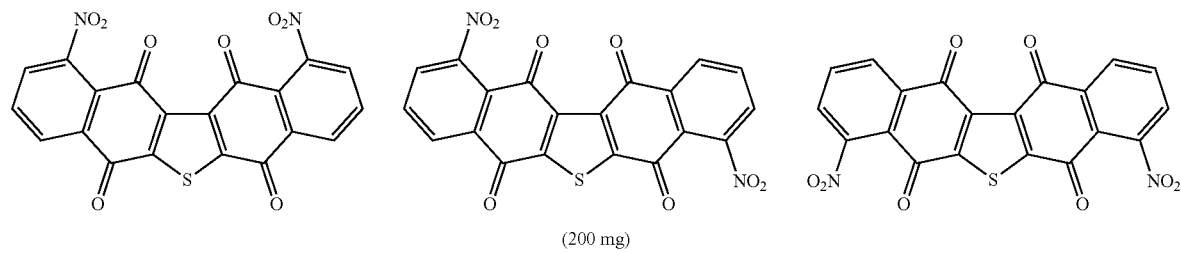
In DMSO (10 ml)
Pd/C (200 mg)
$H_2$ gas
Room temp. 2 h or 40° C. 2-3 h
Filtrate with celite
Wash with DMSO
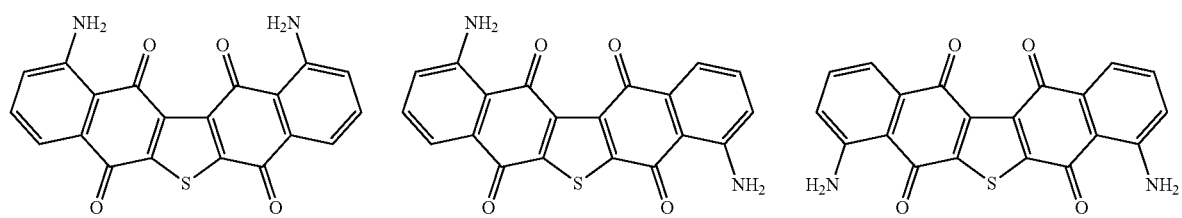
433-1, 456-12, 13, 500-11, 12, 13, 21, 22, 23, 524-1
HPLC

Example 5
Synthesis of substituted seriniquinone. A further schematic depiction of the synthesis of an amine-substituted seriniquinone from the nitro-substituted compound is provided in Scheme 5 following.
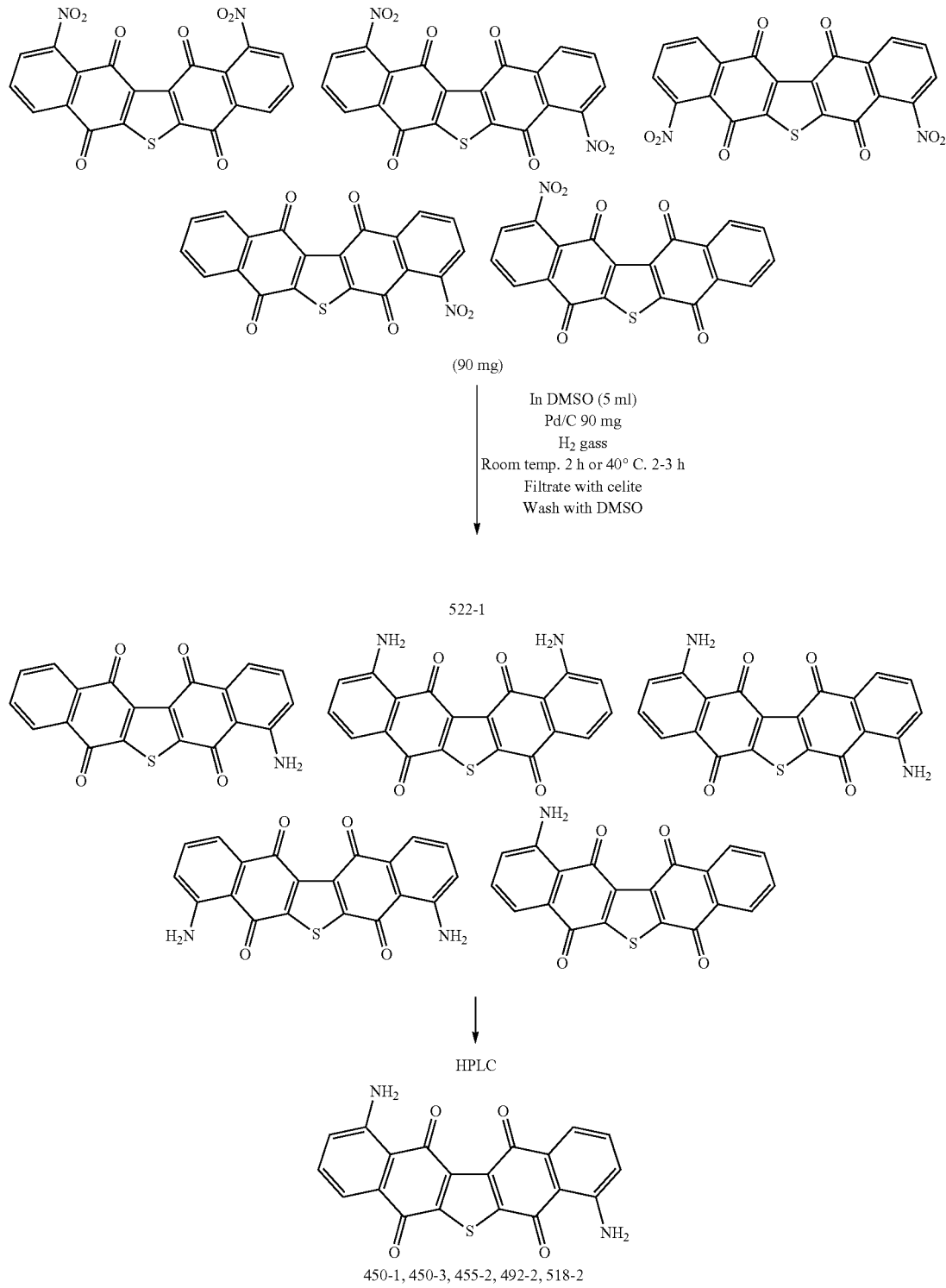

Example 6
Synthesis of substituted seriniquinone. A schematic depiction of the synthesis of a functionalized amine-substituted seriniquinone is provided in Scheme 6 that follows.
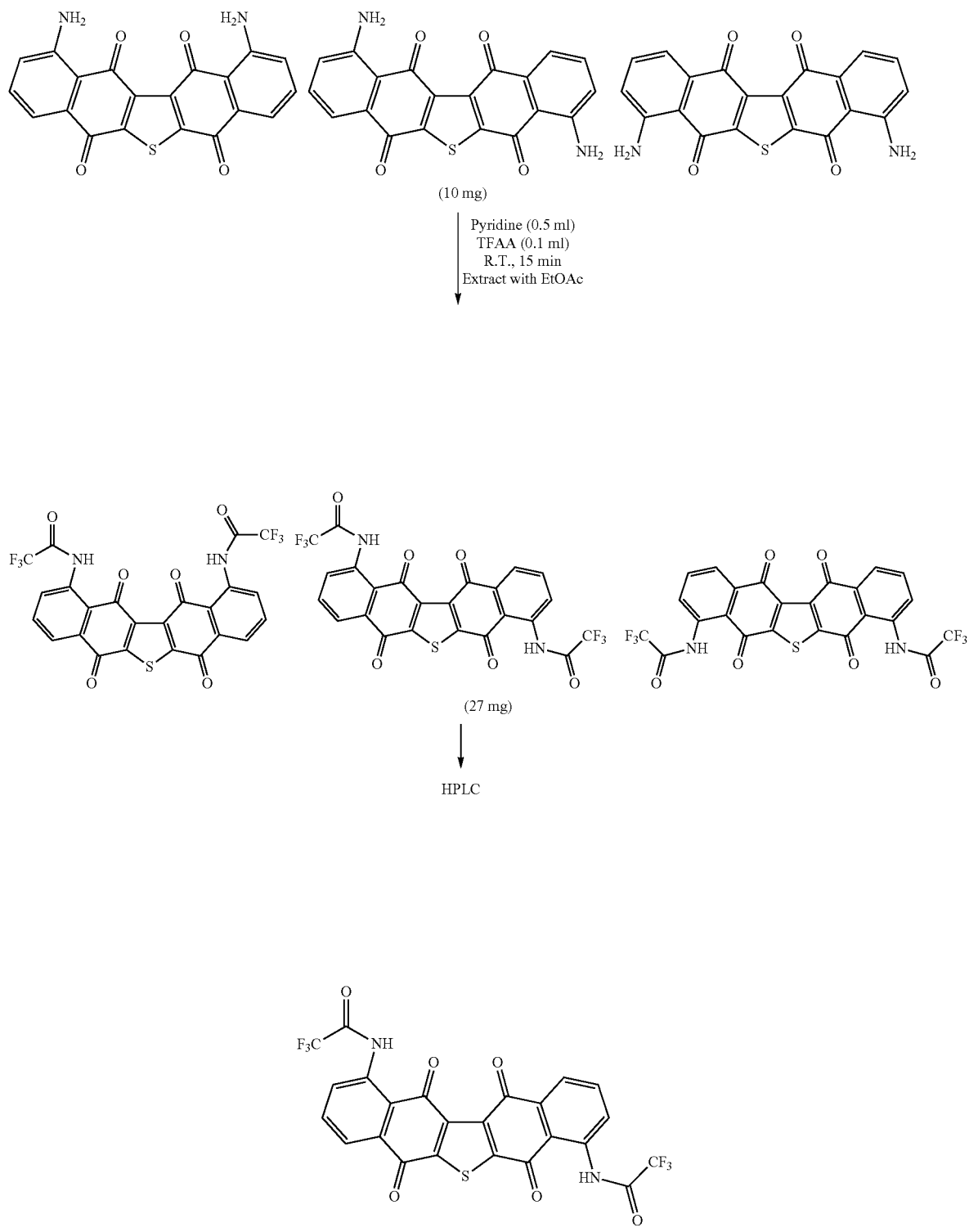

Example 7
Synthesis of substituted seriniquinone. A schematic depiction of the synthesis and purification of a hydroxylated seriniquinone is provided in Scheme 7 following.
Scheme 7.
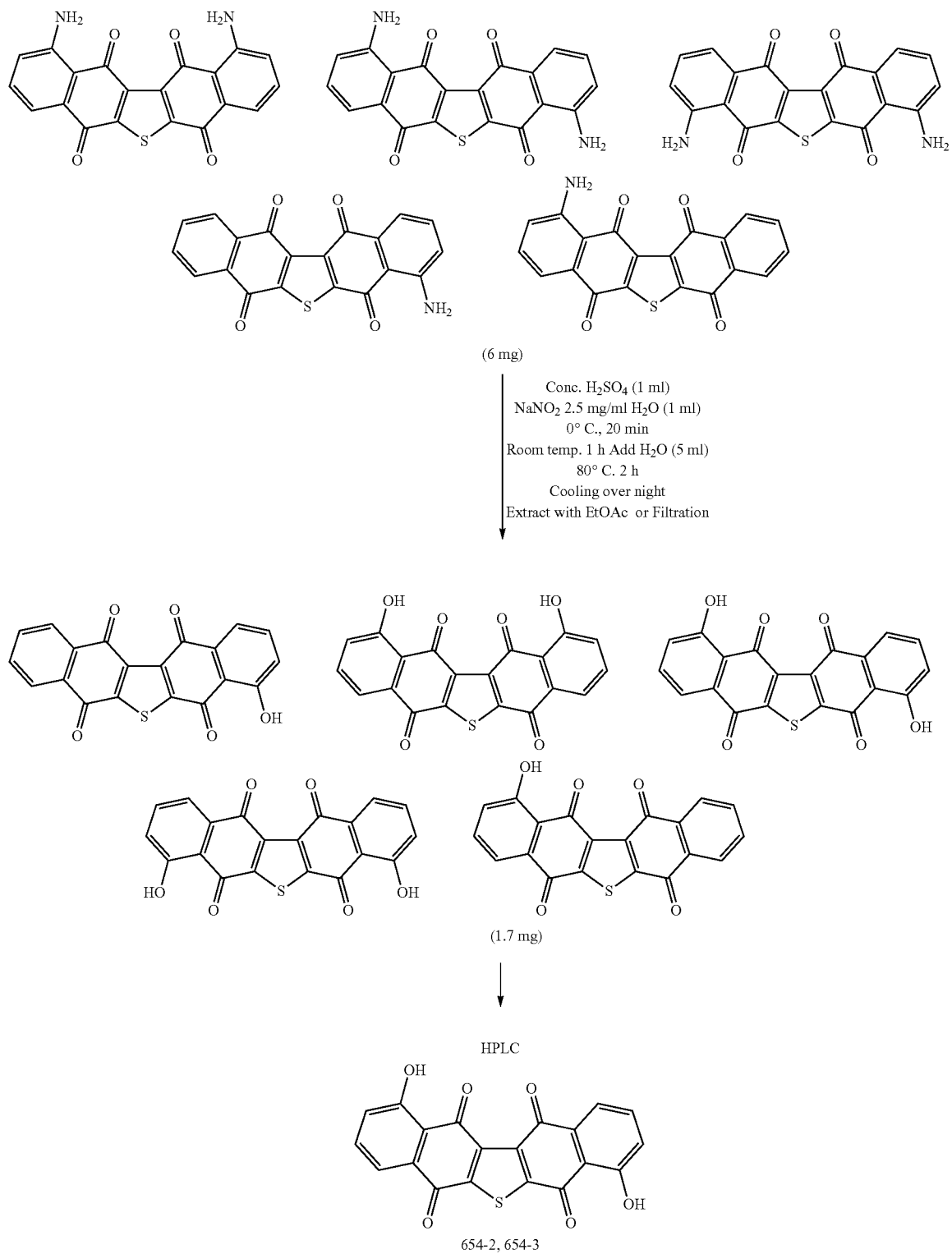

Example 8
Synthesis of substituted seriniquinone. A schematic depiction of the synthesis and purification of a halogenated seriniquinone is provided in Scheme 8 following.
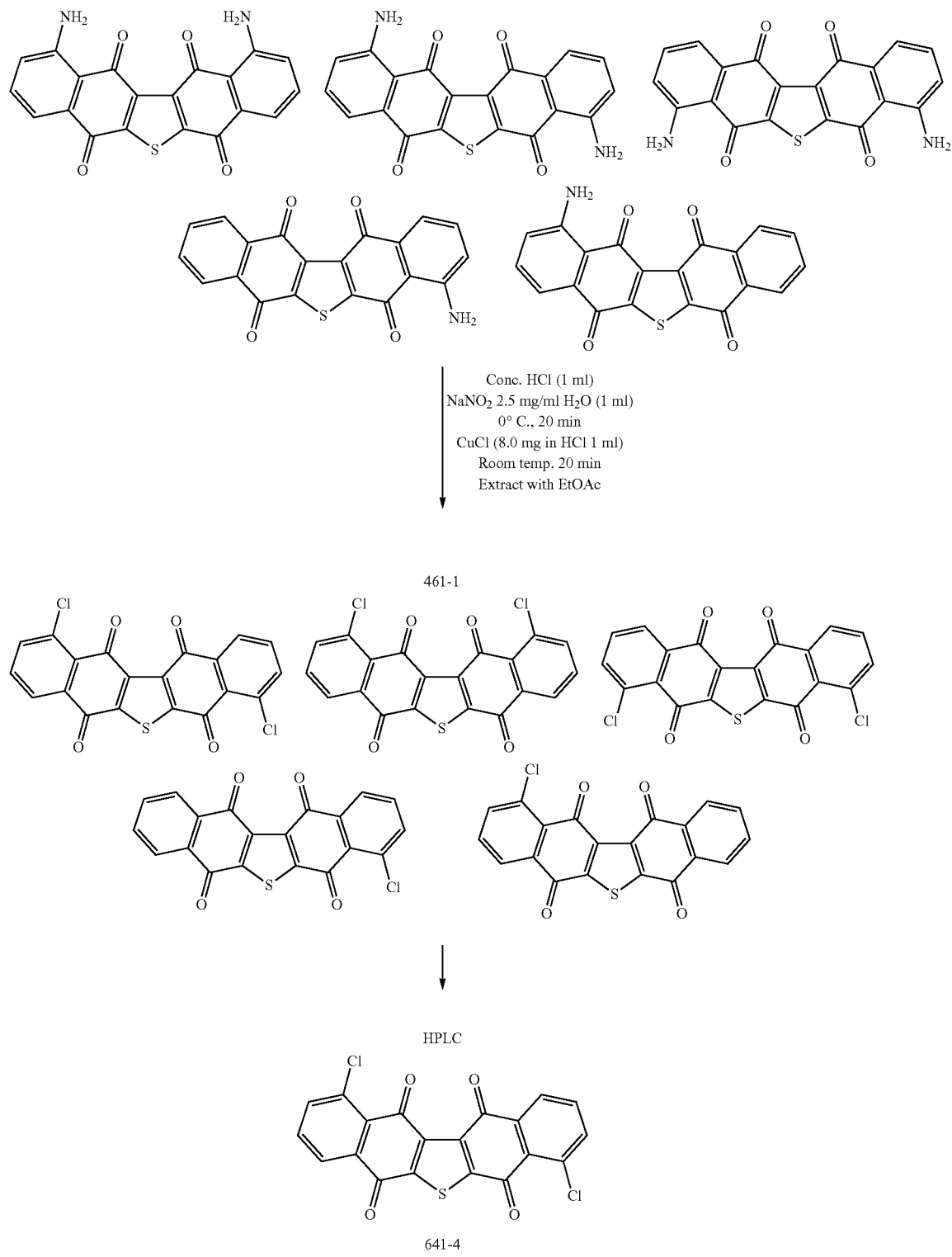

Example 9
Synthesis of substituted seriniquinone. A schematic depiction of the synthesis of a nitrated seriniquinone is provided in Scheme 9 following.
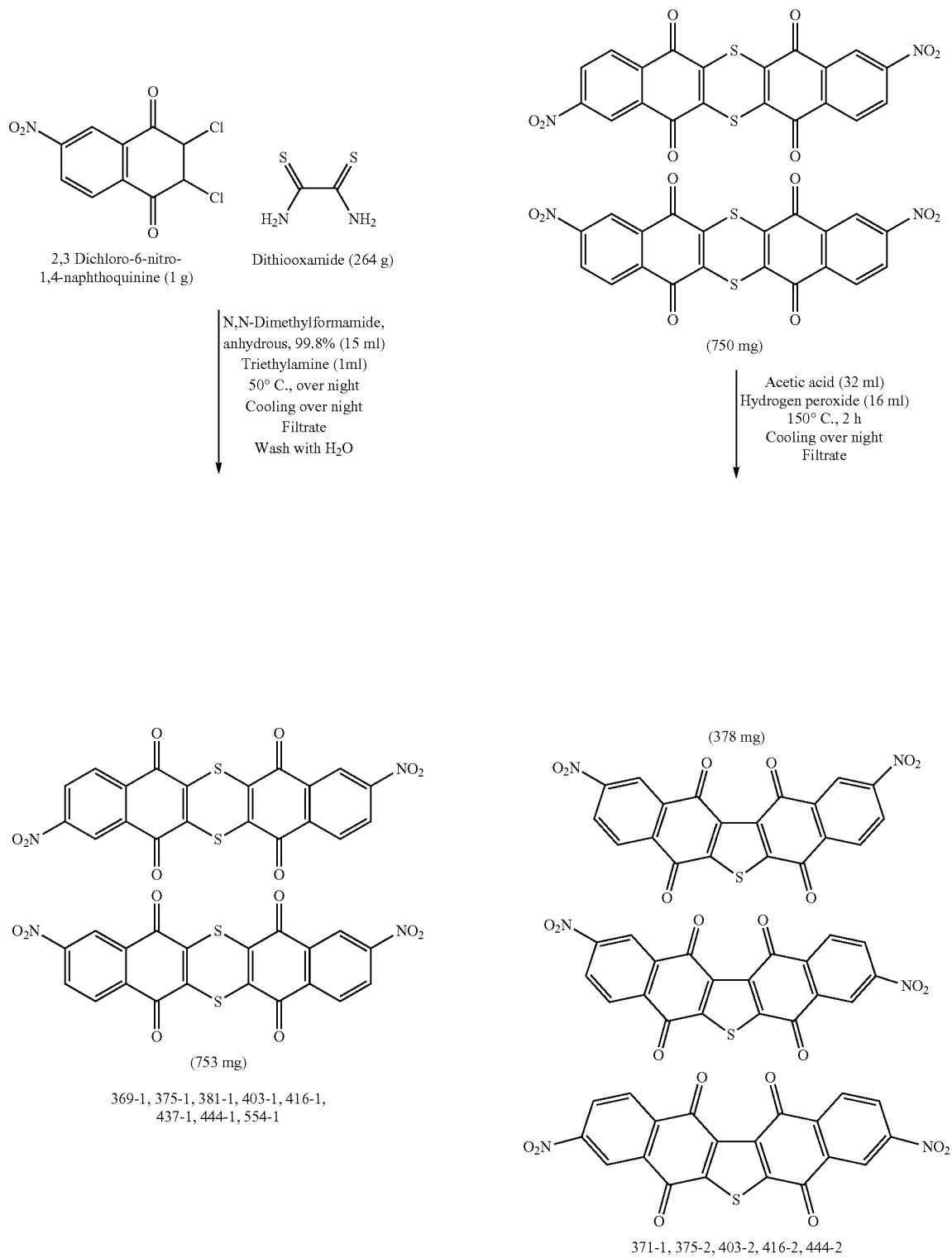
Scheme 9.

Example 10
Synthesis of substituted seriniquinone. A further schematic depiction of the synthesis of an unsubstituted and a nitrated seriniquinone is provided in Scheme 10 following.
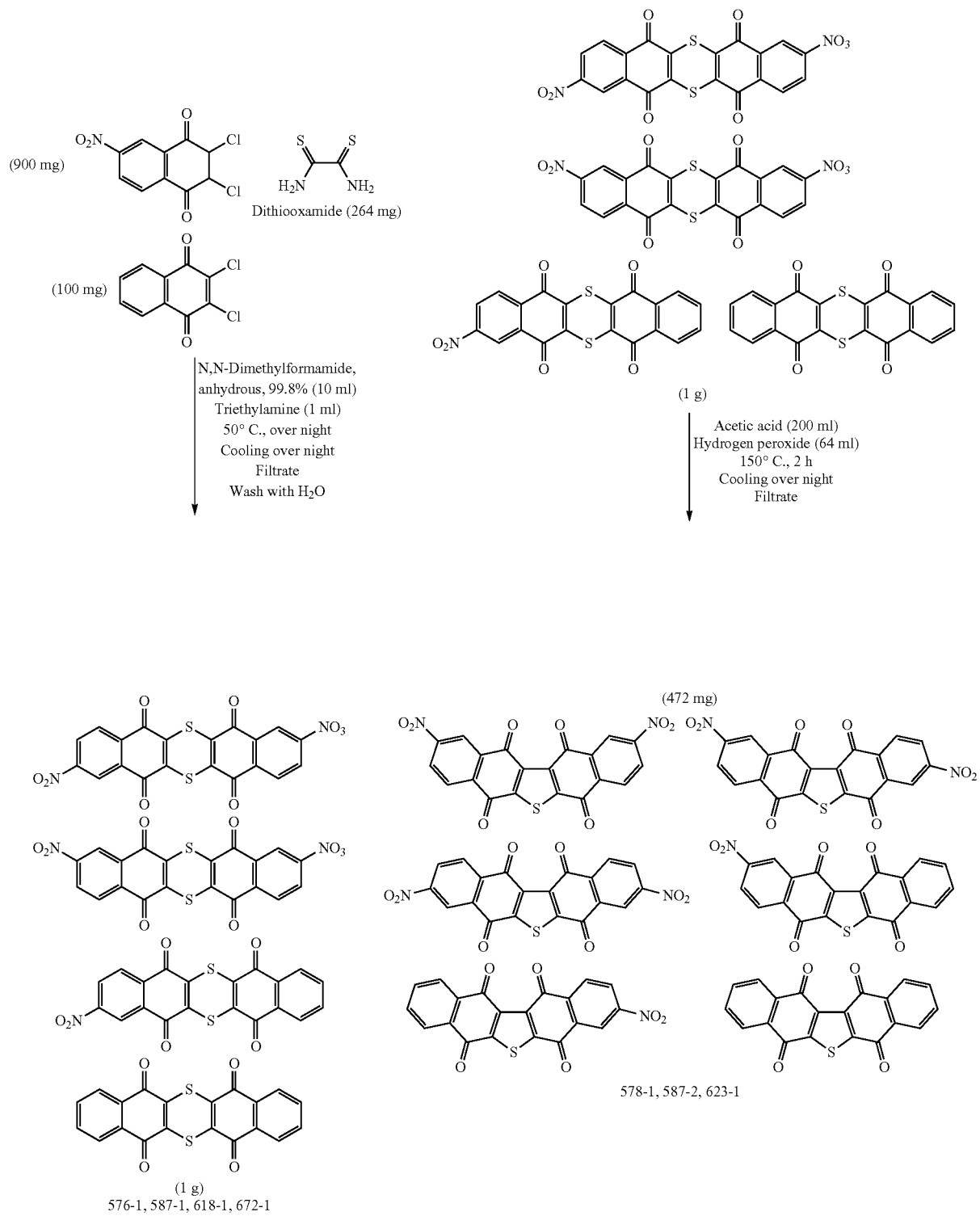

Example 11
Synthesis of substituted seriniquinone. A further schematic depiction of the synthesis of an amine-substituted seriniquinone is provided in Scheme 11 following.
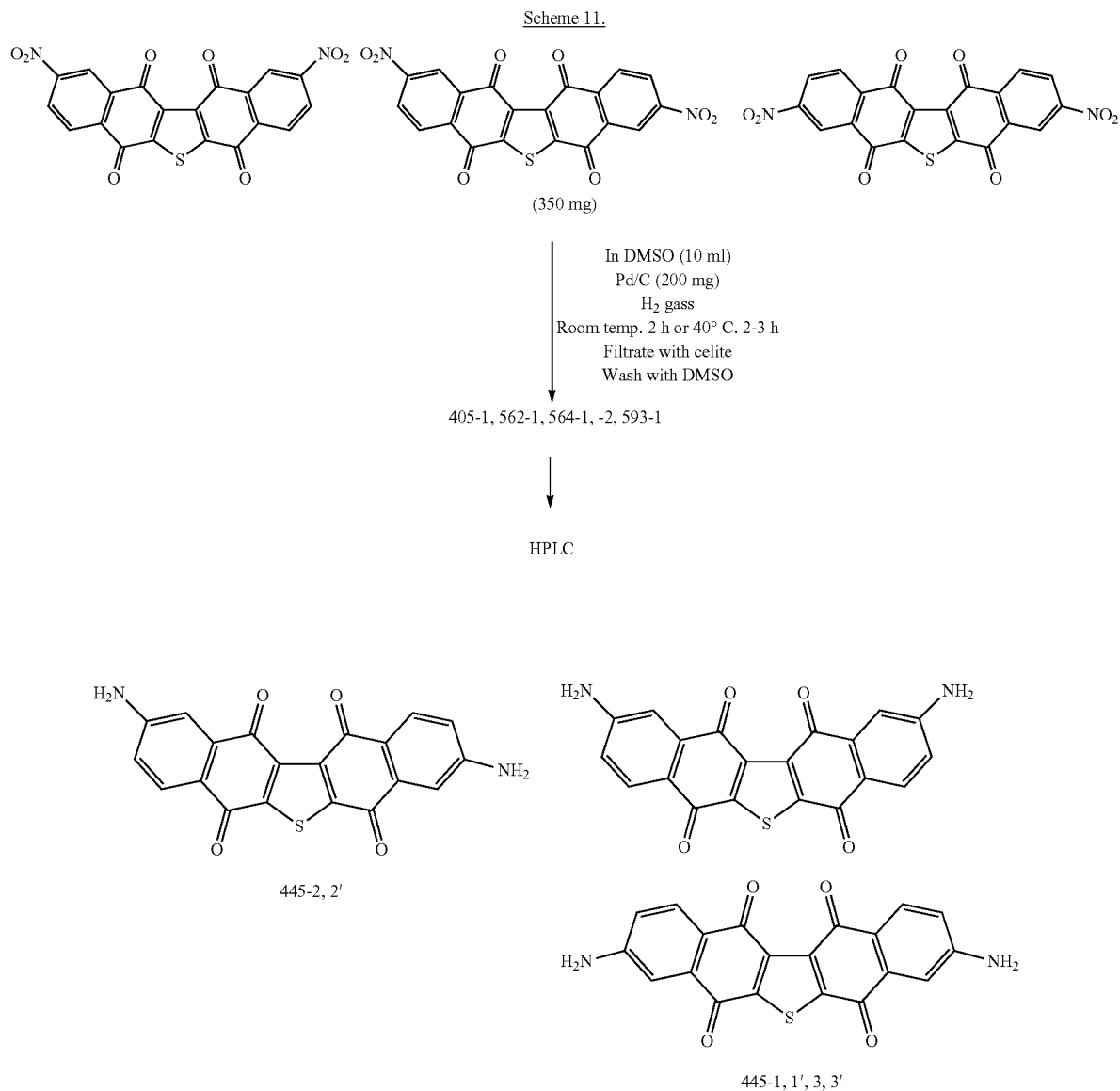
Example 12
Synthesis of substituted seriniquinone. A further schematic depiction of the synthesis of an amine-substituted seriniquinone is provided in Scheme 12 following.
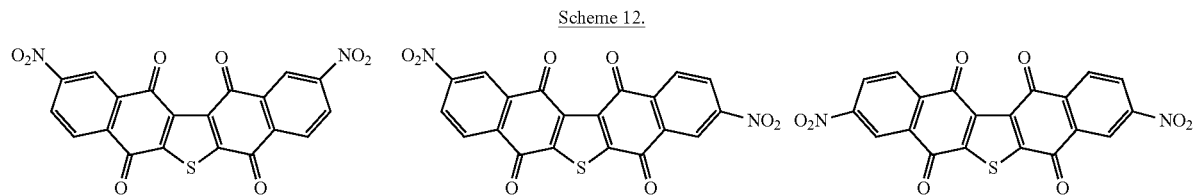

91 92
-continued
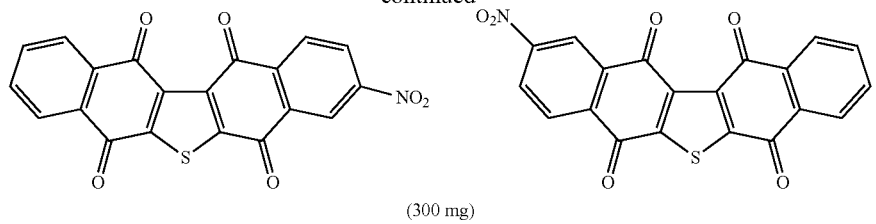
(300 mg)
In DMSO (15 ml)
Pd/C (250 mg)
H₂ gass
Room temp. 2 h or 40° C. 2-3 h
Filtrate with celite
Wash with DMSO
(106 mg)
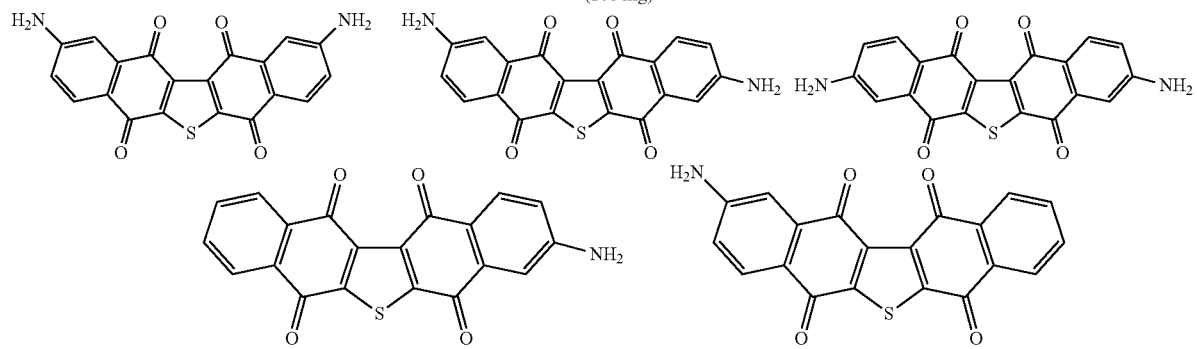
582-1, 592-1, 626-1
HPLC
Example 13
Synthesis of substituted seriniquinone. A further schematic depiction of the synthesis of an amido-substituted seriniquinone is provided in Scheme 13 following.
Scheme 13.
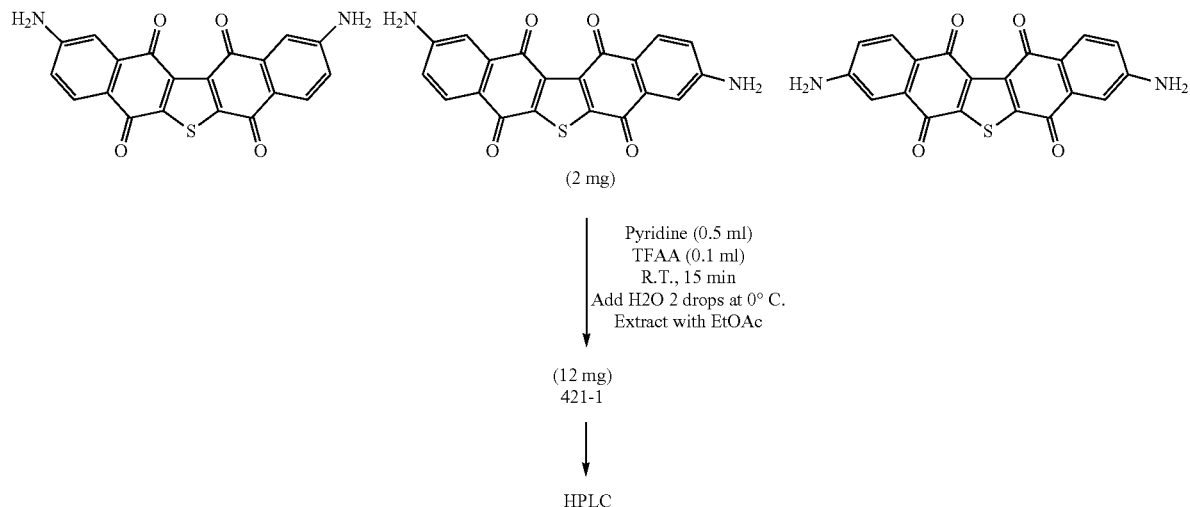
(2 mg)
Pyridine (0.5 ml)
TFAA (0.1 ml)
R.T., 15 min
Add H2O 2 drops at 0° C.
Extract with EtOAc
(12 mg)
421-1
HPLC

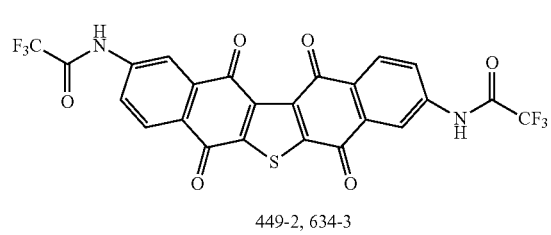
449-2, 634-3
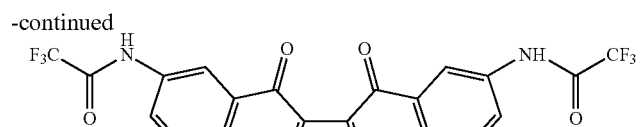
-continued
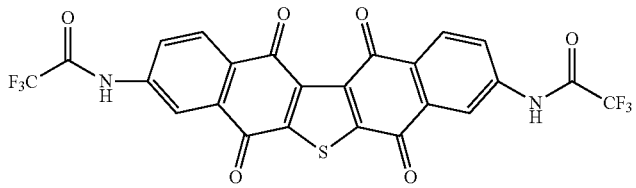
634-2, 634-4
Example 14.
Synthesis of substituted seriniquinone. A further schematic depiction of the synthesis of hydroxylated seriniquinone is provided in Scheme 14 following.
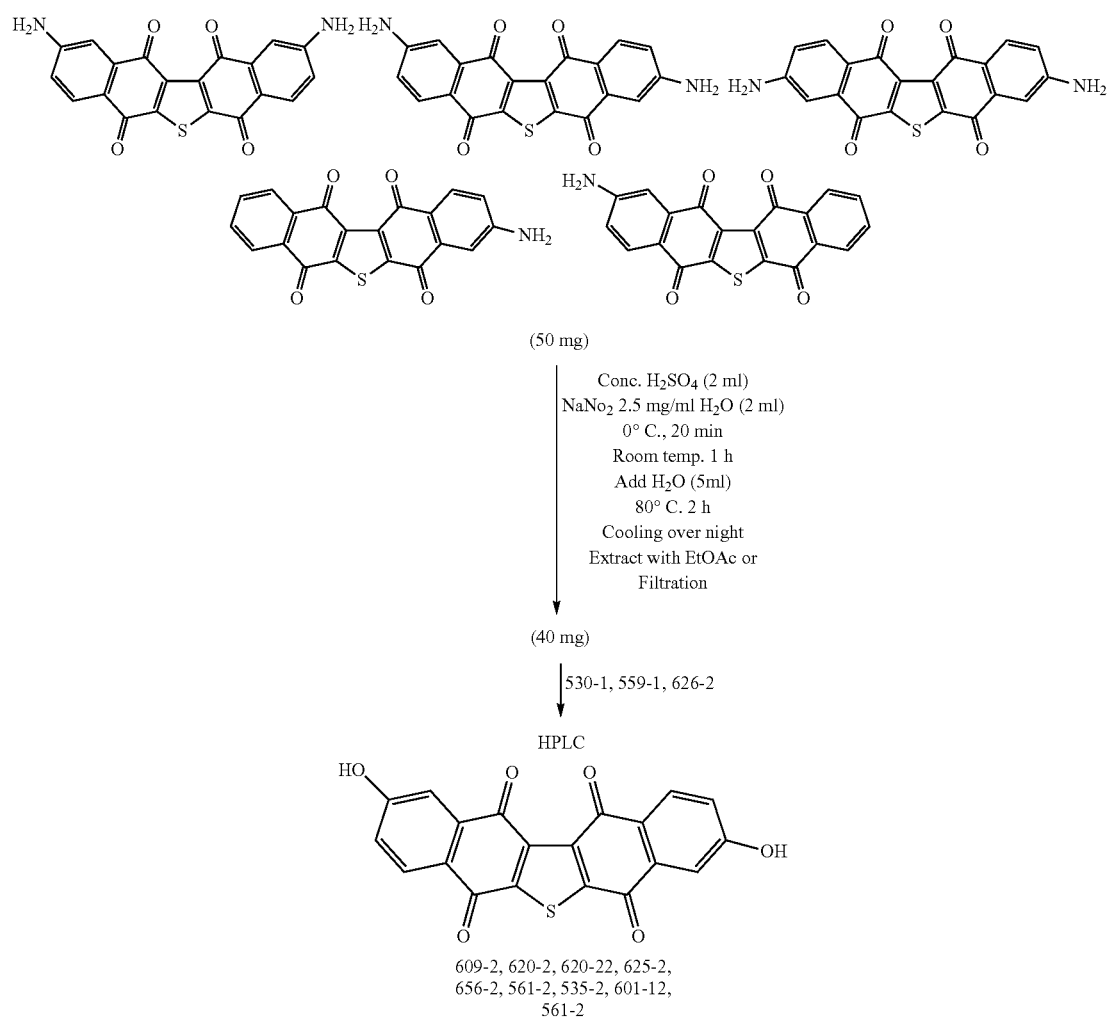
Scheme 14.

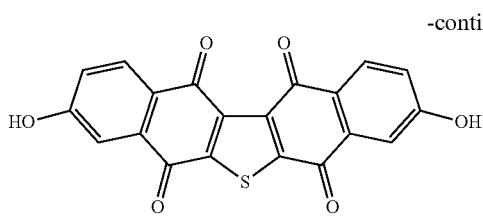
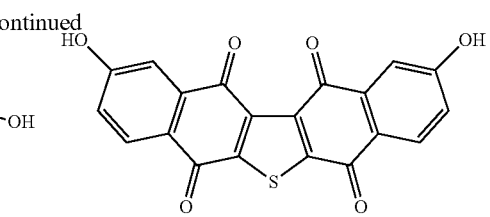
609-1, -3, 620-1, 3, 620-12, -32 625-1, -3
656-1, -3, 561-1, -3, 601-1, -3, 561-1, -3
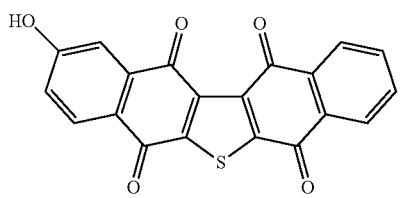
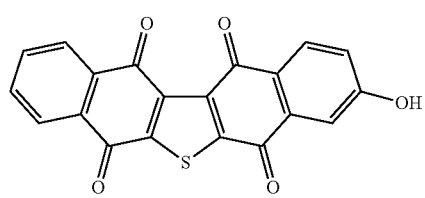
601-4, -5, 609-4, -5, 620-42, -5, 639-4, -5,
656-4, -5.
Example 15.
Synthesis of substituted seriniquinone. A further schematic depiction of the synthesis of hydroxylated and/or esterified seriniquinone is provided in Scheme 15 following.
Scheme 15.
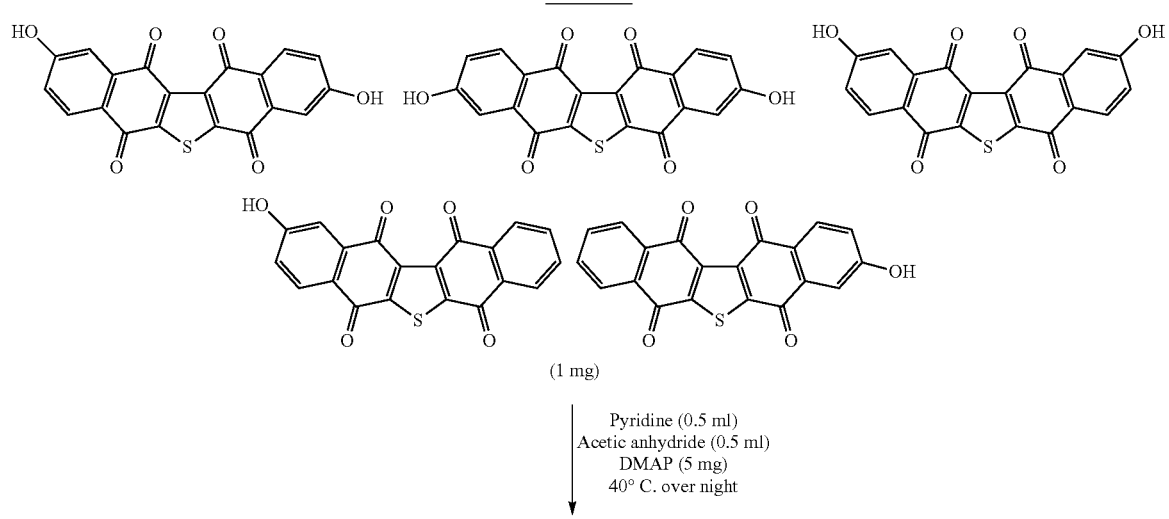
(1 mg)
Pyridine (0.5 ml)
Acetic anhydride (0.5 ml)
DMAP (5 mg)
40° C. over night

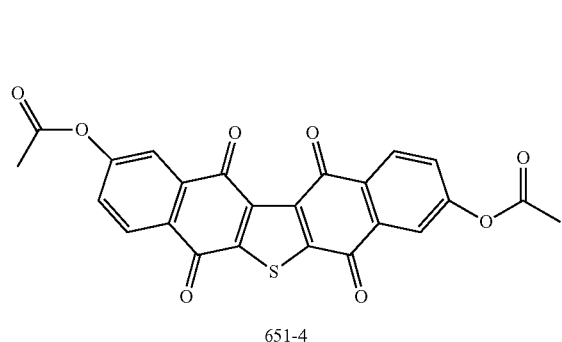
651-4
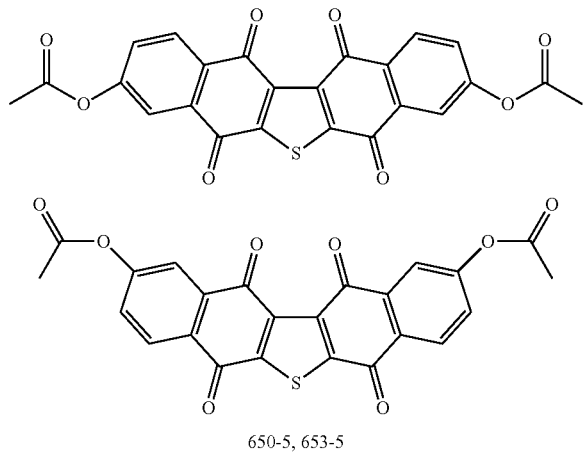
650-5, 653-5
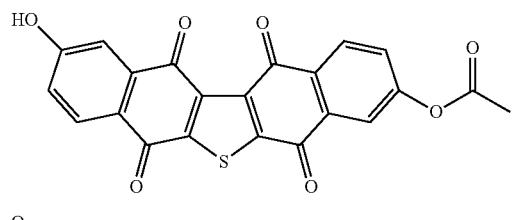
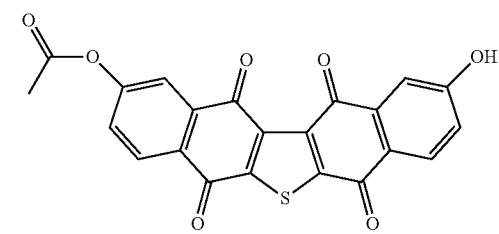
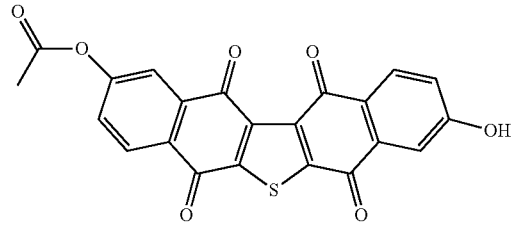
651-2, -3
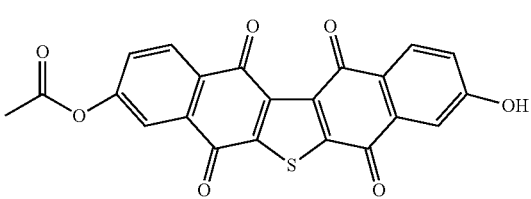
650-4, 653-4
Example 16.
Synthesis of substituted seriniquinone. A further schematic depiction of the synthesis of halogenated seriniquinone is provided in Scheme 16 following.
Scheme 16.
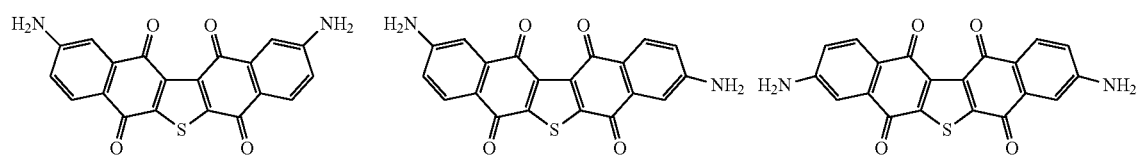

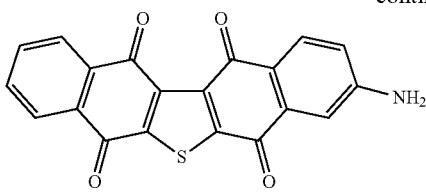
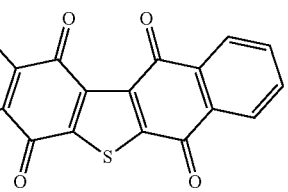

Conc. HCl (1 ml)
NaNO$_2$ 2.5 mg/ml H$_2$O (1 ml)
0° C., 20 min
CuCl (8.0 mg in HCl 1 ml)
Room temp. 20 min
Extract with EtOAc 429-1, 542-2, 579-1
HPLC

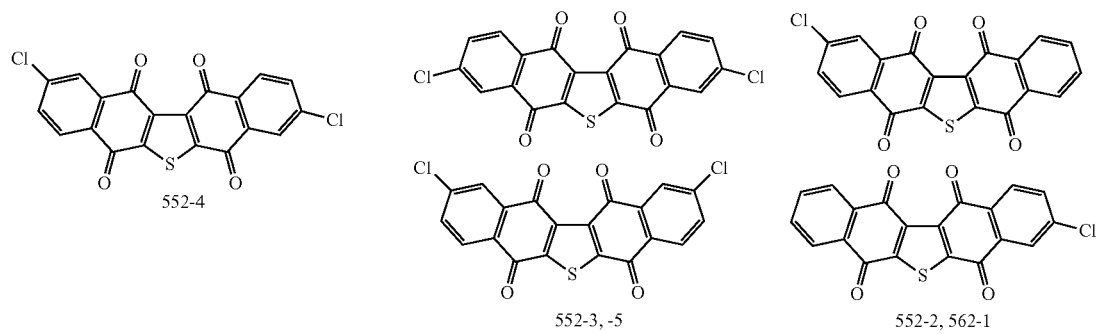

Example 17

Exemplary compounds. Table 1 enumerates compounds 1, p2-p7 and p18-27, based on the synthetic schemes provided above.

Synthesis of Seriniquinone (1).

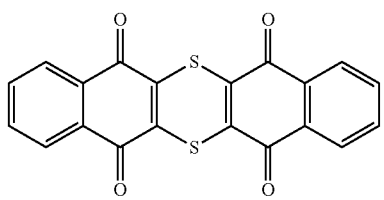

Dibenzo[b,i]thianthrene-5,7,12,14-tetraone

Example 18

2,3-Dichloro-1,4-naphthoquinone (2.00 g, 8.8 mmol) and dithiooxamide (530 mg, 4.4 mmol) were dissolved in dry DMF (30 mL). Et$_3$N (2.6 mL) was added room temperature (rt) and the reaction mixture was heated at 50° C. After 10 h, the mixture was cooled to rt. The dark purple the product was collected by filtration followed by washing with H$_2$O (100 mL) and EtOH (100 mL). Recrystallized from DMF (15 mL) followed by washing with EtOH (2×50 mL) afford dithine 3 (1.46, 88%).[7]

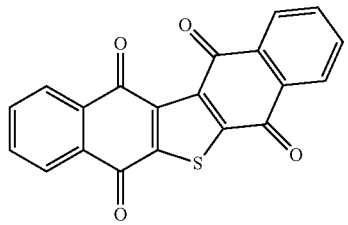

Synthetic Seriniquinone (1)

Example 19

Dithine 3 (1.45 g, 3.8 mmol) was dissolved a mixture of acetic acid (50 mL) and 30% aq. H$_2$O$_2$ (15 mL). The mixture was heated at reflux. After 3 h, the mixture was cooled and the product was collected by filtration, washed with H$_2$O (100 mL), and recrystallized from CHCl$_3$ to afford seriniquinone (1) (1.01 g, 76%) as a yellow-orange solid.

TABLE 1

| Compound | Structure | HCT 116 IC$_{50}$, μM |
|---|---|---|
| 1 | 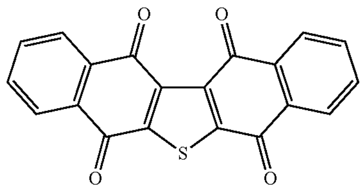 [SMILES: O=c1c2ccccc2c(=O)c2c1sc1c(=O)c3ccccc3c(=O)c12] | 0.35 |
| p2 | 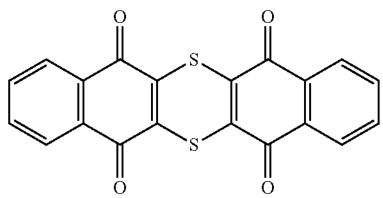 [SMILES: O=c1c2ccccc2c(=O)c2sc3c(=O)c4ccccc4c(=O)c3sc12] | NSA |
| p3 | 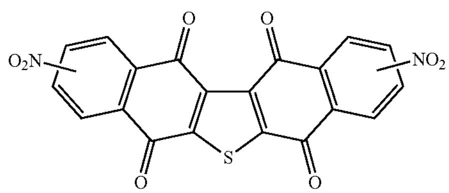 | 5 |
| p4 | 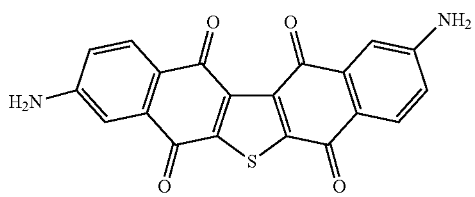 [SMILES: Nc1ccc2c(=O)c3c(sc4c(=O)c5ccc(N)cc5c(=O)c43)c(=O)c2c1] | 2.2 |
| p5 | | 2.7 |
| p6 | 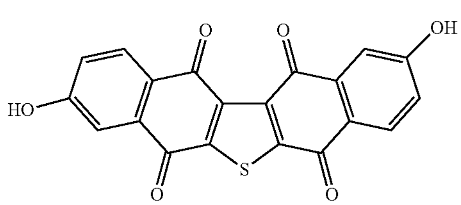 [SMILES: O=c1c2cc(O)ccc2c(=O)c2c1sc1c(=O)c3ccc(O)cc3c(=O)c12] | 1.9 |
| p7 | 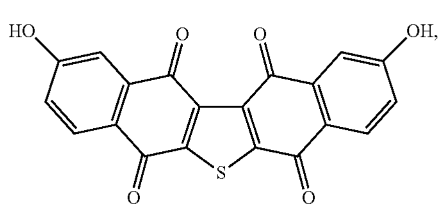 [SMILES: O=c1c2ccc(O)cc2c(=O)c2c1sc1c(=O)c3ccc(O)cc3c(=O)c12] | 1.6, 4.4 |

TABLE 1-continued
| Compound | Structure | HCT 116 IC$_{50}$, μM |
|---|---|---|
| | 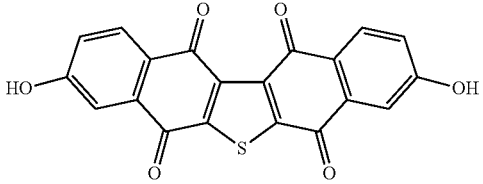 [SMILES: O=c1c2cc(O)ccc2c(=O)c2c1sc1c(=O)c3cc(O)ccc3c(=O)c12] | |
| p8 | 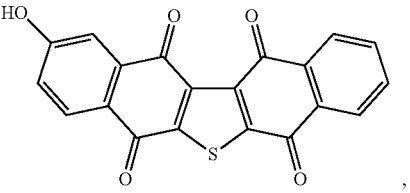 [SMILES: O=c1c2ccccc2c(=O)c2c1sc1c(=O)c3ccc(O)cc3c(=O)c12] | 1.2, 1.3 |
| | 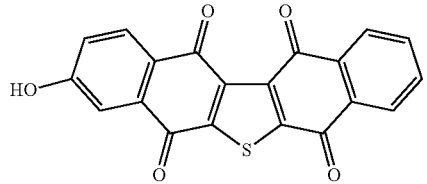 [SMILES: O=c1c2ccccc2c(=O)c2c1sc1c(=O)c3cc(O)ccc3c(=O)c12] | |
| p9 | 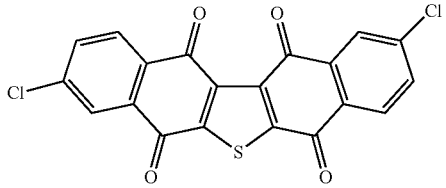 [SMILES: O=c1c2cc(Cl)ccc2c(=O)c2c1sc1c(=O)c3ccc(Cl)cc3c(=O)c12] | 0.55 |
| p10 | 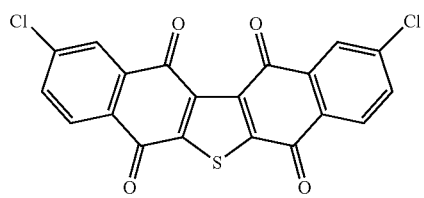 [SMILES: O=c1c2ccc(Cl)cc2c(=O)c2c1sc1c(=O)c3ccc(Cl)cc3c(=O)c12] | 0.78 |
| | 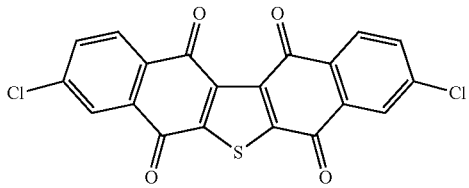 [SMILES: O=c1c2cc(Cl)ccc2c(=O)c2c1sc1c(=O)c3cc(Cl)ccc3c(=O)c12] | |
| p11 | 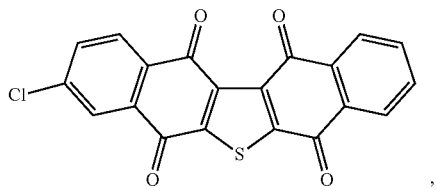 [SMILES: O=c1c2ccccc2c(=O)c2c1sc1c(=O)c3cc(Cl)ccc3c(=O)c12] | 0.15, 0.28 |

TABLE 1-continued

| Compound | Structure | HCT 116 IC$_{50}$, μM |
|---|---|---|
| | (Cl-substituted structure) | |
| p12 | (bis-NHCOCF$_3$ structure) | 0.71 |
| p13 | (bis-NHCOCF$_3$ structure) | 0.48, 0.58 |
| | (bis-NHCOCF$_3$ structure, isomer) | |
| p14 | (bis-OCOCH$_3$ structure) | 2.1 |
| p15 | (bis-OCOCH$_3$ structure) | NSA, 5.8 |
| | (bis-OCOCH$_3$ structure, isomer) | |
| p16 | (HO, OCOCH$_3$ structure) | 3.5, 1.8 |

TABLE 1-continued

| Compound | Structure | HCT 116 IC$_{50}$, μM |
|---|---|---|
| p17 | 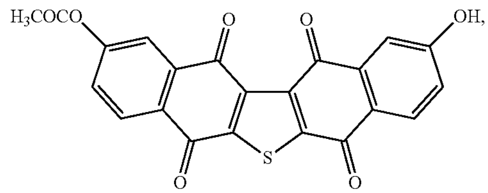 | NSA, 1.6 |
| p19 | 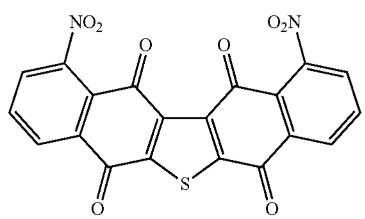 | 0.025 |
| p20 | 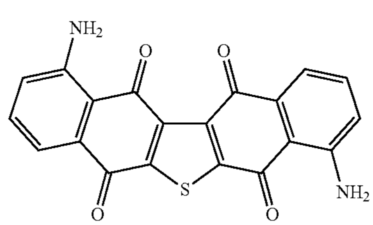 [SMILES: Nc1cccc2c(=O)c3c(sc4c(=O)c5cccc(N)c5c(=O)c43)c(=O)c12] | 0.78 |

TABLE 1-continued
| Compound | Structure | HCT 116 IC$_{50}$, μM |
|---|---|---|
| p21 | 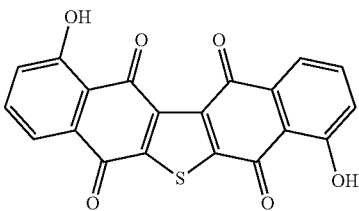 [SMILES: O=c1c2cccc(O)c2c(=O)c2c1sc1c(=O)c3c(O)cccc3c(=O)c12] | 0.7 |
| p22 | 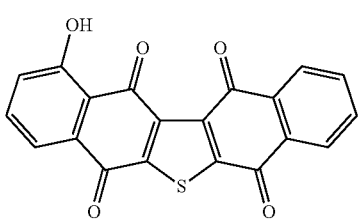 [SMILES: O=c1c2ccccc2c(=O)c2c1sc1c(=O)c3cccc(O)c3c(=O)c12] | 0.54 |
|  | 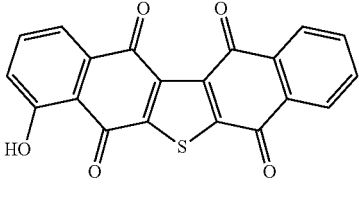 [SMILES: O=c1c2ccccc2c(=O)c2c1sc1c(=O)c3c(O)cccc3c(=O)c12] |  |
| p23 | 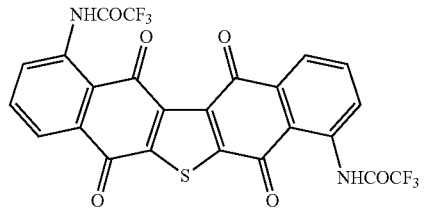 | 0.078 |
| p24 | 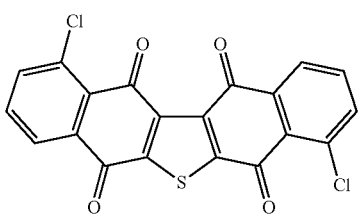 [SMILES: O=c1c2cccc(Cl)c2c(=O)c2c1sc1c(=O)c3c(Cl)cccc3c(=O)c12] |  |
| p25 | 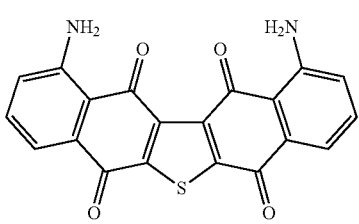 [SMILES: Nc1cccc2c(=O)c3sc4c(=O)c5cccc(N)c5c(=O)c4c3c(=O)c12] |  |
|  | 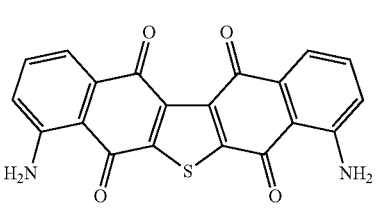 |  |

TABLE 1-continued
| Compound | Structure | HCT 116 IC$_{50}$, μM |
|---|---|---|
| p26 | 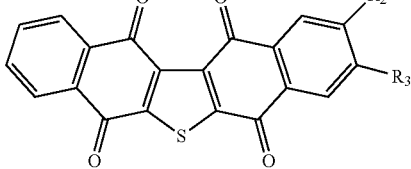 | |
| p27 | 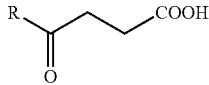 | |
Example 20
Biological Activity of Seriniquinones
Biological data on various seriniquinones disclosed herein is provided in Appendix 1.
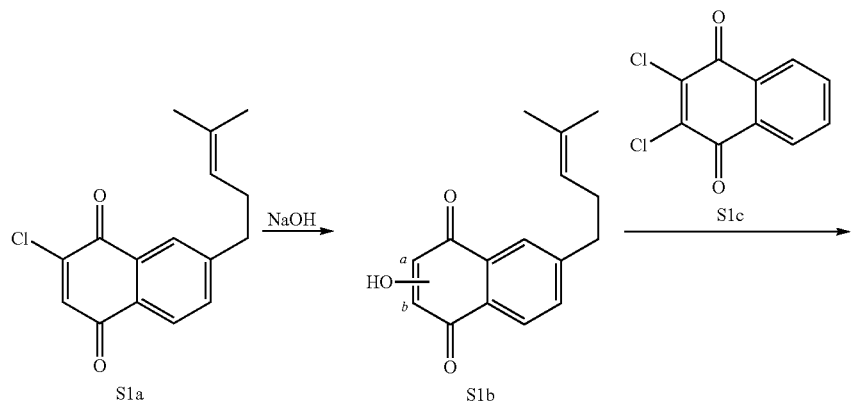

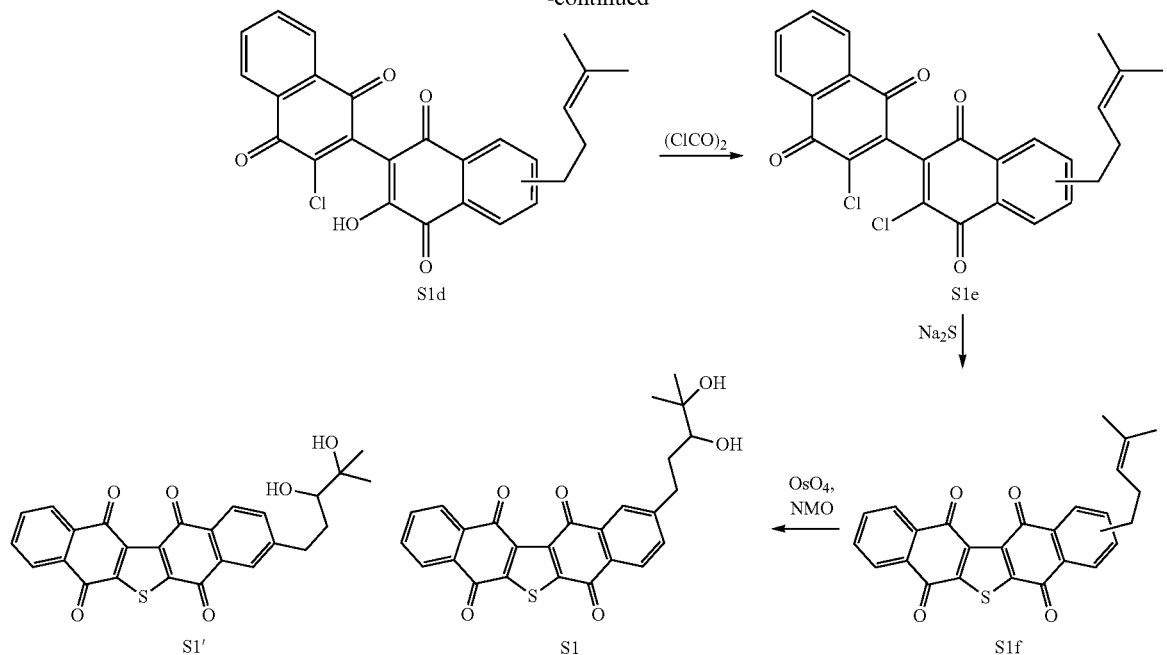

Preparation of compound S1 and S1'

Example 21

2-chloro-7-(4-methylpent-3-enyl)naphthalene-1,4-dione (S1a, 2.78 g, 10.1 mmol), prepared in accordance to procedure described in publication, Bioorganic & Medicinal Chemistry, 14 (21), 7231-7240 (2006), was added to a mixture of MeOH (100 mL) and aqueous NaOH solution (0.5 M, 100 mL) at 25° C. The reaction mixture was stirred for 1 hour. Upon completion, water (100 mL) was added and the pH of the reaction was adjusted to 4-5 by addition of 2N HCl. MeOH was then removed under reduced pressure and the resulting mixture was extracted with EtOAc (3×80 mL). The combined organic extracts were washed with brine, dried over $Na_2SO_4$ and concentrated under reduced pressure. The crude S1b was obtained as mixture of regioisomers (2.60 g) and used directly without future purification.

A solution of compound S1b (2.60 g, 10.1 mmol) was dissolved in anhydrous $CH_3CN$ (200 mL). To this solution was added 2,3-dichloro-1,4-naphthalene (S1c, 2.30 g, 10.1 mmol) followed by anhydrous $CsCO_3$ (6.61 g, 20.2 mmol). The reaction was stirred under Ar atmosphere for 16 h before quenching with water (200 mL). The pH of the mixture was adjusted to 2-3 by addition of 2N HCl. $CH_3CN$ was removed under reduced pressure and the resulting mixture was extracted with EtOAc (3×80 mL). The combined organic extracts were washed with brine, dried over $Na_2SO_4$ and concentrated under reduced pressure. The residue obtained Sid was then dissolved in anhydrous DCM (200 mL). To this solution was added oxalyl chloride (1.78 mL, 20.2 mmol) dropwise followed by 5 drops of anhydrous DMF. The reaction mixture was stirred for 4 h at 25° C. under Ar atmosphere before slowly pouring into water (200 mL). The organic layer was separated and the aqueous layer was extracted with DCM (3×60 mL). The combined organic extracts were washed with brine, dried over $Na_2SO_4$ and concentrated under reduced pressure. The residue was passed through a short silica column (elute with DCM, 2000 mL), concentrated under reduced pressure to afford S1e and was used in the next step without future purification.

To a solution of S1e (2.33 g, 4.94 mmol) in THF (330 mL) was added $Na_2S$ (0.77 g, 9.89 mmol) in water (165 mL). The reaction was stirred at 25° C. for 1 h before additional water (100 mL) was added. The organic layer was separated and the aqueous layer was extracted with EtOAc (3×100 mL). The combined organic extracts were washed with brine, dried over $Na_2SO_4$ and concentrated under reduced pressure. The residue was passed through a short silica column (elute with EtOAc, 2000 mL), concentrated under reduced pressure to afford S1f.

The crude material S1f (2.20, 5.16 mmol) was dissolved in acetone-$H_2O$ (100 mL, 3:1 v/v), NMO (1.81 g, 15.5 mmol) and $K_2OsO_4$ (95.0 mg, 0.26 mmol) was added. The reaction was stirred at 25° C. for 16 h. Upon completion, water (100 mL) was added to the reaction and the acetone was removed under reduced pressure. The mixture was extracted with EtOAc (3×60 mL) and the combined organic extracts were washed with brine, dried over $Na_2SO_4$ and concentrated. The crude product was purified by silica flash column chromatography (DCM:MeOH=1000:1 to 100:3, v/v) to afford compound S1 as a yellow solid (1.59 g, 67%). The two regioisomers were separated by RP-HPLC (S1: S1'=3:1). LC-HRMS, m/z 461.1060 $[M+H]^+$; Calcd for $C_{26}H_{21}O_6S^+$: 461.1014.

Synthesis of Seriniquinone Probe (13)

Example 22

The following section provides a description of the methods and spectroscopic data for the synthetic efforts in FIG. 2B. Structures are noted throughout with compound numbers such as 8 defined as a mixture of isomers 8a (major) and 8b (minor), as shown in the structure below. When possible isomers were purified at the last step by HPLC purification.

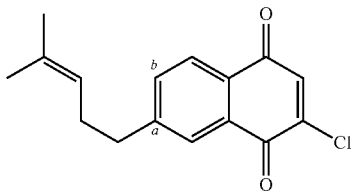

Example 23

2-Chloro-7-(4-methylpent-3-en-1-yl)naphthalene-1,4-dione (6). α-Myrcene (4) (9.24 mL, 67.84 mmol) and 2,5-dichloro-1,4-benzoquinone (5) (12.00 g, 67.84 mmol) were dissolved in benzene (1.4 L). Activated $MnO_2$ (35.38 g, 407.03 mmol) was added and the contents were charged with an Ar atmosphere by repeated degassing (3×). The slurry was brought to a reflux with vigorous stirring. After 48 h, the slurry was cooled to rt and filtered through a pad of $SiO_2$ (400 g) washing with EtOAc (3×500 mL). The resulting solutions were combined, the solvent removed via rotary evaporation, and the residue was purified by flash chromatography (hexanes to 2:1 hexanes/EtOAc) to provide chloronapthylquinone 6 (15.21 g, 82%), as a yellow wax. Over multiple batches the isomer mixture of 2-chloro-7-(4-methylpent-3-en-1-yl)naphthalene-1,4-dione (6a): 2-chloro-6-(4-methylpent-3-en-1-yl)naphthalene-1,4-dione (6b) deviated from 2.5:1 to 9:1. Higher yields of the major isomer, 2-chloro-7-(4-methylpent-3-en-1-yl)naphthalene-1,4-dione (8a) were obtained when the $MnO_2$ was vigorously stirred and did not settle in the reaction flask, as this was often difficult to control at larger scale, different mixtures were obtained.

Chloronapthylquinone 6: $^1$H-NMR ($CDCl_3$, 400 MHz) δ 8.08* (d, J=7.5 Hz, 1H), 7.97 (d, J=8.0 Hz, 1H), 7.96 (d, J=1.8 Hz, 1H), 7.89* (d, J=1.8 Hz, 1H), 7.84* (dd, J=1.8, 8.0 Hz, 1H), 7.58 (dd, J=1.8, 8.0 Hz, 1H), 7.50 (dd, J=1.8, 8.0 Hz, 1H), 7.19* (s, 1H), 7.17 (s, 1H), 5.21* (m, 1H), 5.19 (m, 1H), 2.78 (t, J=2.7 Hz, 2H), 2.34 (m, 2H), 1.67* (s, 3H), 1.66 (s, 3H), 1.52 (s, 3H); $^{13}$C-NMR ($CDCl_3$, 100 MHz) δ 183.1*, 182.5, 178.1, 177.9*, 150.3*, 149.7, 146.5*, 146, 135.8*, 135.8, 134.6, 134.4*, 133.4*, 133.2, 131.8*, 131.1, 129.7, 129.3*, 127.7*, 127.3, 126.8, 126.7*, 122.4*, 122.4, 36.3*, 36.1, 29.3*, 29.2, 25.7*, 25.6, 17.7*, 17.6; FTIR (film) vmax 3060, 1682, 1665, 1600, 1570, 1060, 820 cm$^{-1}$; ESI-MS m/z 275.11 [M+H]$^+$; HR-ESI-MS m/z calcd. for $C_{16}H_{16}ClO_2$ [M+H]+: 275.0833, found 275.0827. Compound 6 was isolated as a mixture of isomers 6a:6b with * denoting the minor isomer (6b).

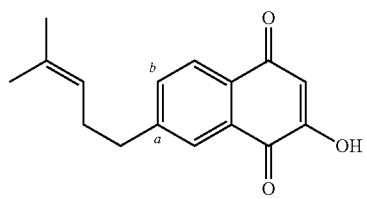

Example 24

2-Hydroxy-7-(4-methylpent-3-en-1-yl)naphthalene-1,4-dione (7). Chloronapthyl-quinone 6 (15.5 mL, 56.3 mmol) was dissolved in MeOH (565 mL). A 0.5 M solution of aq. NaOH (565 mL) was added, and the mixture was brought to reflux. After 1 h, TLC analysis indicated that the reaction was complete. The mixture was cooled briefly (15 min) and then poured on ice (0.5 kg). Once the ice melted, the pH was adjusted to 4.5 by the addition of 2 N HCl. The aqueous mixture was extracted with EtOAc (2×1 L). The organic layers were then combined, washed with brine (500 mL), dried over $Na_2SO_4$, and concentrated via rotary evaporation. The crude product was purified by flash chromatography (hexanes to 1:1 hexanes/EtOAc) to provide the hydroxynapthylquinone 7 (13.9 g, 96%) as a red wax. Compound 7 was obtained a mixture of major isomer, 2-hydroxy-7-(4-methylpent-3-en-1-yl)naphthalene-1,4-dione (7a), and minor isomer 2-hydroxy-6-(4-methylpent-3-en-1-yl)naphthalene-1,4-dione (7b), respectively.

Hydroxynapthylquinone 7: $^1$H-NMR ($CD_3OD$, 500 MHz) δ 7.88 (d, J=7.9 Hz, 1H), 7.85* (d, J=7.9 Hz, 1H), 7.81 (d, J=7.8 Hz, 1H), 7.78 (s, 1H), 7.76 (s, 1H), 7.51 (dd, J=1.9, 8.1 Hz, 1H), 7.45* (dd, J=1.8, 7.8 Hz, 1H), 7.43 (d, J=7.3 Hz, 1H), 5.13* (t, J=7.2 Hz, 1H), 5.10 (t, J=7.2 Hz, 1H), 2.68 (m, 2H), 2.28 (m, 2H), 1.63* (s, 3H), 1.62 (s, 3H), 1.49* (s, 3H), 1.47 (s, 3H); FTIR (film) vmax 3350, 1670, 1650, 1600, 1570, 985, 850 cm$^{-1}$; ESI-MS m/z 257.14 [M+H]$^+$; HR-ESI-MS m/z calcd. for $C_{16}H_{17}O_2$ [M+H]$^+$: 257.1172, found 257.1171. Compound 7 was isolated as a mixture of isomers 7a:7b with * denoting the minor isomer (7b).

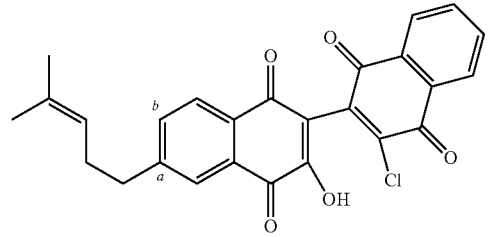

Example 25

3'-Chloro-3-hydroxy-6-(4-methylpent-3-en-1-yl)-[2,2'-binaphthalene]-1,1',4,4'-tetraone (8). This reaction was optimally conducted with batches at a 20-50 mmol scale. Hydroxynapthylquinone 7 (10.13 g, 39.5 mmol) and 2,3-dichloro-1,4-naphthoquinone (2) (9.87 g, 43.4 mmol) was dissolved in anhydrous $CH_3CN$ (810 mL). The flask was charged with an Ar atmosphere by repeated degassing (3×). $CsCO_3$ (25.8 g, 79.1 mmol) was added and the contents were recharged with an Ar atmosphere by repeated degassing (3×). The flask was wrapped in foil (to exclude light) and the slurry was stirred at rt. After 96 h, 2 N HCl was added until the pH was 2. The mixture was diluted with $H_2O$ (100 mL) and extracted with EtOAc (3×500 mL). The organic layers were then combined, washed with water (100 mL) then brine (200 mL), dried over $Na_2SO_4$, and concentrated via rotary evaporation. The crude product was dried by azeotropic removal of benzene (3×100 mL), and used directly for the next step. Samples of pure adduct 8 could be obtained by flash chromatography using a column coated with oxalic acid. This silica gel column was prepared by treating the silica gel with a saturated solution of oxalic acid in methanol for 1 h at rt, loading the column, then washing the column sequentially with 4:1 EtOAc/MeOH, EtOAc, 2:1 hexanes/EtOAc and hexanes. The column was dried with airflow.

Flash chromatography (hexanes to EtOAc) on this treated SiO$_2$ provided a red wax 8. Adduct 8 was obtained as a mixture of a major isomer, 3'-chloro-3-hydroxy-6-(4-methylpent-3-en-1-yl)-[2,2'-binaphthalene]-1,1',4,4'-tetraone (8a) and minor isomer 3'-chloro-3-hydroxy-7-(4-methylpent-3-en-1-yl)-[2,2'-binaphthalene]-1,1',4,4'-tetraone (8b).

Adduct 8: $^1$H-NMR (CDCl$_3$, 400 MHz) δ 8.24 (m, 1H), 8.15 (m, 1H), 8.08 (d, J=8.9 Hz, 1H), 8.00 (d, J=1.8 Hz, 1H), 7.80 (m, 2H), 7.66 (bs, 1H), 7.64 (dd, J=1.8, 7.9 Hz, 1H), 5.13 (tp, J =7.2, 1.4 Hz, 1H), 2.80 (d, J=7.6 Hz, 1H), 2.37 (q, J=7.3 Hz, 1H), 1.69 (s, 3H), 1.55 (s, 3H); $^{13}$C-NMR (CDCl3, 125 MHz) δ 179.9, 179.7, 177.3, 177.1, 176.2, 150.2, 145.2, 145.1, 145.0, 143.7, 140.1, 139.9, 135.1, 134.9, 134.8, 134.7, 133.6, 133.5, 131.6, 131.6, 131.4, 131.3, 131.1, 129.6, 128.0, 128.0, 127.8, 127.7, 127.7, 127.5, 122.5, 36.3, 29.4, 25.8, 17.9.

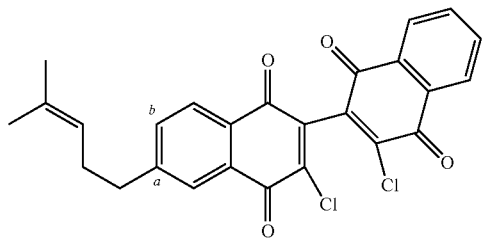

Example 26

3,3'-Dichloro-6-(4-methylpent-3-en-1-yl)-[2,2'-binaphthalene]-1,1',4,4'-tetraone (9). This reaction was optimally conducted directly after preparation of 8. Crude and dried adduct 8 (39.5 mmol) was dissolved in dry CH$_2$Cl$_2$ (1.2 L). After cooling to 0 OC, neat oxalyl chloride (8.5 mL, 98.8 mmol) was added via syringe. Over 45 min, anhydrous N,N-dimethylformamide (15.3 mL, 197.7 mmol) was added in a drop wise fashion so that the temperature of the reaction mixture remained at 0-5° C. After the addition was complete, the mixture was warmed to rt. The flask was wrapped in foil (to exclude light) and stirred at rt. After 12 h, H$_2$O (100 mL) was added and the mixture was extracted with CH$_2$Cl$_2$ (3×250 mL). The organic layers were then combined, washed with brine (200 mL), dried over Na$_2$SO$_4$, and concentrated via rotary evaporation. The crude product was purified by flash chromatography (hexanes to 2:1 hexanes/EtOAc). Recrystallization from hexanes/CH$_2$Cl$_2$ provided dichloride 9 (14.2 g, 77% in two steps from 7), a yellow-orange crystalline material.

Dichloride 9: $^1$H-NMR (CDCl$_3$, 500 MHz) δ 8.25 (m, 1H), 8.15 (m, 1H), 8.05* (s, 1H), 8.05 (s, 1H), 8.03 (s, 1H), 7.94* (d, J=1.8 Hz, 1H), 7.84 (m, 1H), 7.83 (s, 1H), 7.82* (m, 1H), 7.62* (dd, J=1.8, 8.0 Hz, 1H), 7.61 (dd, J=1.8, 8.0 Hz, 1H), 5.12 (m, 1H), 2.82 (t, J=7.6 Hz, 2H), 2.79* (t, J=7.8 Hz, 2H), 2.37 (q, J=7.8 Hz, 2H), 1.68 (d, J=1.5 Hz, 3H), 1.67* (d, J=1.4 Hz, 3H), 1.55 (d, J=1.4 Hz, 3H), 1.54* (d, J=1.3 Hz, 3H); $^{13}$C-NMR (CDCl$_3$, 125 MHz) δ 180.2, 179.9, 179.7, 177.3, 177.1, 176.8, 150.8, 150.5, 145.3, 145.2, 145.1, 145.0, 140.0, 140.0, 139.9, 139.7, 135.1, 134.9, 134.9, 134.7, 133.6, 133.5, 131.6, 131.5, 131.4, 131.3, 129.5, 129.3, 128.0, 128.0, 127.8, 127.7, 127.7, 127.5, 127.4, 122.5, 122.5, 36.4, 36.3, 29.4, 25.8, 17.9; ESI-MS m/z 465.08 [M+H]$^+$; HR-ESI-MS m/z calcd. for C$_{26}$H$_{19}$Cl$_2$O$_5$ [M+H]$^+$: 447.0994, found 447.0992. Dichloride 9 existed as a mixture of isomers with the minor isomer is noted by a *.

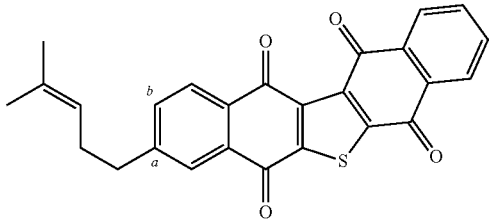

Example 27

3-(4-Methylpent-3-en-1-yl)dinaphtho[2,3-b:2',3'-d]thiophene-5,7,12,13-tetraone (10). This reaction was optimally conducted at batches of 5-10 mmol scale. Dichloride 9 (2.33 g, 4.94 mmol) was dissolved in THF (330 mL). Na$_2$S (770 mg, 9.89 mmol) dissolved in H$_2$O (165 mL) was added at rt. The reaction was stirred at rt for 1 h before addition of water (100 mL). The suspension was extracted with EtOAc (3×100 mL). The organic layers were combined, washed with brine (5 mL), dried over Na$_2$SO$_4$, filtered through a pad of silica gel (100 g) washing with EtOAc (2000 mL). The combined organic washes were concentrated via rotary evaporation. The crude product was used directly for the next stage. Analytical samples were purified by flash chromatography (hexanes to 1:1 hexanes/EtOAc) to provide the alkene 10. This compound was rather unstable and was best processed immediately after preparation (significant decomposition observed on pure material after 1 month of storage at −20° C.

Alkene 10: $^1$H-NMR (CDCl$_3$, 500 MHz) δ 8.03 (m, 1H), 8.22 (m, 2H), 8.12* (m, 1H), 8.08 (s, 1H), 7.82 (m, 1H), 7.77 (m, 1H), 7.65 (m, 1H), 5.12 (m, 1H), 2.80 (m, 2H), 2.37 (m, 2H), 1.67 (s, 3H), 1.53 (s, 3H); ESI-MS m/z 449.10 [M+Na]$^+$; HR-ESI-MS m/z calcd. for C$_{26}$H$_{18}$O$_4$SNa [M+Na]$^+$: 449.0819, found 449.0817.

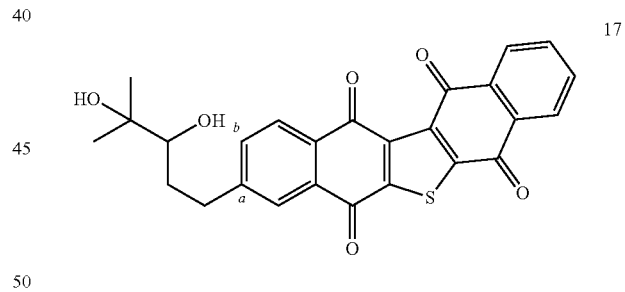

Example 28

3-(3,4-Dihydroxy-4-methylpentyl)dinaphtho[2,3-b:2',3'-d]thiophene-5,7,12,13-tetraone (17). Alkene 10 (2.20, 5.16 mmole) was dissolved in a mixture of acetone (75 mL) and H$_2$O (25 mL). N-Methylmorpholine-N-oxide (1.81 g, 15.50 mmol) and K$_2$OsO$_4$.2 H$_2$O (95.0 mg, 0.26 mmol) were added sequentially as solids. The mixture was stirred at rt. After 16 h, mixture was extracted with EtOAc (3×60 mL). The organic layers were combined, washed with brine (5 mL), dried over Na$_2$SO$_4$, and concentrated via rotary evaporation. The crude product was purified by flash chromatography (1000:1 CH$_2$Cl$_2$/MeOH to 30:1 CH$_2$Cl$_2$/MeOH) to provide diol 15 (1.59 g, 67% over 2 steps). The two isomers 17a and 17b could be separated by RP-HPLC using an isocratic run with 13:7 mixture CH$_3$CN/H$_2$O.

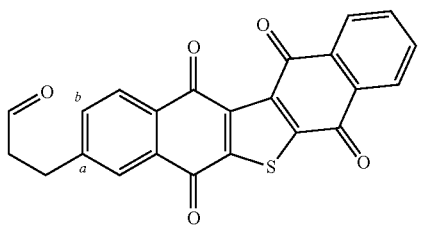

Example 29

3-(5,7,12,13-tetraoxo-5,7,12,13-tetrahydrodinaphtho[2,3-b:2',3'-d]thiophen-3-yl)-propanal (23). Silica gel supported NaIO$_4$ was prepared by dissolving NaIO$_4$ (2.00 g, 5.42 mmol) in H$_2$O (4 mL) heated to 70 OC. Silica gel (230-400 mesh, 8.0 g) was added to this hot solution with vigorous swirling and shaking. After 5 min, the silica gel was collected by filtration, washed with EtOAc (50 mL) and CH$_2$Cl$_2$ (2×50 ml). The silica gel supported NaIO$_4$ was then added to a solution of diol 17 (1.25 g, 2.71 mmol) dissolved CH$_2$Cl$_2$ (65 mL). After stirring at rt for 2 h, the reaction mixture was filtered through Celite® washing with EtOAc (3×50 ml). The washes were collected and concentrated via rotary evaporation to yield aldehyde 16 (1.06 g, 99%) as a yellow solid. Aldehyde 23 was used directly without further purification.

Aldehyde 23: $^1$H-NMR (CDCl$_3$, 400 MHz) δ 9.87 (s, 1H), 8.35 (m, 1H), 8.28 (m, 2H), 8.06 (s, 1H), 7.89 (m, 1H), 7.80 (m, 1H), 7.66 (m, 1H), 3.16 (m, 2H), 2.95 (m, 2H). (HR-ESI-MS m/z calcd. for C$_{23}$H$_{12}$O$_5$SNa [M+Na]$^+$: 423.0298, found 423.0296.

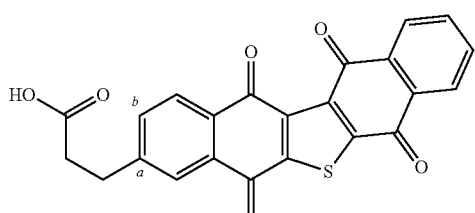

Example 30

3-(5,7,12,13-Tetraoxo-5,7,12,13-tetrahydrodinaphtho[2,3-b:2',3'-d]-thiophen-3-yl)-propanoic acid (11). Oxone (1.86 g, 60.5 mmol) was added to aldehyde 16 (1.21 g, 3.03 mmol) dissolved in DMF (20 mL). The mixture for was stirred for 2 h at rt. Et$_2$O (100 mL) and 1 N HCl (30 mL). The organic layer was washed excessively with water and brine, dried over Na$_2$SO$_4$, and concentrated via rotary evaporation. This material was used without further purification. Analytical samples were purified by flash chromatography (hexanes to 1:1 EtOAc/MeOH) to provide acid 11 (887.1 mg, 98%).

Acid 11: $^1$H-NMR (500 MHz, DMSO-d$_6$) δ 12.19 (bs, 1H), 8.19 (d, 1H), 8.16 (d, 1H), 8.11 (d, 1H), 8.01 (s, 1H), 7.97 (t, 1H), 7.92 (t, 1H), 7.85 (d, 1H), 3.04 (t, 2H), 2.68 (t, 2H). HR-ESI-MS m/z calcd. for C$_{23}$H$_{12}$O$_6$SNa [M+Na]$^+$: 439.02177, found 439.0388.

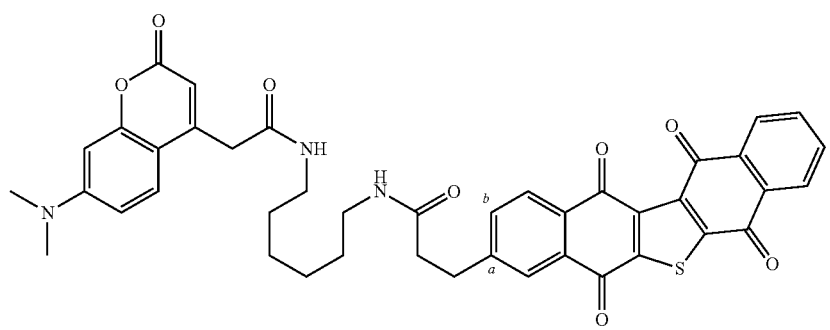

Example 31

N-(6-(2-(7-(dimethylamino)-2-oxo-2H-chromen-4-yl)acetamido)hexyl)-3-(5,7,12,13-tetraoxo-5,7,12,13-tetrahydrodinaphtho[2,3-b:2',3'-d]thiophen-3-yl)propanamide (13). Acid 11 (210.0 mg, 0.50 mmol) and 6-(2-(7-(dimethylamino)-2-oxo-2H-chromen-4-yl)acetamido)hexan-1-aminium chloride (12) (192.6 mg. 0.50 mmol) were dissolved in DMF (1 mL) and dried by rotary evaporation of toluene (3×10 ml). The resulting wax was dissolved in anhydrous DMF (2 mL). EtN$^i$Pr$_2$ (0.35 mL, 2.52 mmol) was added followed by HATU (287.6 mg, 0.75 mmol). A second aliquot of HATU (287.6 mg, 0.75 mmol) was added after stirring at rt for 2 h. The mixture was then stirred for 12 h at rt at which point EtOAc (50 mL) and MeOH (5 mL) were added and the mixture was dried via rotary evaporation. The crude product was purified by flash chromatography (hexanes to 1:1 EtOAc/MeOH) to provide unstable probe 13 (210.5 mg, 57%).

Example 32

Further synthesis of Seriniquinone Derivatives. The synthesis of compounds detailed in Examples 20-33 is set forth schematically in Scheme 17 following.

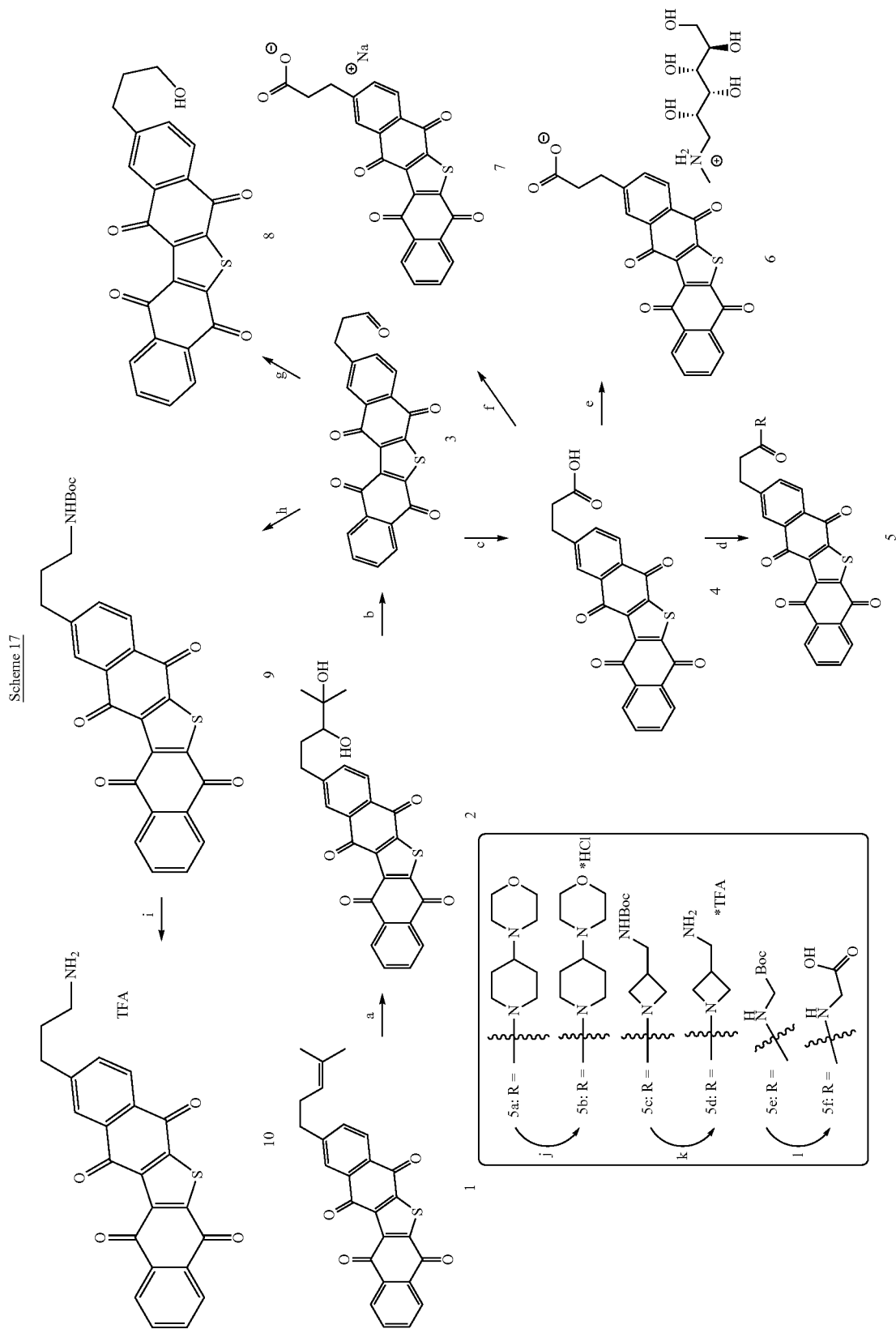

Reagent and conditions for Scheme 1: (a) OsO₄ (cat.), NMO, Acetone-H₂O (3:1 v/v), 16 h, 25° C., 67%; (b) NaIO₄—SiO₂, DCM, 2 h, 25° C., 100%; (c) Oxone, DMF, 2 h, 25° C., 100%; (d) HATU, DIPEA, DMF, 2-3 h, 0 to 25° C., 47-71%; (e) D-glutamine, MeOH, 24 h, 25° C., 34%; (f) NaOMe, MeOH, 2 h, 25° C., 63%; (g) NaBH₄, THF, 0.5 h, −78 to 0° C., 33%; (h) TESH, TFA, NH₂Boc, MeCN, 16 h, 25° C., 48%; (i) TFA-DCM (1:3 v/v), 2 h, 25° C.; (j) 1N HCl, THF, 25° C., 37%; (k) TFA-DCM (1:3 v/v), 1 h, 25° C., 42%; (l) TFA-DCM (1:3 v/v), 1 h, 25° C., 67%.

Example 33

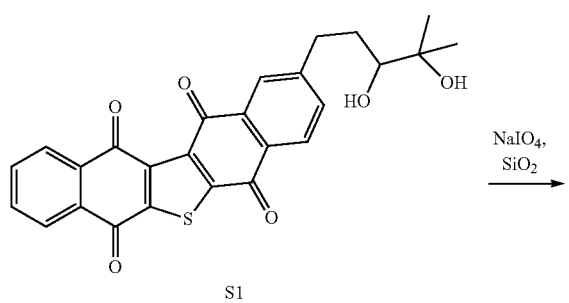

S1

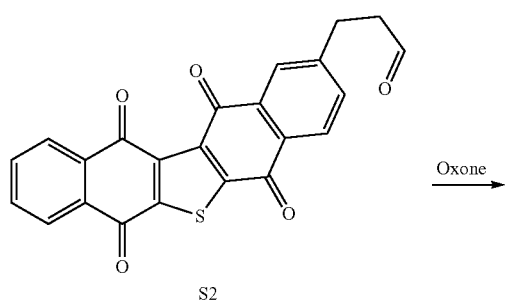

S2

Preparation of compound S2: To a solution of diol S1 (40 mg, 0.087 mmol) in DCM (2 mL) was added silica gel supported NaIO₄ [NaIO₄ (35 mg, 0.16 mmol) dissolved in 0.7 mL of hot water (approximately 70° C.). To the hot solution was added silica gel (230-400 mesh, 140 mg) with vigorous swirling and shaking. The resultant silica gel coated with NaIO₄ was in a powder form. The resulting mixture was stirred at 25° C. for 2 h. Upon completion, the reaction mixture was filtered through Celite® and the solvent was removed under reduced pressure to afford aldehyde S2 (35 mg, 100%) as a yellow solid. Aldehyde S2 was used directly without further purification. LC-HRMS, m/z 401.0478 [M+H]⁺; Calcd for C₂₃H₁₃O₅S⁺: 401.0439.

Example 34

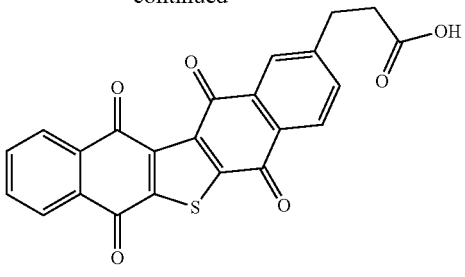

S3

Preparation of compound S3: To a solution of aldehyde S2 (20 mg, 0.05 mmol) in DMF (0.5 mL) was added Oxone® (30 mg, 0.05 mmol). The reaction was stirred at 25° C. for 2 h before 1N HCl (3 mL) was added. The mixture was extracted with EtOAc (3×10 mL) and the combined organic layers were washed excessively with water (5×1 mL), brine (10 mL) and dried over Na₂SO₄. The solvent was removed under reduced pressure to afford compound S3 (20 mg, 100%) as a yellow solid and was used without further purification. LC-HRMS, m/z 417.0412 [M+H]⁺; Calcd for C₂₃H₁₃O₆S⁺: 417.0388.

Example 35

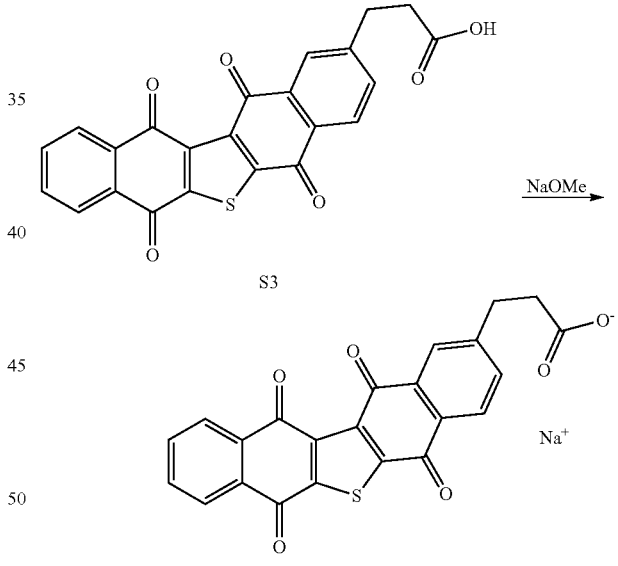

S3

S4

Preparation of compound S4: To a solution of acid S3 (15 mg, 0.036 mmol) in anhydrous MeOH (20 mL) was added NaOMe (0.05 M, 0.72 mL, 0.036 mmol). The reaction mixture was stirred at 25° C. for 2 h under N₂ until all solid dissolved. Upon completion, solvent was removed until the final volume was 2 mL. To this mixture, ether (15 mL) was added with vigorous stirring. The yellow-orange precipitate was isolated by filtration and washed excessively with ether (5×2 mL), then dried under high vacuum. The title compound S4 (10 mg, 63%) was obtained as orange solid. LC-HRMS, m/z 415.0463 [M−H]⁻; Calcd for C₂₃H₁₁O₆S⁻: 415.0276.

Example 36

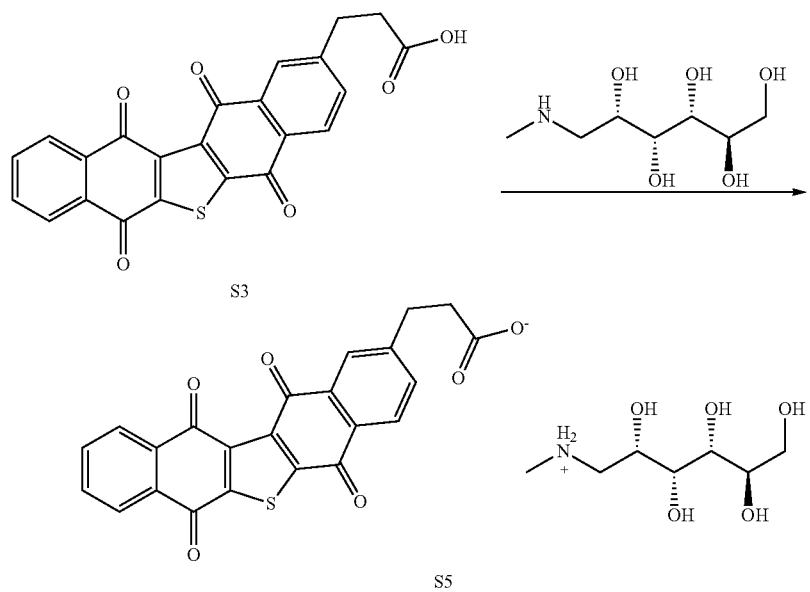

Preparation of compound S5: To a solution of acid S3 (10 mg, 0.024 mmol) in anhydrous MeOH (15 mL) was added N-methyl-D-glucamine (5 mg, 0.024 mmol). The reaction mixture was stirred at 25° C. for 24 h under $N_2$ until all solid dissolved. Upon completion, solvent was removed until the final volume was 2 mL. To this mixture, ether (15 mL) was added with vigorous stirring. The yellow-brown precipitate was isolated by filtration and washed with ether (5×2 mL), then dried under high vacuum. The title compound S5 (5 mg, 34%) was obtained as brown solid. LC-HRMS, m/z 415.0463 [M−H]$^-$; Calcd for $C_{23}H_{11}O_6S^-$: 415.0276.

Example 37

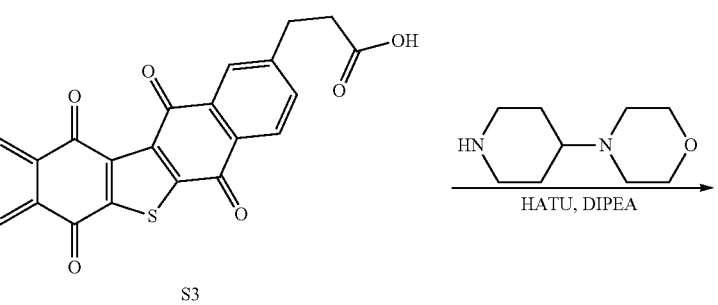

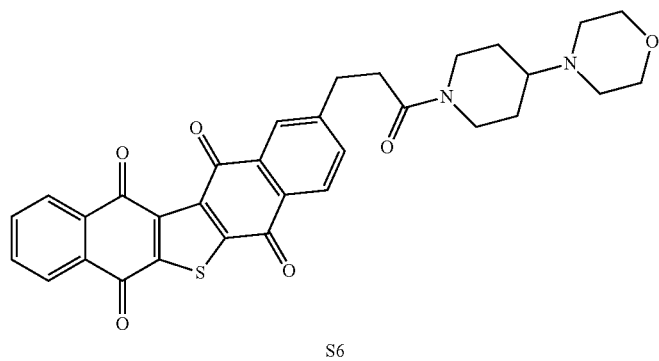

Preparation of compound S6: To a solution of acid S3 (20 mg, 0.048 mmol) in anhydrous DMF (0.5 mL) was added 4-(piperidin-4-yl)morpholine (16 mg, 0.096 mmol) followed by DIPEA (0.025 mL, 0.144 mmol). The reaction mixture was cooled to 0° C. and HATU (24 mg, 0.062 mmol) was added. Upon complete addition, the reaction was warmed up to 25° C. and stirred for 3 h under $N_2$. The reaction was then quenched with pH 7 buffer (phosphate, 5 mL) and extracted with EtOAc (3×5 mL). The combined organic extracts were washed with water (3 mL) and brine (3 mL), dried over $Na_2SO_4$ and concentrated. The mixture was purified by RP-HPLC (isocratic 70% MeCN in water) to afford title compound S6 (16 mg, 59%) as a yellow solid. LC-HRMS, m/z 569.1751 [M+H]$^+$; Calcd for $C_{32}H_{29}N_2O_6S^+$: 569.1702.

Example 38

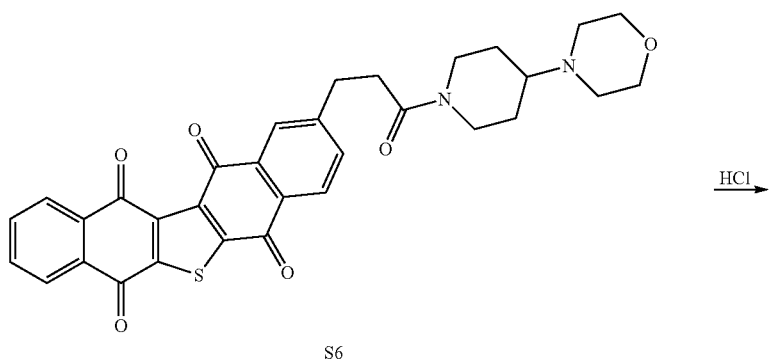

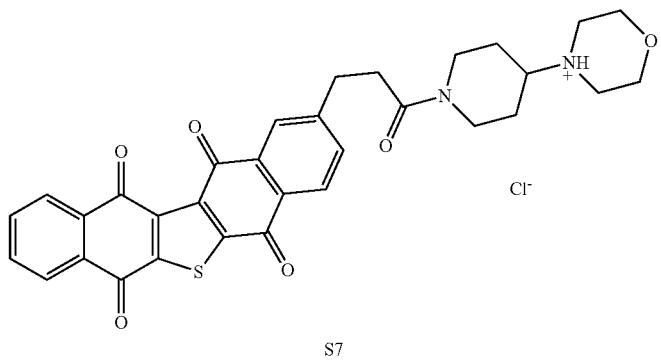

Preparation of compound S7: To a solution of compound S6 (20 mg, 0.035 mmol) in THF (0.3 mL) was added 1N HCl dropwise until pH 4 was obtained. Diethyl ether (10 mL) was added to the reaction with vigorous stirring. The yellow precipitate formed was isolated by filtration and washed with ether (5×2 mL), then dried under high vacuum. The title compound 5b (8 mg, 37%) was obtained as a brown-yellow solid. LC-HRMS, m/z 569.1751 [M+H]$^+$; Calcd for $C_{32}H_{29}N_2O_6S^+$: 569.1702.

Example 39

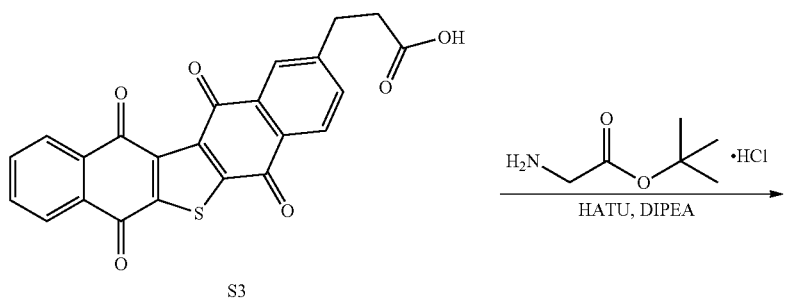

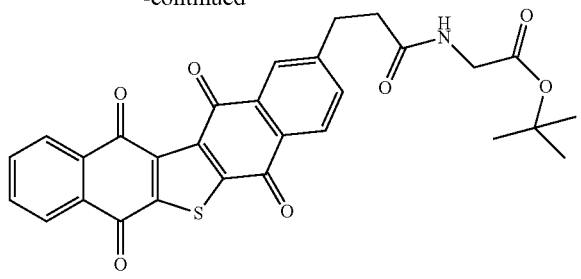

S8

Preparation of compound S8: To a solution of acid S3 (10 mg, 0.024 mmol) in anhydrous DMF (0.25 mL) was added glycine tert-butyl ester hydrochloride (8 mg, 0.096 mmol) followed by DIPEA (0.020 mL, 0.12 mmol). The reaction mixture was cooled to 0° C. and HATU (12 mg, 0.031 mmol) was added. Upon complete addition, the reaction was warmed to 25° C. and stirred for 2 h under $N_2$. The reaction was then quenched with pH 7 buffer (phosphate, 5 mL) and extracted with EtOAc (3×5 mL). The combined organic extracts were washed with water (3 mL) and brine (3 mL), dried over $Na_2SO_4$ and concentrated. The mixture was purified by silica flash column chromatography (DCM:MeOH=1000:1 to 100:1) to afford title compound S8 (6 mg, 47%) as a yellow solid. LC-HRMS, m/z 530.1270 [M+H]$^+$; Calcd for $C_{29}H_{24}NO_7S^+$: 530.1229.

Example 40

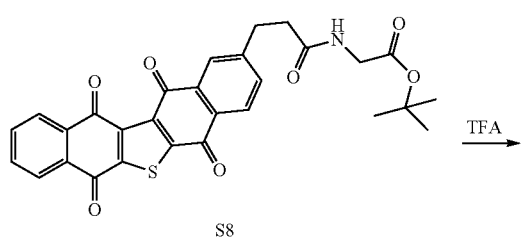

S8

→ TFA

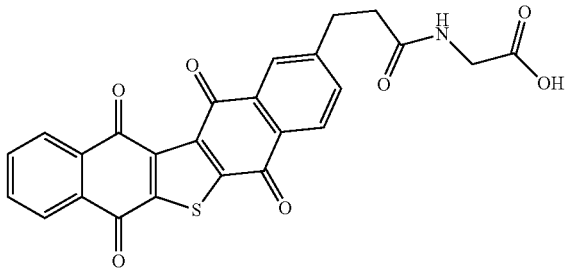

S9

Preparation of compound S9: Compound S8 (10 mg, 0.019 mmol) was dissolved in DCM-TFA (3:1, 1.0 mL) at 25° C. and stirred for 1 h. Upon completion, the reaction was concentrated and purified by silica flash chromatography (DCM:MeOH=1000:1 to 50:1) to afford the title compound S9 (6 mg, 67%) as a yellow solid. LC-HRMS, m/z 474.0648 [M+H]$^+$; Calcd for $C_{25}H_{16}NO_7S^+$: 474.0603.

Example 41

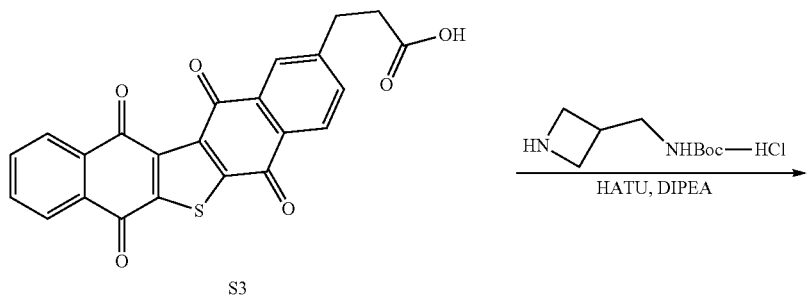

S3 → HATU, DIPEA

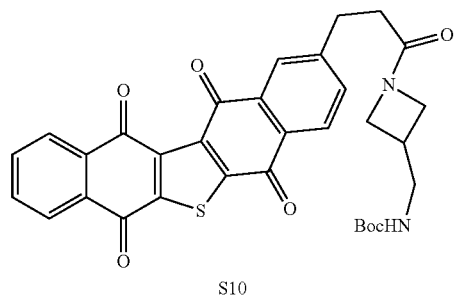

S10

Preparation of compound S10: To a solution of acid S3 (45 mg, 0.11 mmol) in anhydrous DMF (1.5 mL) was added tert-butyl azetidin-3-ylmethylcarbamate hydrochloride (53 mg, 0.14 mmol) followed by DIPEA (0.1 mL, 0.54 mmol). The reaction mixture was cooled to 0° C. and HATU (48 mg, 0.216 mmol) was added. Upon complete addition, the reaction as warmed up to 25° C. and stirred for 2 h under $N_2$. The reaction was then quenched with pH 7 buffer (phosphate, 10 mL) and extracted with EtOAc (3×15 mL). The combined organic extracts were washed with water (5 mL) and brine (5 mL), dried over $Na_2SO_4$ and concentrated. The mixture was purified by silica flash column chromatography (DCM: MeOH=1000:1 to 100:1) to afford title compound S10 (45 mg, 71%) as a yellow solid. LC-HRMS, m/z 607.1433 [M+Na]$^+$; Calcd for $C_{32}H_{28}N_2O_7SNa^+$: 607.1617.

Example 42

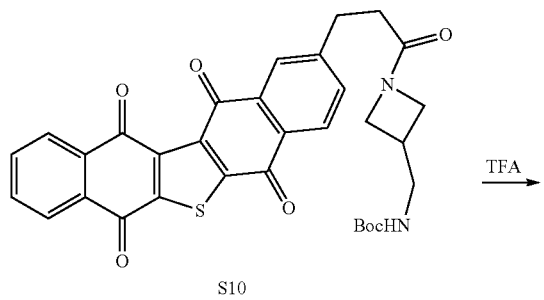

S10

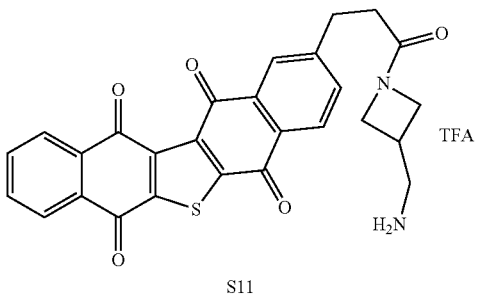

S11

Preparation of compound S11: Amide S10 (20 mg, 0.034 mmol) was dissolved in DCM-TFA (3:1, 1.0 mL) at 25° C. and stirred for 1 h. Upon completion, diethyl ether (10 mL) was added with vigorous stirring. The yellow precipitate was isolated by filtration, washed excessively with ether (5×2 mL) and dried under high vacuum. The title compound S11 (7 mg, 42%) was obtained as a yellow solid. LC-HRMS, m/z 485.1211 [M+H]$^+$; Calcd for $C_{27}H_{21}N_2O_5S^+$: 485.1126.

Example 43

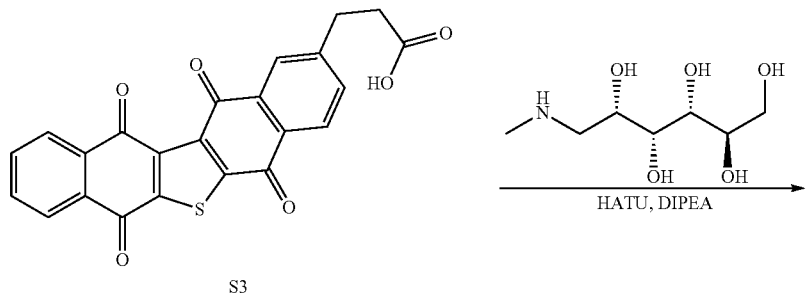

S3

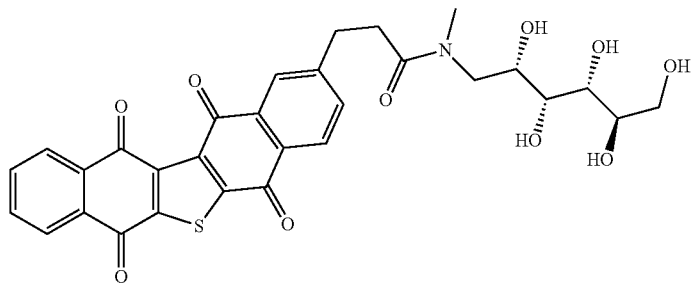

S12

Preparation of compound S12: To a solution of acid S3 (10 mg, 0.024 mmol) in anhydrous DMF (0.25 mL) was added N-methyl-glucamine (9.5 mg, 0.048 mmol) followed by DIPEA (0.013 mL, 0.072 mmol). The reaction mixture was cooled to 0° C. and HATU (12 mg, 0.031 mmol) was added. Upon complete addition, the reaction as warmed up to 25° C. and stirred for 2 h under $N_2$. The DMF was removed under reduced pressure and the mixture was purified by silica flash column chromatography (DCM:MeOH=1000:1 to 100:1) to afford the title compound S12 (9 mg, 63%) as a yellow-brown solid. LC-HRMS, m/z 594.1439 [M+H]$^+$; Calcd for $C_{30}H_{28}NO_{10}S^+$: 594.1389.

Example 44

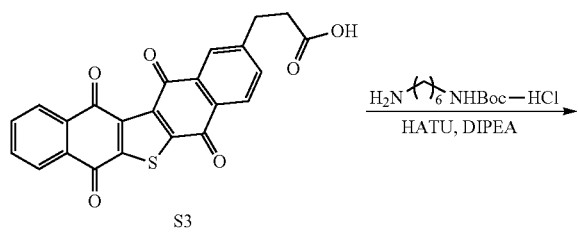

Preparation of compound S13: To a solution of acid S3 (10 mg, 0.024 mmol) in anhydrous DMF (0.5 mL) was added 1,6-hexadiamine hydrochloride (9.2 mg, 0.036 mmol) followed by DIPEA (0.013 mL, 0.072 mmol). The reaction mixture was cooled to 0° C. and HATU (48 mg, 0.22 mmol) was added. Upon complete addition, the reaction as warmed up to 25° C. and stirred for 2 h under $N_2$. The reaction was then quenched with pH 7 buffer (phosphate, 5 mL) and extracted with EtOAc (3×10 mL). The combined organic extracts were washed with water (5 mL) and brine (5 mL), dried over $Na_2SO_4$ and concentrated. The mixture was purified by silica flash column chromatography (DCM:MeOH=1000:1 to 100:1) to afford title compound S13 (12 mg, 81%) as a bright yellow solid. LC-HRMS, m/z 637.1986 [M+Na]$^+$; Calcd for $C_{34}H_{34}N_2O_7SNa^+$: 637.2087.

Example 45

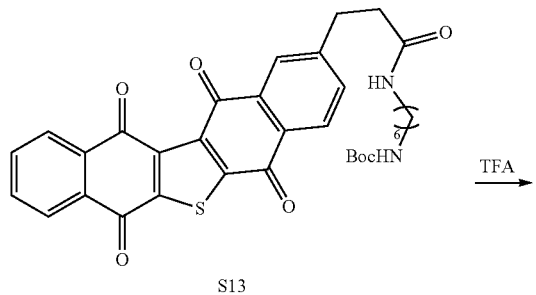

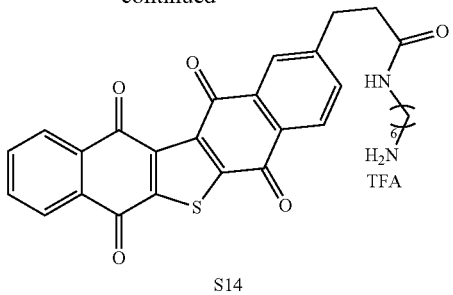

Preparation of compound S14: Amide S13 (20 mg, 0.034 mmol) was dissolved in DCM-TFA (3:1, 0.2 mL) at 25° C. and stirred for 1 h. Upon completion, diethyl ether (10 mL) was added with vigorous stirring. The yellow precipitate was isolated by filtration, washed excessively with ether (5×2 mL) and dried under high vacuum. The title compound S14 (5 mg, 41%) was obtained as a yellow solid. LC-HRMS, m/z 515.1627 [M+H]$^+$; Calcd for $C_{29}H_{27}N_2O_5S^+$: 515.1596.

Example 46

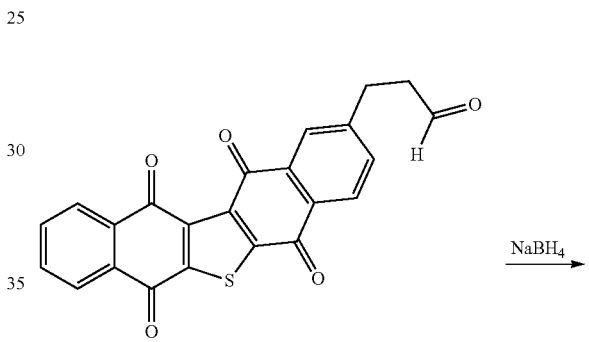

Preparation of compound S15: To a solution of aldehyde S2 (10 mg, 0.018 mmol) in anhydrous THF (4 mL) was added $NaBH_4$ (3 mg dissolved in 1 mL of anhydrous MeOH) dropwise at −78° C. over 5 min. The reaction was stirred for an additional 20 min before another portion of $NaBH_4$ (3 mg dissolved in 1 mL of anhydrous MeOH) was added. The reaction was then warmed up to 0° C. and stirred for an additional 30 min under $N_2$ before pH 7 buffer (phosphate, 5 mL) was added. The reaction was warmed to 25° C. and diluted with EtOAc (10 mL), washed with water (5 mL) and brine (5 mL), dried over $Na_2SO_4$ and concentrated. The crude product was then purified by silica flash chromatography (DCM:MeOH=1000:1 to 100:1) to afford alcohol S15 (4 mg, 40%) as a bright yellow solid, and 2 mg of aldehyde S2 was recovered. LC-HRMS, m/z 403.0651 [M+H]$^+$; Calcd for $C_{23}H_{15}O_5S^+$: 403.0595.

Example 47

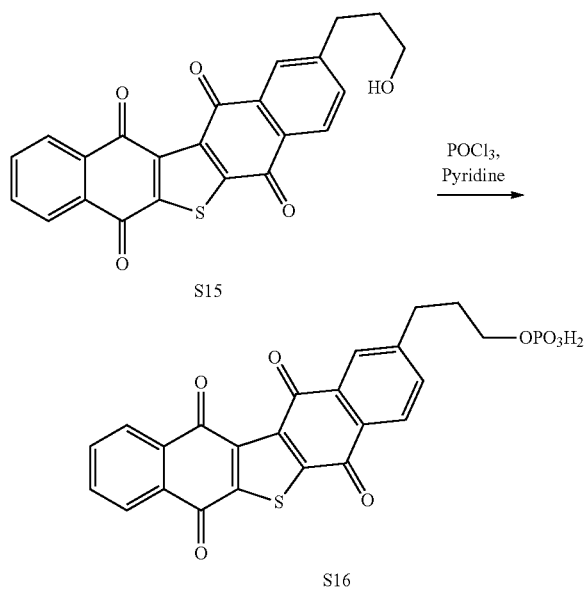

Preparation of compound S16: To a solution alcohol S15 (10 mg, 0.025 mmol) in anhydrous THF-Pyridine (5:1, 600 µL, v/v) was added POCl$_3$ (7 µL, 0.075 mmol) dropwise at 0° C. The reaction was stirred for additional 30 min before poured into 10 mL of ice water. The mixture was extracted with CHCl$_3$ excessively (5×10 mL), dried over Na$_2$SO$_4$ and concentrated. The product was purified by RP-HPLC to afford S16 as a brown-yellow solid (2 mg, 17%). LC-HRMS, m/z 483.0315 [M+H]$^+$; Calcd for C$_{23}$H$_{16}$O$_8$PS$^+$: 483.0225.

Example 48

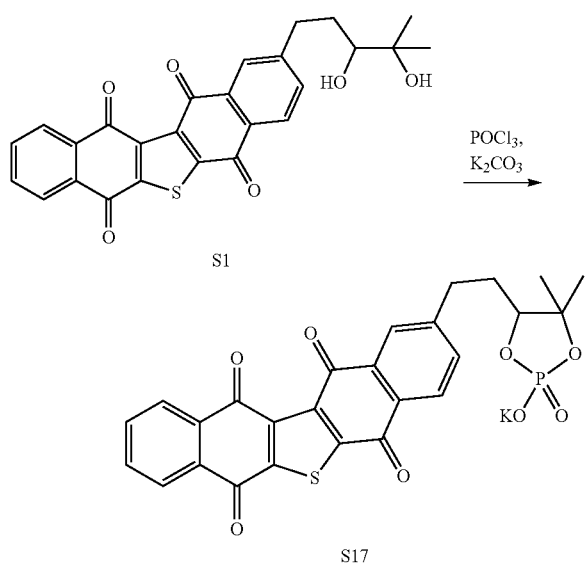

Preparation of compound S17: To a solution of POCl$^3$ (0.040 m, 0.43 mmol) in anhydrous THF-Pyridine (5:1, 600 µL, v/v) was added a solution of diol S1 (20 mg, 0.043 mmol) in anhydrous THF (500 µL) dropwise at −78° C. under Ar. The reaction mixture was stirred for additional 2 h before warmed up to 0° C. The mixture was then poured into 10 mL of ice water and K$_2$CO$_3$ (300 mg, 2.17 mmol) was added. The mixture was washed with diethyl ether (5×5 mL) and freeze-dried. The resulting yellow solid was dissolved in water (5 mL) followed by addition of a 1:1 mixture of CH$_3$CN/Isopropanol (10 mL), followed by vigorous stirring, leading to a liquid-liquid two-phase system. The organic phase, containing the target compound, was collected, dried over Na$_2$SO$_4$ and concentrated to afford S17 as a yellow solid (5 mg, 21%). LC-HRMS, m/z 523.0620 [M+H]$^+$; Calcd for C$_{26}$H$_{19}$O$_8$PS$^+$: 523.0572.

Example 49

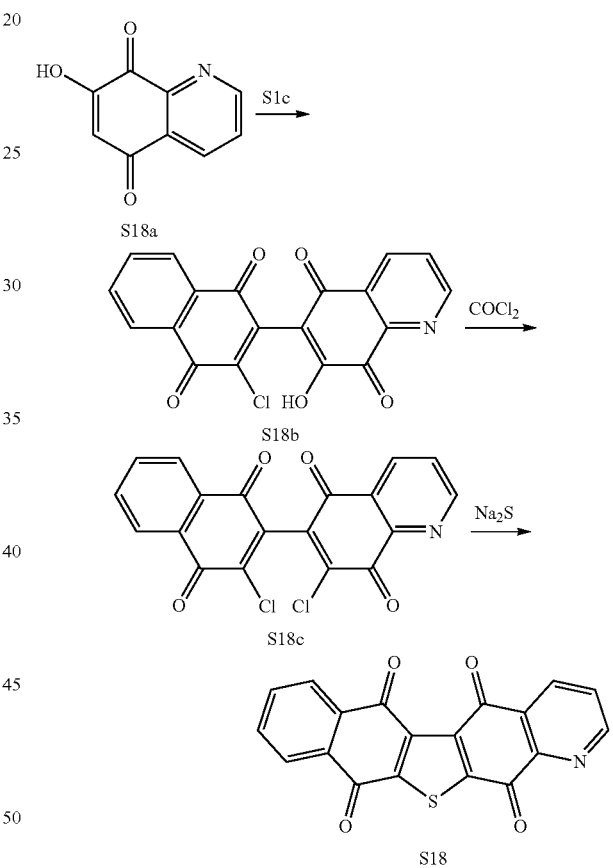

Preparation of compound S18: 7-Hydroxy-5,8-quinoline-quinone (S18a, 0.045 g, 0.26 mmol), prepared in accordance with the procedure described in: *J. Am. Chem. Soc.*, 79, 5024-5026 (1957), was dissolved in anhydrous CH$_3$CN (5 mL). To this solution was added 2,3-dichloro-1,4-naphthalene (S1c, 0.058 g, 1.01 mmol) followed by anhydrous CsCO$_3$ (0.17 g, 0.52 mmol). The reaction was stirred under an Ar atmosphere for 16 h before it was quenched with water (10 mL). The pH of the mixture was adjusted to 2-3 by addition of 2N HCl. CH$_3$CN was removed under reduced pressure and the resulting mixture was extracted with DCM (3×10 mL). The combined organic extracts were washed with brine, dried over Na$_2$SO$_4$ and concentrated under reduced pressure. The crude material obtained S18b was then dissolved in anhydrous DCM (5 mL). To this solution was added oxalyl chloride (0.05 mL, 0.55 mmol) dropwise followed by 2 drops of anhydrous DMF. The reaction mixture was stirred for 4 h at 25° C. under an Ar atmosphere before being slowly poured into water (10 mL). The organic layer was separated and the aqueous layer was extracted with DCM (3×10 mL). The combined organic extracts were washed with brine, dried over $Na_2SO_4$ and concentrated under reduced pressure. The crude product S18c was used without further purification.

The crude S18c was dissolved in THF (3.5 mL), $Na_2S$ (20 mg, 0.26 mmol) in water (1.5 mL) was added slowly. The reaction was stirred at 25° C. for 1 h before additional water (10 mL) was added. The organic layer was separated and the aqueous layer was extracted with EtOAc (3×10 mL). The combined organic extracts were washed with brine, dried over $Na_2SO_4$ and concentrated under reduced pressure. The residue was purified by silica flash chromatography (Hexanes:DCM:MeOH=1:1:0 to 0:1000:1) to afford S18 as a yellow-orange solid (12 mg, 14%, 3 steps). LC-HRMS, m/z 346.0175 $[M+H]^+$; Calcd for $C_{19}H_8NO_4S^+$: 346.0129.

Example 50

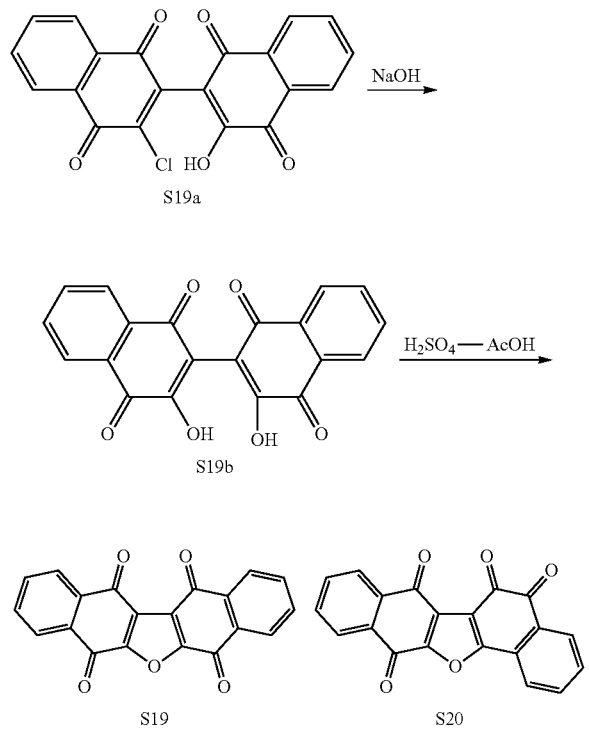

Preparation of compound S19 and S20: The chlorohydroxybiquinone S19a (100 mg, 0.27 mmol), prepared in accordance to the procedure described in Organic Letters, 4 (4), 521-524 (2002), suspended in 4% NaOH (10 mL) was stirred at 25° C. until all solid had dissolved. The solution was washed with diethyl ether (2×5 mL) and then acidified with 3N HCl. The resulting mixture was extracted with DCM (3×10 mL), the combined organic extracts were washed with brine (10 mL), dried over $Na_2SO_4$ and concentrated. The residue was the dihydroxybiquinone S19b obtained as an orange solid. The crude product was used without further purification.

The crude dihydroxybiquinone S19b, obtained as described above, was suspended in glacial acetic acid (8 mL) and 1 mL of a solution of equal parts by volume of concentrated sulfuric acid and water. The mixture was rapidly brought to reflux. After 15 min, the reaction was cooled and the crystalline product that precipitated, was collected and re-dissolved in DCM (50 mL), dried over $Na_2SO_4$ and concentrated. The residue was purified by silica flash chromatography (DCM/Hexanes=50% to 100%) to afford S19 (25 mg, 26% over 2 steps) and S20 (11 mg, 10% over 2 steps) as yellow-orange solids. LC-HRMS, m/z 329.0462 $[M+H]^+$; Calcd for $C_{20}H_9O_5S^+$: 329.0405.

Example 51

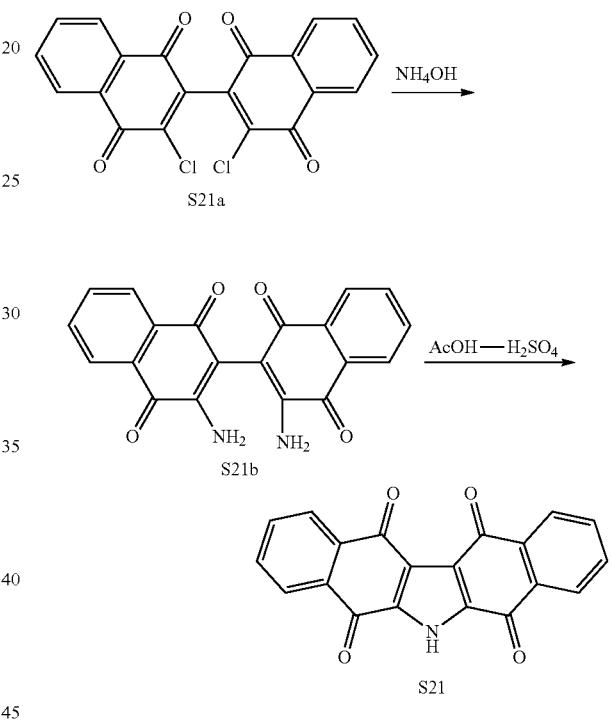

Preparation of compound S21: The dichlorobisquinone S21a (~100 mg, 0.26 mmol), prepared in accordance to procedure described in Organic Letters, 4 (4), 521-524 (2002), was dissolved in anhydrous DCM (10 mL) in a 25-mL pressure tube. Ammonia (0.65 mL, 2M in MeOH) was added at 25° C. and the flask was immediately sealed and stirred for 3 days. The resulting suspension was concentrated, and the precipitate was filtered to yield diaminobisquinone S21b as an orange solid that was used directly to the next step.

The crude diaminobisquinone S21b, obtained above, was suspended in glacial acetic acid (6 mL) and 0.4 mL of a solution of equal parts by volume of concentrated sulfuric acid and water. The mixture was rapidly brought to reflux. After 15 min, the reaction was cooled and the volume was reduced to 2 mL. The residue was purified by silica flash chromatography (DCM:MeOH=1000:1 to 100:3) to afford S21 as a yellow-orange solid (8 mg, 10% 2 steps). LC-HRMS, m/z 328.0614 $[M+H]^+$; Calcd for $C_{20}H_{10}NO_4S^+$: 328.0565.

Example 52

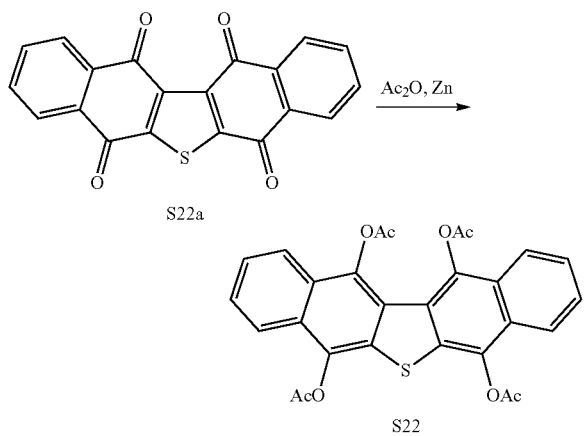

Preparation of compound S22: To a solution of S22a (50 mg, 0.15 mmol) in acetic acid anhydride (1.5 mL) was added Zn-dust (80 mg, 1.23 mmol). The mixture was stirred for 2 h at 90° C. before cooling to 25° C. The un-reacted zinc powder was filtered through Celite@ and ice water (10 mL) was added to the filtrate. The yellow precipitate obtained was filtered, re-dissolved in DCM (20 mL), dried over $Na_2SO_4$ and the DCM concentrated. The crude product was purified by silica gel chromatography (50% to 100% DCM in hexanes) to afford the title compound S22 as a yellow solid (50 mg, 67%). LC-HRMS, m/z 539.0776 [M+Na]$^+$; Calcd for $C_{28}H_{20}O_8SNa^+$: 539.0879.

Example 53

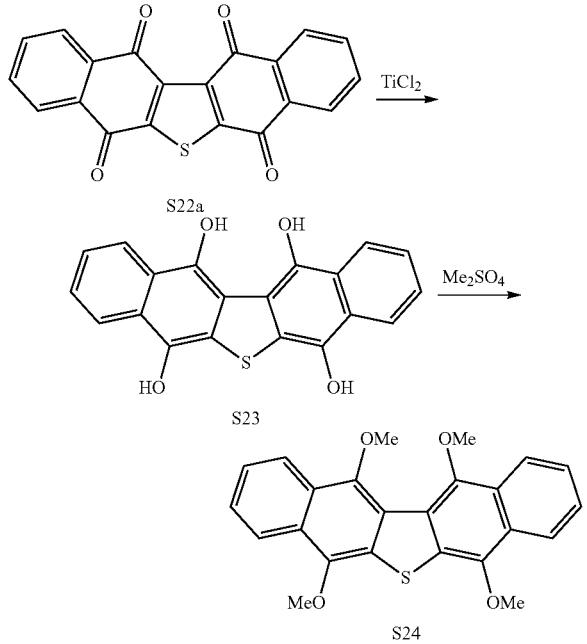

Preparation of compound S23: To a solution of S22a (50 mg, 0.15 mmol) in 95% ethanol (1.5 mL) at 50° C. was added a solution of tin(II) chloride (96 mg, 0.51 mmol) in concentrated HCl (100 µL). The reaction was stirred for an additional 30 min before cold water (10 mL) was added. The green precipitate was filtered, re-dissolved in $CHCl_3$, dried over $Na_2SO_4$ and concentrated. The crude product was purified by using a short silica column (elute with DCM, 1000 mL) and concentrated under reduced pressure to afford S23 (42 mg, 72%). Compound S23 oxidizes rapidly back to S22a in solution, but is more stable as a solid when stored cold.

Preparation of compound S24: To hydroquinone S23 (40 mg, 0.14 mmol) was added dimethyl sulfate (0.20 mL, 2.18 mmol) followed by addition of 50% potassium hydroxide solution (1.5 mL) dropwise at 0° C. The reaction was warmed to 65° C. and stirred for an additional 3 h. Upon completion, the reaction mixture was poured into cold water (20 mL) and extracted with DCM (3×10 mL). The combined organic extracts were washed with saturated $NaHCO_3$ solution (10 mL), brine (10 mL), then dried over $Na_2SO_4$ and concentrated. The residue was purified by silica flash chromatography (50% to 100% DCM in Hexanes) to afford S24 as a yellow solid (27 mg, 68%). LC-HRMS, m/z 427.0977 [M+Na]$^+$; Calcd for $C_{24}H_{20}O_4SNa^+$: 427.1082.

Example 54

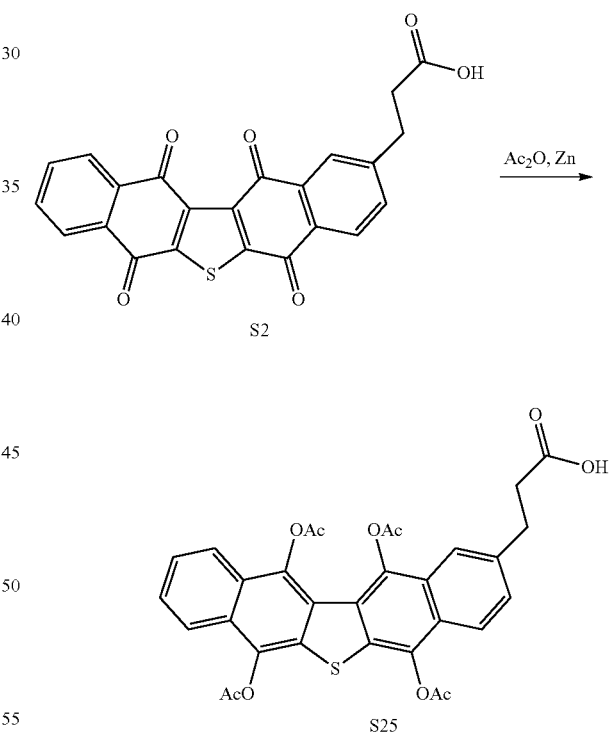

Preparation of compound S25: To a solution of S2 (80 mg, 0.19 mmol) in acetic acid anhydride (1.5 mL) was added Zn-dust (97 mg, 1.48 mmol). The mixture was stirred for 2 h at 90° C. before being cooled to 25° C. The un-reacted zinc powder was filtered through Celite@ and the filtrate was evaporated to dryness under reduced pressure. The residue was purified by silica gel chromatography (DCM: MeOH=1000:1 to 50:1) to afford the title compound S25 as a yellow solid (72 mg, 65%). LC-HRMS, m/z 611.1003 [M+Na]$^+$; Calcd for $C_{31}H_{24}O_{10}SNa^+$: 611.1090.

Example 55

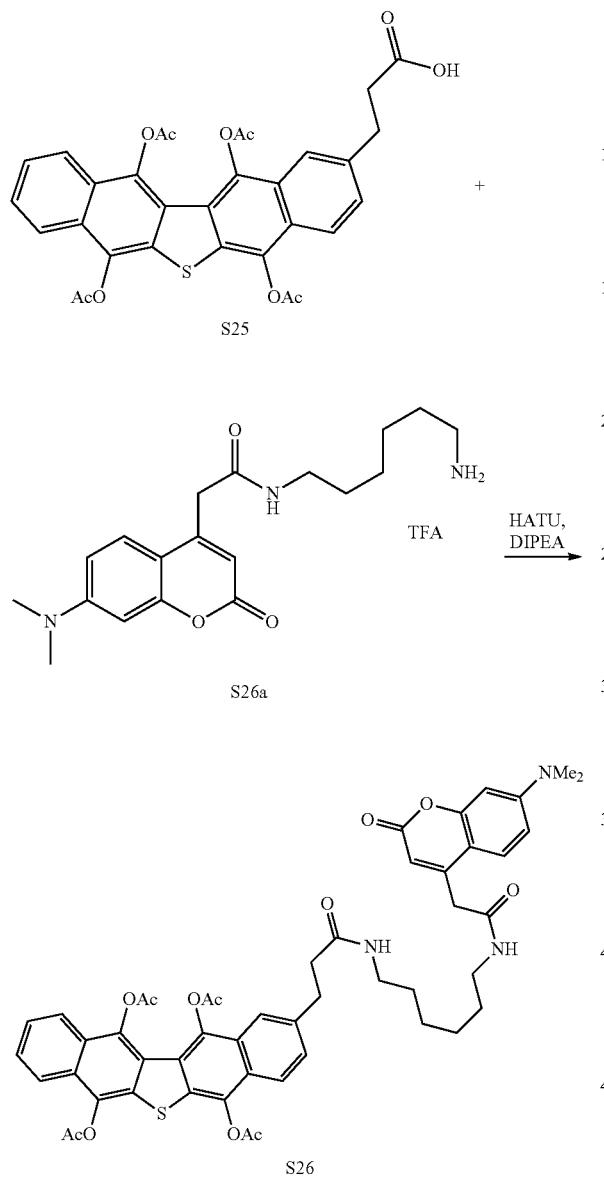

Preparation of compound S26: To a solution of amine trifluoroacetic acid salt S26a (74 mg, 0.12 mmol), prepared in accordance to procedure described in *J. Nat. Prod.* 73 (10), 1659-1666 (2010), was added acid S25 (65 mg, 0.15 mmol) followed by DIPEA (65 μL, 0.37 mmol). The reaction mixture was cooled to 0° C. and HATU (48 mg, 0.216 mmol) was added. Upon complete addition, the reaction was warmed to 25° C. and stirred for 2 h under $N_2$. The reaction was then quenched with pH 7 buffer (phosphate, 10 mL) and extracted with DCM (3×15 mL). The combined organic extracts were washed with water (10 mL) and brine (10 mL), dried over $Na_2SO_4$ and concentrated. The residue was purified by silica flash column chromatography (DCM:MeOH:TEA=1000:1:0.01 to 50:1:0.01) to afford the title compound S26 (32 mg, 29%) as a brownish yellow solid. LC-HRMS, m/z 916.3146 [M+H]$^+$; Calcd for $C_{50}H_{50}N_3O_{12}S^+$: 916.3070.

Example 56

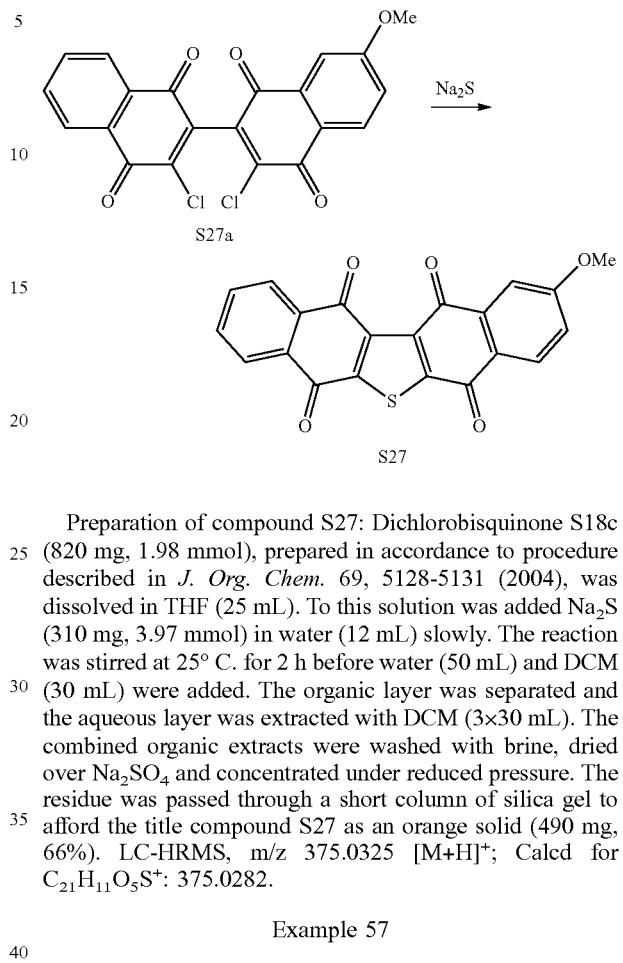

Preparation of compound S27: Dichlorobisquinone S18c (820 mg, 1.98 mmol), prepared in accordance to procedure described in *J. Org. Chem.* 69, 5128-5131 (2004), was dissolved in THF (25 mL). To this solution was added $Na_2S$ (310 mg, 3.97 mmol) in water (12 mL) slowly. The reaction was stirred at 25° C. for 2 h before water (50 mL) and DCM (30 mL) were added. The organic layer was separated and the aqueous layer was extracted with DCM (3×30 mL). The combined organic extracts were washed with brine, dried over $Na_2SO_4$ and concentrated under reduced pressure. The residue was passed through a short column of silica gel to afford the title compound S27 as an orange solid (490 mg, 66%). LC-HRMS, m/z 375.0325 [M+H]$^+$; Calcd for $C_{21}H_{11}O_5S^+$: 375.0282.

Example 57

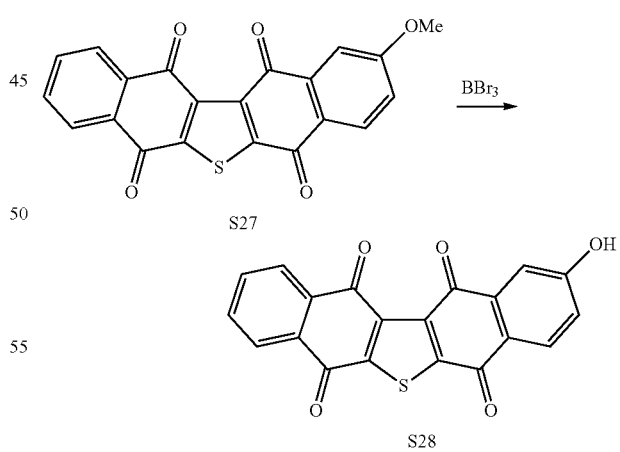

Preparation of compound S28: To a DCM (25 mL) solution of 6-methoxyseriniquinone S27 (400 mg, 1.07 mmol) was added $BBr_3$ (2.67 mL, 1M solution in DCM) slowly at −78° C. The reaction was stirred for 30 min at the same temperature before being warmed to 25° C. for 16 h. Upon completion, the reaction was quenched with pH 7 buffer (phosphate, 50 mL). The organic layer was separated and the aqueous layer was extracted with EtOAc (3×30 mL). The combined organic extracts were washed with water (30 mL) and brine (30 mL), dried over Na$_2$SO$_4$ and concentrated under reduced pressure. The residue was purified by silica flash chromatography (DCM:MeOH=100 to 50:1) to afford 6-hydroxyseriniquinone S28 as a yellow solid (210 mg, 58%). LC-HRMS, m/z 361.0134 [M+H]$^+$; Calcd for C$_{21}$H$_9$O$_5$S$^+$: 361.0126.

Example 58

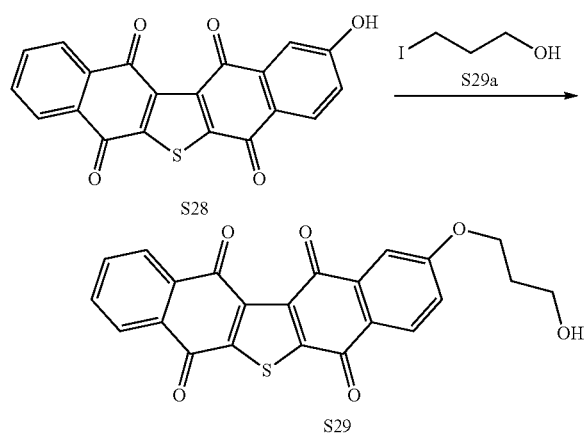

Preparation of compound S29: To a DMF (1 mL) solution of 6-hydroxyseriniquinone S28 (200 mg, 0.56 mmol) was added 3-iodo-1-propanol S29a (53 μL, 0.56 mmol) followed by K$_2$CO$_3$ (153 mg, 1.11 mmol). The reaction was stirred at 25° C. for 24 h before 1N HCl was added to neutralize the reaction. The mixture was extracted with EtOAc (3×10 mL), the combined organic extracts were washed with buffer (10 mL, phosphate pH=7), water (10 mL), brine (10 mL), dried over Na$_2$SO$_4$ and concentrated under reduced pressure. The collected residue was purified by silica flash chromatography (DCM:MeOH=1000:1 to 50:1) to afford alcohol S29 (143 mg, 61%). LC-HRMS, m/z 419.0596 [M+H]$^+$; Calcd for C$_{23}$H$_{15}$O$_6$S$^+$: 419.0545.

Example 59

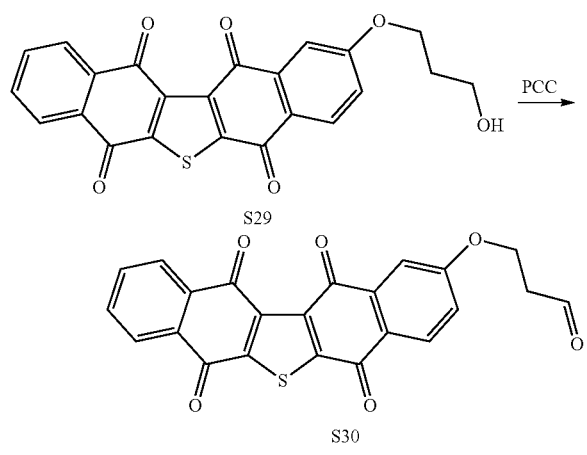

Preparation of compound S30: To a DCM (12 mL) solution of 6-hydroxyseriniquinone S29 (50 mg, 0.12 mmol) was added Celite@ (100 mg) followed by PCC (52 mg, 0.24 mmol) at 0° C. The reaction was then warmed to 25° C. and stirred for 3 h. Upon completion, buffer (15 mL, phosphate pH=7) was added and the organic layer was separated. The aqueous layer was extracted with DCM (3×10 mL) and the combined organic extracts were washed with water (10 mL) and brine (10 mL), dried over Na$_2$SO$_4$ and concentrated under reduced pressure. The collected residue was purified by silica flash chromatography (DCM:hexanes=50% to 100%) to afford aldehyde S30 (26 mg, 52%). LC-HRMS, m/z 438.9264 [M+Na]$^+$; Calcd for C$_{23}$H$_{12}$O$_6$SNa$^+$: 439.0388.

Example 60

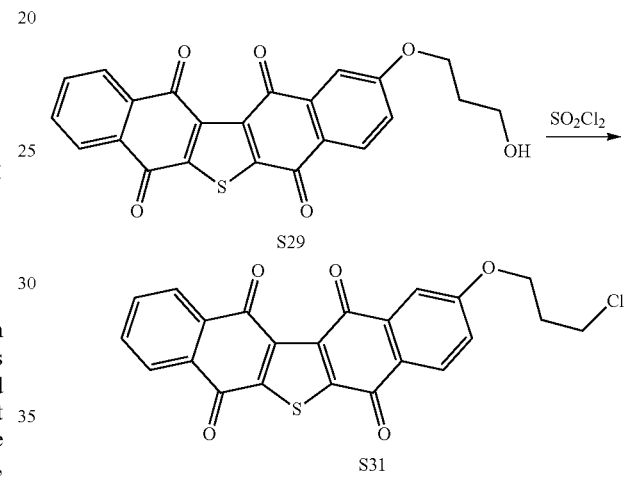

Preparation of compound S31: To a solution of alcohol S29 (5 mg, 0.012 mmol) in DCM (0.3 mL) was added SO$_2$C$_{12}$ (5.0 μL) at 0° C. The reaction was stirred at the same temperature for 2 h before buffer (3 mL, phosphate, pH=7) and DCM (3 mL) were added. The organic layer was separated and the aqueous layer was extracted with DCM (3×3 mL). The combined organic extracts were washed with water (5 mL) and brine (5 mL), dried over Na$_2$SO$_4$ and concentrated under reduced pressure. The collected residue was purified on silica gel coated prep TLC plate (DCM:MeOH=1000:1) to afford aldehyde S31 (2 mg, 38%). LC-HRMS, m/z 437.02442[M+H]$^+$; Calcd for C$_{23}$H$_{14}$ClO$_5$S$^+$: 437.0172.

Example 61

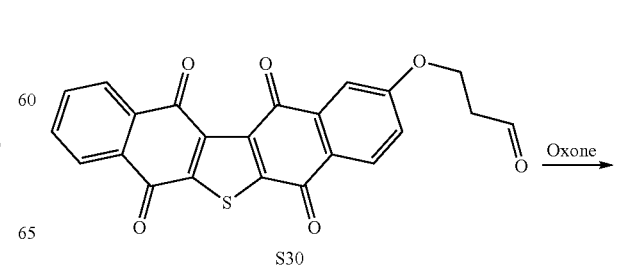

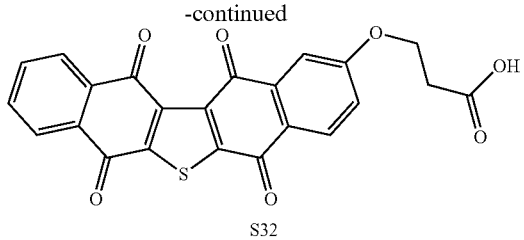

S32

Preparation of compound S32: To a solution of aldehyde S30 (10 mg, 0.024 mmol) in DMF (0.5 mL) was added Oxone® (15 mg, 0.024 mmol). The reaction was stirred at 25° C. for 2 h before 1N HCl (3 mL) was added. The mixture was extracted with EtOAc (3×10 mL) and the combined organic layer was washed excessively with water (5×1 mL), brine (10 mL) and dried over $Na_2SO_4$. The solvent was removed under reduced pressure to afford the title compound S32 (10 mg, 100%) as a yellow solid that was used without further purification. LC-HRMS, m/z 433.0376 $[M+H]^+$; Calcd for $C_{23}H_{13}O_7S^+$: 433.0337.

Example 62

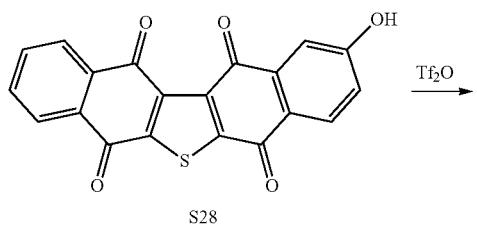

S28

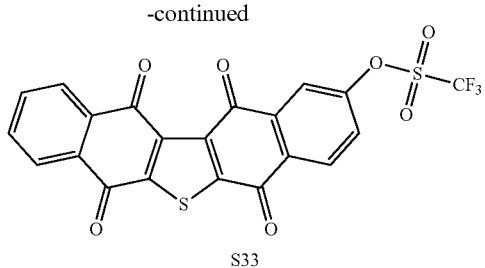

S33

Preparation of compound S33: To a DCM (10 mL) solution of 6-hydroxyseriniquinone S29 (120 mg, 0.33 mmol) was added pyridine (0.80 mL, 0.99 mmol) and a catalytic amount of DMAP. To this solution was added trifluoromethane sulfonic anhydride (0.28 mL, 1.67 mmol) slowly at 0° C. After addition, the mixture was warmed to 25° C. and stirred for 16 h. Upon completion, water (20 mL) was added and the organic layer was separated. The aqueous layer was extracted with DCM (3×10 mL) and the combined organic layer was washed with a 10% HCl solution (15 mL), water (15 mL) and brine (15 mL), dried over $Na_2SO_4$ and concentrated under reduced pressure. The residue was then purified by silica flash chromatography (hexanes: DCM=50% to 100%) to afford the title compound S33 (134 mg, 82%). LC-HRMS, m/z 492.9658 $[M+NH]^+$; Calcd for $C_{21}H_8F_3O_7S_2^+$: 492.9619.

Example 63

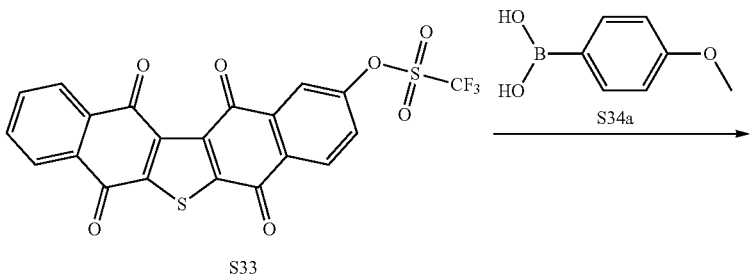

S33

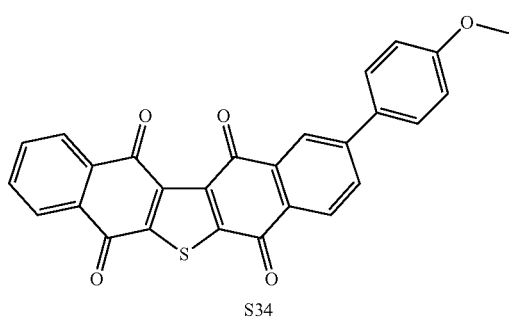

S34

Preparation of compound S34: To a 1,4-dioxane (200 μL) solution of triflate S33 (10 mg, 0.02 mmol) was added Pd(PPh$_3$)$_4$ (2.0 mg, 10% mol) and boric acid (6.2 mg, 0.04 mmol). To this solution was added Na$_2$CO$_3$ solution (0.1 mL, 1M) and the mixture was stirred at 110° C. for 1 h before cooled to 25° C. To the reaction mixture was added buffer (5 mL, phosphate, pH=7) and DCM (5 mL). The organic layer was separated and the aqueous layer was extracted with DCM (3×2 mL). The combined organic extracts were washed with water (5 mL) and brine (5 mL), dried over Na$_2$SO$_4$ and concentrated under reduced pressure. The residue was then purified by silica flash chromatography (hexanes:DCM=50% to 100%) to afford the title compound S34 (3 mg, 33%). LC-HRMS, m/z 451.0638 [M+H]$^+$; Calcd for C$_{27}$H$_{15}$O$_5$S$^+$: 451.0595.

Preparation of Compound 9

Example 64 tert-Butyl-3-(5,7,12,13-tetraoxo-5,7,12,13-tetrahydrodinaphtho[2,3-b:2',3'-d]thiophen-2-yl)propylcarbamate (9). A solution of aldehyde 3 (10 mg, 0.025 mmole), tert-butyl carbamate (9 mg, 0.075 mmole), triethylsilane (0.012 ml, 0.075 mmole) and TFA (4 μl, 0.05 mmole) in MeCN (0.2 ml) was stirred at 25° C. for 16 h. The reaction mixture was diluted with ether (5 ml), washed with saturated NaHCO$_3$ solution (1 ml) and brine (1 ml), dried over Na$_2$SO$_4$ and concentrated. The crude product was purified by silica flash chromatography (DCM:MeOH=1000:1 to 100:1) to afford compound 9 (6 mg, 48%) as a yellow solid. 1H NMR (500 MHz, CDCl$_3$) δ 8.37 (d, 1H), 8.25 (m, 2H), 8.07 (s, 1H), 7.89 (t, 1H), 7.83 (t, 1H), 7.72 (d, 1H), 3.16 (t, 2H), 2.94 (t, 2H), 2.36 (t, 2H), 1.36 (s, 9H); LCMS, m/z 502.0 [M+H$^+$] calcd for C$_{28}$H$_{24}$NO$_6$S$^+$: 502.5.

Preparation of Compound 10

Example 65

2-(3-Aminopropyl)dinaphtho[2,3-b:2',3'-d]thiophene-5,7,12,13-tetraone trifluoroacetic salt (10). Compound 9 (13 mg, 0.026 mmole) was dissolved in DCM-TFA (3:1, 0.4 ml) at 25° C. and stirred for 1 h. Upon completion, ether (10 ml) was added with vigorous stir. The yellow precipitate was isolated through filtration, washed excessively with ether (5×1 ml) and dried under high vacuum. The title compound 10 (5 mg, 36%) was obtained as a yellow solid. $^1$H NMR (500 MHz, CD$_3$OD) δ 8.28 (d, 1H), 8.26 (m, 2H), 8.11 (s, 1H), 7.91 (t, 1H), 7.87 (t, 1H), 7.81 (d, 1H), 3.18 (m, 2H), 2.82 (m, 2H), 2.28 (t, 2H); LCMS, m/z 402.0 [M+H$^+$] calcd for C$_{23}$H$_{16}$NO$_4$S$^+$: 402.4.

Example 66

Chemical characterization for compounds are tabulated in Table 2 following.

TABLE 2

| # | Compound | Formula | MW |
|---|---|---|---|
| 1 (Nat. Prod.) | 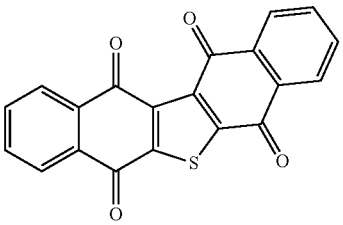 [SMILES: O=c1c2ccccc2c(=O)c2c1sc1c(=O)c3ccccc3c(=O)c12] | C$_{20}$H$_8$O$_4$S | 344 |
| S1 | 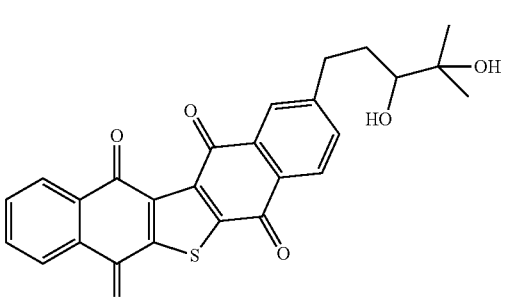 | C$_{26}$H$_{20}$O$_6$S | 460 |
| S2 | 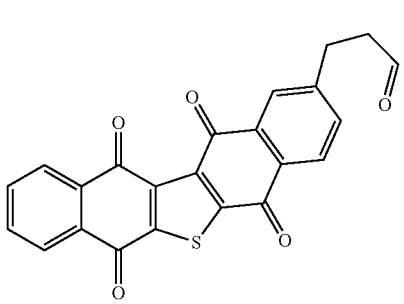 [SMILES: O=CCCc1ccc2c(=O)c3sc4c(=O)c5ccccc5c(=O)c4c3c(=O)c2c1] | C$_{23}$H$_{12}$O$_5$S | 400 |

TABLE 2-continued

| # | Compound | Formula | MW |
|---|---|---|---|
| S3 | | $C_{23}H_{12}O_6S$ | 416 |
| S4 | | $C_{23}H_{11}NaO_6S$ | 438 |
| S5 | | $C_{31}H_{29}NO_{11}S$ | 611 |
| S6 | | $C_{32}H_{28}N_2O_6S$ | 568 |

TABLE 2-continued

| # | Compound | Formula | MW |
|---|---|---|---|
| S7 | (structure shown, HCl salt) | $C_{32}H_{29}ClN_2O_6S$ | 604 |
| S8 | (structure shown) | $C_{29}H_{23}NO_7S$ | 529 |
| S9 | (structure shown) | $C_{25}H_{15}NO_7S$ | 473 |
| S10 | (structure shown, NHBoc) | $C_{32}H_{28}N_2O_7S$ | 584 |
| S11 | (structure shown, TFA salt) | $C_{29}H_{21}F_3N_2O_7S$ | 598 |

TABLE 2-continued

| # | Compound | Formula | MW |
|---|---|---|---|
| S12 | | $C_{30}H_{27}NO_{10}S$ | 593 |
| S13 | | $C_{34}H_{34}N_2O_7S$ | 614 |
| S14 | | $C_{31}H_{27}F_3N_2O_7S$ | 628 |
| S15 | | $C_{23}H_{14}O_5S$ | 402 |
| S16 | | $C_{23}H_{15}O_8PS$ | 482 |

TABLE 2-continued

| # | Compound | Formula | MW |
|---|---|---|---|
| S17 | | $C_{26}H_{18}KO_8PS$ | 560 |
| S18 | | $C_{19}H_7NO_4S$ | 345 |
| S19 | | $C_{20}H_8O_5$ | 328 |
| S20 | | $C_{20}H_8O_5$ | 328 |
| S21 | | $C_{20}H_9O_4N$ | 327 |
| S22 | | $C_{28}H_{20}O_8S$ | 516 |

TABLE 2-continued

| # | Compound | Formula | MW |
|---|---|---|---|
| S23 | | $C_{20}H_{12}O_4S$ | 348 |
| S24 | | $C_{24}H_{20}O_4S$ | 404 |
| S25 | | $C_{31}H_{24}O_{10}S$ | 588 |
| S26 | | $C_{50}H_{49}N_3O_{12}S$ | 915 |
| S27 | | $C_{21}H_{10}O_5S$ | 374 |

TABLE 2-continued
| # | Compound | Formula | MW |
|---|---|---|---|
| S28 | 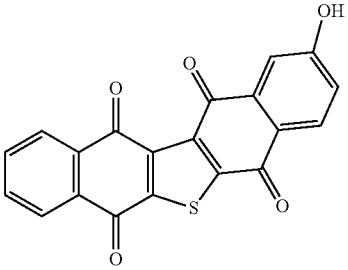 [SMILES: O=c1c2ccccc2c(=O)c2c1sc1c(=O)c3ccc(O)cc3c(=O)c12] | $C_{21}H_8O_5S$ | 360 |
| S29 | 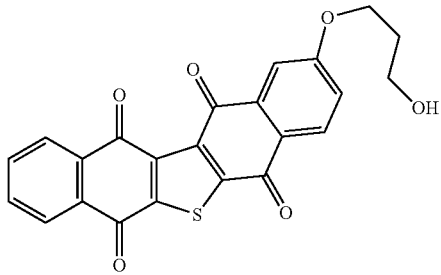 [SMILES: O=c1c2ccccc2c(=O)c2c1sc1c(=O)c3ccc(OCCCO)cc3c(=O)c12] | $C_{23}H_{14}O_6S$ | 418 |
| S30 | 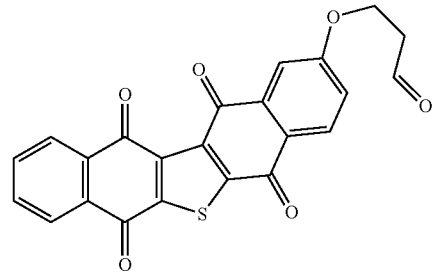 [SMILES: O=CCCOc1ccc2c(=O)c3sc4c(=O)c5ccccc5c(=O)c4c3c(=O)c2c1] | $C_{23}H_{12}O_6S$ | 416 |
| S31 | 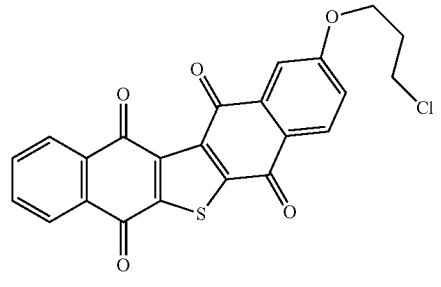 [SMILES: O=c1c2ccccc2c(=O)c2c1sc1c(=O)c3ccc(OCCCCl)cc3c(=O)c12] | $C_{23}H_{13}ClO_5S$ | 436 |
| S32 | 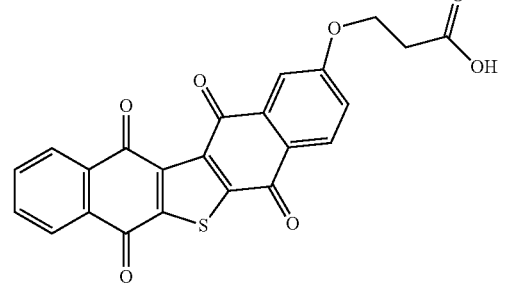 | $C_{23}H_{12}O_7S$ | 432 |

TABLE 2-continued

| # | Compound | Formula | MW |
|---|---|---|---|
| S33 | [structure] | $C_{21}H_7F_3O_7S_2$ | 491 |
| S34 | [structure] | $C_{27}H_{14}O_5S$ | 450 |
| 10 | [structure] | $C_{25}H_{15}F_3NO_5S$ | 498 |

Selection and Characterization of *Serinicoccus* sp.

Example 66

Strain CNJ927 was isolated from a sediment sample collected at a depth of 50 m near Palau in 2004. By analysis of the 16S rDNA gene sequence, CNJ927 was identified as *Serinicoccus* sp. A picture of this strain was provided in FIG. 1A. Strain CNJ927 was cultured at 27° C. with shaking at 215 rpm in the medium AlBFe+C (10 g of starch, 4 g of yeast extract, 2 g of peptone, 1 g of $CaCO_3$, 40 mg of $Fe_2(SO_4)_3 \cdot 4H_2O$, 100 mg of KBr per 1 L of seawater) in a 2.8 L Fembach flask. After 7 d, the 36 L broth (36 flasks) was extracted using with ethyl acetate (36 L). The EtOAc layer was dried over $Na_2SO_4$ and concentrated by rotary evaporation to yield 2.0 g of crude extract.

Isolation of Seriniquinone (1)

Example 67

The crude extract was dissolved in a small volume of chloroform, applied on a silica gel column (50 g, 3.2×20 cm, 200-450 mesh), and eluted stepwise with 100% $CHCl_3$, 50:1, 25:1, 10:1, 5:1, 1:1 (v/v) of $CHCl_3$/MeOH solvent and 100% MeOH (150 mL/fraction). Seriniquinone was observed in the first fraction eluted with chloroform. This fraction was purified by HPLC; ODS column (250×10 mm, Phenomenex), eluting with 70% $CH_3CN$ at a flow rate 2.5 mL/min with detection at 210 nm by a UV detector. Under this condition, seriniquinone (1) was eluted as peak with retention time of 28.0 min. This peak was collected and concentrated to afford 2.4 mg as yellow needles. A picture of these needles are provided in the inset of FIG. 1A.

Figure 1C:
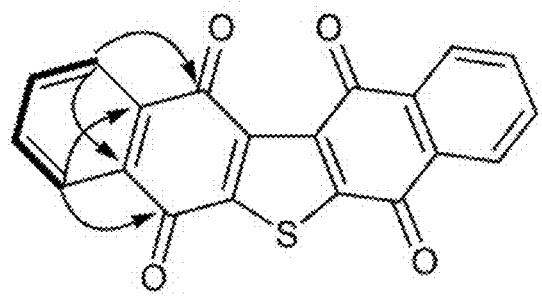

Seriniquinone (1). IR (plate) vmax 1664, 1588, 1500, 1258 cm−1; UV ($CHCl_3$) $\lambda_{max}$ (ε) 342 (6900), 289 (24,000), 250 (20,700); $^1$H and $^{13}$C NMR data are provided in Table 3; HR-ESI-TOFMS [M+H]$^+$ m/z 345.0210 ($C_{20}H_9O_4S$, calcd 345.0222). The structure and key COSY and HMBC correlations from 1 are provided in FIGS. 1B-1C.

TABLE 3

NMR spectroscopic data for seriniquinone (1) in CDCl$_3$. Assignments are based on COSY, HSQC and HMBC analyses. Carbons C1 and C4, C4a and C8a, C5 and C8 or C6 and C7 could not be distinguished using this methods. $^1$H and $^{13}$C NMR data were collected at 500 MHz and 125 MHz, respectively.

| # | δ H, mult (J in Hz) | δ C, type | COSY | HMBC |
|---|---|---|---|---|
| 1 | | 177.3, C | | |
| 2 | | 152.6, C | | |
| 3 | | 141.0, C | | |
| 4 | | 178.6, C | | |
| 4a | | 131.9, C | | |
| 5 | 8.25, d (6.6) | 127.0, CH | 6 | C4, C7, C8a |
| 6 | 7.81, t (6.6) | 133.9, CH | 5, 7 | C4a, C8 |
| 7 | 7.87, t (6.6) | 135.3, CH | 6, 8 | C5, C8a |
| 8 | 8.35, d (6.6) | 128.6, CH | 7 | C1, C4a, C6 |
| 8a | | 134.8, C | | |

Biological Studies. All reagents and media were used at molecular or cellular biological grades. Unless stated, all antibodies were purchased from Cell Signaling Technology Inc.

Tissue Culture

Example 68

HCT-116 (ATCC# CCL-247), PC-3M (DCTD tumor repository, NCI) and SF-295 (DCTD tumor repository, NCI) cells were cultivated in RPMI media (GIBCO-BRL), supplemented with 10% inactivated fetal calf serum (FCS) and 1% penicillin/streptomycin (GIBCO-BRL). Malme-3M cells (ATCC# HTB-64) were grown in Iscove's modified Dulbecco's medium (GIBCO-BRL) supplemented with 20% inactivated FCS and 1% penicillin/streptomycin. All cells were manipulated under sterile conditions provided by a class II biohazard safety flow hood and incubated at 37° C. in a 5% $CO_2$ atmosphere. Every 3-4 d, cells were detached from flask using a 0.05% trypsin-EDTA solution (GIBCO-BRL) and split 1:4 for routine passage.

Mammalian Cell Lysate

Example 69

All samples of cell lysate were prepared fresh, stored on ice and used within 4 h of production. For the preparation of HCT-116 cell lysates, the PBS-washed cells from 75 cm$^2$ culture flask were scraped and suspended in 5 mL of PBS containing 10 μL protease inhibitor cocktail. The cell suspension was then passed through 27.5 gauge needle multiple times using syringe. The crude cell lysate centrifuged at 13,000 and stored at 4° C. until used. The concentration of protein in the lysates was check via Bradford analyses.

Trypan Blue Assays

Example 70

Cell viability was determined using the Trypan blue dye exclusion test after incubation of HCT-116 cells (1×10$^5$ cells/mL) with 0.3 μM seriniquinone (1), 3 μM 1, and 30 μM 1. Aliquots were removed from cultures after 24 and 48 h, and the cells that excluded (viable) or not (non-viable) Trypan blue were differentially counted using a Neubauer chamber.

Cytotoxicity Analyses

Example 71

HCT-116 colon carcinoma cells were plated in 96-well plates at 2.5×10$^4$ cells/well. After 24 h, the cultures were treated with a single concentration seriniquinone (1) within the range of 0.02-20.0 μM, etoposide (positive control) in the range of 0.05-50 μM or 1% DMSO (negative control). The cells were incubated for either 24 h, 48 h or 72 h. At the end of the incubation period, cultures were added with 3-(4,5-dimethylthiazol-2-yl)-5-(3-carboxymethoxyphenyl)-2-(4-sulfophenyl)-2H-tetrazolium (MTS) for 3 h. Cell viability was quantified by the ability of living cells to reduce the yellow MTS dye to a purple formazan product. Time course experiments were also conducted in HCT-116 cells. Cells were exposed to 1 over short periods (1 h, 3 h, 6 h, and 9 h) followed by incubation in drug-free media to complete a total of 24 h incubation before addition of MTS.

Cell Cycle and DNA Fragmentation Analysis

Example 72

Cell cycle was analyzed by the ImageStream® cell analysis system (Amnis). Briefly, HCT-116 cells (1×10$^5$ cells/mL) were seeded in 24-well plates, and 24 h later, 0.3 μM 1, 3 μM 1, 30 μM 1 or 17 μM etoposide (positive control) or 1% DMSO (negative control) was added to the cultures. After 18 h or 24 h incubation, cells were recovered by treatment with 0.05% trypsin-EDTA solution (GIBCO-BRL). An 100 μL aliquot of these cells were incubated for 30 min in the dark with a hypotonic solution containing 50 μg/mL propidium iodide, 0.1% sodium citrate, and 0.1% Triton X-100. Fluorescence was measured and DNA fragmentation and cell cycle were analyzed using ModFit LT for Win32 version 3.1.

Western Blot Analysis of Cell Cycle and Apototic Markers

Example 73

HCT-116 cells (1×10$^6$ cells/mL) were seeded in 75 cm$^2$ cell culture flasks and, 24 h later, treated with 3 μM 1, 30 μM 1, 17 μM etoposide (positive control), or 0.3% DMSO (negative control). After 24 h incubation, cells were washed in PBS, harvested and lysed in RIPA buffer. Protein extracts were quantified by an adapted micro-method of the Lowry assay using the DC Protein Assay kit (BioRad Laboratories). Equal amounts of protein (30 μg) from each treatment were fractionated using SDS-PAGE 5-15% gel and transferred to a PVDF membrane (BioRad Laboratories). The membranes were incubated overnight at 4° C. with primary antibodies for caspase-3, cleaved caspase-3, caspase 7, cleaved caspase-7, caspase-9, cleaved caspase-9, PARP, cleaved PARP, cyclin A, cyclin B1, cyclin D1, cyclin D3, cyclin D3, cyclin E1, cyclin E2, LC3A, LC3B or dermcidin (Santa Cruz Biotech). β-actin (Abcam) was used to normalize protein loading. After washing with TBS containing 0.1% Tween-20, the membranes were incubated with the appropriate secondary antibody alkaline phosphatase conjugate (Cell Signaling Technology Inc.), followed by BCIP/NBT color development substrate (Perkin-Elmer).

Confocal Microscopy

Example 74

Confocal studies were conducted on a LSM 710 inverted confocal microscope (Zeiss) with scanning module with 3 detection channels, Plan-Apochromat 63×/1.4 na objective, diode laser (405 nm, CW pulsed, 30 mW), Ar-laser (458 nm, 488 nm, 514 nm, 25 mW), HeNe-laser (543 nm, 1 mW) and HeNe-laser (633 nm, 5 mW). For all procedures, cells were seeded 24 h prior to treatment, to allow for adequate attachment to the well or flask bottom. Cells were plated in glass-bottom dishes (MatTek Corporation) for microscopic analyses at $1\times10^5$ cells/mL. Compounds were added to cells under 1 mL of media from 100× DMSO stocks such that the DMSO content remained under 0.1%. Cells were cultured for the ascribed periods at 37° C. in a 5% $CO_2$ atmosphere.

Time Course Imaging

Example 75

HCT-116, PC-3M, SF-295 HCT-8 and MALME-3M cells were incubated at a density of $1\times10^5$ cells/cm² in a 35 mm glass-bottom dish (MatTek Corporation). After 24 h, seriniquinone (1) was added as a 100× stock in media such that the DMSO content remained under 0.1%. After incubation, the cells were fixed by treatment with 4% formaldehyde in PBS followed by washing twice with 1 mL of PBS. Images were collected within a few h of fixation.

Colocalization Studies

Example 76

Colocalization studies were conducted by treating cells (HCT-116 or MALME-3M) at a density of $1\times10^5$ cells/cm² in a 35 mm glass-bottom dish (MatTek Corporation). Compounds were added to cells under 1 mL of media from 100×DMSO stocks such that the DMSO content remained under 0.1%. Cells were cultured for the ascribed periods at 37° C. in a 5% $CO_2$ atmosphere. For the endoplasmatic reticulum co-staining, cells were treated with 1 and then stained with 0.5 µM ER-tracker™ blue-White DPX (Life Technologies) at 37° C. After 30 min, cells were washed PBS (4×1 mL) and immediately analyzed by confocal microscope. Live cells were used for confocal analysis. The localization of seriniquinone (1) was acquired by red fluorescence with emission at 550-631 nm, while the ER-tracker was acquired by blue florescence with emission at 406-450 nm. For autophagosomal co-staining, cells were treated with 1 and then 0.05 mM dansylcadaverine 0 at 37° C. After 15 min, cells were washed PBS (4×1 mL) and immediately analyzed by confocal microscope. Live cells were used for confocal analysis. The localization of seriniquinone (1) was acquired by red fluorescence with emission at 550-631 nm, while the ER-tracker was acquired by blue florescence with emission at 415-530 nm.

Immunoprecipitation with Probe 14a/14b

Example 77

An 1 mg/mL stock of probe 14a/14b in DMSO solution was added to 1 mL of cell lysate containing ~1 mg/mL in net protein to provide a net concentration of 3 µM 14a/14b or 30 µM 14a/14b. This solution was added to a tube containing 100 µL of Affi-Gel 10 resin (Bio-Rad) containing the 1.5 mg/mL of covalently attached XRI-TF35 mAb. The resulting mixture was shaken on a Thermo Scientific Labquake rotator for 12 h at 4° C. The resin was then collected and washed three times with 1000 µL of ice-cold RIPA buffer. After washing was complete, 50 µL of 1 mM 7-dimethyl-amino-coumarin-4-acetic acid in PBS at pH 7.2 was added and the mixture was centrifuged at 13,000. The supernate was removed (referred to as the IP fraction from probe 11b) was collected and used for SDS-PAGE analysis, Western blot analysis as well as iodoacetamide treatment. Briefly, SDS PAGE analysis was conducted by diluting the IP fraction from probe 11b in a 1:1 ratio with SDS-PAGE gel loading buffer. A 15-20 µL aliquot was loaded per lane of a NuPage 3-8% Tris-acetate gradient gel.

Target Identification

Example 78

Silver Stained bands were excised from the polyacrylamide gel and destained. After destaining, the bands were submitted to LC-MS/MS Protein-ID analysis conducted by the Biomolecular and Proteomics Mass Spectrometry Facility at UC San Diego. General procedure was using in-gel trypsin digest and then the trypsin-digested peptides were analyzed by liquid chromatography LC-MS/MS with electrospray ionization. All nanospray ionization experiments were performed by using a QSTAR-Elite hybrid mass spectrometer (AB/MDS Sciex) interfaced to a nanoscale reversed-phase high-pressure liquid chromatograph (Tempo) using a 10 cm-180 ID glass capillary packed with 5-µm $C_{18}$ Zorbax™ beads (Agilent). The buffer compositions were as follows: Buffer A was composed of 98% H2O, 2% $CH_3CN$, 0.2% formic acid, and 0.005% trifluoracetic acid (TFA); buffer B was composed of 100% $CH_3CN$, 0.2% formic acid, and 0.005% TFA. Peptides were eluted from the $C_{18}$ column into the mass spectrometer using a linear gradient of 5-60% Buffer B over 60 min at 400 µl/min. LC-MS/MS data were acquired in a data-dependent fashion by selecting the 4 most intense peaks with charge state of 2 to 4 that exceeds 20 counts, with exclusion of former target ions set to "360 seconds" and the mass tolerance for exclusion set to 100 ppm. Time-of-flight MS were acquired at m/z 400 to 1600 Da for 1 s with 12 time bins to sum. MS/MS data were acquired from m/z 50 to 2,000 Da by using enhance all and 24 time bins to sum, dynamic background subtract, automatic collision energy, and automatic MS/MS accumulation with the fragment intensity multiplier set to 6 and maximum accumulation set to 2 s before returning to the survey scan. Peptide identifications were made using paragon algorithm executed in Protein Pilot 2.0 software (Life Technologies).

Iodoacetamide Treatment after IP Analysis

Example 79

A 20 µL sample of IP fraction from an experiment using 30 µM 11a, as described in above procedure describing immunoprecipitation with probe 14a/14b, was treated with 5 mM iodoacetamide (freshly prepared) for 1 h at 23° C. After exposure, the resulting fraction was diluted 1:1 in gel loading buffer was subjected to SDS-PAGE analysis on a NuPage 3-8% Tris-acetate gradient gel.

Iodoacetamide Treatment before IP Analysis

Example 80

Cell lysate (5 mL) containing ~1 mg/mL in net protein was treated with 0.5 mM iodoacetamide for 1 h at 4 OC. The remaining iodoacetamide was removed by spin dialysis with five 10 mL washes. The lysate was concentrated from 15 mL to 2.5 mL during each wash. A 1 mg/mL stock of probes 14a/14b in DMSO solution was added to 1000 µL of cell lysate containing ~1 mg/mL in net protein to provide a net concentration of 30 µM 14a/14b. This solution was added to a tube containing 100 µL of Affi-Gel 10 resin (Bio-Rad) containing the 1.5 mg/mL of covalently attached XRI-TF35 mAb. The resulting mixture was shaken on a Thermo Scientific Labquake rotator for 12 h at 4° C. The resin was then collected and washed three times with 1000 µL of ice-cold RIPA buffer. After washing was complete, 50 µL of 1 mM 7-dimethylaminocoumarin-4-acetic acid in PBS pH 7.2 was added and the mixture was centrifuged at 13,000. The supernate was removed (referred to as the IP fraction from probe 11b) was collected and used for SDS-PAGE analysis, Western blot analysis as well as iodoacetamide treatment. Briefly, SDS PAGE analysis was conducted by diluting the IP fraction from probe 11b in a 1:1 ratio with SDS-PAGE gel loading buffer A 15-20 µL aliquot was loaded per lane of a NuPage 3-8% Tris-acetate gradient gel.

Western Blot Validation DCD·GAPDH Identified by Immunopreciptation with Probes 14a/14b Example 81

A 20 µL sample of the IP fraction from an experiment using 30 µM 14a/14b, as described in above procedure describing immunoprecipitation with probe 14a/14b, was diluted 1:1 in gel loading buffer (LIST) as subjected to SDS-PAGE analysis on a NuPage 3-8% Tris-acetate gradient gel and transferred to polyvinylidene difluoride (PVDF) membrane (GE Healthcare). The blotting membrane was blocked with 5% non-fat milk and hybridized with either the mouse anti-IAF TF35 mAb (Xenobe Research Institute) diluted 1:2000 (lanes L1-L2, FIG. 5C), a mouse anti-DCD mAB (NAME) diluted 1:1000 (lane L3, FIG. 5C), or a mouse anti-GAPDH (BRAND) diluted 1:1000 (lane L4, FIG. 5C). The membrane was incubated with alkaline phosphatase-conjugated goat-anti-mouse secondary antibody #69266 (Novagen), washed, and stained with BCIP/NBT color development substrate S3771 (Promega).

Immunoprecipitation with Probe 15a/15b

Example 82

The following procedure was used for the studies shown in lane L1 of FIG. 5D. An 40 µL aliquot of a 1 mg/mL stock of probe 13a in DMSO solution was added to 1000 µL of cell lysate containing ~1 mg/mL in net protein. This solution was added to a tube containing 100 µL of Affi-Gel 10 resin (Bio-Rad) containing the 1.5 mg/mL of covalently attached XRI-TF35 mAb. The resulting mixture was shaken on a Thermo Scientific Labquake rotator for 12 h at 4° C. The resin was then collected and washed three times with 500 µL of ice-cold RIPA buffer. After washing was complete, 50 µL of 1 mM 7-dimethylaminocoumarin-4-acetic acid in PBS pH 7.2 was added and the mixture was centrifuged at 13,000. The mixture was diluted 1:1 with SDS-PAGE gel loading buffer and a 20 µL aliquot was subjected to SDS-PAGE analysis on a NuPage 3-8% Tris-acetate gradient gel.

Western Blot Validation DCD*GAPDH Identified by Immunopreciptation with Probes 15a/15b Example 83

Western blot analyses were conducted to validate the protein targets identified via IP analyses as shown in FIG. 5E. A 20 µL sample of the ascribed IP fraction diluted 1:1 in gel loading buffer (LIST) as subjected to SDS-PAGE analysis on a NuPage 3-8% Tris-acetate gradient gel and transferred to polyvinylidene difluoride (PVDF) membrane (GE Healthcare). The blotting membrane was blocked with 5% non-fat milk and hybridized with either the mouse anti-IAF TF35 mAb diluted 1:2000, a mouse anti-DCD mAB (NAME) diluted 1:1000, or a mouse anti-GAPDH (BRAND) diluted 1:1000. The membrane was incubated with alkaline phosphatase-conjugated goat-anti-mouse secondary antibody #69266 (Novagen), washed, and stained with BCIP/NBT color development substrate S3771 (Promega).

REFERENCES

1. Newman, D. J. & Cragg, G. M. Natural Products As Sources of New Drugs over the 30 Years from 1981 to 2010. *J. Nat. Prod.* 75, 311-335 (2012).
2. Li, J. W. & Vederas, J. C. Drug discovery and natural products: end of an era or an endless frontier? *Science.* 324, 161-165 (2009).
3. Carlson, E. E. Natural products as chemical probes. *ACS Chem. Biol.* 5, 639-653 (2010).
4. La Clair, J. J. Natural product mode of action (MOA) studies: a link between natural and synthetic worlds. *Nat. Prod. Rep.* 27, 969-995 (2010).
5. Hughes, C. C. & Fenical W. Antibacterials from the sea. *Chemistry,* 16, 12512-12525 (2010).
6. Sumantran, V. N. Cellular chemosensitivity assays: an overview. *Methods Mol. Biol.* 731, 219-236 (2011).
7. Matsuoka, M., Iwamoto, A. & Kitao, T. Reaction of 2,3-dichloro-1,4-naphthoquinone with dithiooxamide. Synthesis of dibenzo[b,i]thianthrene-5,7,12,14-tetrone. *J. Heterocyclic Chem.* 28, 1445-1447 (1991).
8. Shoemaker R. H. The NCI60 human tumour cell line anticancer drug screen. Nat. Rev. Cancer. 6, 813-823 (2006).
9. Cole, L., Davies, D., Hyde, G. J. & Ashford, A. E. ER-Tracker dye and BODIPY-brefeldin A differentiate the endoplasmic reticulum and golgi bodies from the tubular-vacuole system in living hyphae of *Pisolithus tinctorius.* *J. Microsc.* 197, 239-249 (2000).
10. Biederbick, A., Kern, H. F. & Elsässer, H. P. Monodansylcadaverine (MDC) is a specific in vivo marker for autophagic vacuoles. *Eur. J. Cell Biol.* 66, 3-14 (1995).
11. Barth, S., Glick, D. & Macleod K F. Autophagy: assays and artifacts. *J. Pathol.* 221, 117-124 (2010).
12. Musgrove, E. A., Caldon, C. E., Barraclough, J., Stone, A. & Sutherland, R. L. Cyclin D as a therapeutic target in Cancer. *Nat. Rev. Cancer* 11, 558-572 (2011).
13. Yu, W. L., Guizzunti, G., Foley, T. L., Burkart, M. D. & La Clair, J. J. An optimized immunoaffinity fluorescent method for natural product target elucidation. *J. Nat. Prod.* 73, 1659-1666 (2010).

14. Hughes, C. C., MacMillan, J. B., Gaudêncio, S. P., Fenical, W. & La Clair, J. J. Ammosamides A and B target myosin. *Angew. Chem. Int. Ed. Engl.* 48, 728-732 (2009).

15. Miguel del Corral, J. M., Castro, M. A., Gordaliza, M., Martin, M. L., Oliveira, A. B., Gualberto, S. A., García-Grávalos, M. D., San Feliciano, A. Synthesis and biological evaluation of cytotoxic 6(7)-alkyl-2-hydroxy-1,4-naphthoquinones. *Arch. Pharm (Weinheim).* 335, 427-437 (2002).

16. Stocki, P., Wang, X. N., Morris, N. J. & Dickinson A. M. Hsp70 natively and specifically associates with an N-terminal dermcidin-derived peptide that contains an HLA-A*03 antigenic epitope. *J. Biol. Chem.* 286, 12803-12811 (2011).

What is claimed is:

1. A compound of Formula (I):

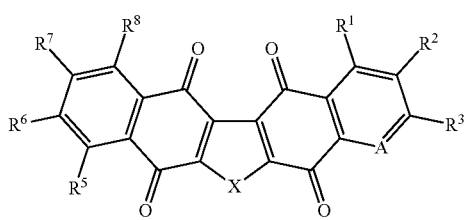

or pharmaceutically acceptable salt thereof,
wherein
A is N or —$CR^4$;
X is —S—;
$R^1$, $R^4$, $R^5$, $R^6$, $R^7$, and $R^8$ are independently hydrogen, halogen, —$NH_2$, —OH, —$NO_2$, —$C(O)CH_3$, —$NHC(O)CF_3$, —$OC(O)CH_3$, or unsubstituted $C_{1-4}$ alkyl;
$R^2$ and $R^3$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{2a}$-substituted or unsubstituted $C_1$-$C_8$ alkyl, $R^{2a}$-substituted or unsubstituted 2-8 membered heteroalkyl, $R^{2a}$-substituted or unsubstituted $C_3$-$C_8$ cycloalkyl, $R^{2a}$-substituted or unsubstituted 3-6 membered heterocycloalkyl, $R^{2a}$-substituted or unsubstituted phenyl, or $R^{2a}$-substituted or unsubstituted 5 or 6 membered heteroaryl;
$R^{2a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{2b}$-substituted or unsubstituted $C_1$-$C_8$ alkyl, $R^{2b}$-substituted or unsubstituted 2-8 membered heteroalkyl, $R^{2b}$-substituted or unsubstituted $C_3$-$C_8$ cycloalkyl, $R^{2b}$-substituted or unsubstituted 3-6 membered heterocycloalkyl, $R^{2b}$-substituted or unsubstituted phenyl, or $R^{2b}$-substituted or unsubstituted 5 or 6 membered heteroaryl; and
$R^{2b}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, an unsubstituted $C_1$-$C_8$ alkyl, an unsubstituted 2-8 membered heteroalkyl, an unsubstituted $C_3$-$C_8$ cycloalkyl, an unsubstituted 3-6 membered heterocycloalkyl, an unsubstituted phenyl, or an unsubstituted 5 or 6 membered heteroaryl;

wherein if A is —$CR^4$ then at least one of $R^1$, $R^2$, $R^3$, $R^4$, $R^5$, $R^6$, $R^7$, and $R^8$ is not hydrogen or alkyl.

2. The compound of claim 1, wherein A is —$CR^4$; and $R^1$, $R^4$, $R^5$, and $R^8$ are hydrogen.

3. The compound of claim 1, wherein
A is —$CR^4$—;
$R^1$, $R^3$, $R^4$, $R^5$, $R^6$, $R^7$, and $R^8$ are hydrogen; and
$R^2$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{2a}$-substituted or unsubstituted $C_1$-$C_8$ alkyl, $R^{2a}$-substituted or unsubstituted 2-8 membered heteroalkyl, $R^{2a}$-substituted or unsubstituted $C_3$-$C_8$ cycloalkyl, $R^{2a}$-substituted or unsubstituted 3-6 membered heterocycloalkyl, $R^{2a}$-substituted or unsubstituted phenyl, or $R^{2a}$-substituted or unsubstituted 5 or 6 membered heteroaryl.

4. The compound of claim 1, wherein the compound is:

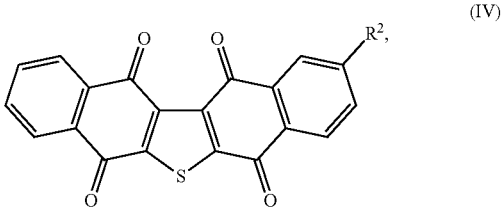

wherein $R^2$ is $R^{2a}$-substituted or unsubstituted $C_1$-$C_8$ alkyl, $R^{2a}$-substituted or unsubstituted 2-8 membered heteroalkyl, $R^{2a}$-substituted or unsubstituted $C_3$-$C_8$ cycloalkyl, $R^{2a}$-substituted or unsubstituted 3-6 membered heterocycloalkyl, $R^{2a}$-substituted or unsubstituted phenyl, or $R^{2a}$-substituted or unsubstituted 5 or 6 membered heteroaryl.

5. The compound of claim 1, wherein $R^2$ is —$(CH_2)_2C(O)$—$R^{2b}$.

6. The compound of claim 1, wherein
A is —$CR^4$—; and
$R^1$, $R^2$, $R^3$, $R^4$, $R^5$, $R^6$, $R^7$, and $R^8$ are independently hydrogen, halogen, —$NH_2$, —OH, —$NO_2$, —$C(O)CH_3$, —$NHC(O)CF_3$, —$OC(O)CH_3$, or unsubstituted $C_{1-4}$ alkyl.

7. The compound of claim 6, wherein
$R^1$, $R^4$, $R^5$, and $R^8$ are hydrogen;
one of $R^2$ and $R^3$ is hydrogen and the other of $R^2$ and $R^3$ is halogen, —$NH_2$, —OH, —$NO_2$, —$C(O)CH_3$, —$NHC(O)CF_3$, or —$OC(O)CH_3$; and
one of $R^6$ and $R^7$ is hydrogen and the other of $R^6$ and $R^7$ is halogen, —$NH_2$, —OH, —$NO_2$, —$C(O)CH_3$, —$NHC(O)CF_3$, or —$OC(O)CH_3$.

8. A method of treating melanoma or prostate cancer in a subject in need thereof, said method comprising administering to a subject a therapeutically effective amount of a compound of claim 1 to treat the melanoma or prostate cancer.

9. A compound of Formula (VII):

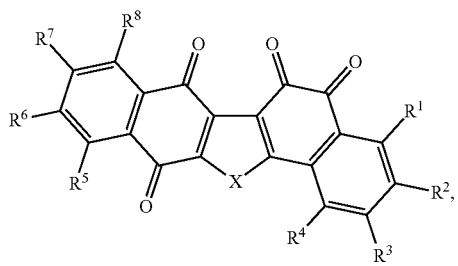

(VII)

or pharmaceutically acceptable salt thereof,
wherein
X is —S— or —NR$^{21}$;
R$^1$, R$^4$, R$^5$, R$^6$, R$^7$ and R$^8$ are independently hydrogen, halogen, —NH$_2$, —OH, —NO$_2$, —C(O)CH$_3$, —NHC(O)CF$_3$, —OC(O)CH$_3$, or unsubstituted C$_{1-4}$ alkyl;
R$^2$ and R$^3$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{2a}$-substituted or unsubstituted C$_1$-C$_8$ alkyl, R$^{2a}$-substituted or unsubstituted 2-8 membered heteroalkyl, R$^{2a}$-substituted or unsubstituted C$_3$-C$_8$ cycloalkyl, R$^{2a}$-substituted or unsubstituted 3-6 membered heterocycloalkyl, R$^{2a}$-substituted or unsubstituted phenyl, or R$^{2a}$-substituted or unsubstituted 5or 6 membered heteroaryl;
R$^{2a}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{R2b}$-substituted or unsubstituted C$_1$-C$_8$ alkyl, R$^{2b}$-substituted or unsubstituted 2-8 membered heteroalkyl, R$^{2b}$-substituted or unsubstituted C$_3$-C$_8$ cycloalkyl, R$^{2b}$-substituted or unsubstituted 3-6 membered heterocycloalkyl, R$^{2b}$-substituted or unsubstituted phenyl, or R$^{2b}$-substituted or unsubstituted 5or 6 membered heteroaryl;
R$^{2b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2-8 membered heteroalkyl, unsubstituted C$_3$-C$_8$ cycloalkyl, unsubstituted 3-6 membered heterocycloalkyl, unsubstituted phenyl, or unsubstituted 5or 6 membered heteroaryl;
R$^2$ and R$^3$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, R$^{2a}$-substituted or unsubstituted C$_1$-C$_8$ alkyl, R$^{2a}$-substituted or unsubstituted 2-8 membered heteroalkyl, R$^{2a}$-substituted or unsubstituted C$_3$-C$_8$ cycloalkyl, R$^{2a}$-substituted or unsubstituted 3-6 membered heterocycloalkyl, R$^{2a}$-substituted or unsubstituted phenyl, or R$^{2a}$-substituted or unsubstituted 5or 6 membered heteroaryl; and
R$^{21}$ is hydrogen or unsubstituted C$_1$-C$_5$ alkyl;
wherein at least one of R$^1$, R$^2$, R$^3$, R$^4$, R$^5$, R$^6$, R$^7$, and R$^8$ is not hydrogen or alkyl.

10. A method of treating melanoma or prostate cancer in a subject in need thereof, said method comprising administering to a subject a therapeutically effective amount of a compound of claim 9 to treat the melanoma or prostate cancer.

11. A compound of Formula (VIII):

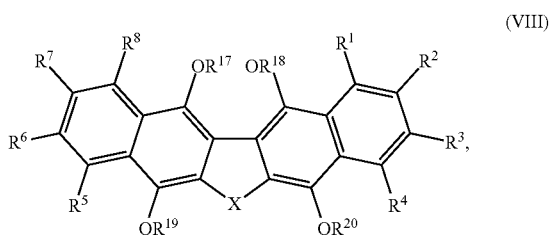

(VIII)

or pharmaceutically acceptable salt thereof,
wherein
X is —S— or —O—;
R$^1$, R$^4$, R$^5$, R$^6$, R$^7$, and R$^8$ are independently hydrogen, halogen, —NH$_2$, —OH, —NO$_2$, —C(O)CH$_3$, —NHC(O)CF$_3$, —OC(O)CH$_3$, or unsubstituted C$_1$-C$_4$ alkyl;
R$^2$ and R$^3$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, SO$_3$H, —SO$_4$H, —SO$_2$NH$_2$, —NHNH$_2$, —ONH$_2$, —NHC(O)NHNH$_2$, R$^{2a}$-substituted or unsubstituted C$_1$-C$_8$ alkyl, R$^{2a}$-substituted or unsubstituted 2-8 membered heteroalkyl, R$^{2a}$-substituted or unsubstituted C$_3$-C$_8$ cycloalkyl, R$^{2a}$-substituted or unsubstituted 3-6 membered heterocycloalkyl, R$^{2a}$-substituted or unsubstituted phenyl, or R$^{2a}$-substituted or unsubstituted 5or 6 membered heteroaryl;
R$^{2a}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —NHC(O)NHNH$_2$, R$^{2b}$-substituted or unsubstituted C$_1$-C$_8$ alkyl, R$^{2b}$-substituted or unsubstituted 2-8 membered heteroalkyl, R$^{2b}$-substituted or unsubstituted C$_3$-C$_8$ cycloalkyl, R$^{2b}$-substituted or unsubstituted 3-6 membered heterocycloalkyl, R$^{2b}$-substituted or unsubstituted phenyl, or R$^{2b}$-substituted or unsubstituted 5or 6 membered heteroaryl;
R$^{2b}$ is independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted C$_1$-C$_8$ alkyl, unsubstituted 2-8 membered heteroalkyl, unsubstituted C$_3$-C$_8$ cycloalkyl, unsubstituted 3-6 membered heterocycloalkyl, unsubstituted phenyl, or unsubstituted 5or 6 membered heteroaryl; and
R$^{17}$, R$^{18}$, R$^{19}$, and R$^{20}$ are independently hydrogen or substituted or unsubstituted alkyl.

12. The compound of claim 11, wherein R$^1$, R$^2$, R$^3$, R$^4$, R$^5$, R$^6$, R$^7$, and R$^8$ are hydrogen.

13. The compound of claim 11, wherein $R^{17}, R^{18}, R^{19}$, and $R^{20}$ are identical.

14. The compound of claim 11, wherein $R^{17}, R^{18}, R^{19}$, and $R^{20}$ are hydrogen, methyl, or acetyl.

15. The compound of claim 11, wherein $R^{17}, R^{18}, R^{19}$, and $R^{20}$ are acetyl.

16. A method of treating melanoma or prostate cancer in a subject in need thereof, said method comprising administering to a subject a therapeutically effective amount of a compound of claim 11 to treat the melanoma or prostate cancer.

17. A method of inhibiting a dermcidin protein in vitro, comprising:
 (i) contacting a dermcidin protein having at least 75% sequence identity to SEQ ID NO:1, 2, 3, or 4 in vitro with a compound of claim 1; and
 (ii) detecting formation of a dermcidin—seriniquinone complex, wherein formation of the complex is indicative of inhibition of the dermcidin protein, and further wherein the complex is detected using fluorescence detection.

18. A compound selected from the group consisting of:

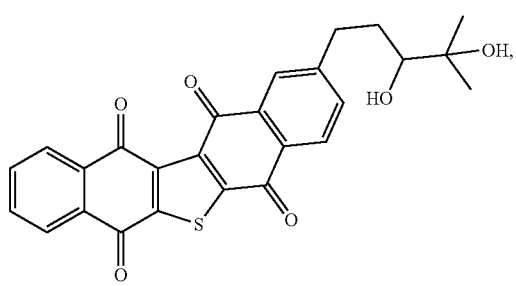

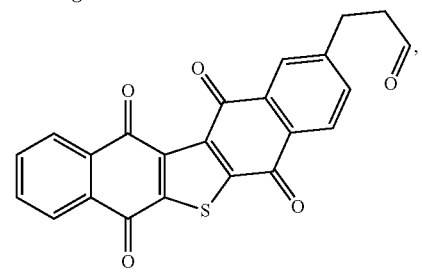

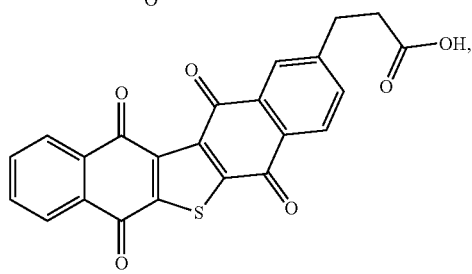

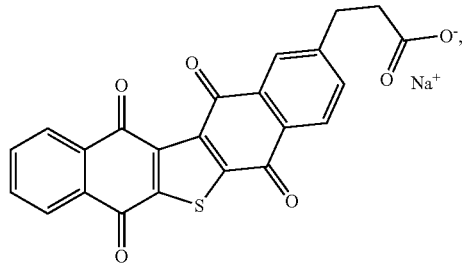

-continued

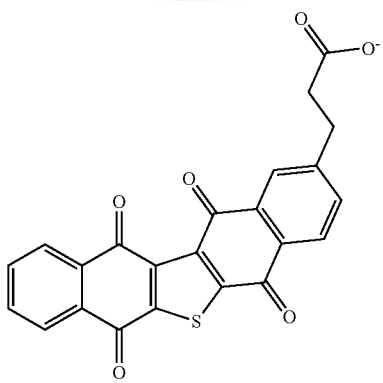

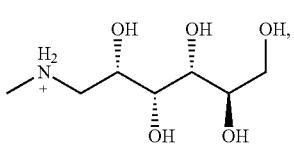

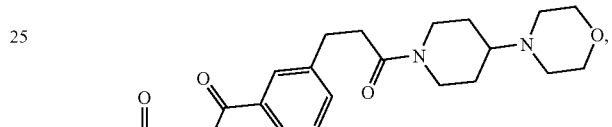

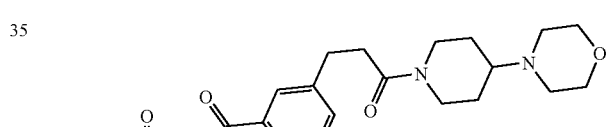

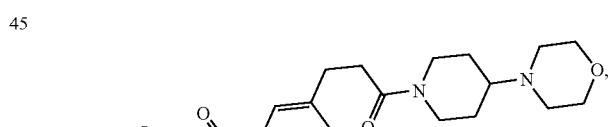

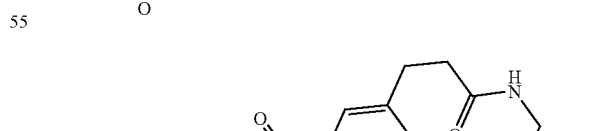

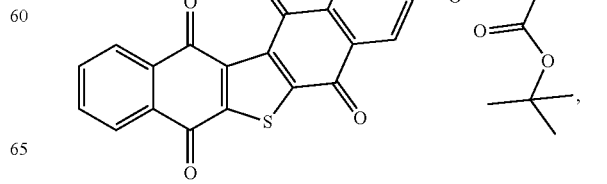

181
-continued
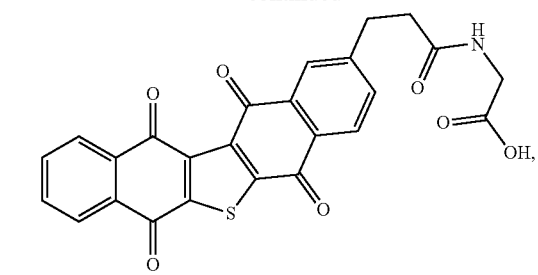
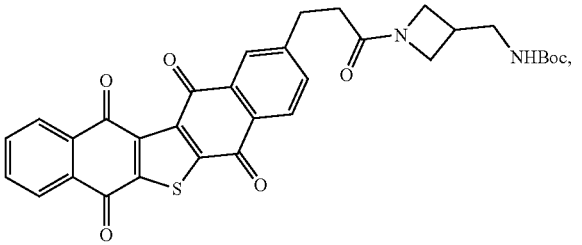
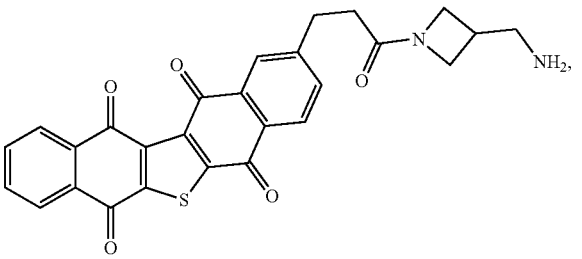
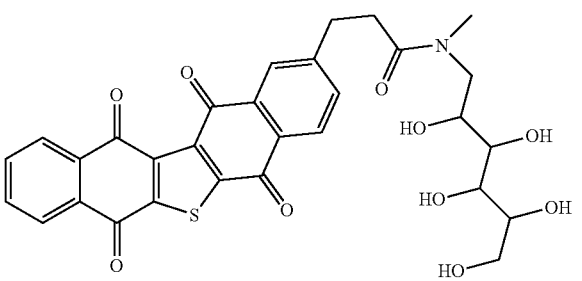
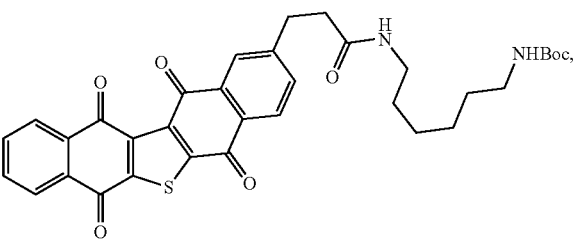
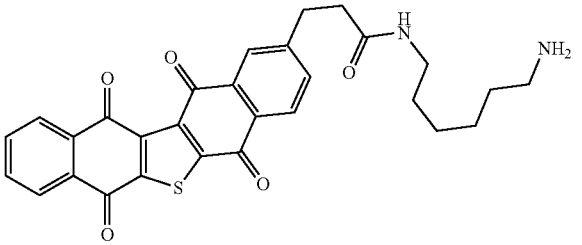
182
-continued
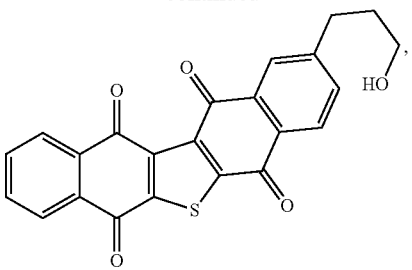
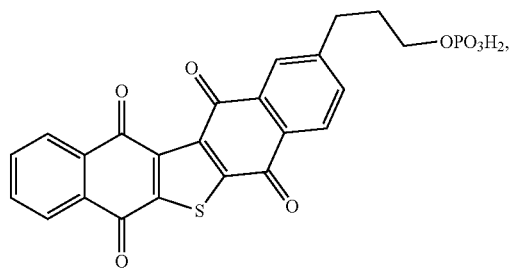
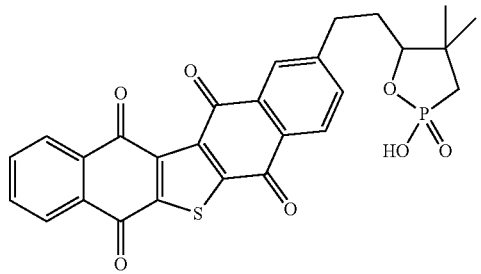
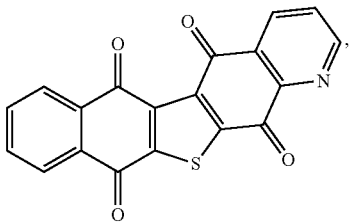
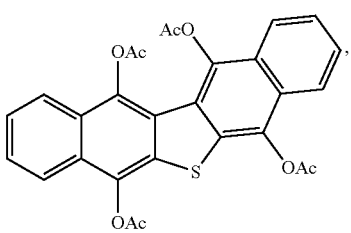
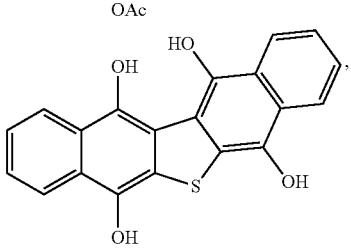
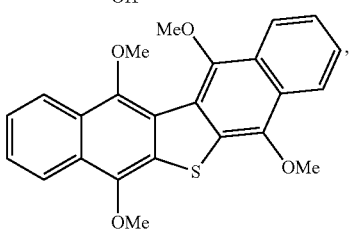

183
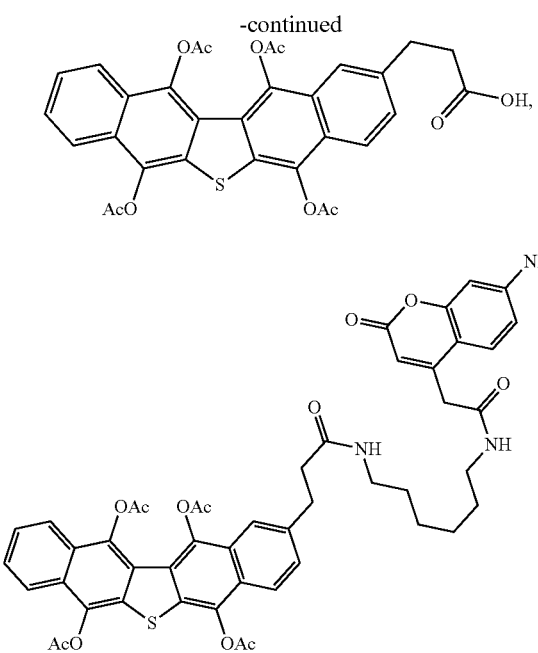
184
-continued
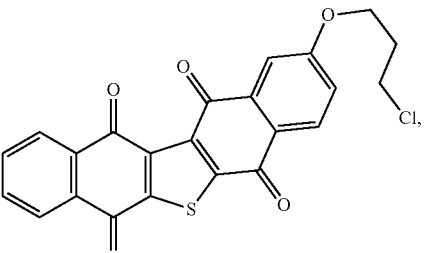
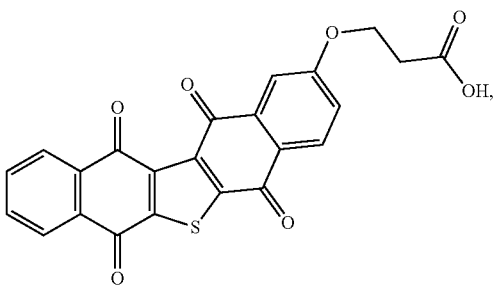
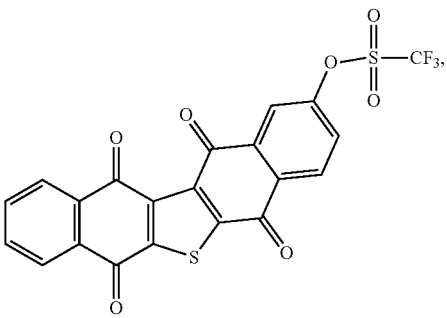
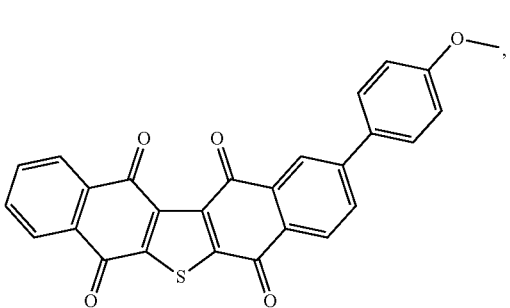
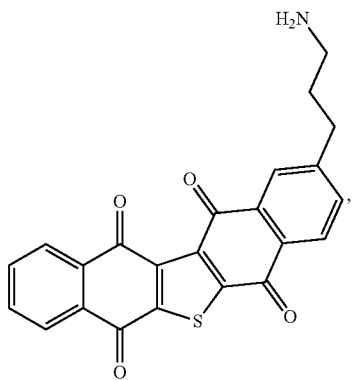

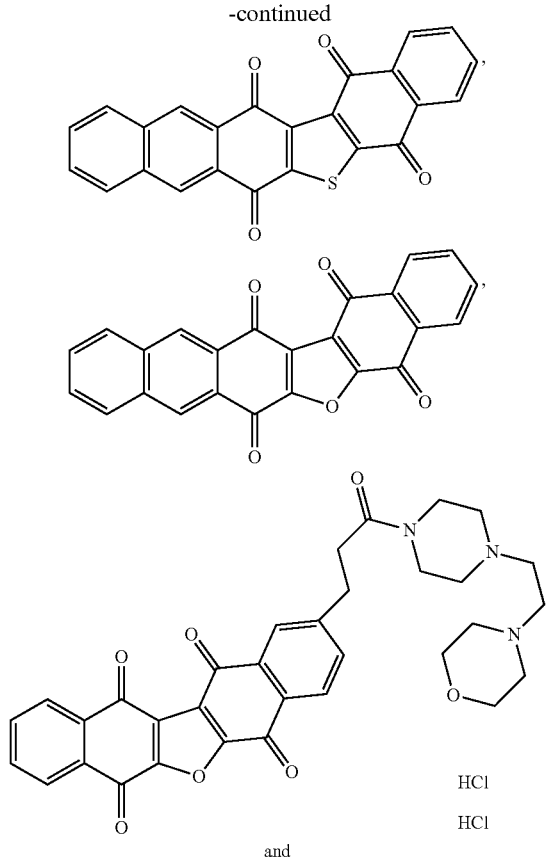
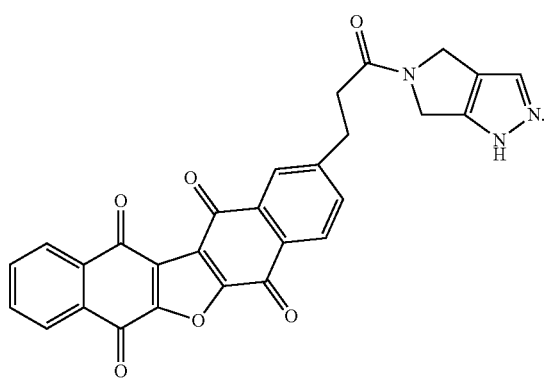 [SMILES: O=C(CCc1ccc2c(=O)c3oc4c(=O)c5ccccc5c(=O)c4c3c(=O)c2c1)N1Cc2cn[nH]c2C1]
19. A compound selected from the group consisting of:
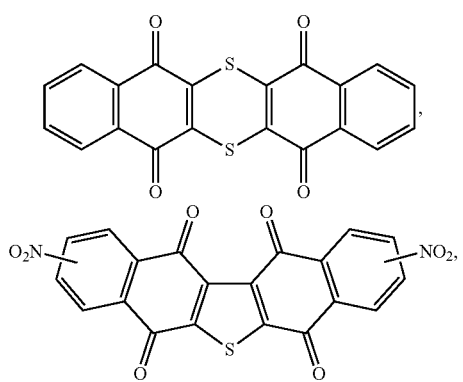
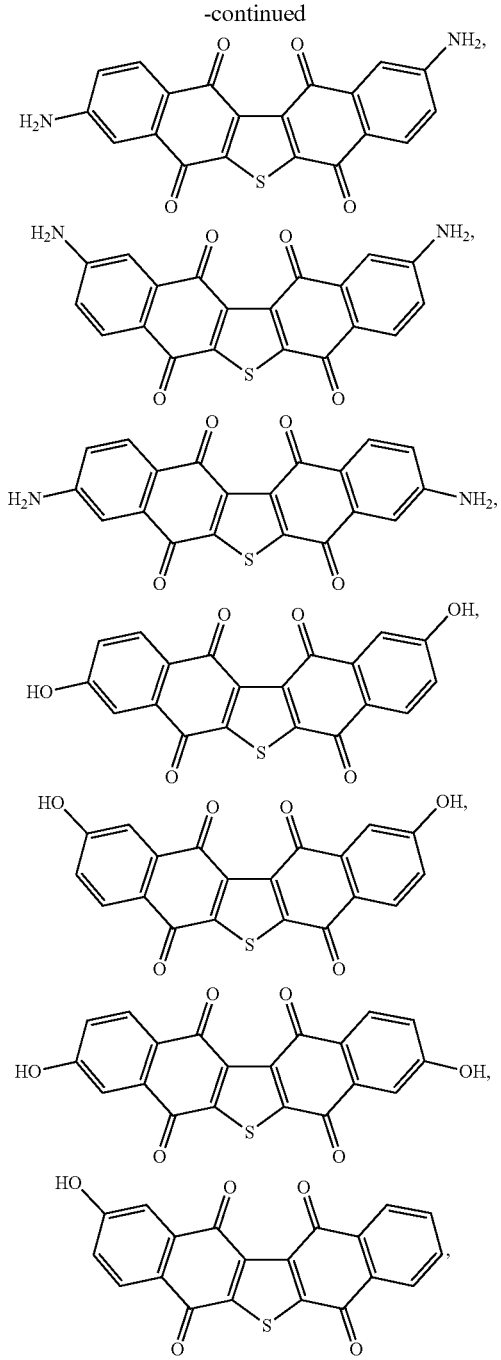
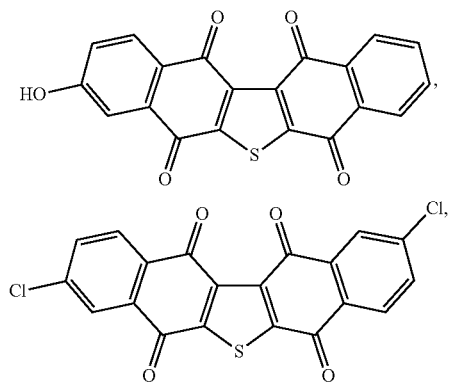

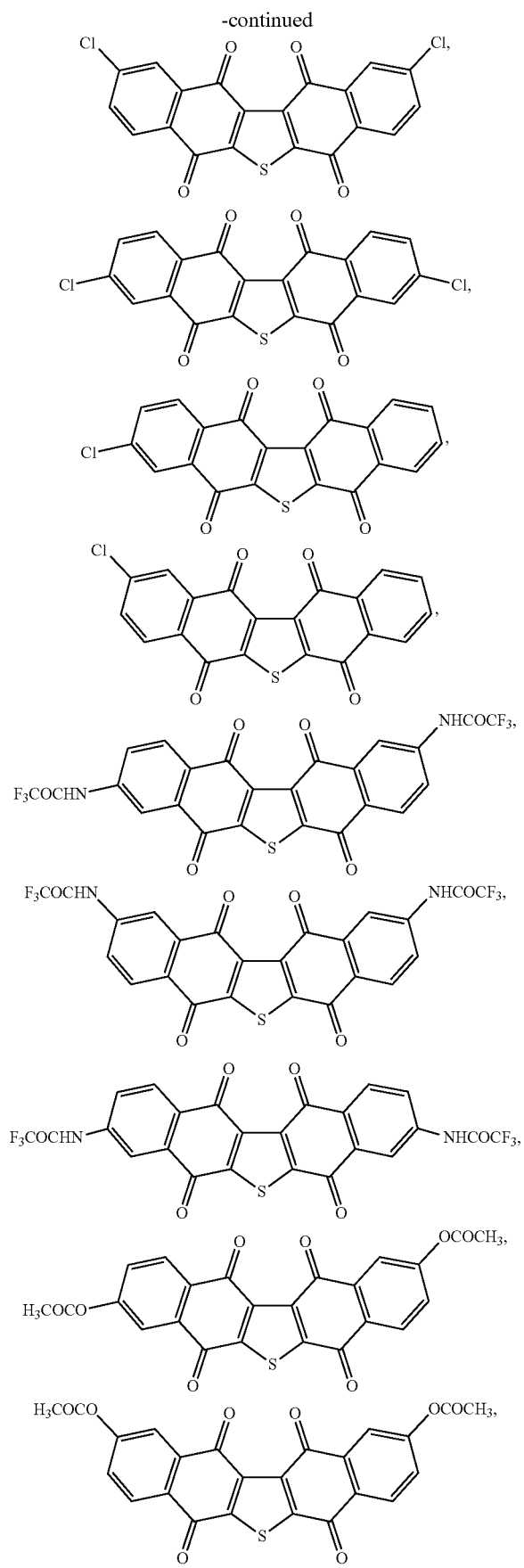
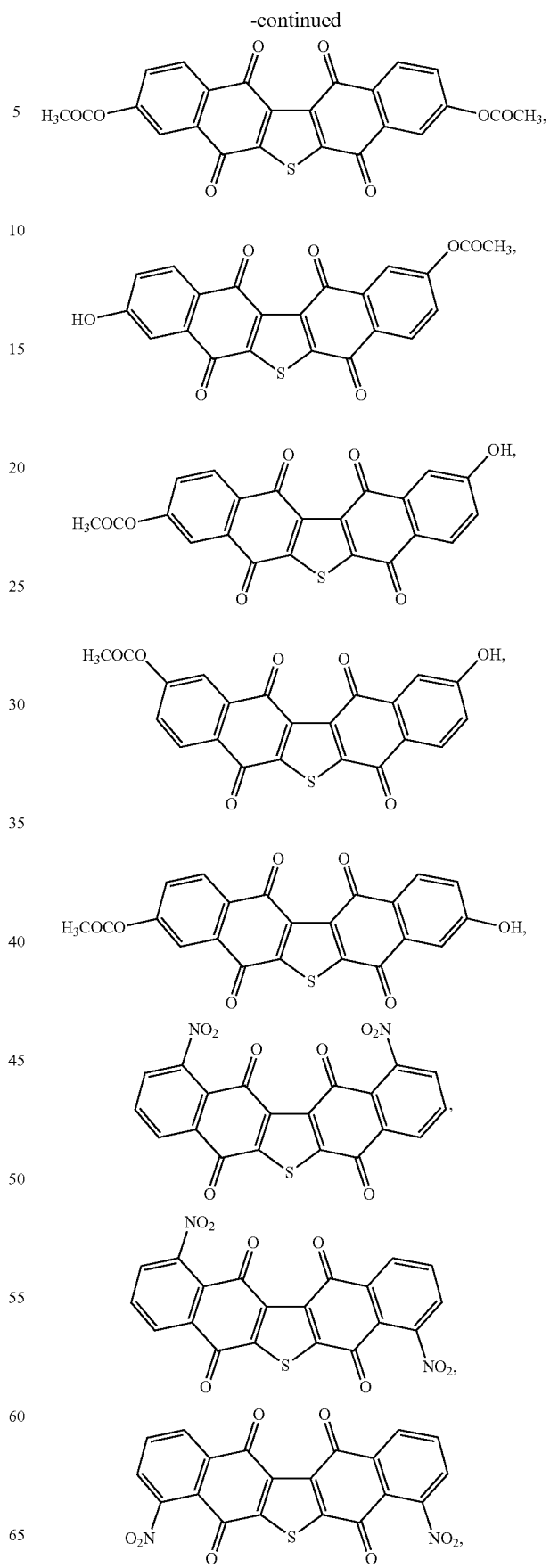

189
-continued
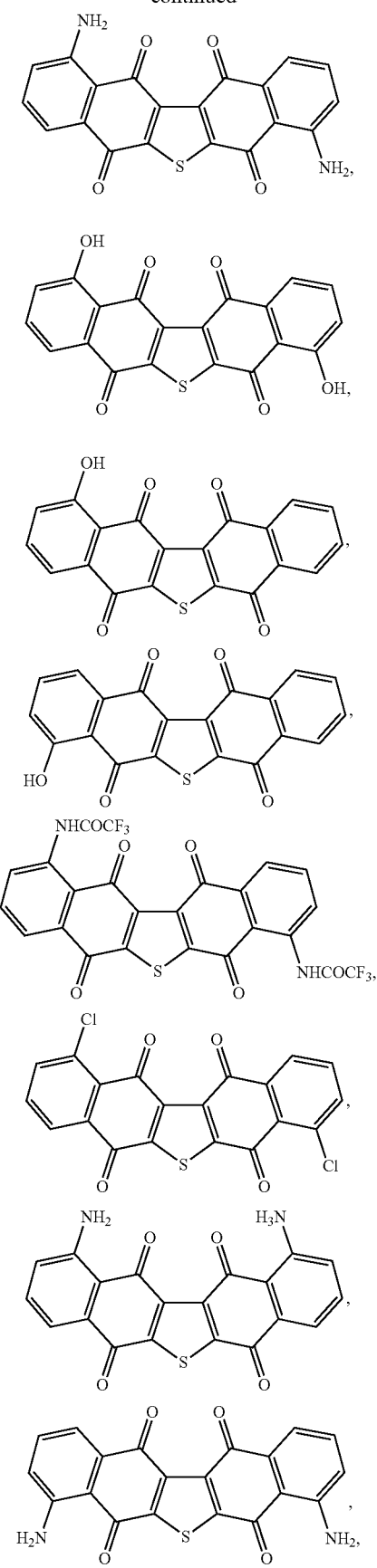
190
-continued
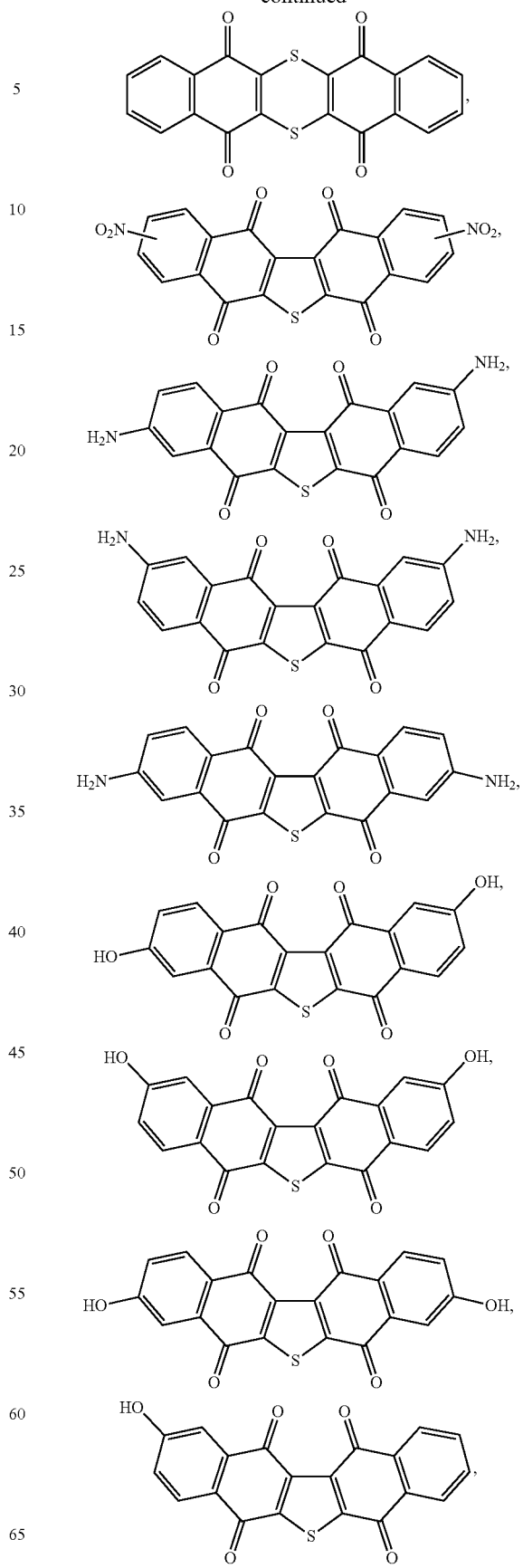

191
-continued
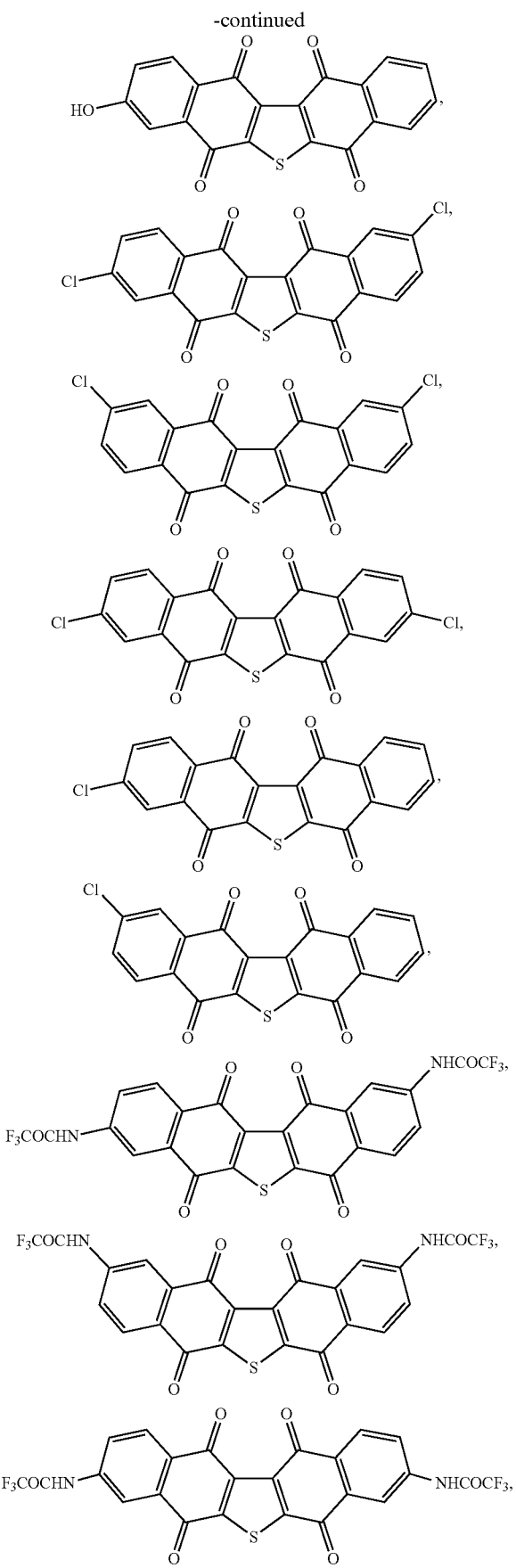
192
-continued
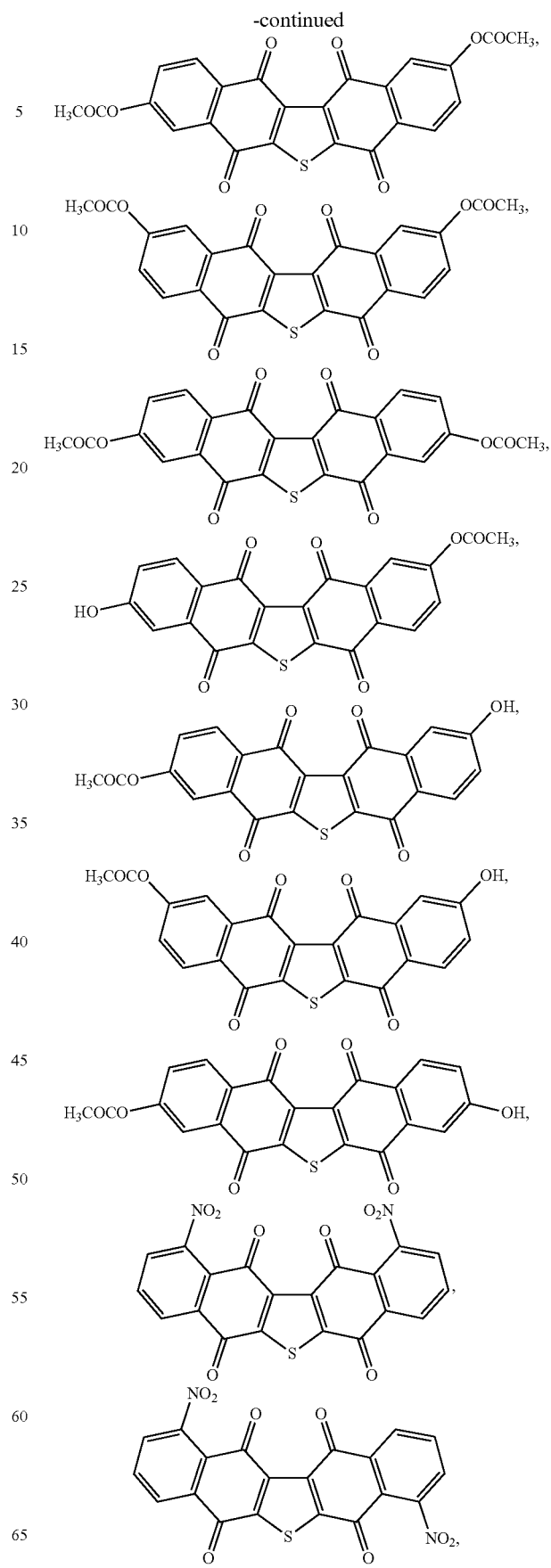

193
-continued
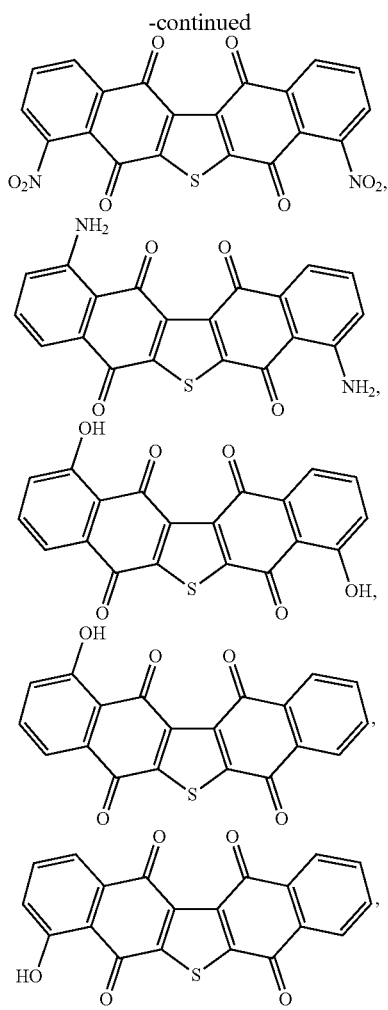
194
-continued
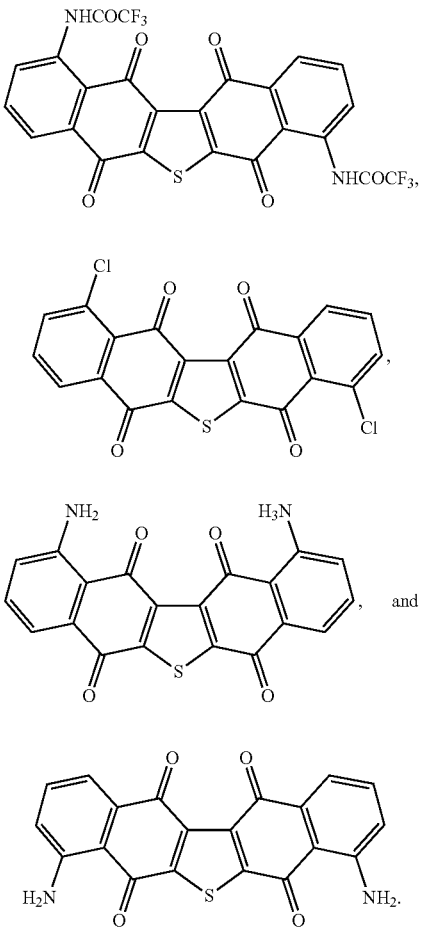
* * * * *

SEQUENCE LISTING

```
<160> NUMBER OF SEQ ID NOS: 4

<210> SEQ ID NO 1
<211> LENGTH: 110
<212> TYPE: PRT
<213> ORGANISM: Homo sapiens

<400> SEQUENCE: 1

Met Arg Phe Met Thr Leu Leu Phe Leu Thr Ala Leu Ala Gly Ala Leu
1               5                   10                  15

Val Cys Ala Tyr Asp Pro Glu Ala Ala Ser Ala Pro Gly Ser Gly Asn
            20                  25                  30

Pro Cys His Glu Ala Ser Ala Ala Gln Lys Glu Asn Ala Gly Glu Asp
        35                  40                  45

Pro Gly Leu Ala Arg Gln Ala Pro Lys Pro Arg Lys Gln Arg Ser Ser
    50                  55                  60

Leu Leu Glu Lys Gly Leu Asp Gly Ala Lys Lys Ala Val Gly Gly Leu
65                  70                  75                  80

Gly Lys Leu Gly Lys Asp Ala Val Glu Asp Leu Glu Ser Val Gly Lys
                85                  90                  95

Gly Ala Val His Asp Val Lys Asp Val Leu Asp Ser Val Leu
            100                 105                 110

<210> SEQ ID NO 2
<211> LENGTH: 48
<212> TYPE: PRT
<213> ORGANISM: Homo sapiens

<400> SEQUENCE: 2

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45

<210> SEQ ID NO 3
<211> LENGTH: 109
<212> TYPE: PRT
<213> ORGANISM: Homo sapiens

<400> SEQUENCE: 3

Met Arg Phe Met Thr Leu Leu Phe Leu Thr Ala Leu Ala Gly Ala Leu
1               5                   10                  15

Val Cys Ala Tyr Asp Pro Glu Ala Ala Ser Ala Pro Gly Ser Gly Asn
            20                  25                  30

Pro Cys His Glu Ala Ser Ala Ala Gln Lys Glu Asn Ala Gly Glu Asp
        35                  40                  45

Pro Gly Leu Ala Arg Gln Ala Pro Lys Pro Arg Lys Gln Arg Ser Ser
    50                  55                  60
```

```
Leu Leu Glu Lys Gly Leu Asp Gly Ala Lys Ala Val Gly Gly Leu
 65                  70                  75                  80

Gly Lys Leu Gly Lys Asp Ala Val Glu Asp Leu Glu Ser Val Gly Lys
                 85                  90                  95

Gly Ala Val Asp Val Lys Asp Val Leu Asp Ser Val Leu
                100                 105

<210> SEQ ID NO 4
<211> LENGTH: 333
<212> TYPE: PRT
<213> ORGANISM: Homo sapiens

<400> SEQUENCE: 4

Met Gly Lys Val Lys Val Gly Val Asn Gly Phe Gly Arg Ile Gly Arg
  1               5                  10                  15

Leu Val Thr Arg Ala Ala Phe Asn Ser Gly Lys Val Asp Ile Val Ala
                 20                  25                  30

Ile Asn Asp Pro Phe Ile Asp Leu Asn Tyr Met Val Tyr Met Phe Gln
             35                  40                  45

Tyr Asp Ser Thr His Gly Lys Phe His Gly Thr Val Lys Ala Glu Asn
 50                  55                  60

Gly Lys Leu Val Ile Asn Gly Asn Pro Ile Thr Ile Phe Gln Glu Arg
 65                  70                  75                  80

Asp Pro Ser Lys Ile Lys Trp Gly Asp Ala Gly Ala Glu Tyr Val Val
                 85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Trp Ser Ser Asp Phe Asn Ser Asp
        275                 280                 285

Thr His Ser Ser Thr Phe Asp Ala Gly Ala Gly Ile Ala Leu Asn Asp
290                 295                 300
```

```
His Phe Val Lys Leu Ile Ser Trp Tyr Asp Asn Glu Phe Gly Tyr Ser
305                 310                 315                 320

Asn Arg Trp Asp Leu Met Ala His Met Ala Ser Lys Glu
                325                 330
```